(12) United States Patent
Li et al.

(10) Patent No.: US 10,615,349 B2
(45) Date of Patent: Apr. 7, 2020

(54) DONOR-ACCEPTOR TYPE THERMALLY ACTIVATED DELAYED FLUORESCENT MATERIALS BASED ON IMIDAZO[1,2-F]PHENANTHRIDINE AND ANALOGUES

(71) Applicant: Arizona Board of Regents on behalf of Arizona State University, Scottsdale, AZ (US)

(72) Inventors: Jian Li, Tempe, AZ (US); Zhi-Qiang Zhu, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/984,157

(22) Filed: May 18, 2018

(65) Prior Publication Data
US 2018/0337345 A1 Nov. 22, 2018

Related U.S. Application Data

(60) Provisional application No. 62/508,518, filed on May 19, 2017.

(51) Int. Cl.
| | | |
|---|---|---|
| C07D 471/22 | (2006.01) | |
| H01L 51/00 | (2006.01) | |
| C09K 11/06 | (2006.01) | |
| C07D 495/22 | (2006.01) | |
| C07D 471/14 | (2006.01) | |
| C07D 495/14 | (2006.01) | |
| C07D 491/147 | (2006.01) | |
| C07D 471/20 | (2006.01) | |
| C07D 491/22 | (2006.01) | |
| H01L 51/50 | (2006.01) | |

(52) U.S. Cl.
CPC ........ *H01L 51/0072* (2013.01); *C07D 471/14* (2013.01); *C07D 471/20* (2013.01); *C07D 471/22* (2013.01); *C07D 491/147* (2013.01); *C07D 491/22* (2013.01); *C07D 495/14* (2013.01); *C07D 495/22* (2013.01); *C09K 11/06* (2013.01); *H01L 51/0071* (2013.01); *C09K 2211/1018* (2013.01); *H01L 51/5012* (2013.01)

(58) Field of Classification Search
CPC .. C07D 471/14; C07D 495/22; C07D 471/20; C07D 491/147; C07D 491/22; C07D 471/22; C07D 495/14; H01L 51/0072; H01L 51/0071
USPC ....................................................... 544/230
See application file for complete search history.

(56) References Cited

U.S. PATENT DOCUMENTS

| | | |
|---|---|---|
| 2009/0136779 A1 | 5/2009 | Cheng et al. |
| 2012/0202997 A1 | 8/2012 | Parham et al. |
| 2017/0077420 A1 | 3/2017 | Li et al. |

FOREIGN PATENT DOCUMENTS

| | | |
|---|---|---|
| KR | 2011066763 A | 6/2011 |
| KR | 2014027030 A | 3/2014 |
| WO | WO2010050778 A | 5/2010 |
| WO | WO2015099507 | 7/2015 |

OTHER PUBLICATIONS

Yan, et al. Organic & Biomolecular Chemistry, 11(45), 2013, 7966-7977.
U.S. Appl. No. 15/984,102, filed May 18, 2018, Thermally Assisted Delayed Fluorescent Materials With Triad-Type Materials, Jian Li.
U.S. Appl. No. 15/246,754, filed Aug. 25, 2016, US-2017-0077420-A1, Thermally Activated Delayed Fluorescent Material Based on 9,10-Dihydro-9,9-Dimethylacridine Analogous for Prolonging Device Longevity, Jian Li; Daijun Feng.
Uoyama et al., "Highly efficient organic light-emitting diodes from delayed fluorescence" Nature, 492:234-238, (2012).

*Primary Examiner* — Kahsay Habte
(74) *Attorney, Agent, or Firm* — Riverside Law LLP

(57) ABSTRACT

Donor-acceptor type thermally activated delayed fluorescent emitters based on imidazo[1,2-F]phenanthridine and analogues for full color displays and lighting applications.

3 Claims, 1 Drawing Sheet

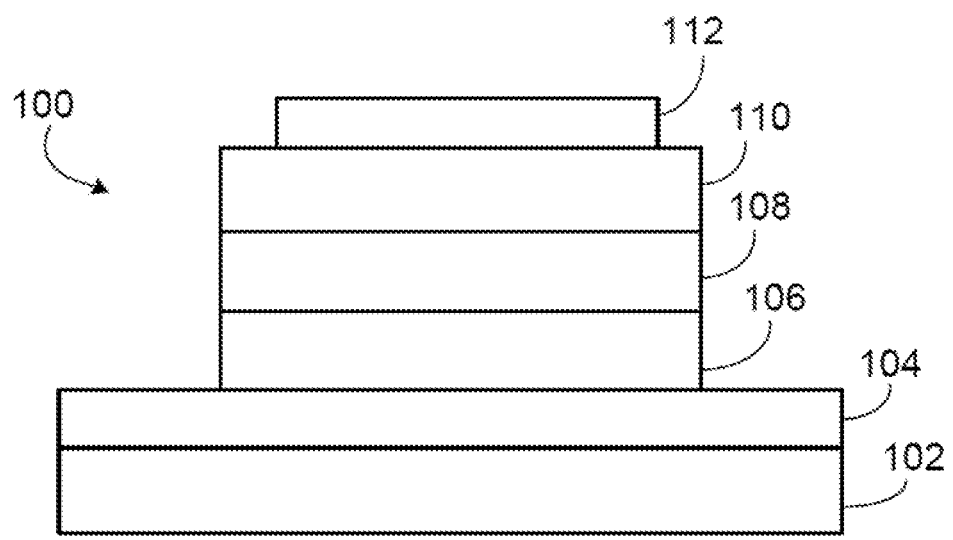

DONOR-ACCEPTOR TYPE THERMALLY ACTIVATED DELAYED FLUORESCENT MATERIALS BASED ON IMIDAZO[1,2-F]PHENANTHRIDINE AND ANALOGUES

CROSS-REFERENCE TO RELATED APPLICATION

This application claims the benefit of U.S. patent application Ser. No. 62/508,518 entitled "DONOR-ACCEPTOR TYPE THERMALLY ACTIVATED DELAYED FLUORESCENT MATERIALS BASED ON IMIDAZO[1,2-F] PHENANTHRIDINE AND ANALOGUES" filed May 19, 2017, which is incorporated by reference herein in its entirety.

TECHNICAL FIELD

This invention relates to donor-acceptor type thermally activated delayed fluorescent materials based on imidazo[1,2-F]phenanthridine and analogues for full color displays and lighting applications.

BACKGROUND

Compounds capable of absorbing or emitting light can be used in a variety of optical and electro-optical devices, including photo-absorbing devices (e.g., solar- and photo-sensitive devices), photo-emitting devices, organic light-emitting diodes (OLEDs), and devices capable of photo-absorption and photo-emission. Much research has been devoted to the discovery and optimization of organic and organometallic materials for use in optical and electro-optical devices. Metal complexes can be used for many applications, such as emitters for OLEDs. Despite advances in research devoted to optical and electro-optical materials, many currently available materials exhibit a number of disadvantages, including poor processing ability, inefficient emission or absorption, and insufficient stability.

SUMMARY

General Formulas I-IV include donor-acceptor type thermally activated delayed fluorescent materials based on imidazo[1,2-f]phenanthridine and analogues for organic light emitting diodes (OLEDS) suitable for full color displays and lighting applications.

General Formula I

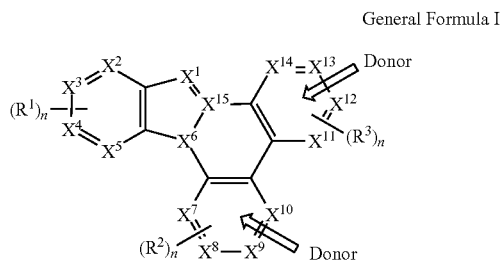

General Formula II

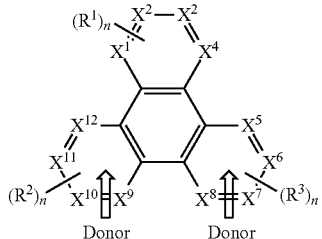

General Formula III

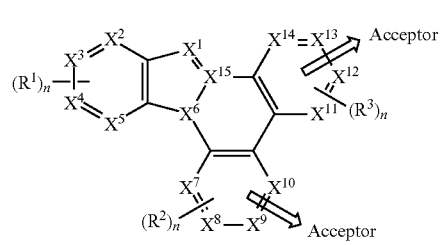

General Formula IV

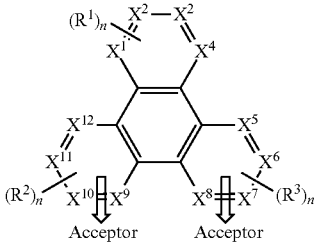

In General Formulas I-IV:

$R^1$, $R^2$, and $R^3$ each independently represents hydrogen, cyanide, halogen, hydroxy, amino, nitro, thiol, or substituted or unsubstituted $C_1$-$C_4$ alkyl, alkoxy, or aryl, and $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ each independently represents substituted or unsubstituted C, N, Si, O, or S, valency permitting, and each n is independently an integer as permitted by valence.

These general and specific aspects may be implemented using a device, system or method, or any combination of devices, systems, or methods. The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1 depicts a cross-sectional view of an organic light emitting device.

DETAILED DESCRIPTION

General Formulas I-IV include donor-acceptor type thermally activated delayed fluorescent materials based on imidazo[1,2-f]phenanthridine and analogues for organic light emitting diodes (OLEDS) suitable for full color displays and lighting applications.

Implementations of General Formulas I-IV are shown below.

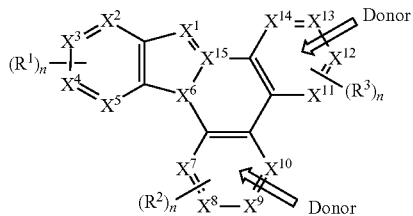

General Formula I

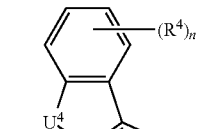

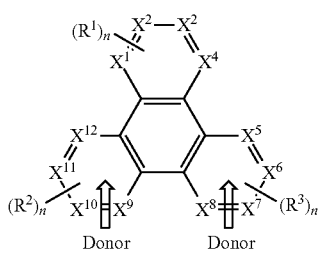

General Formula II

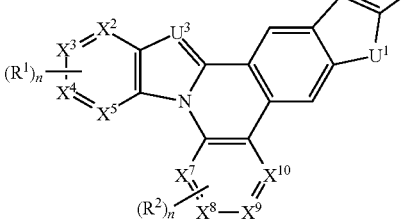

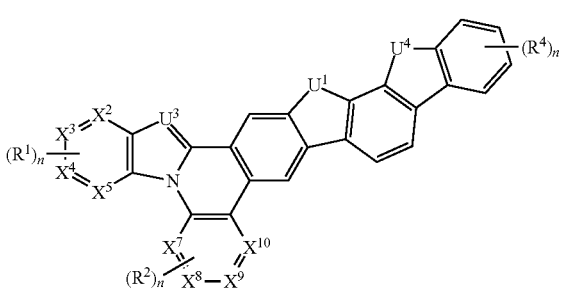

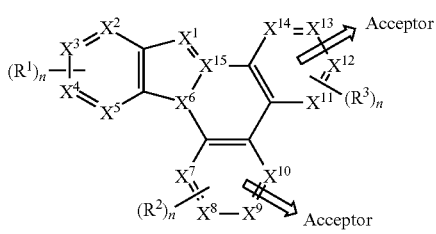

General Formula III

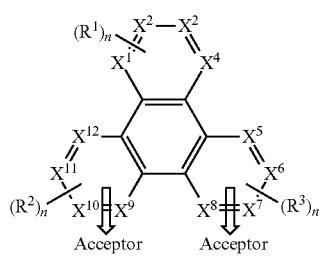

General Formula IV

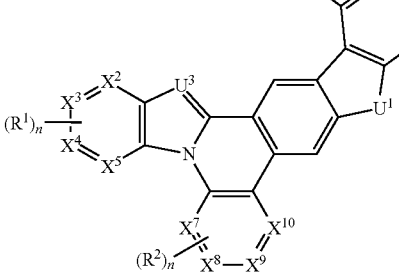

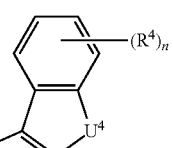

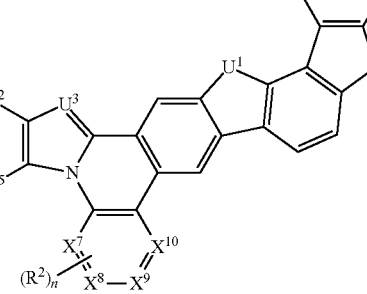

In General Formulas I-IV:

$R^1$, $R^2$, and $R^3$ each independently represents hydrogen, cyanide, halogen, hydroxy, amino, nitro, thiol, or substituted or unsubstituted $C_1$-$C_4$ alkyl, alkoxy, or aryl, and $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ each independently represents substituted or unsubstituted C, N, Si, O, or S, valency permitting, and each n is independently an integer as permitted by valence.

-continued
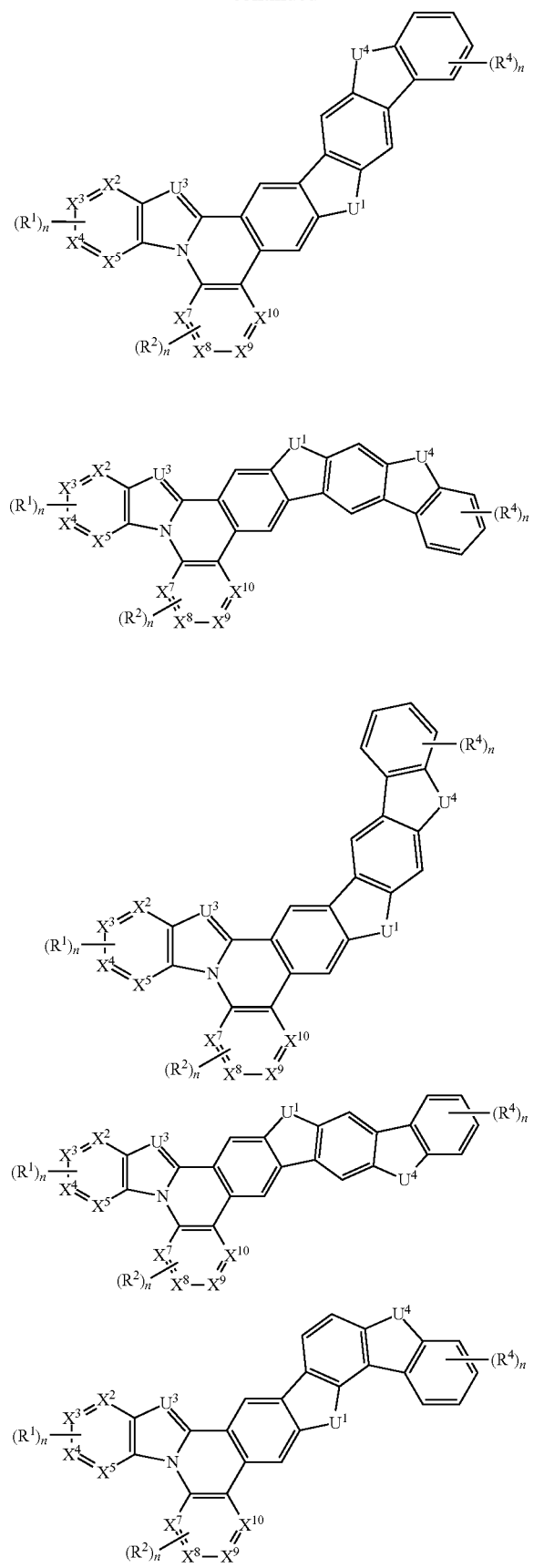
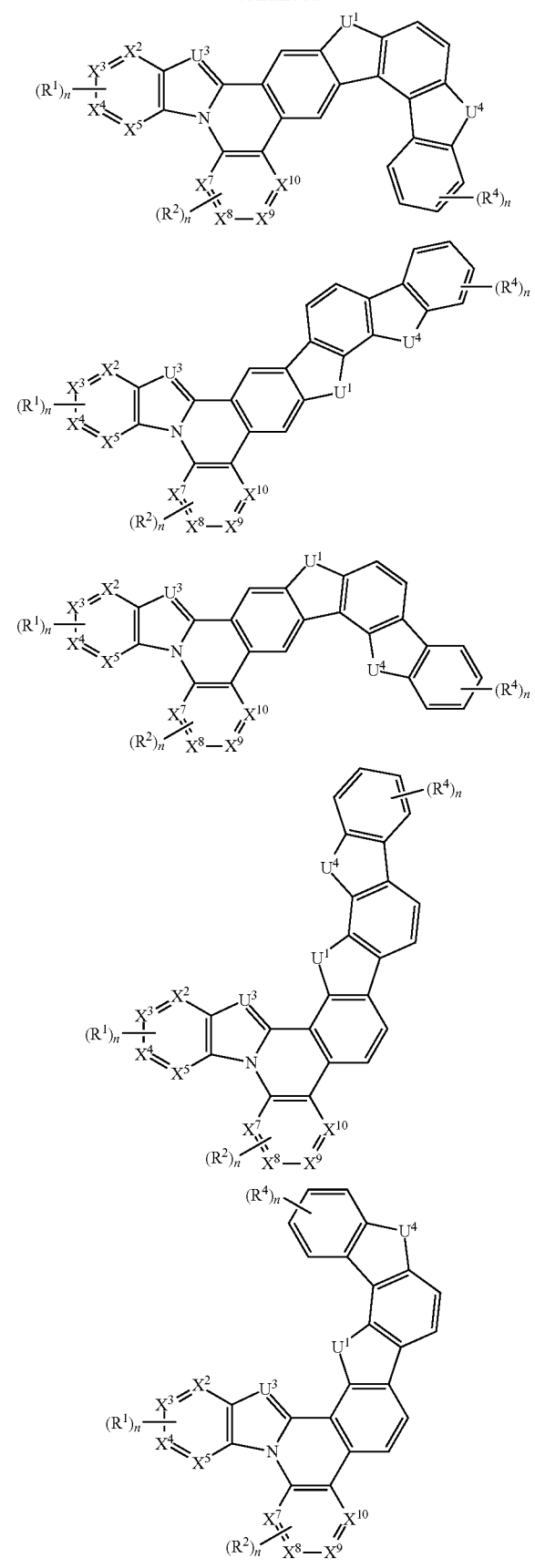

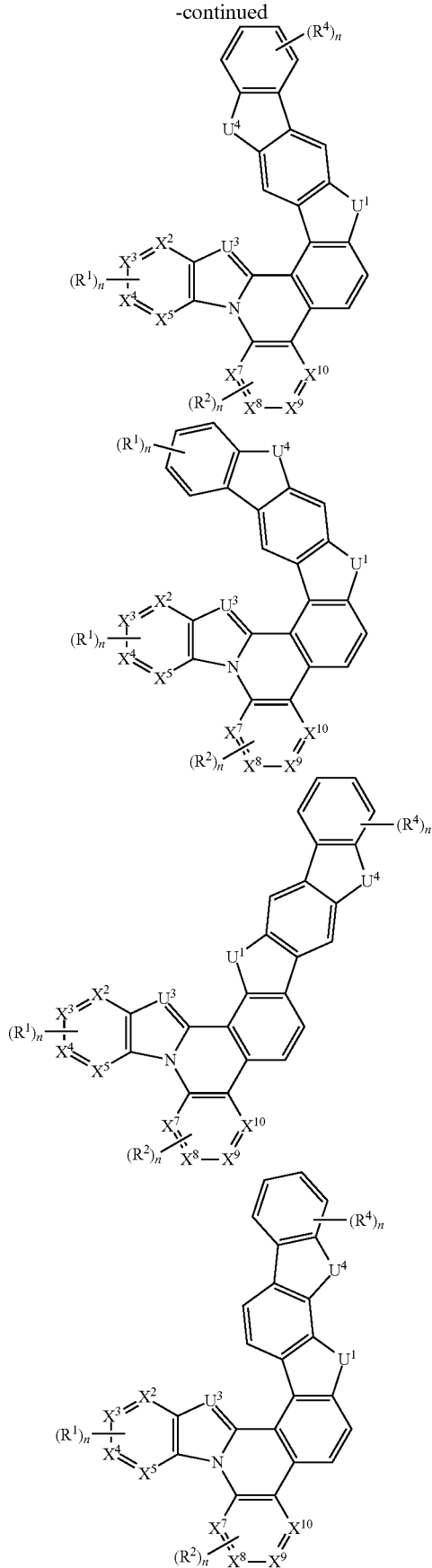
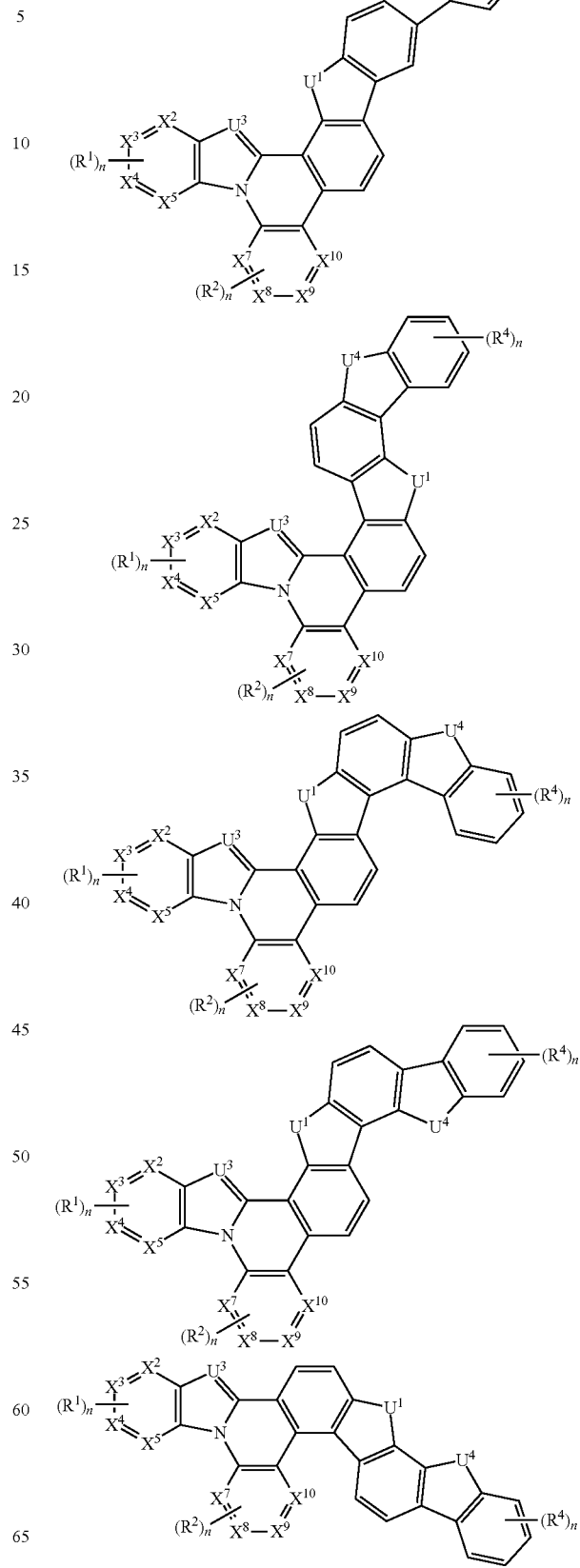

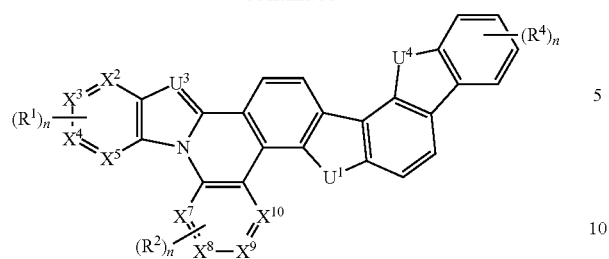
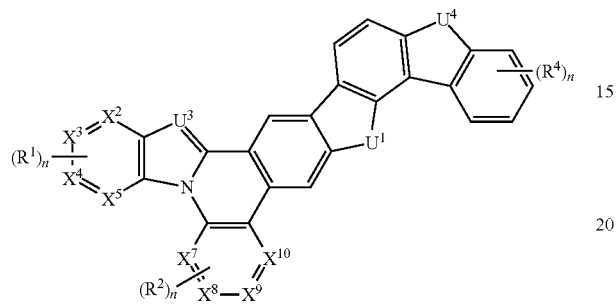
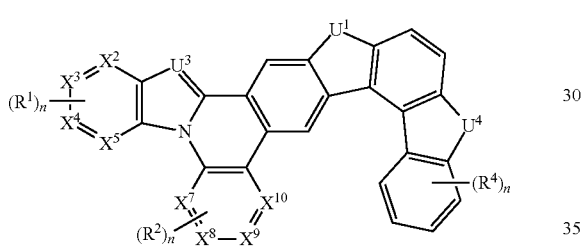
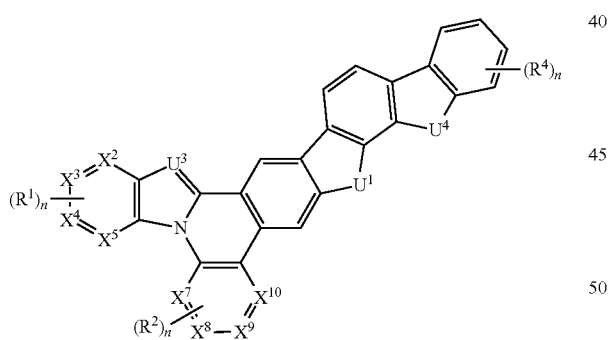
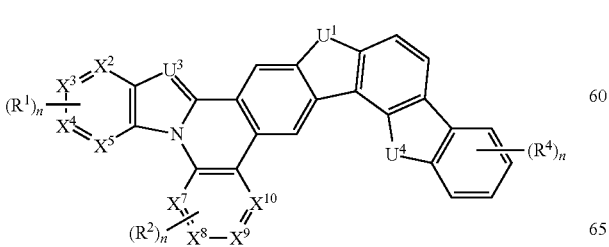
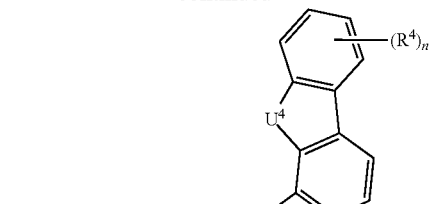
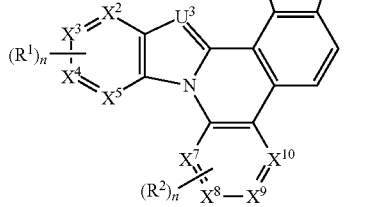

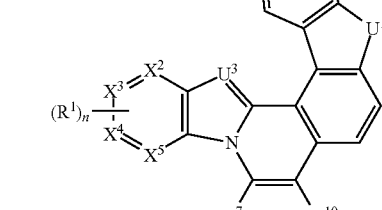

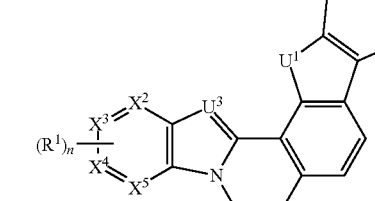
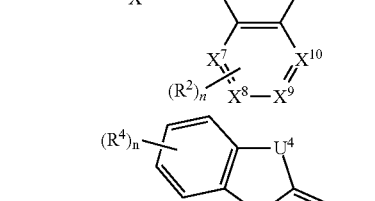
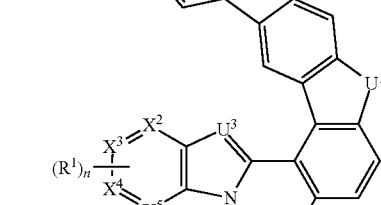
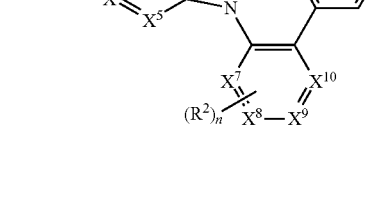

-continued
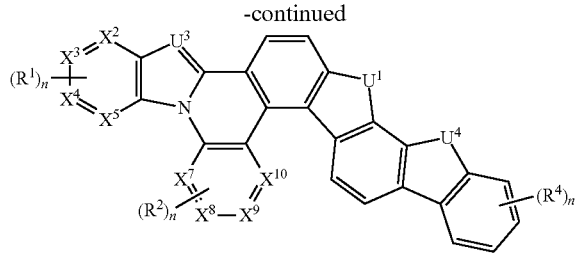
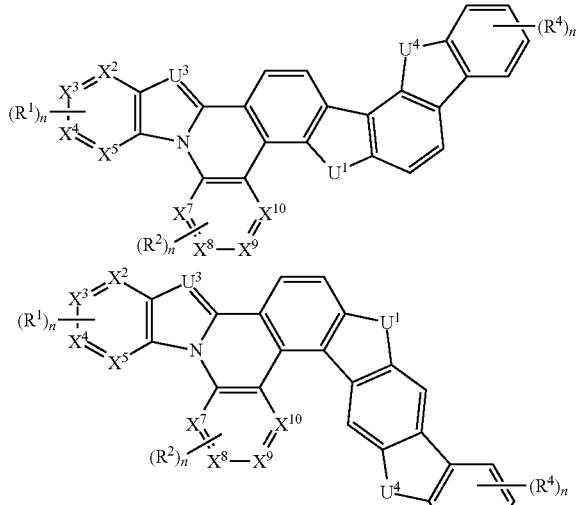
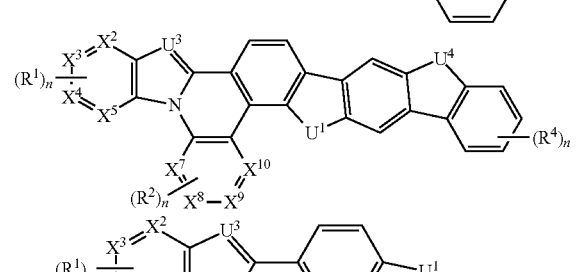
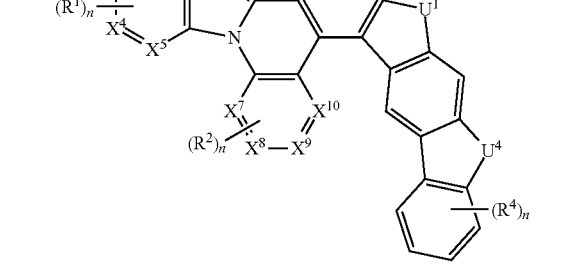
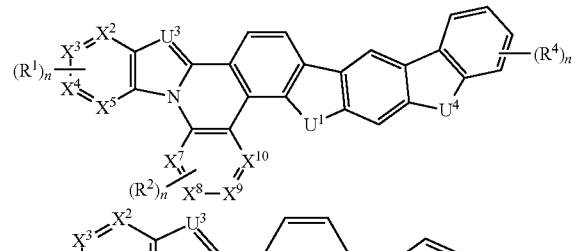
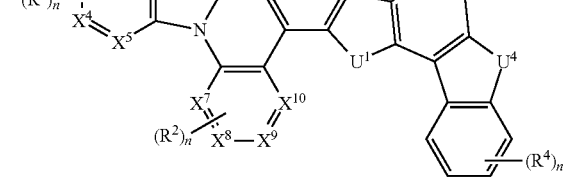
-continued
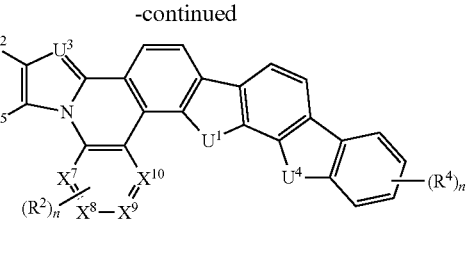
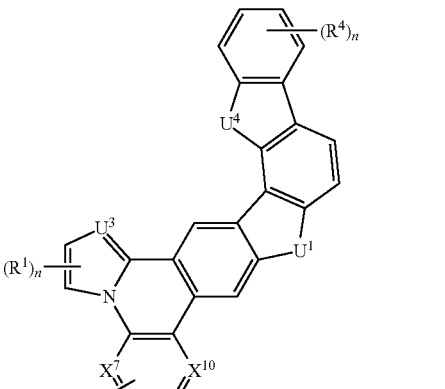
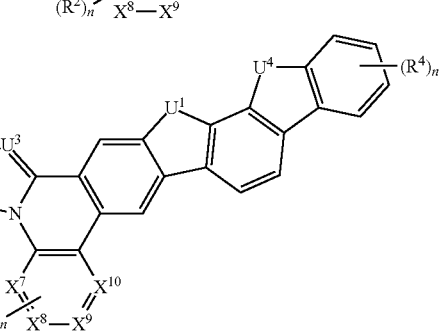
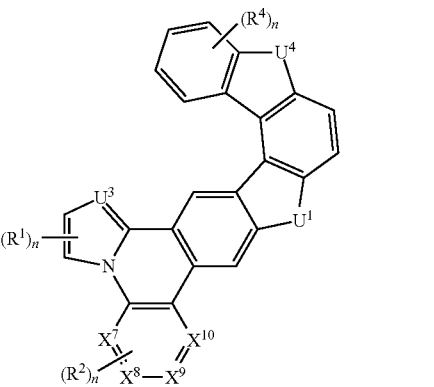
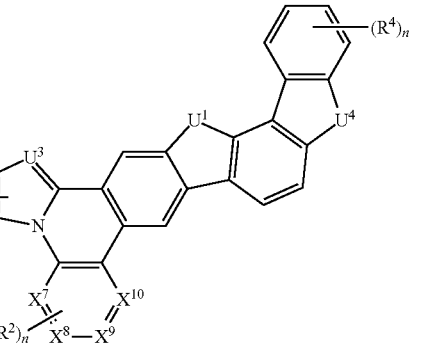

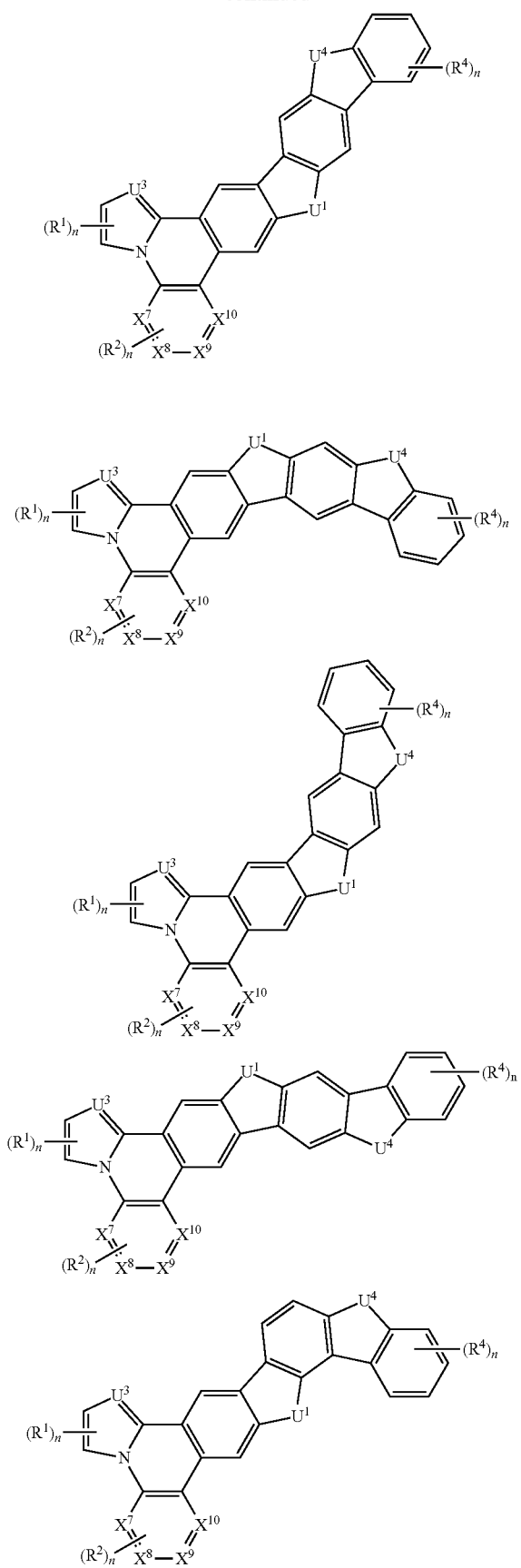
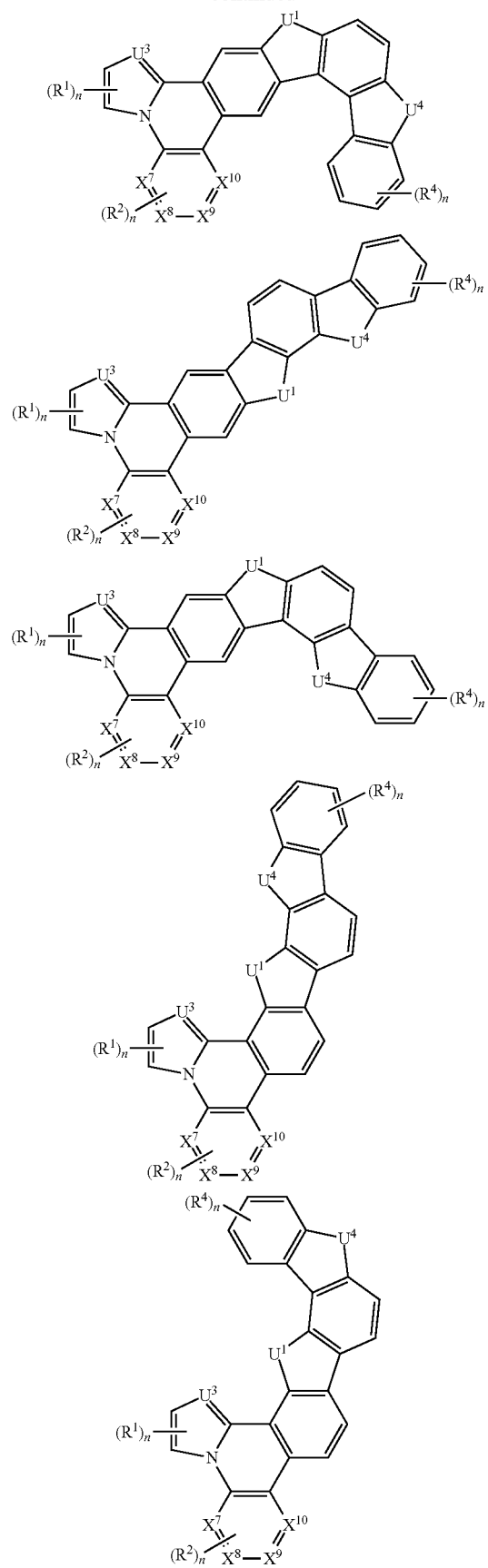

-continued
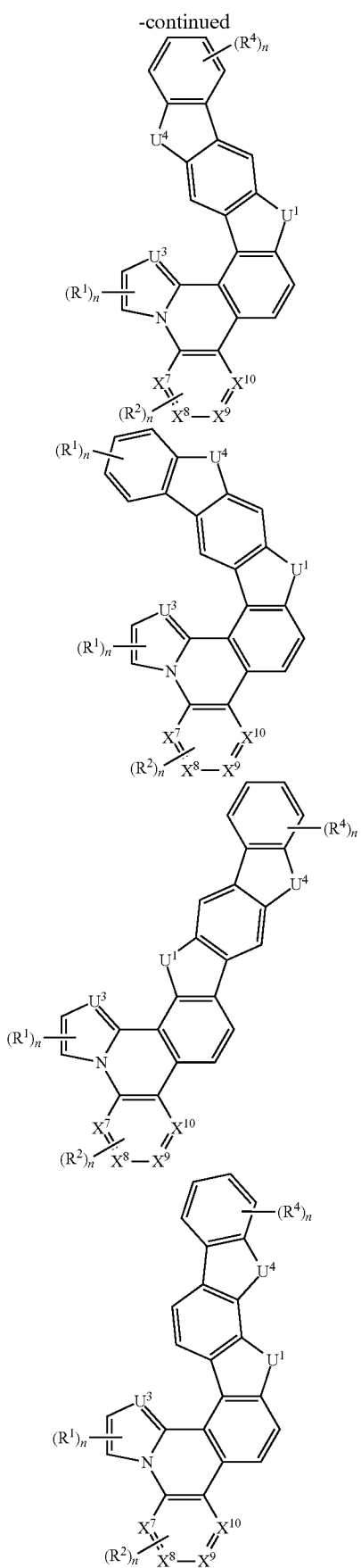
-continued
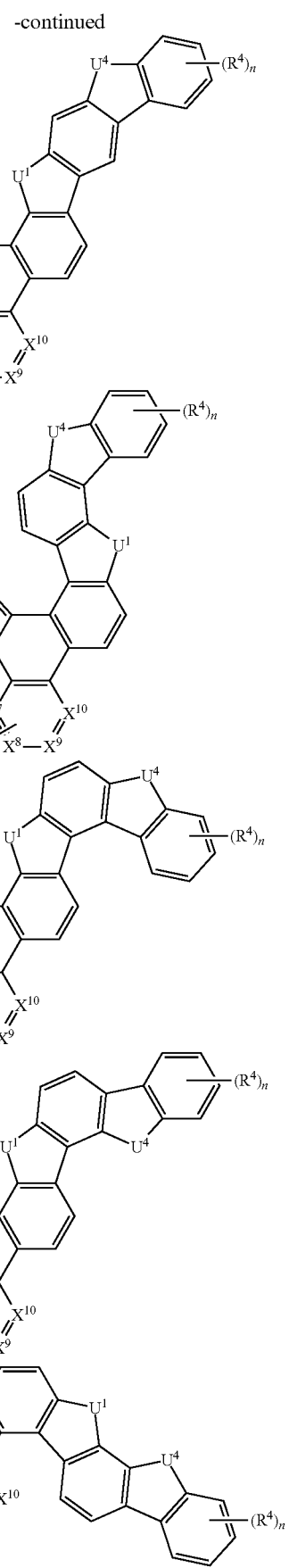

-continued
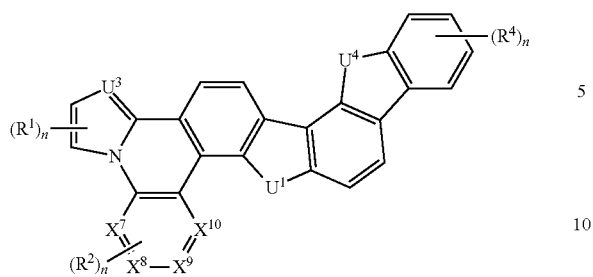
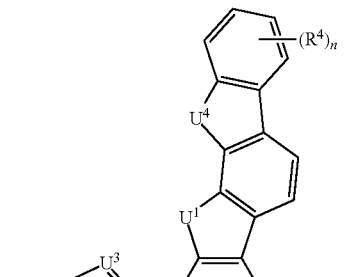
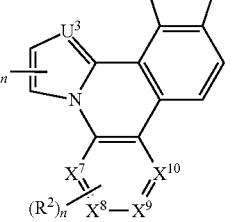
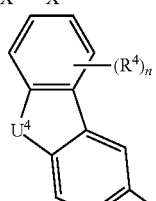
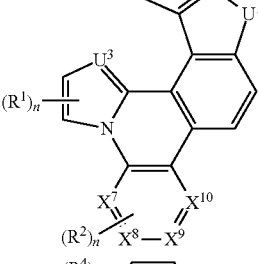
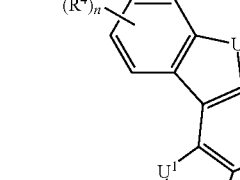
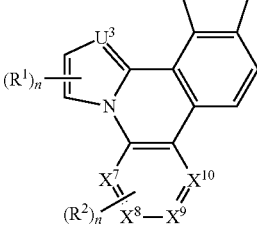
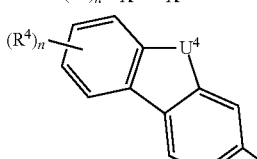
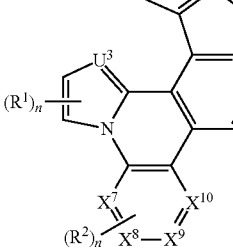

-continued
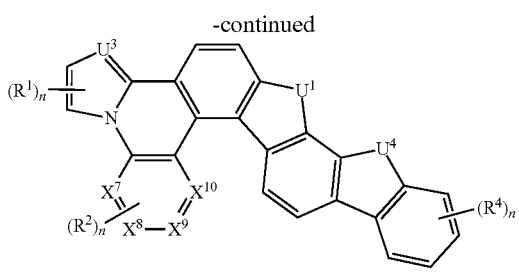
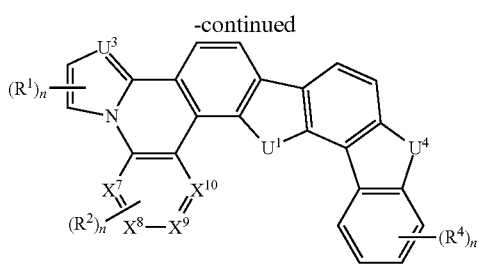
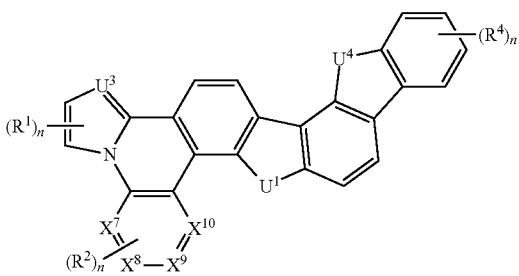
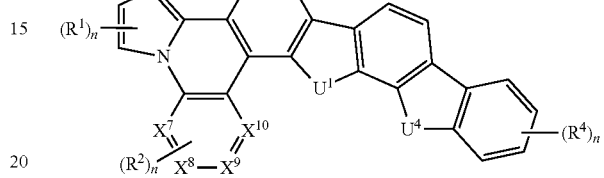
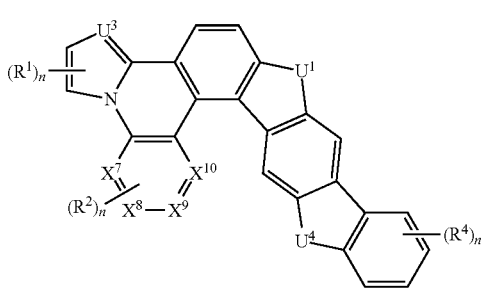
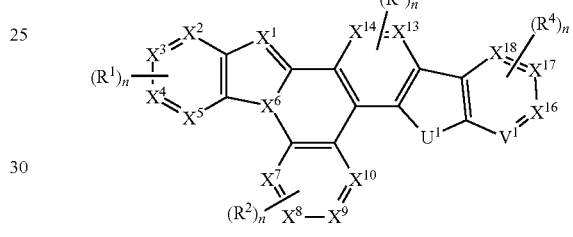
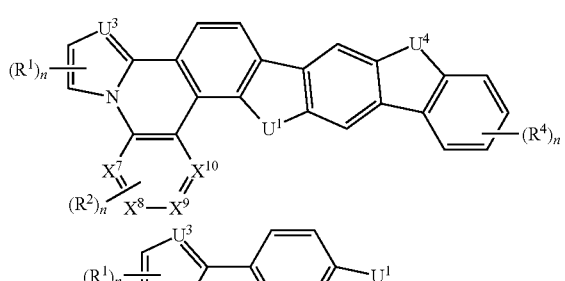
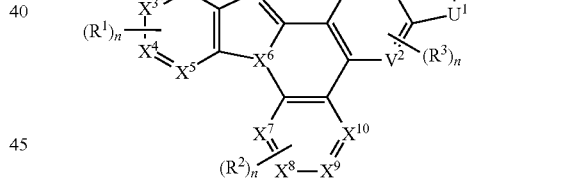
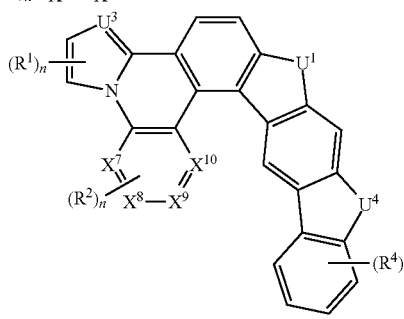
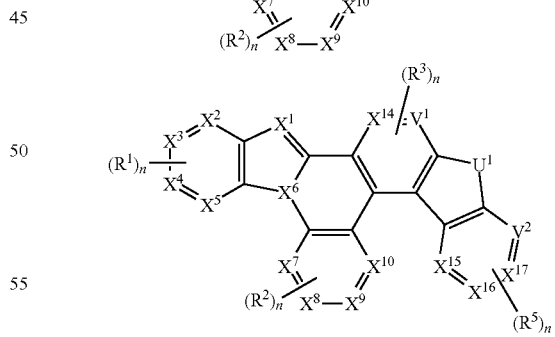
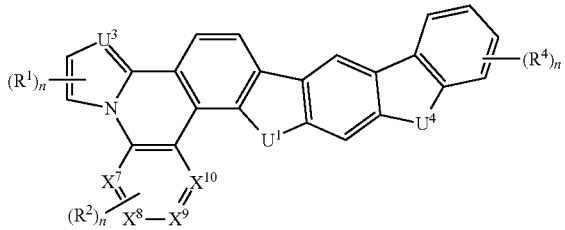
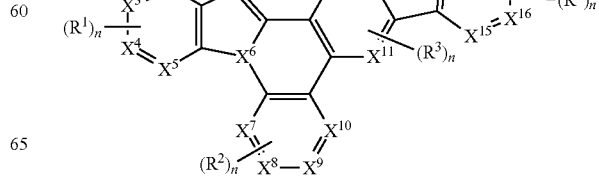

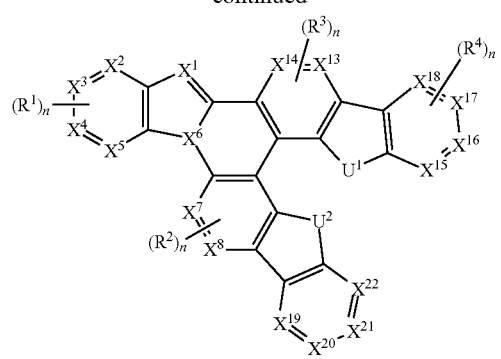
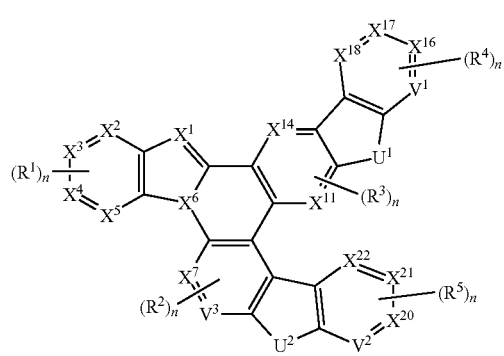
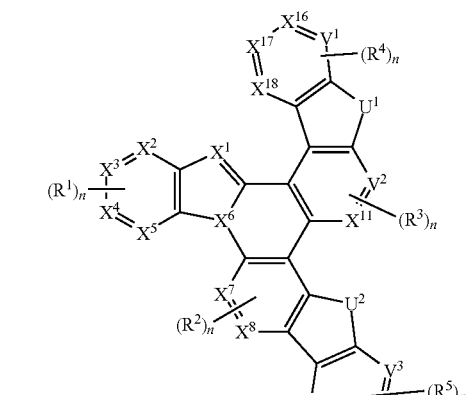
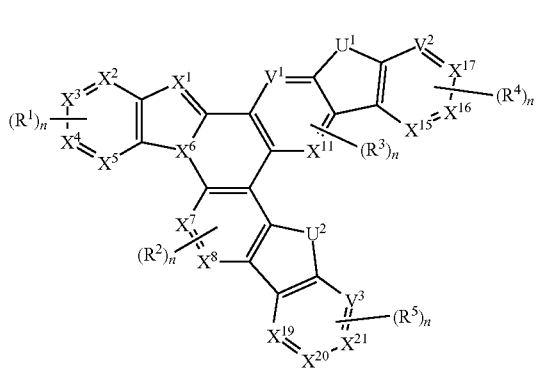
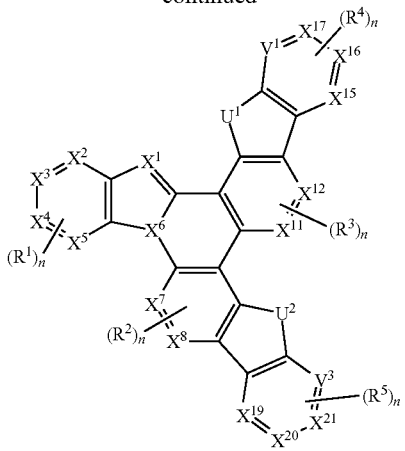
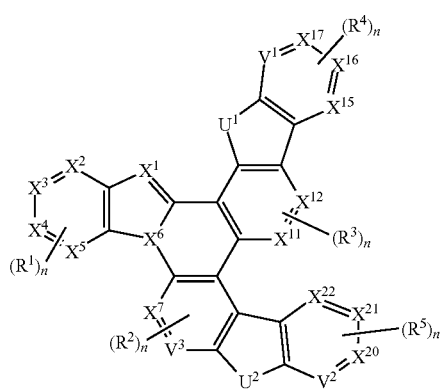
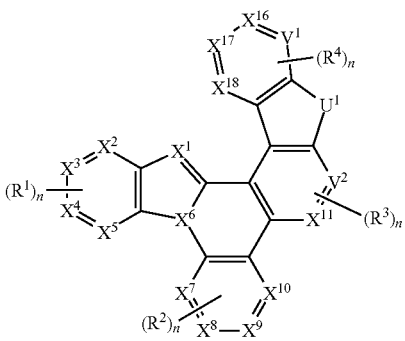
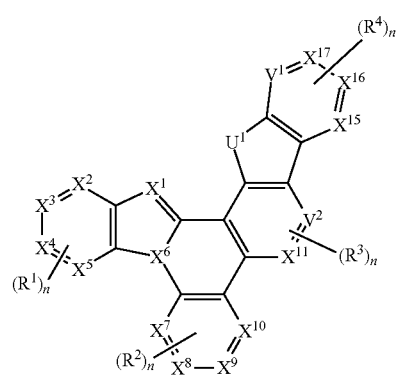

-continued
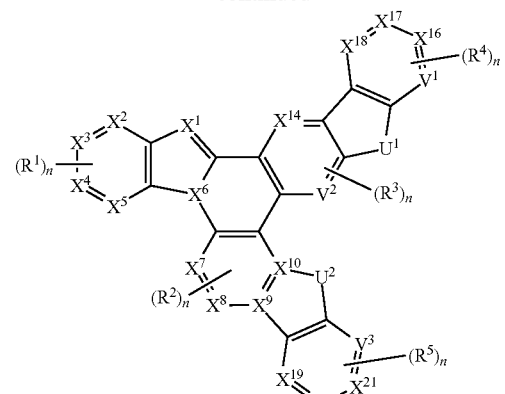
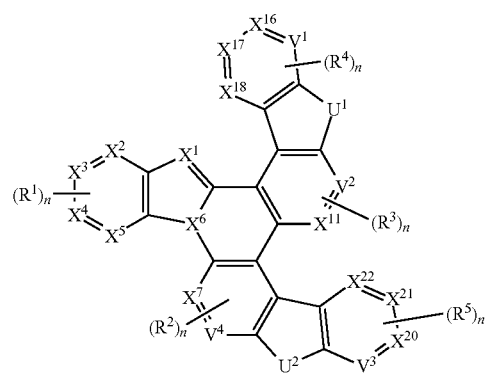
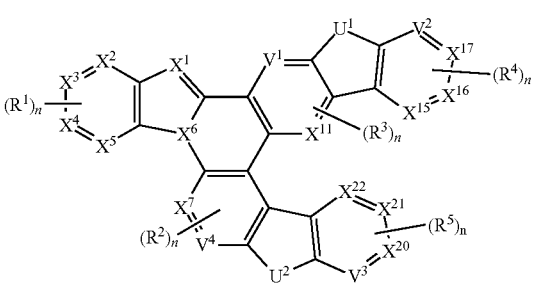
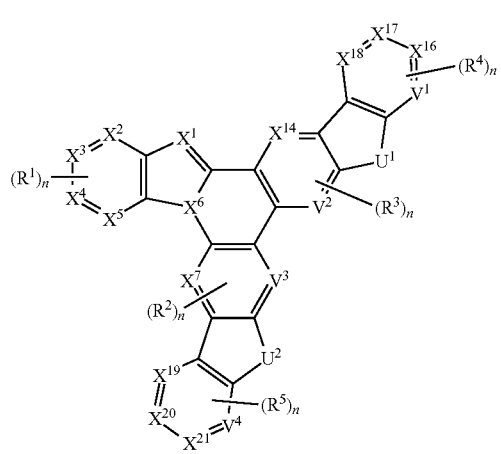
-continued
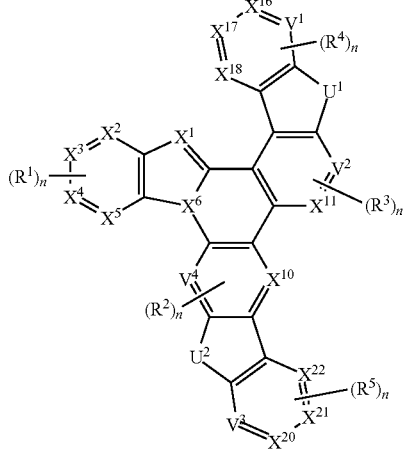
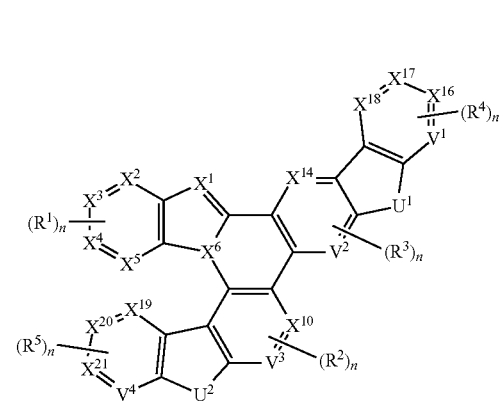
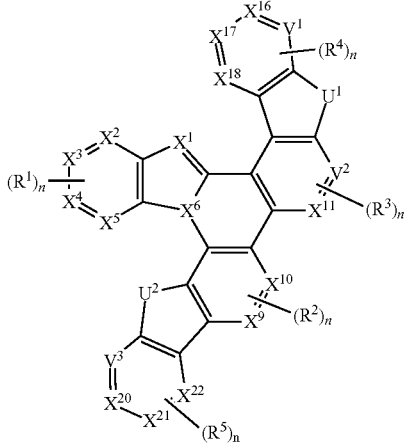
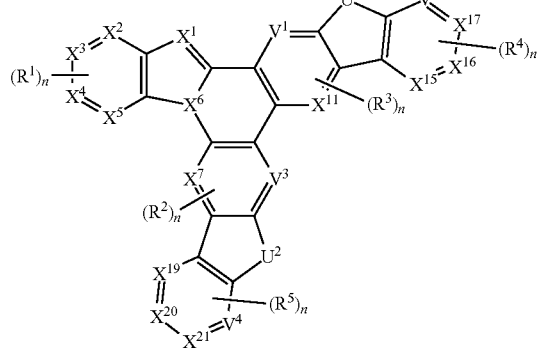

-continued
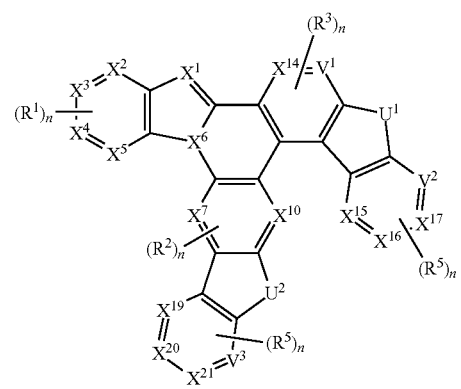
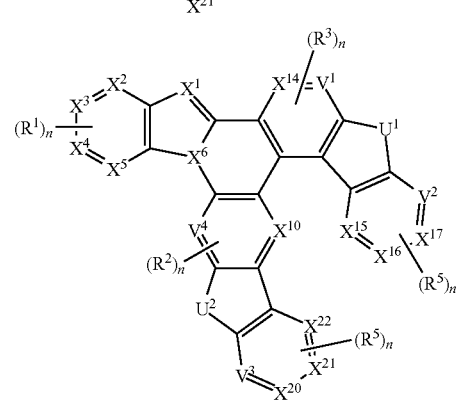
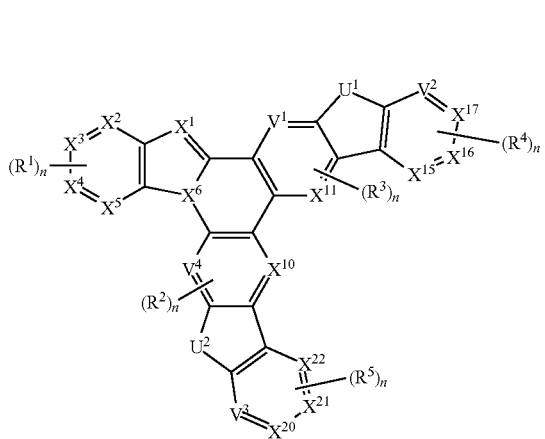
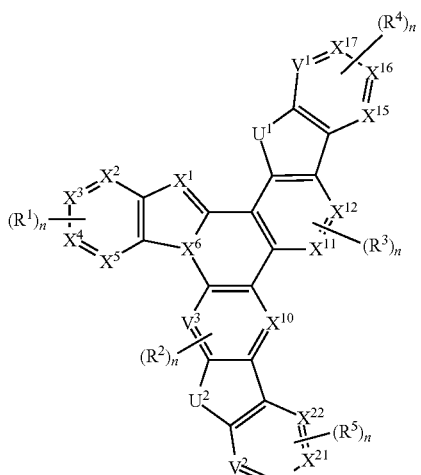
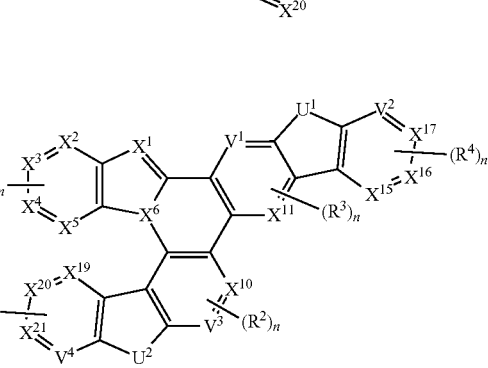
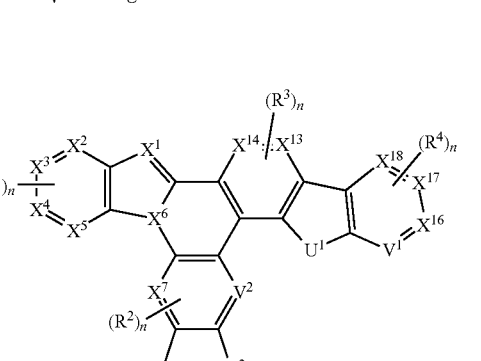
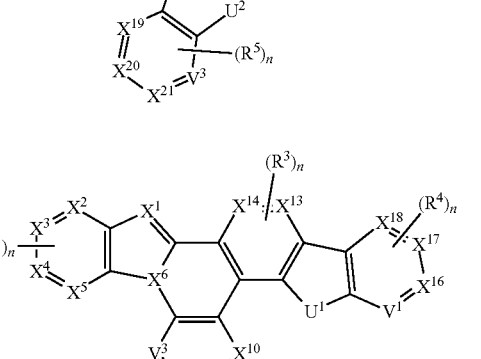

-continued
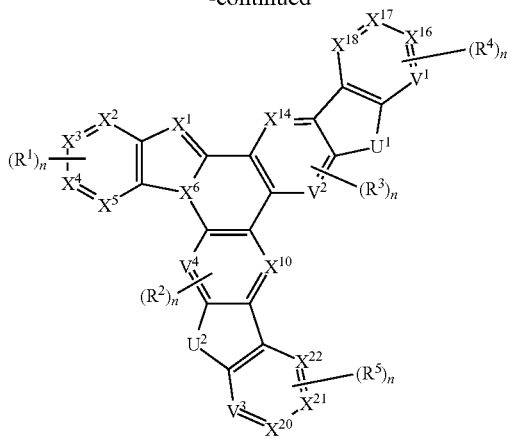
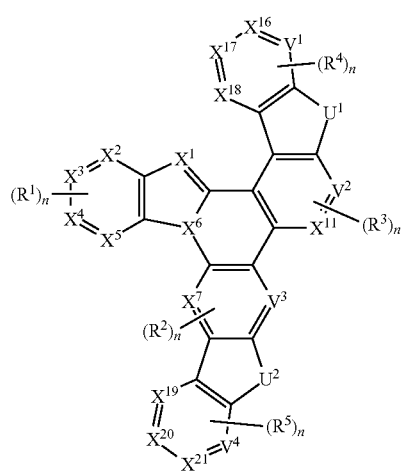
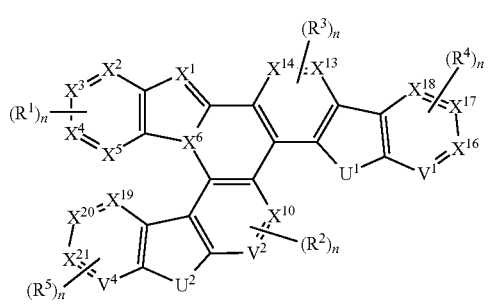
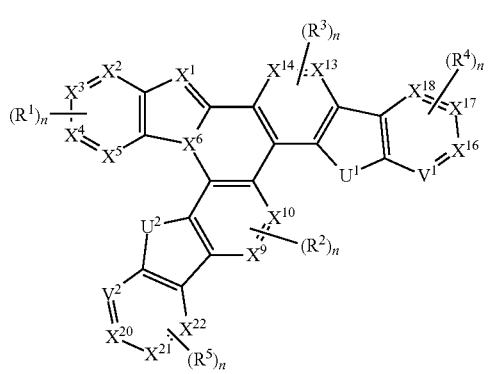
-continued
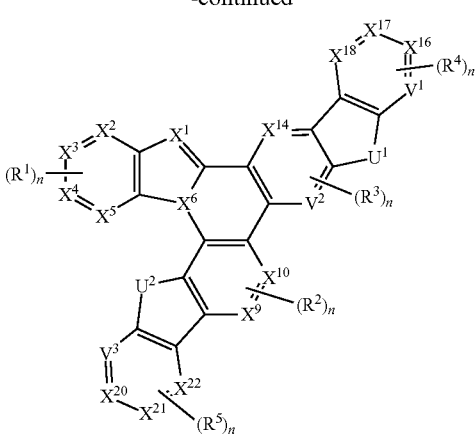
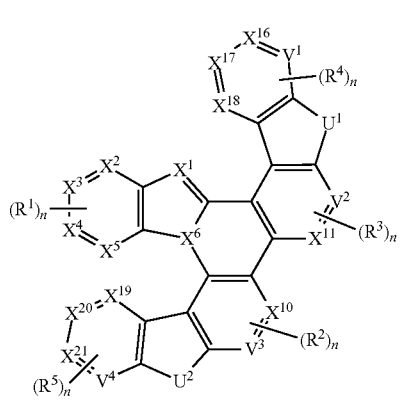
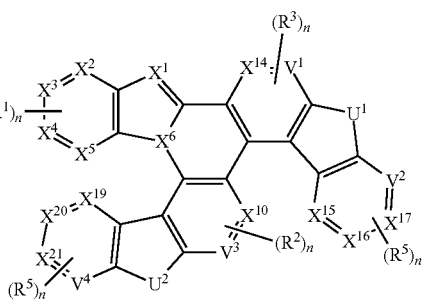
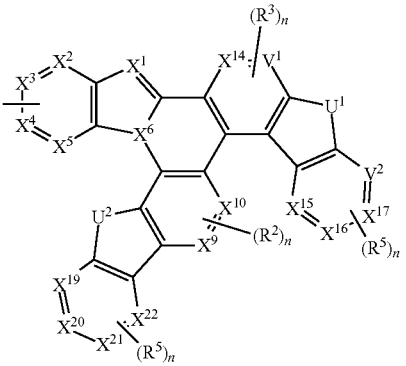

-continued
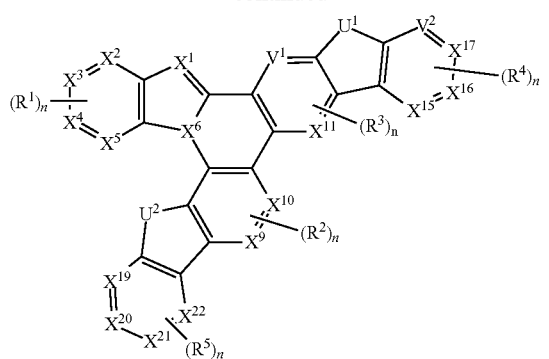
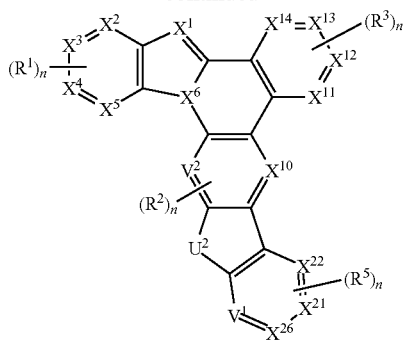
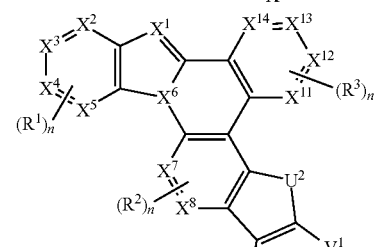
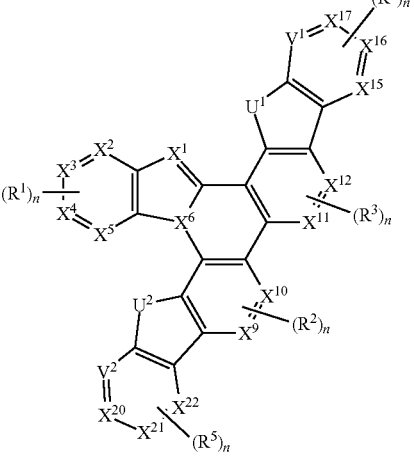
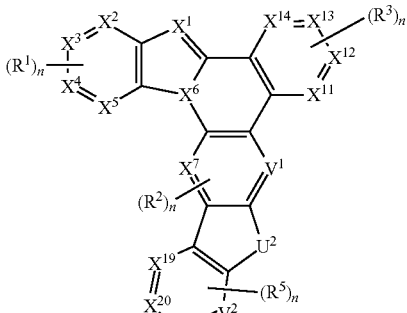
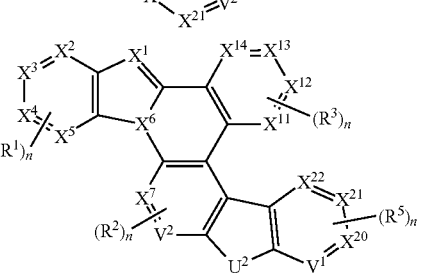

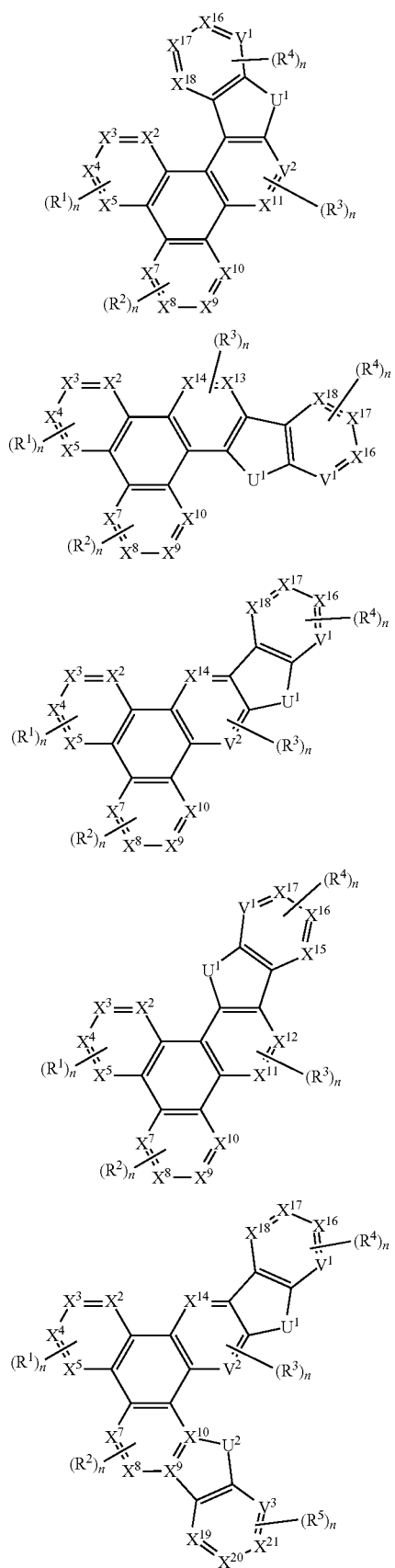
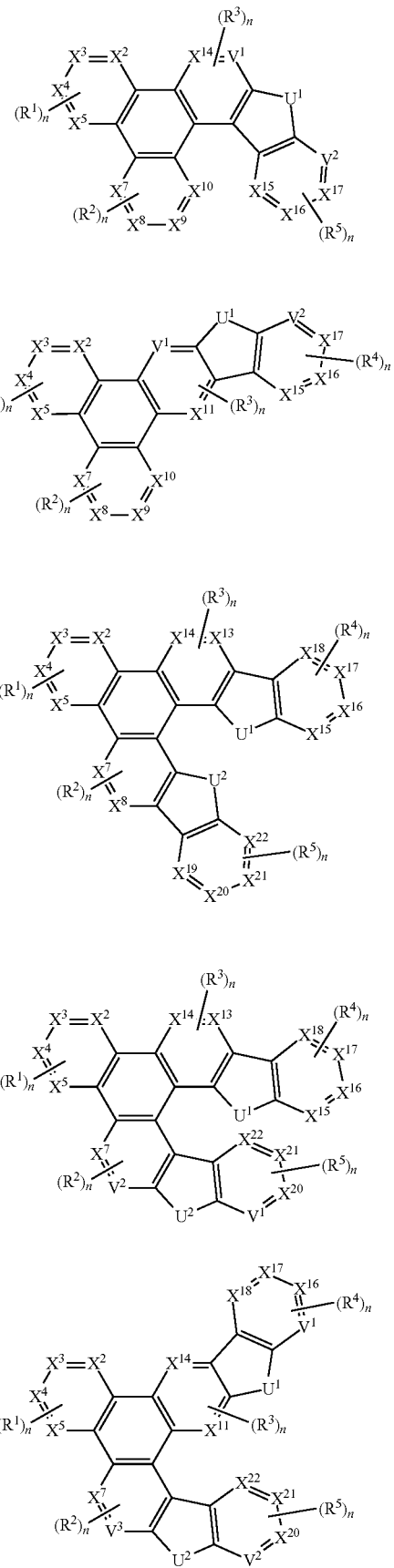

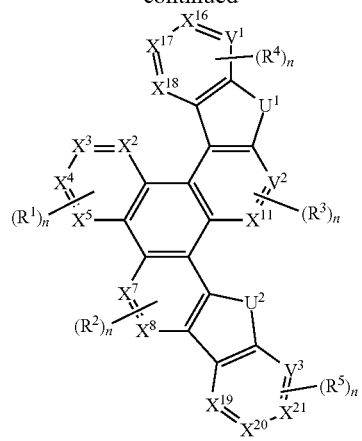
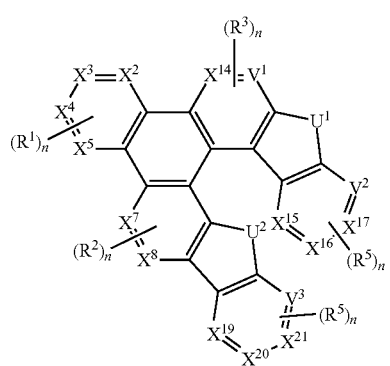
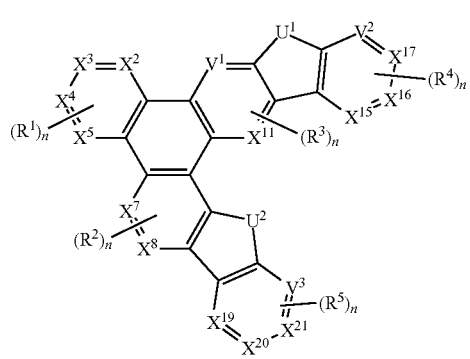
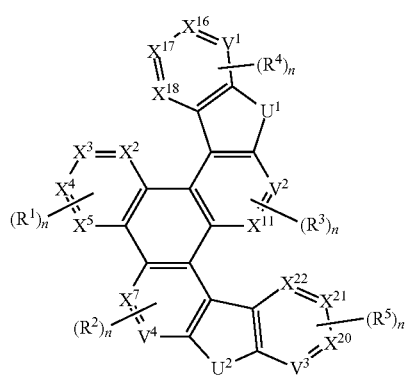
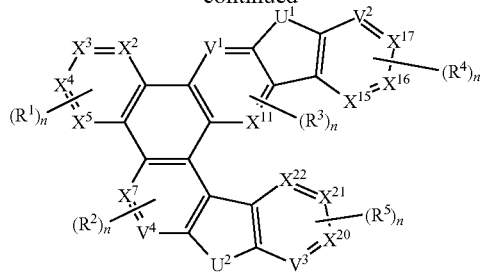
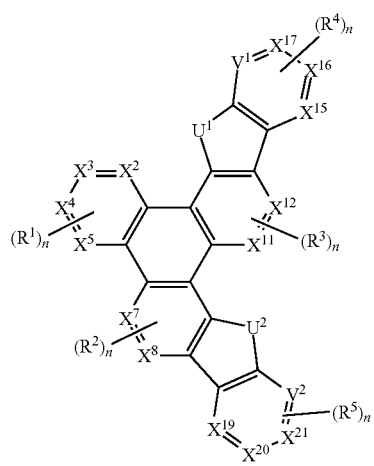
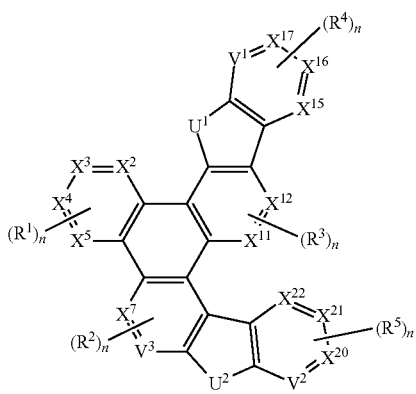
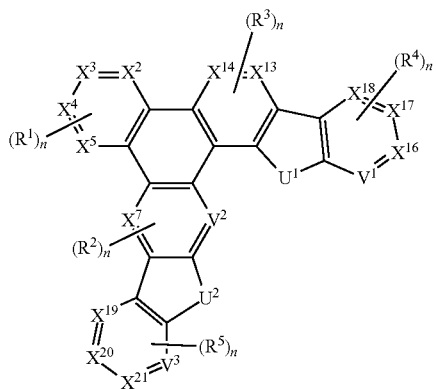

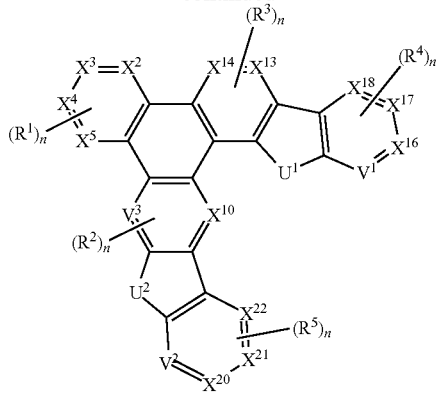
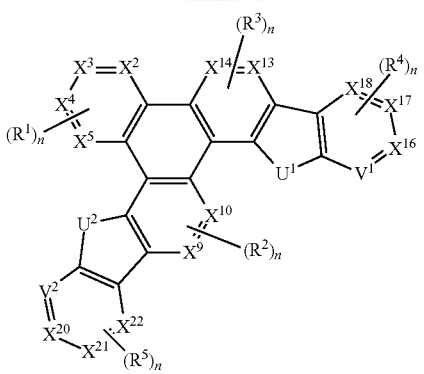
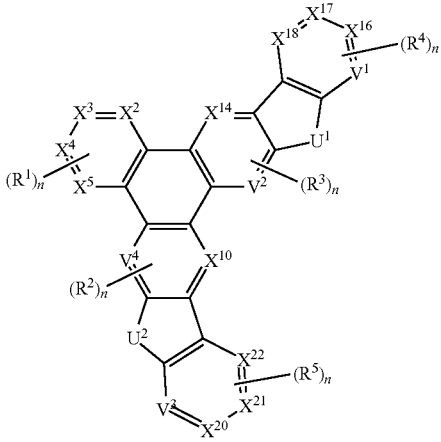
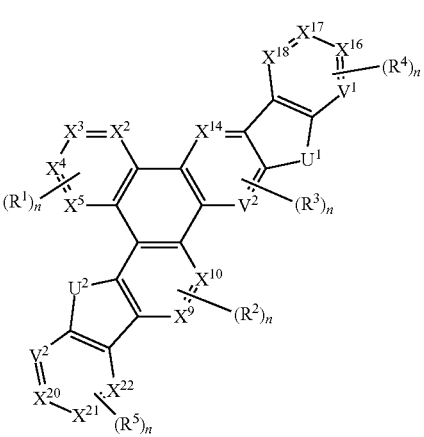
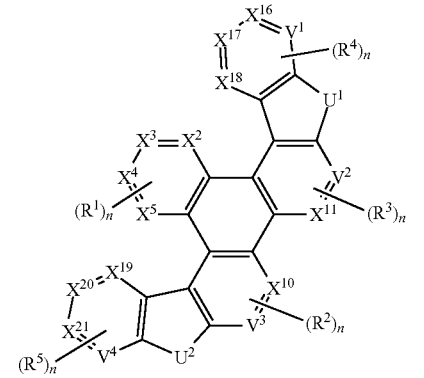
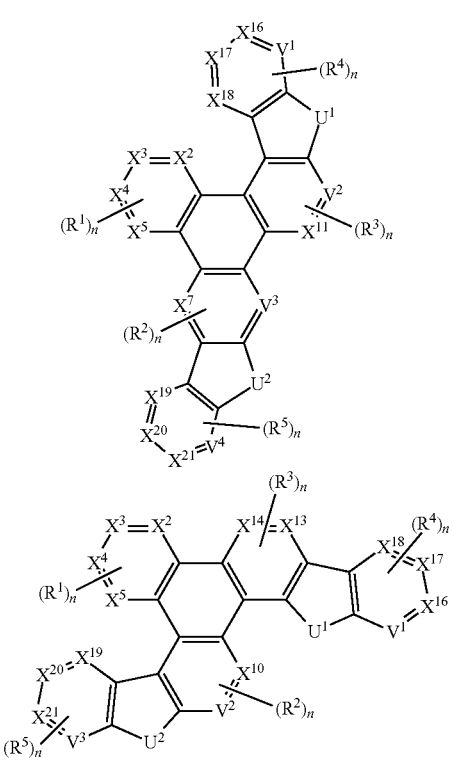
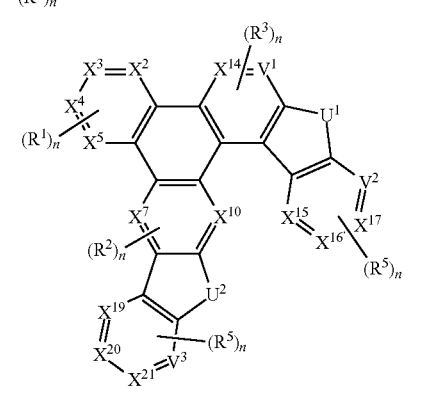
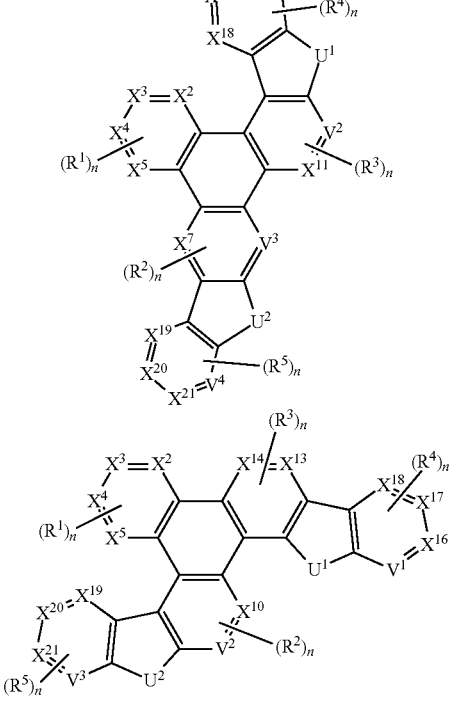

37
-continued
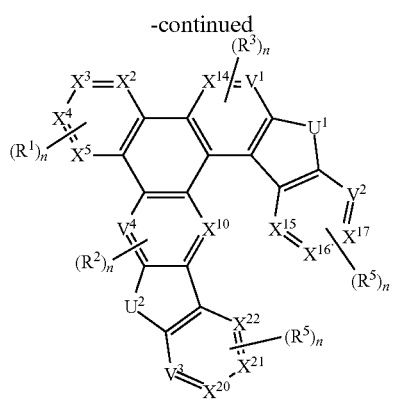
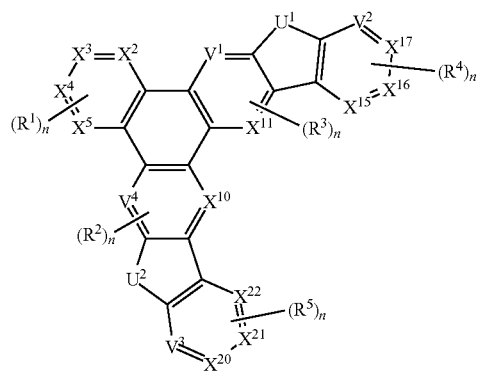
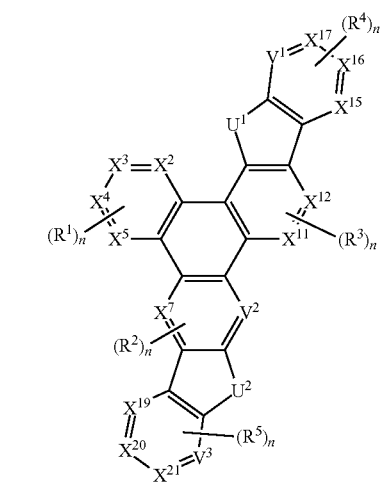
38
-continued
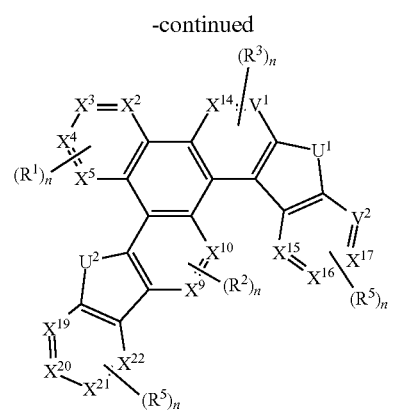
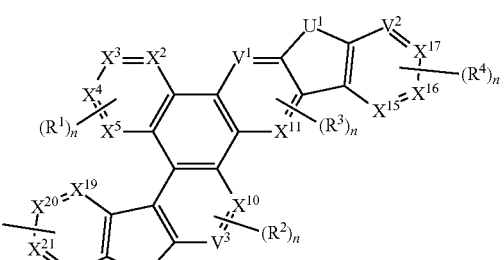
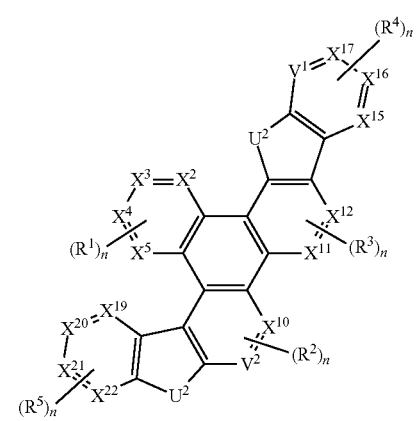

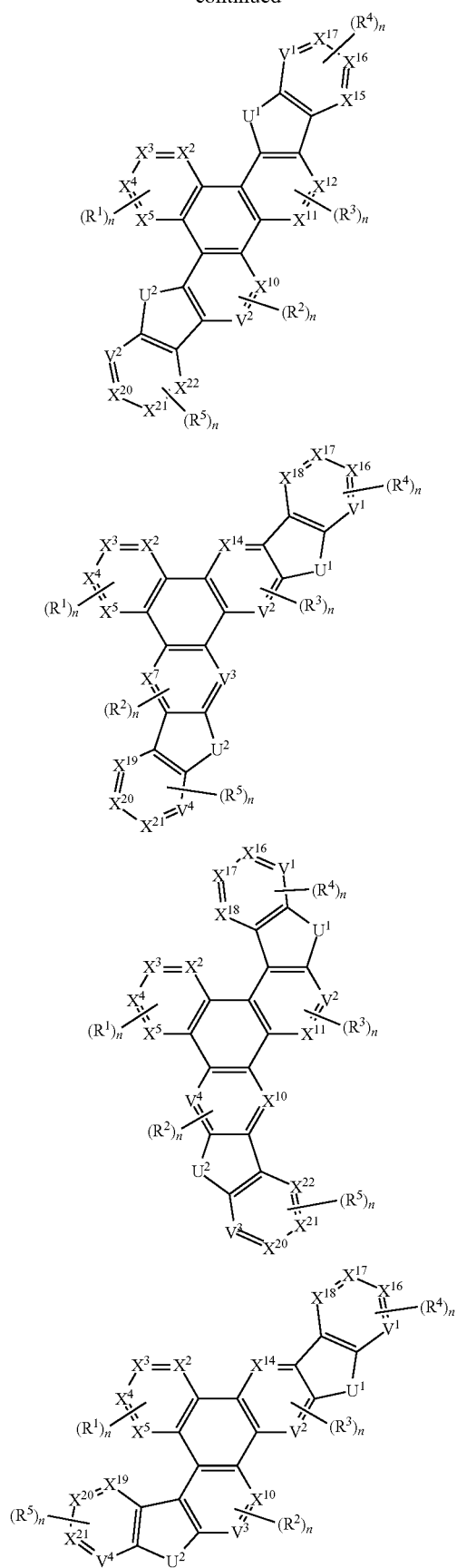
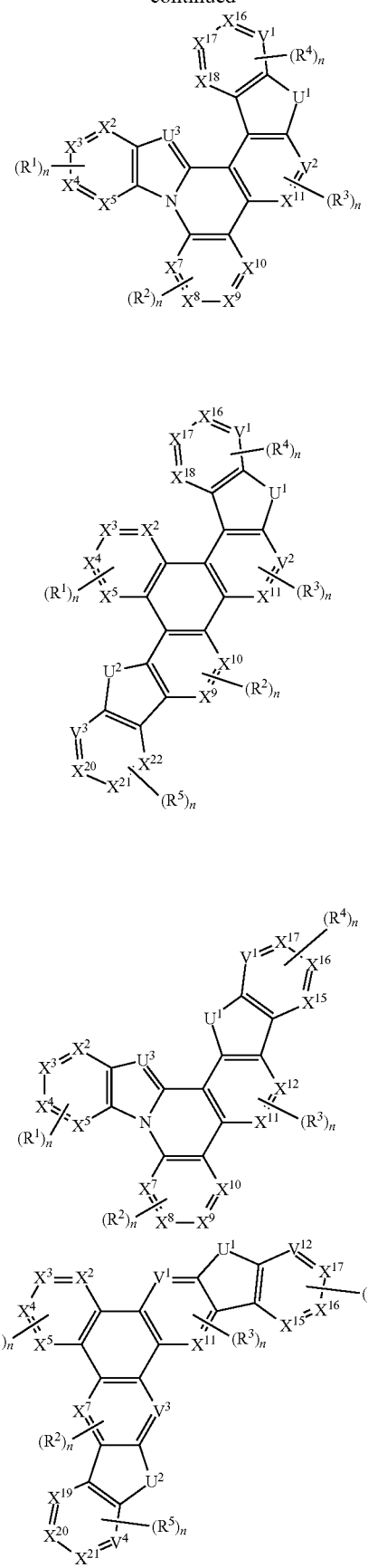

-continued
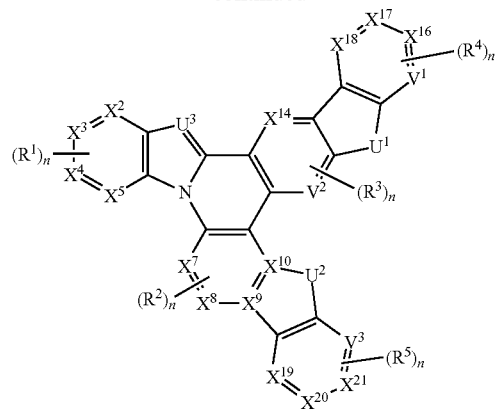
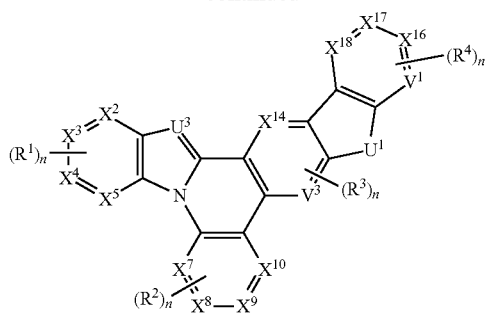
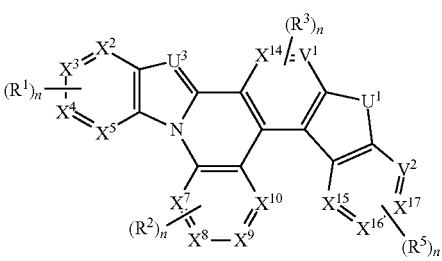
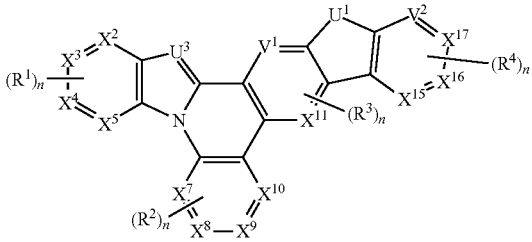
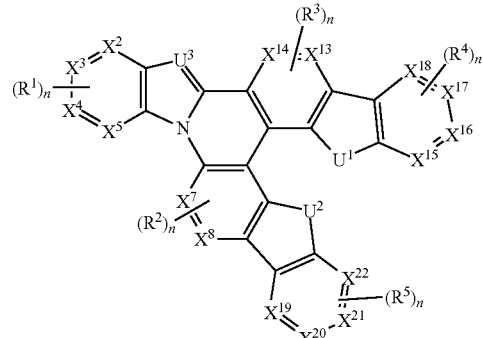
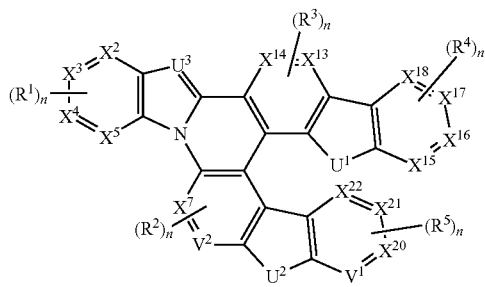

-continued
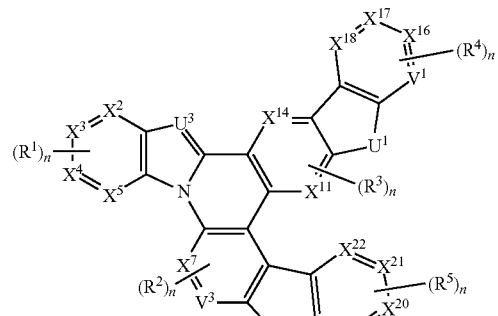
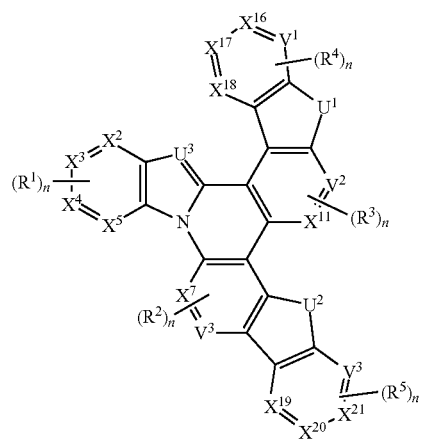
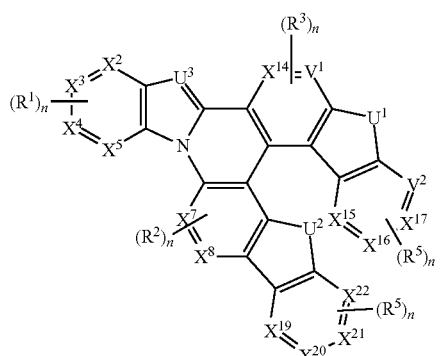
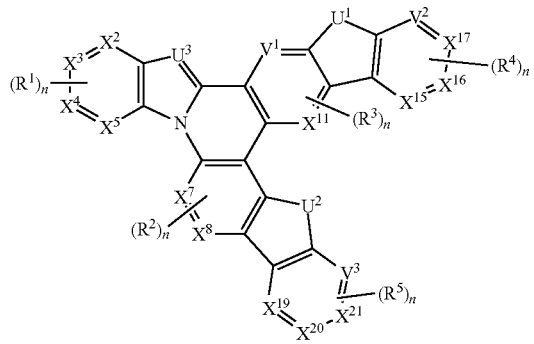
-continued
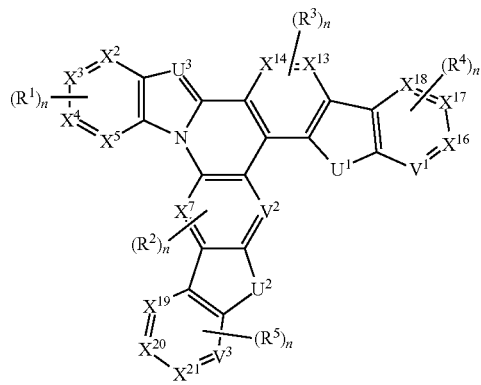
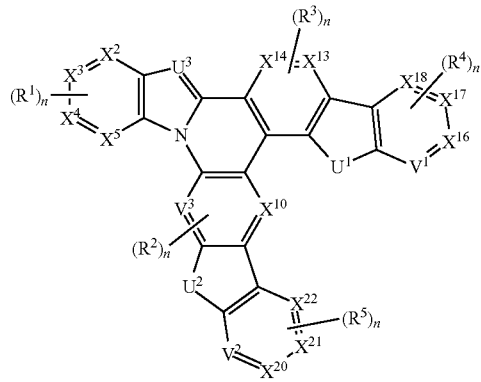
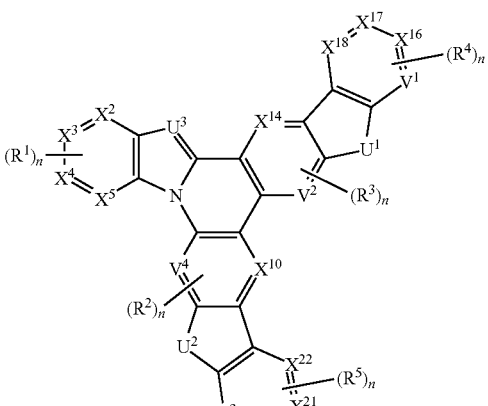
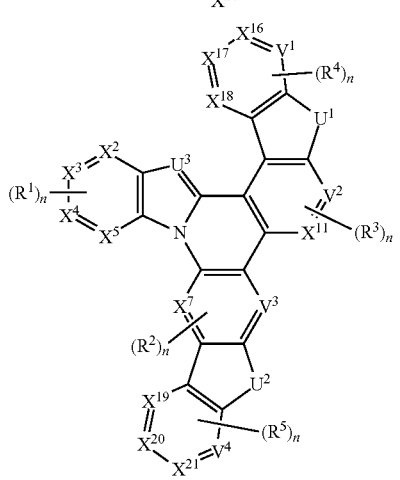

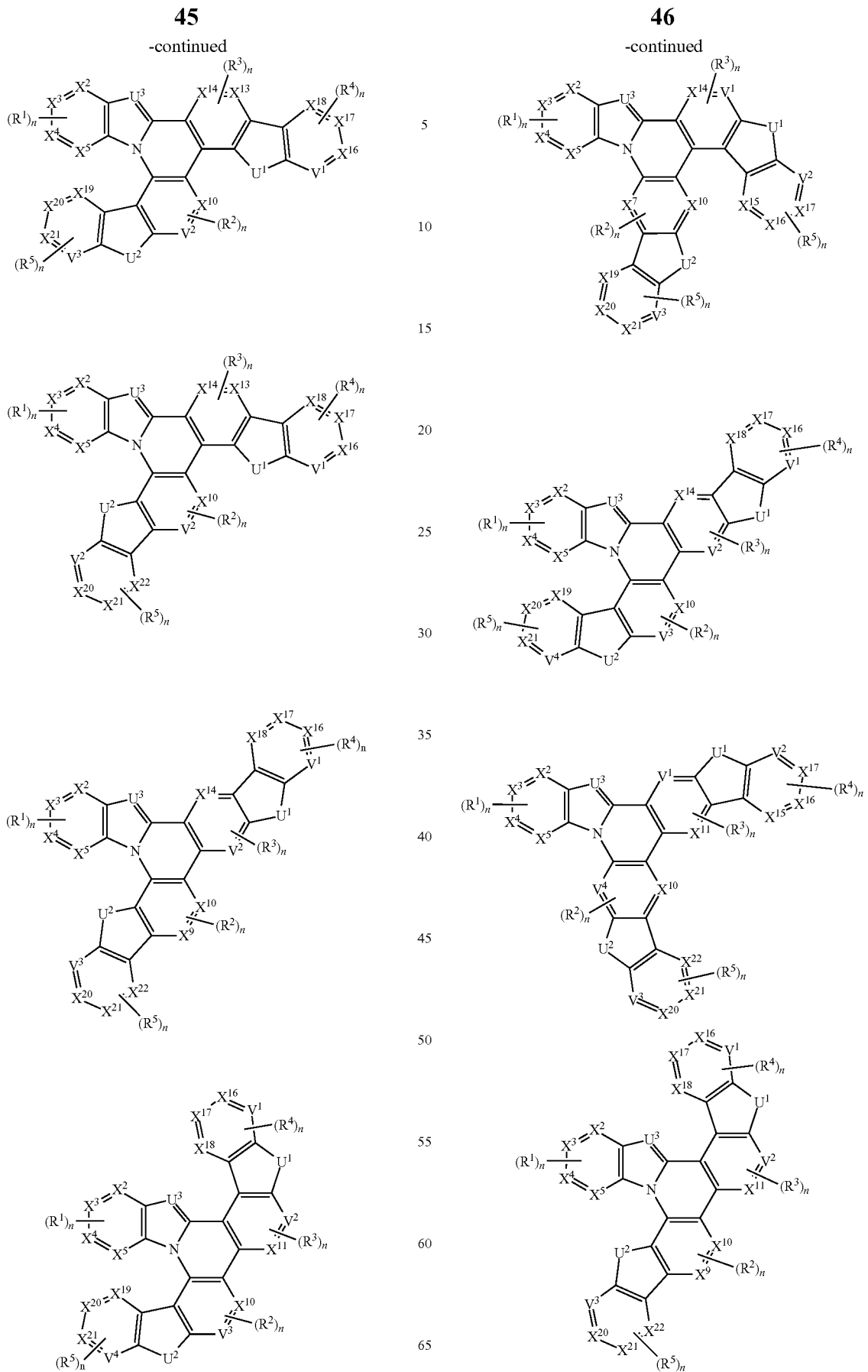

47
-continued
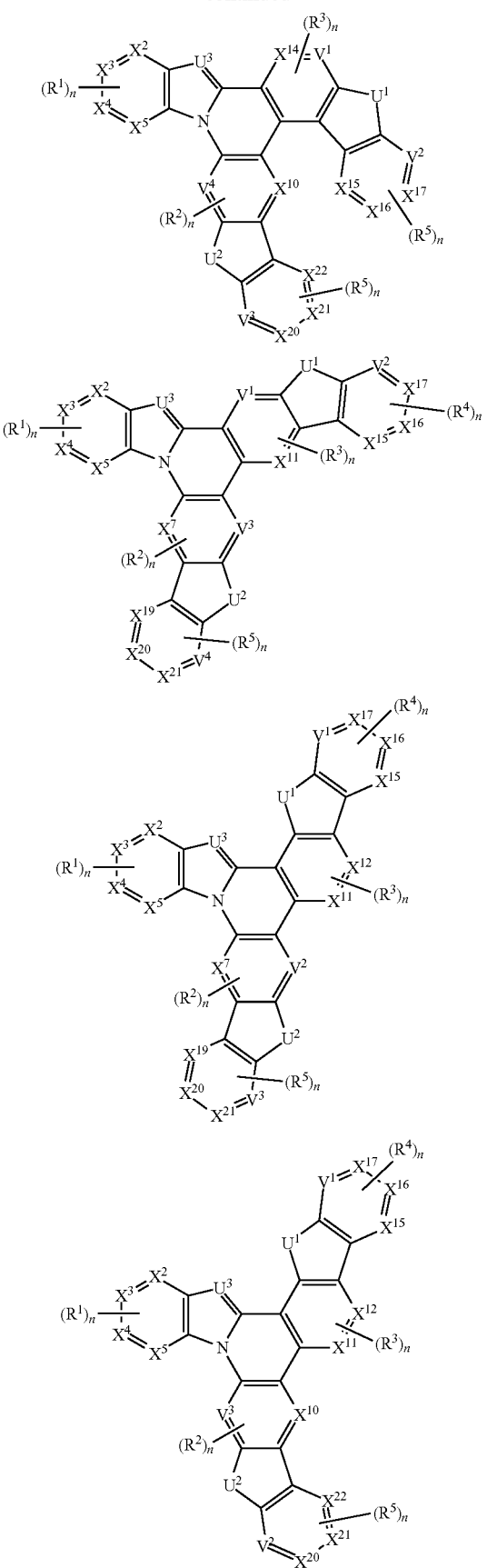
48
-continued
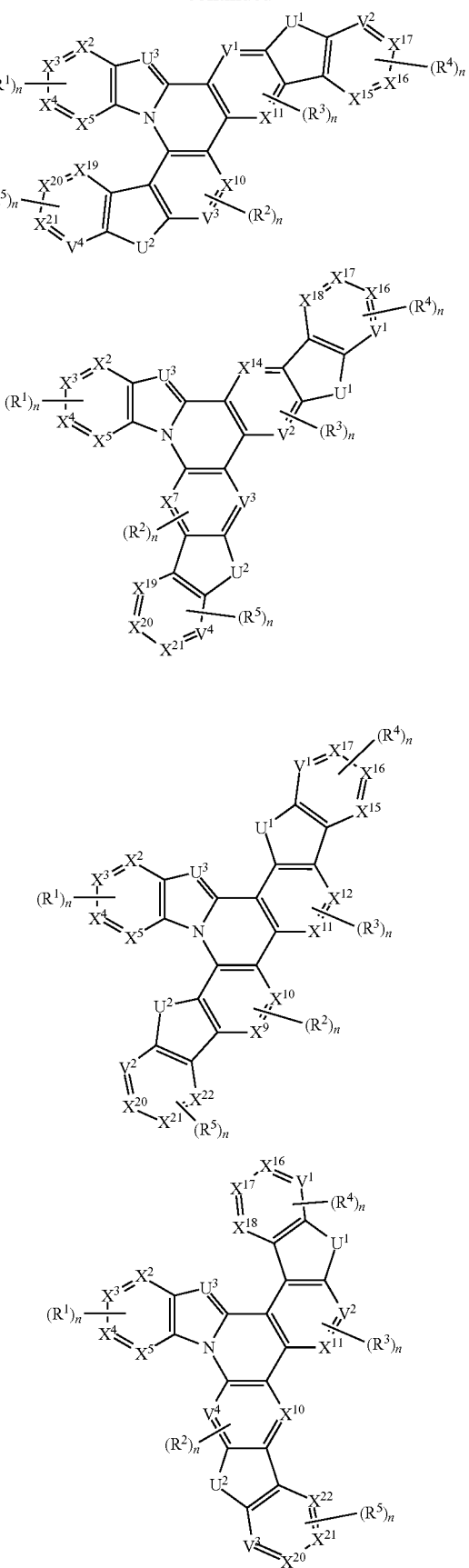

-continued

-continued
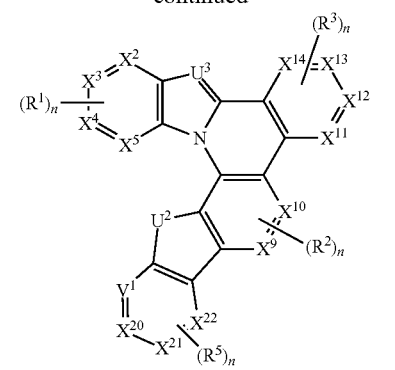
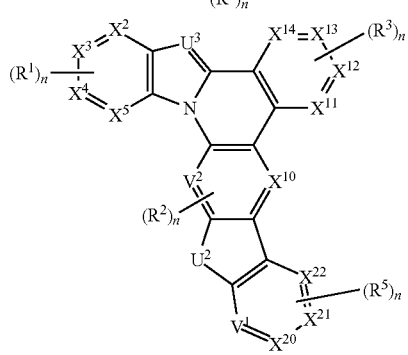
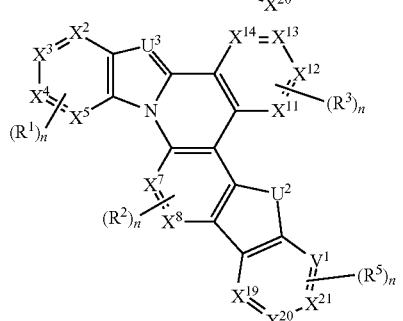
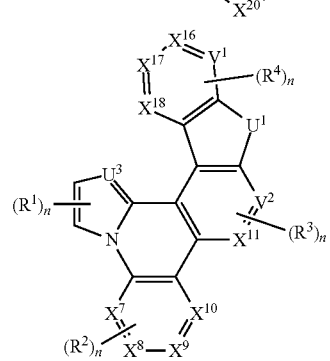
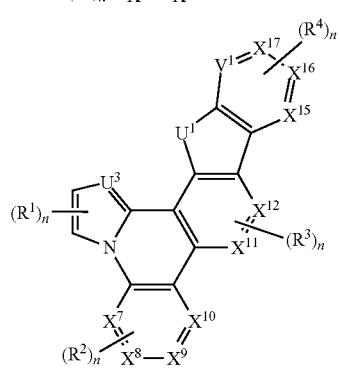
-continued
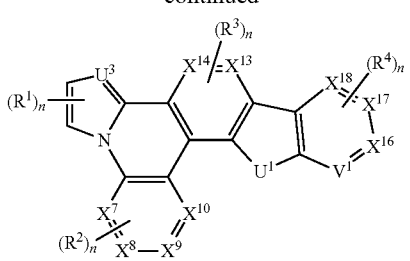
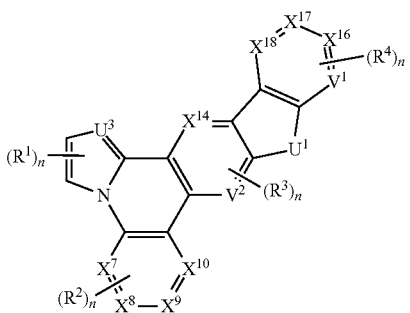
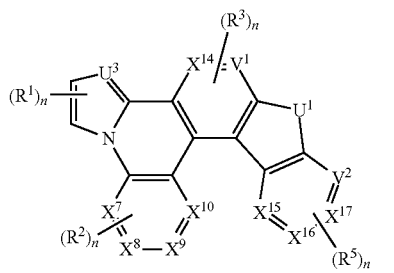
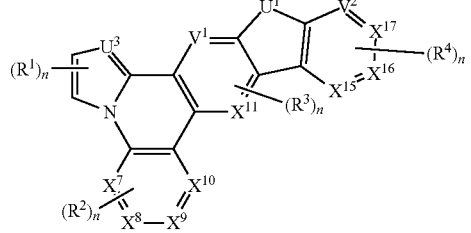
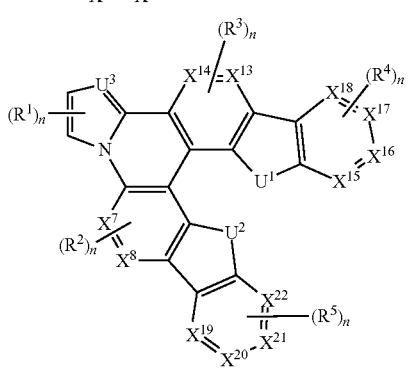

-continued
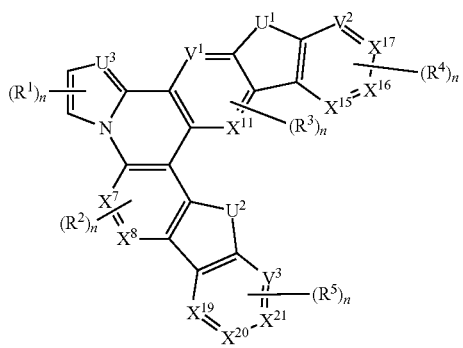
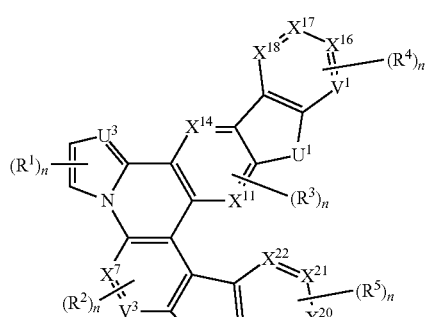
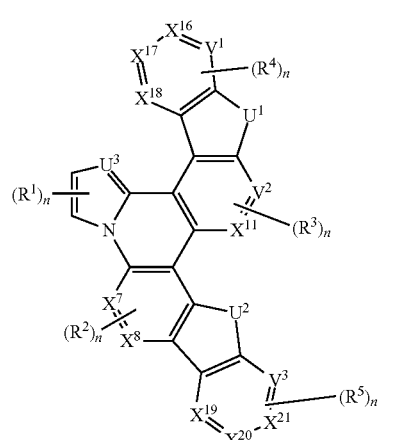
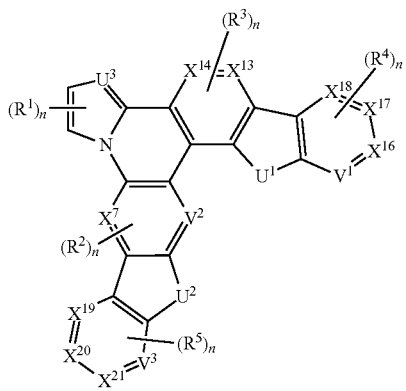
-continued
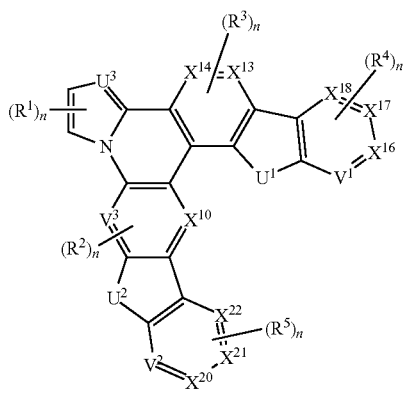
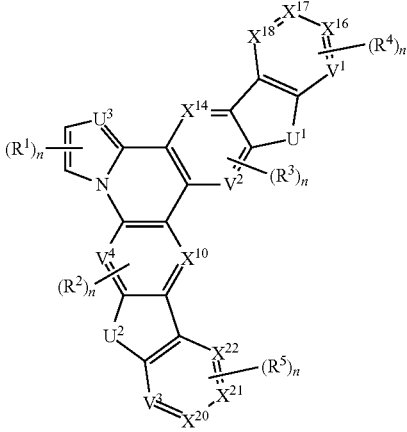
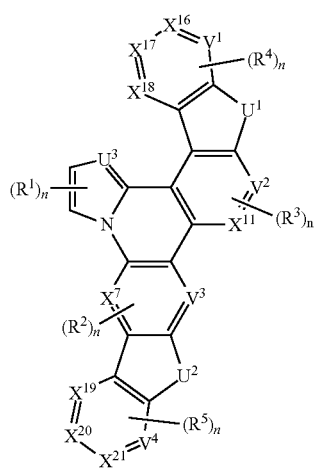
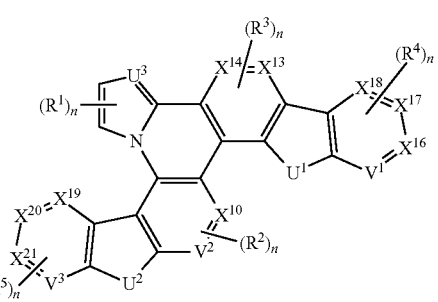

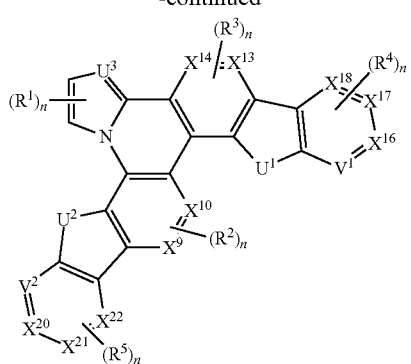
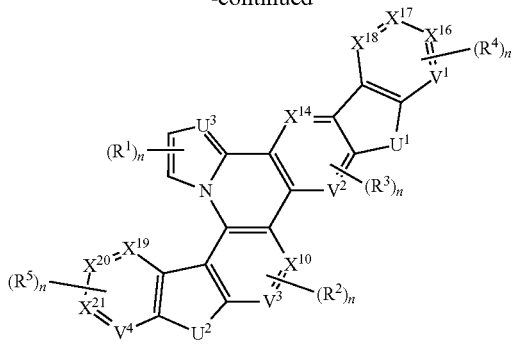
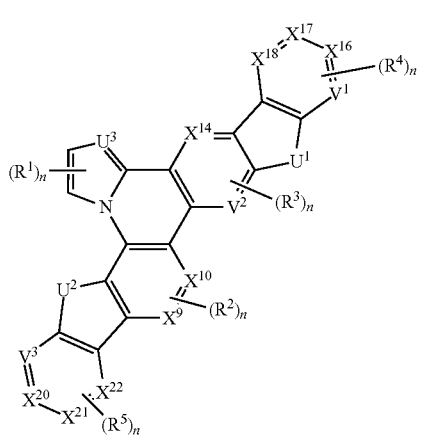
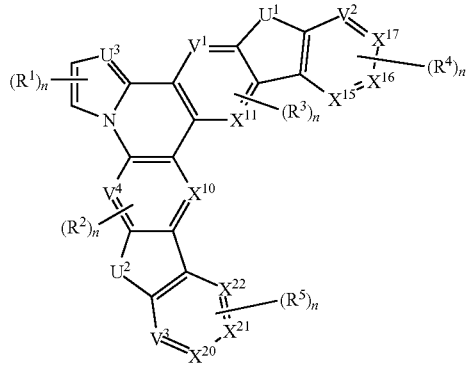
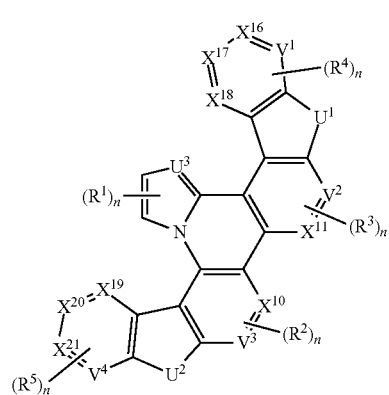
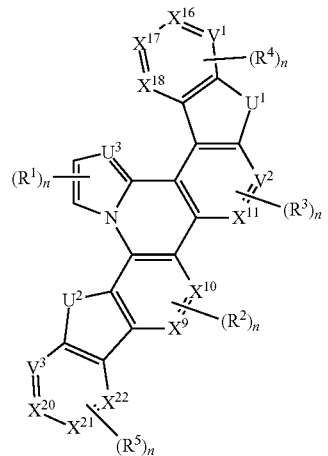
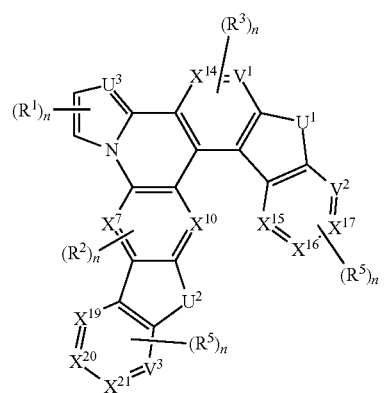
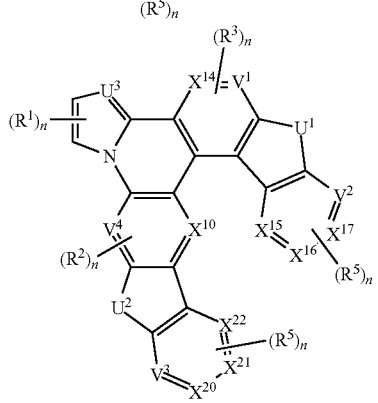

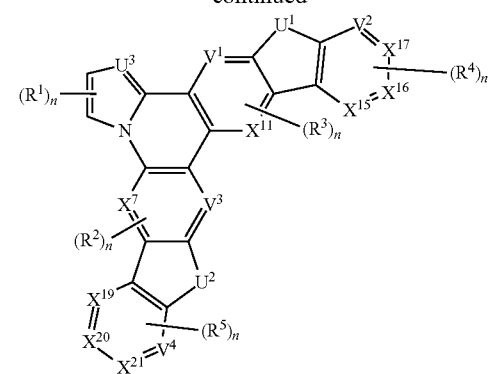
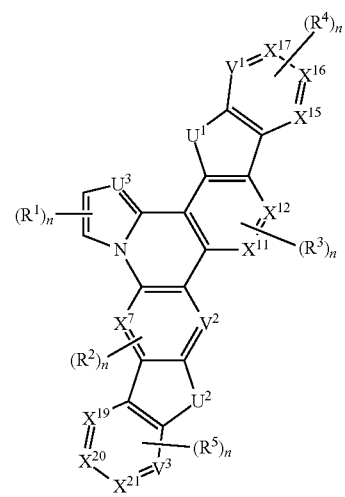
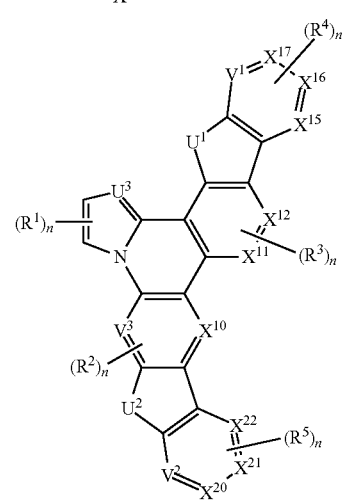
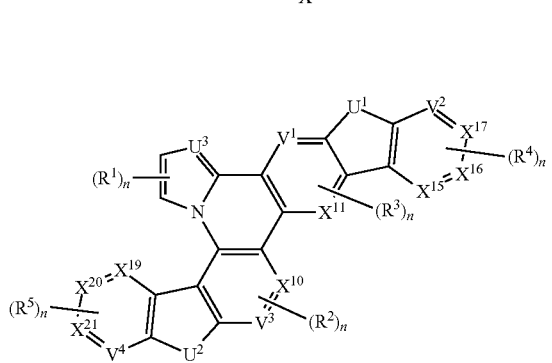
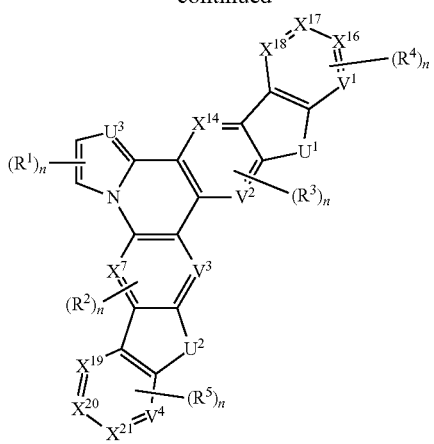
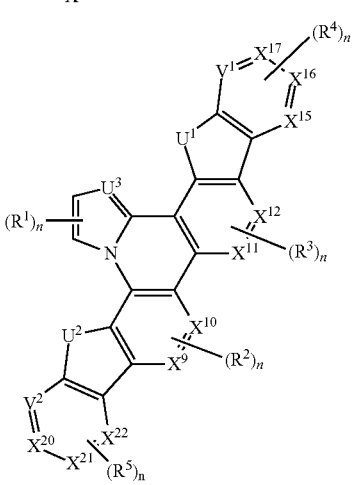
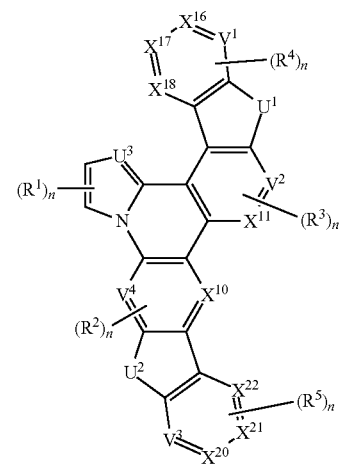
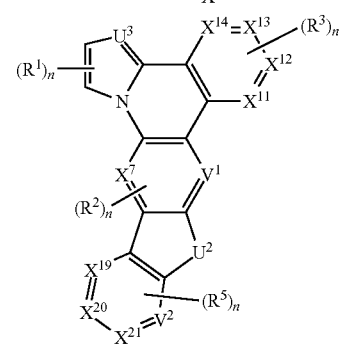

-continued
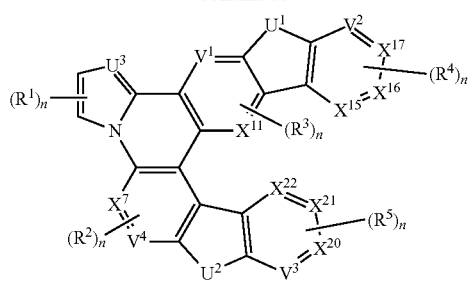
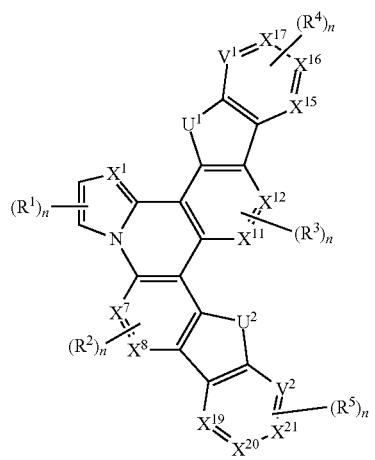
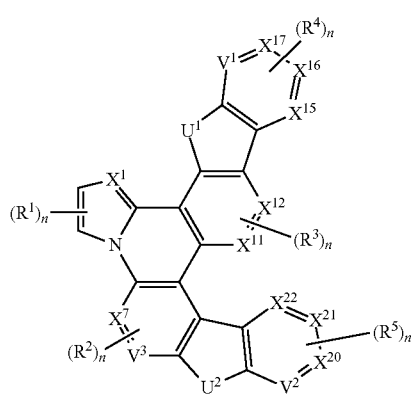
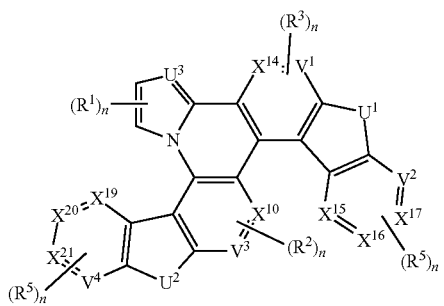
-continued
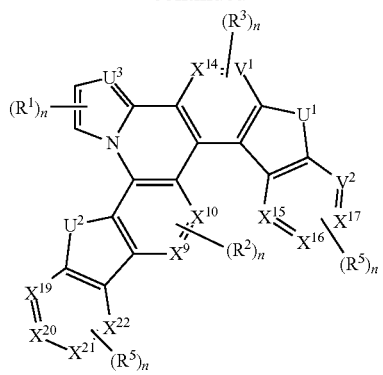
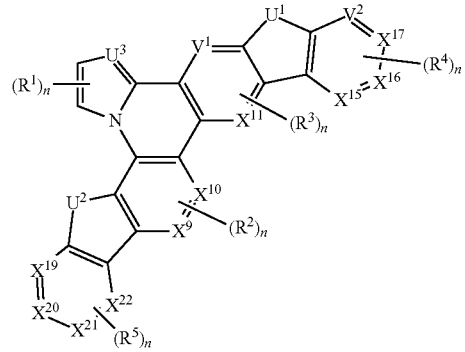
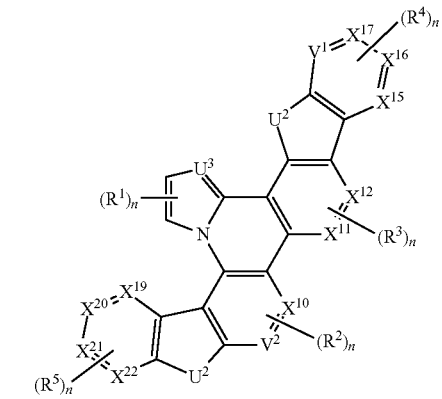
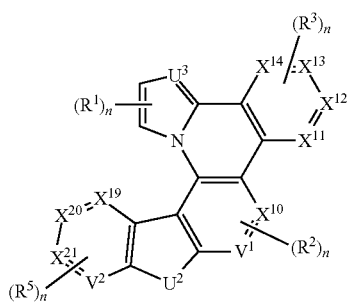

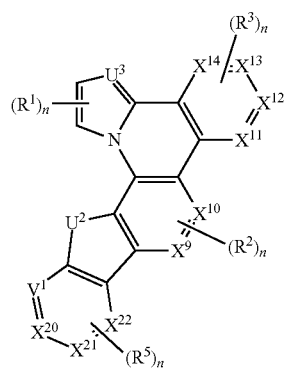
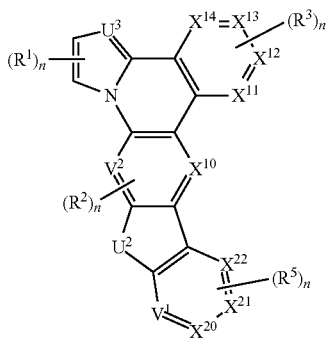
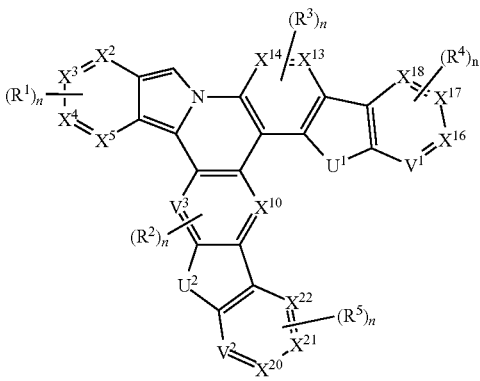
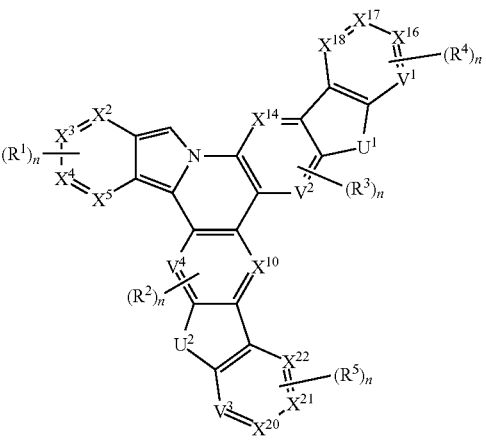
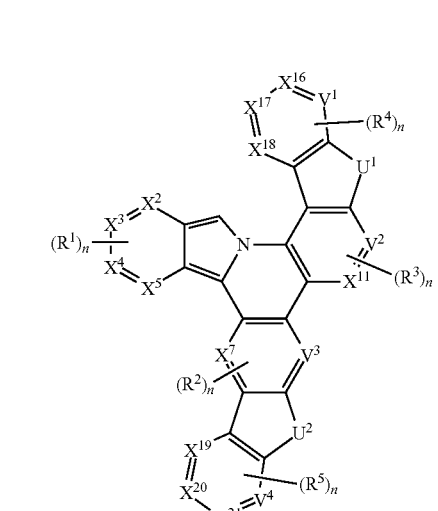
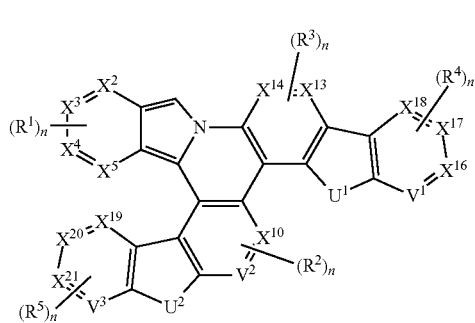

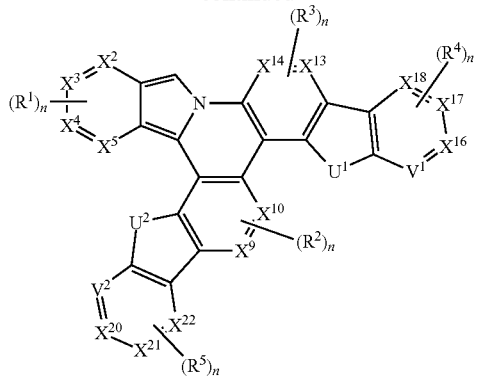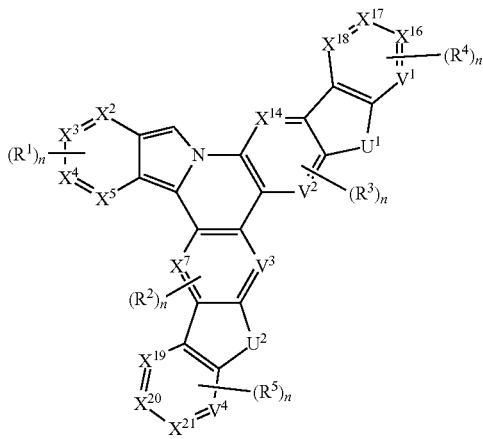

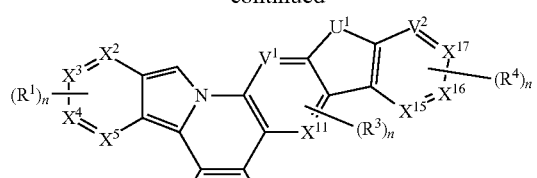
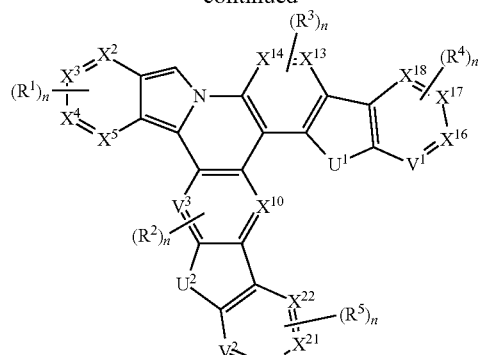
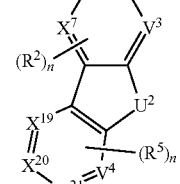
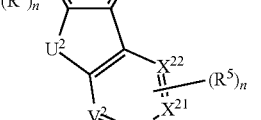
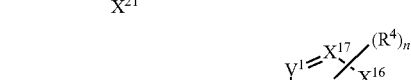
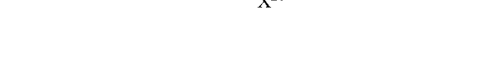
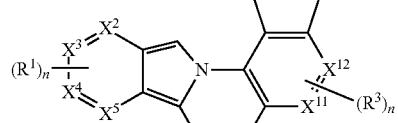
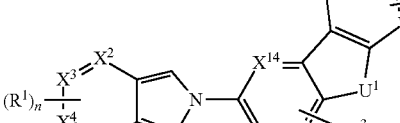
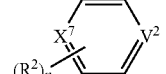
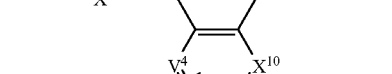
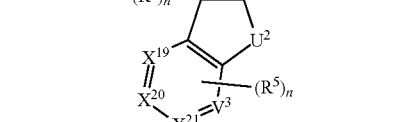
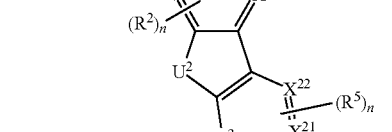
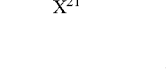
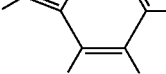
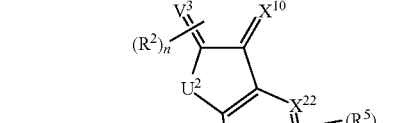
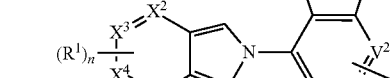
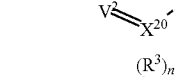
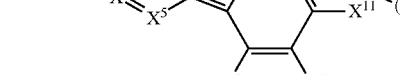
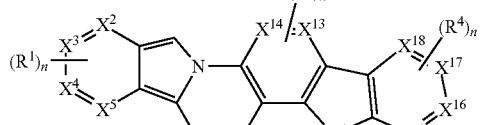
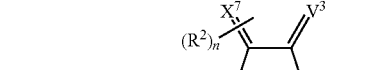
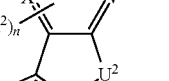
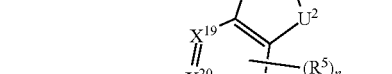
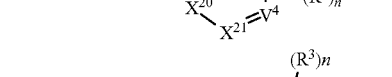

-continued
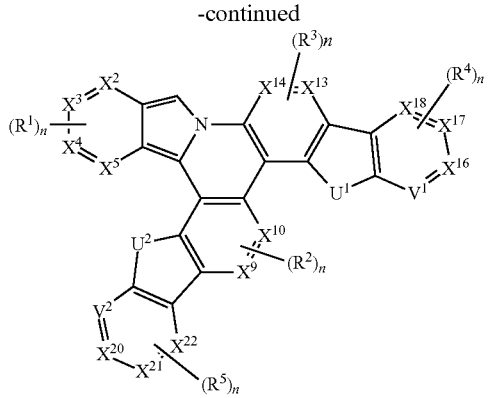
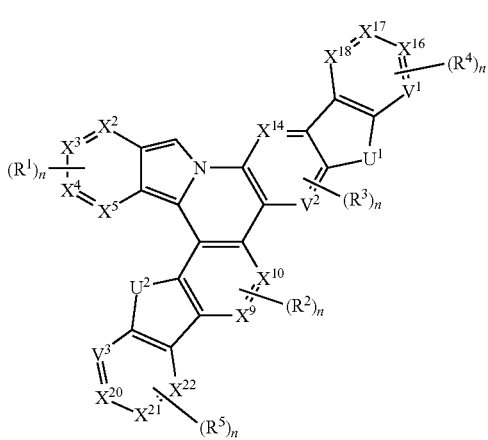
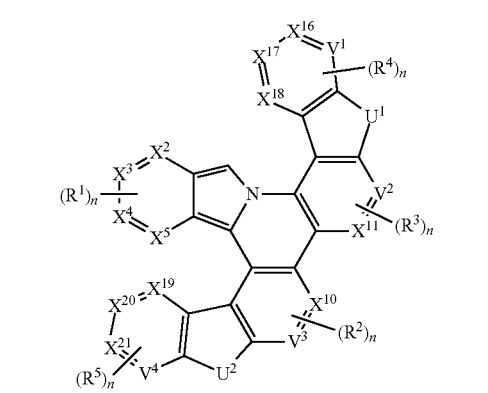
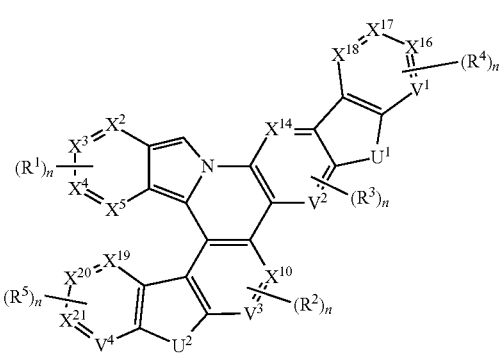
-continued
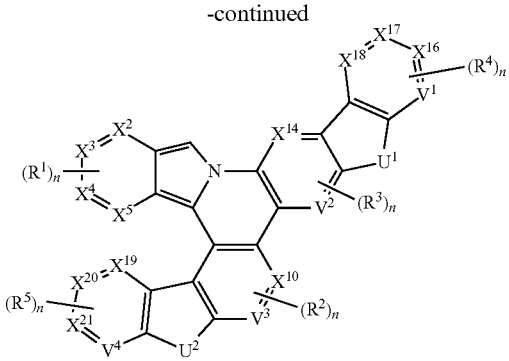
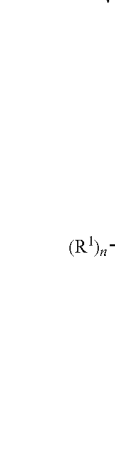
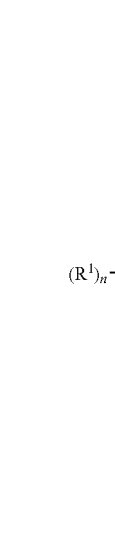
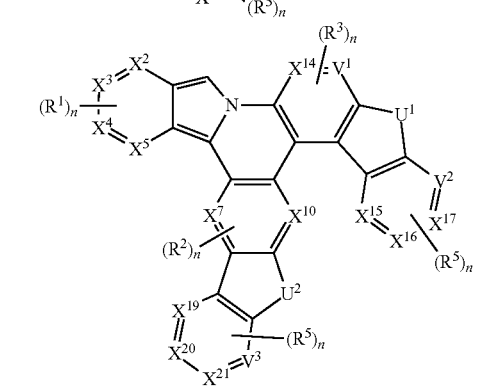

-continued
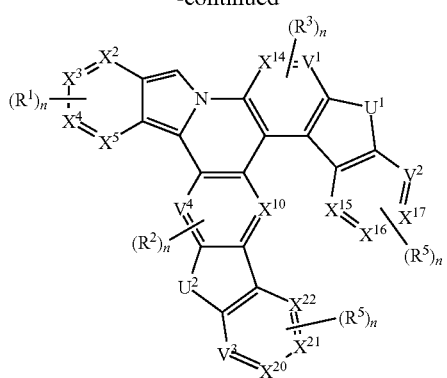
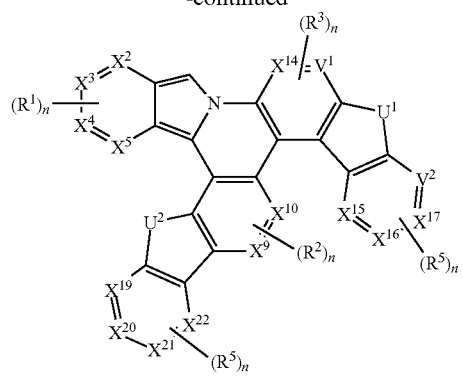
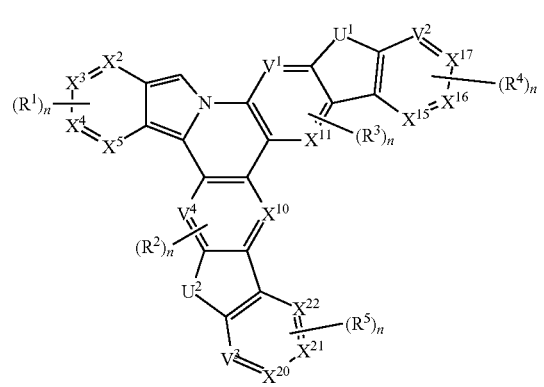
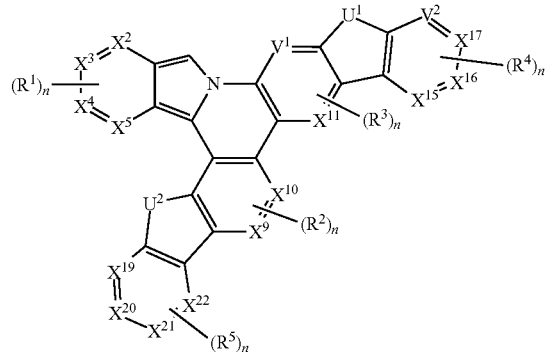
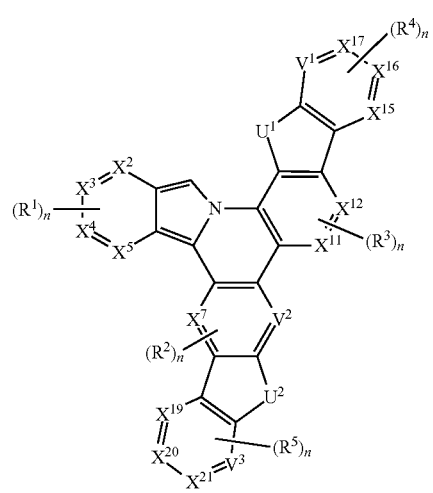
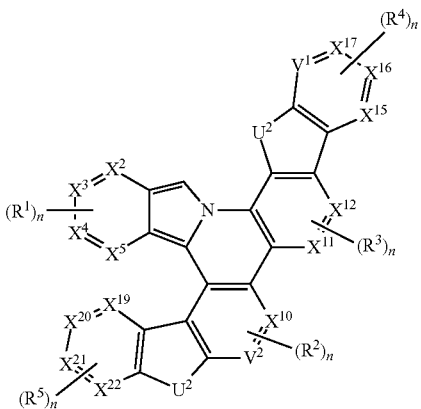
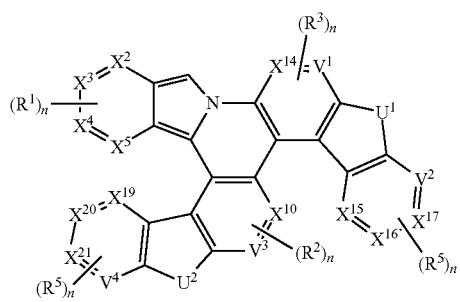
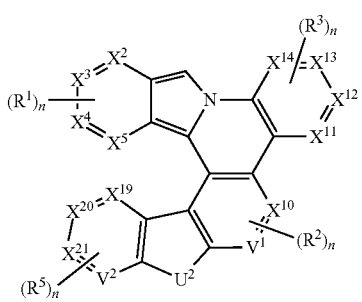

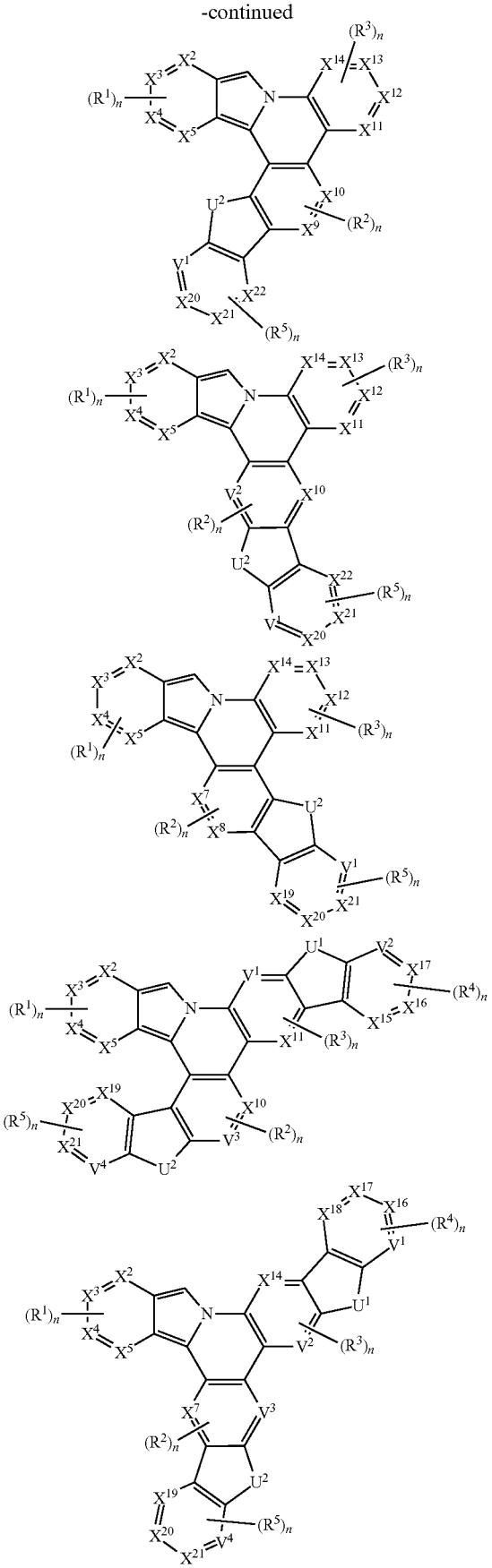
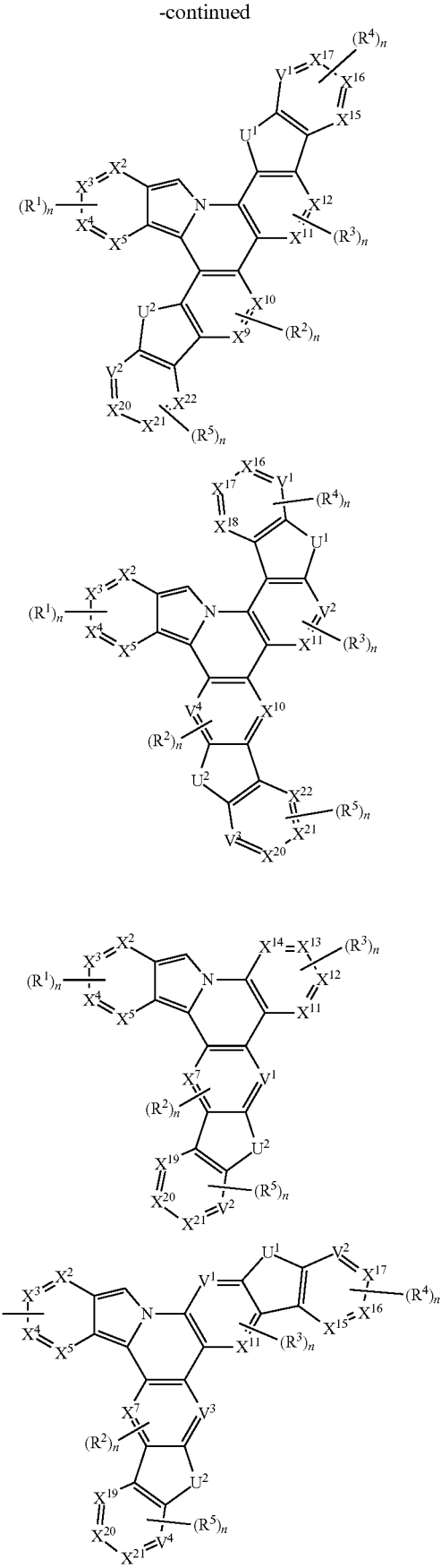

-continued

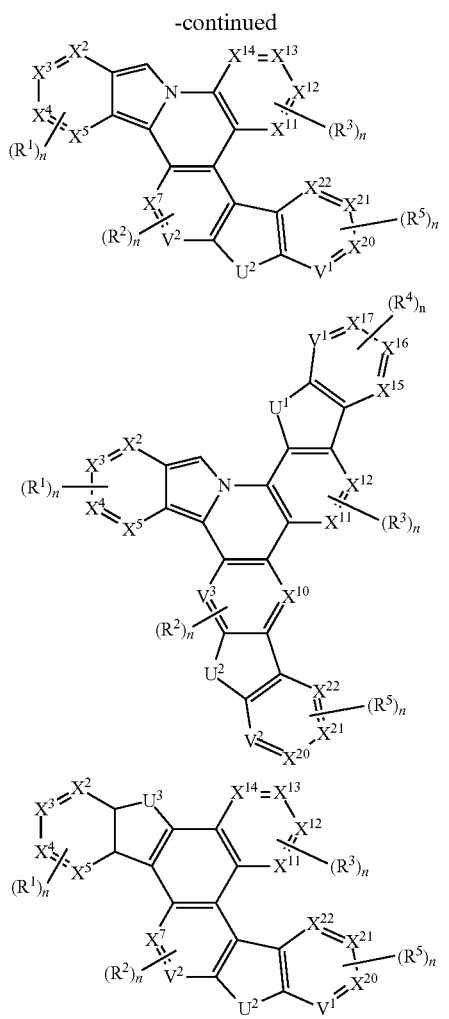

In these implementations of General Formulas I-IV, $R^1$, $R^2$, $R^3$, $R^4$, and $R^5$ each independently represents hydrogen, cyanide, halogen, hydroxy, amino, nitro, thiol, or substituted or unsubstituted $C_1$-$C_4$ alkyl, alkoxy, or aryl, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, and $X^{22}$ each independently represents substituted or unsubstituted C, N, Si, O, or S, valency permitting.

$V^1$, $V^2$, $V^3$, and $V^4$ each independently represents substituted or unsubstituted C or N, valency permitting.

$U^1$ and $U^2$ each independently represents O, S, CRR', SiRR', or NAr*, where R and R' each independently represents hydrogen, cyanide, halogen, hydroxy, amino, nitro, thiol, or optionally substituted $C_1$-$C_4$ alkyl, alkoxy, or aryl, and Ar* represents a substituted phenyl, pyridyl, naphthyl, pyrimidyl, pyridazinyl, pyrazinyl, pyrazolyl, imidazolyl, oxazolyl, or thiazolyl ring, and Ar* is optionally covalently bonded to $V^1$, $V^2$, $V^3$, or $V^4$ to form one or more 5-membered or 6-membered rings, $U^3$ and $U^4$ each independently represents CR, SiR, or N, where R represents optionally substituted $C_1$-$C_4$ alkyl, alkoxy, aryl or heteroaryl, and each n is independently an integer as permitted by valence.

Compounds of General Formulas I-IV are shown below.

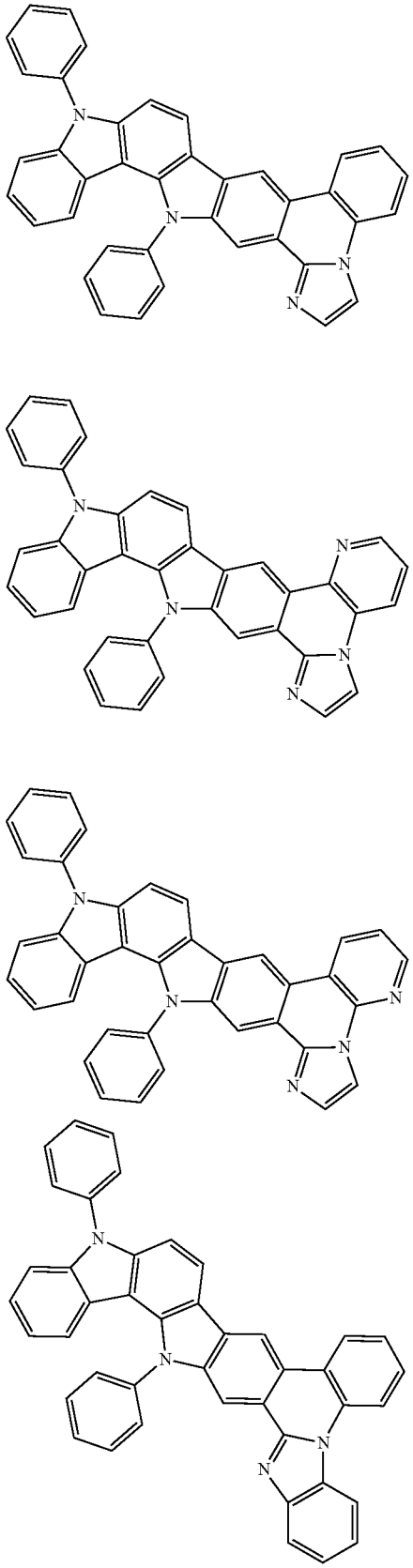

75
-continued
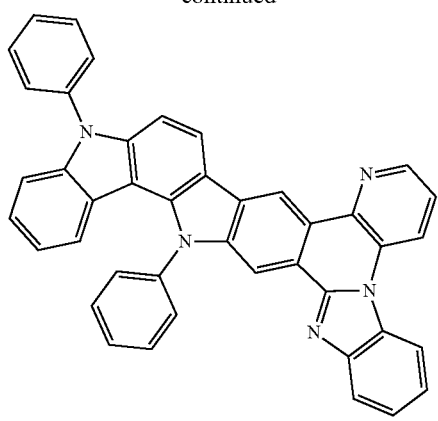
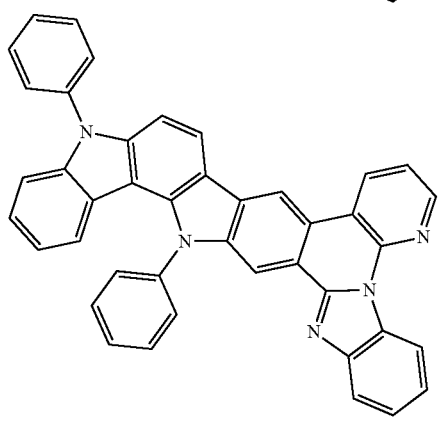
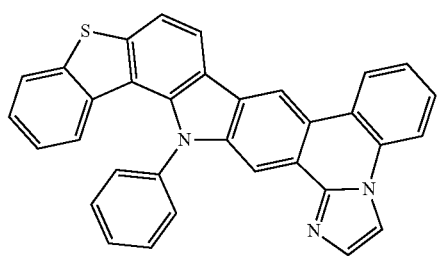
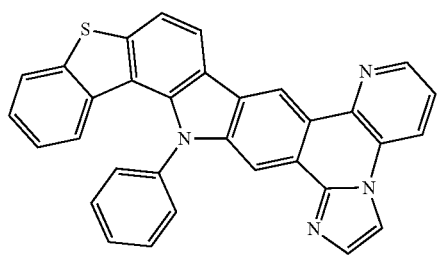
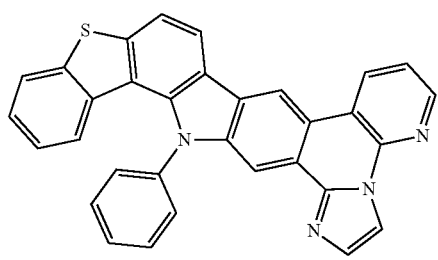
76
-continued
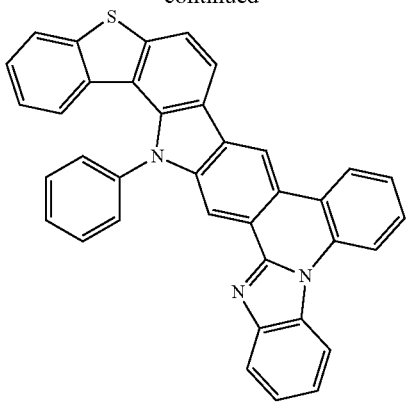
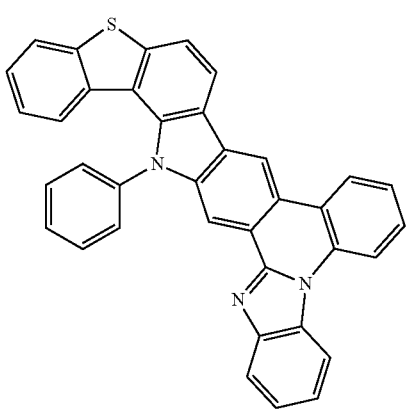
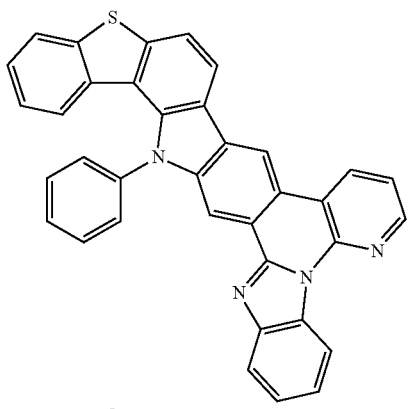
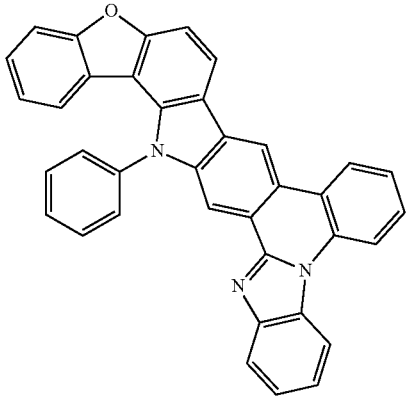

77
-continued
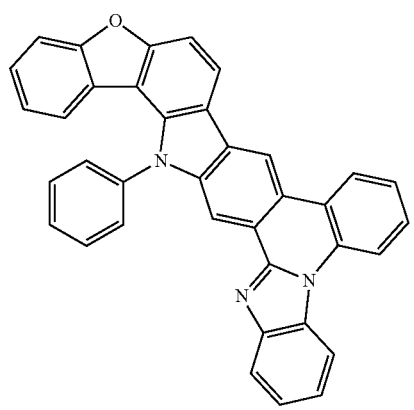
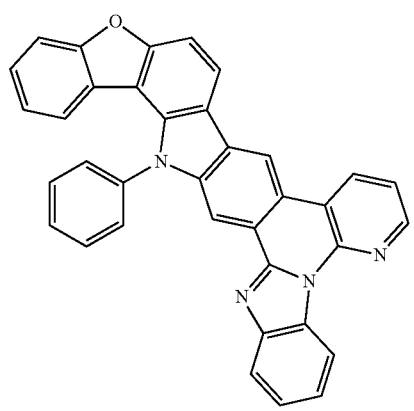
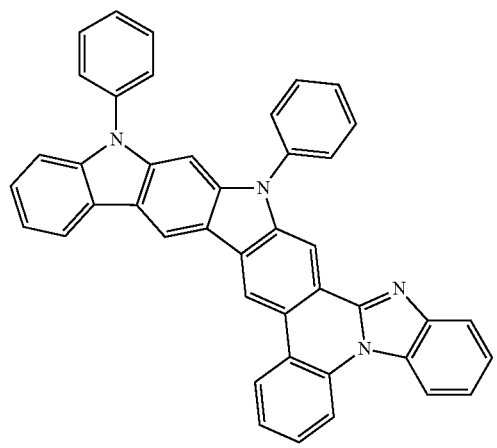
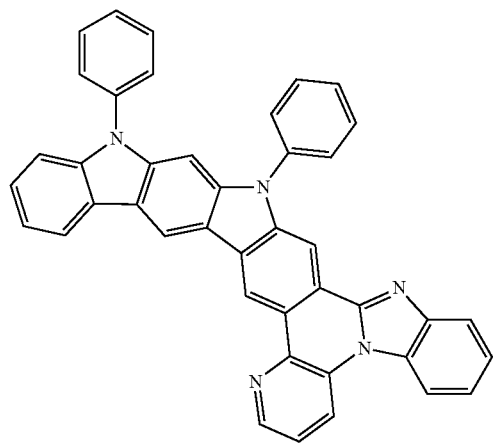
78
-continued
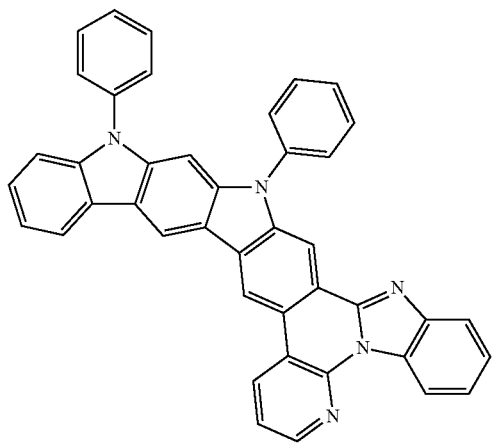
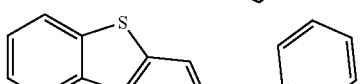
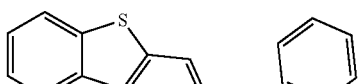
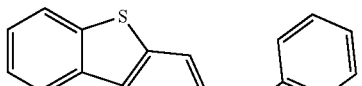

-continued
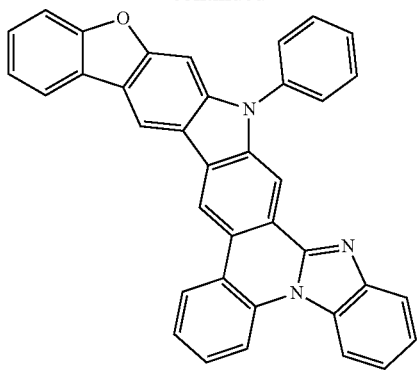
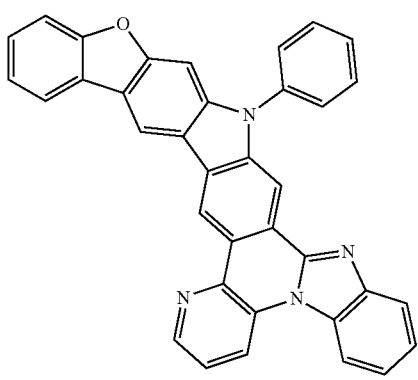
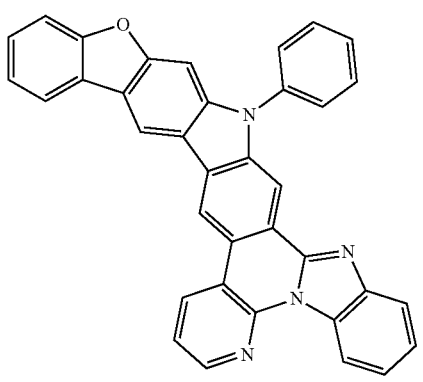
-continued
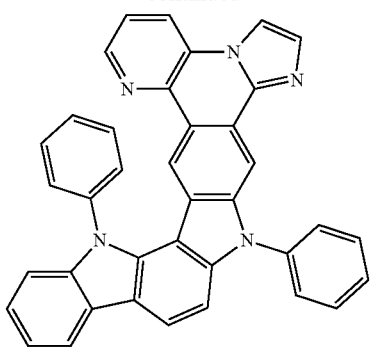
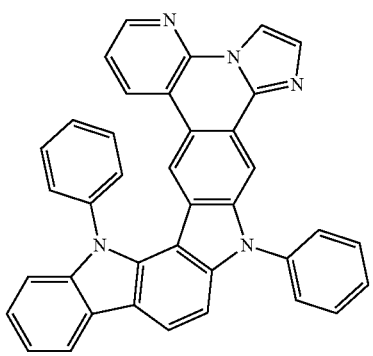
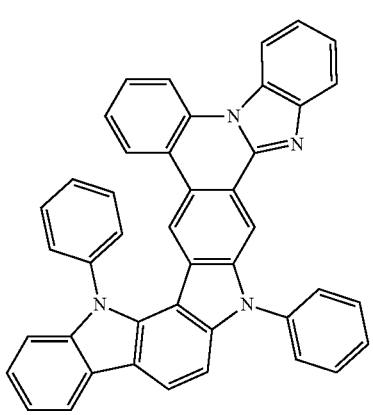
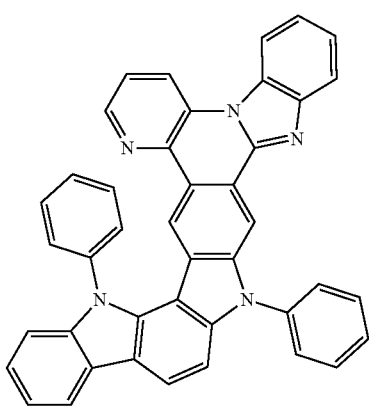

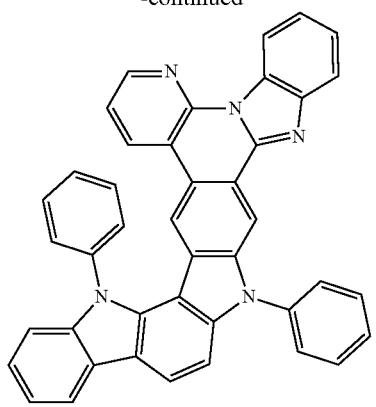
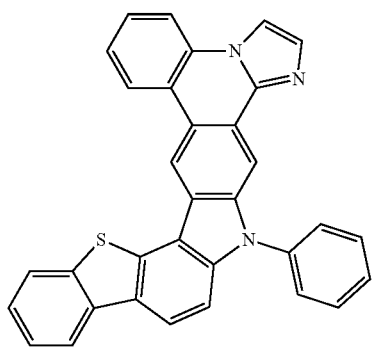
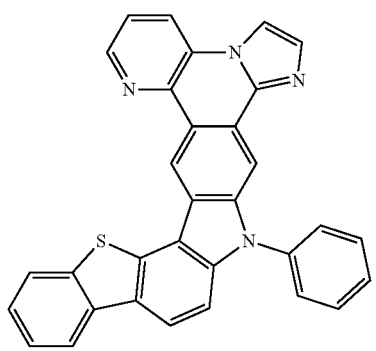
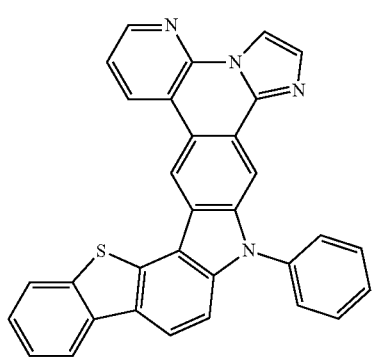
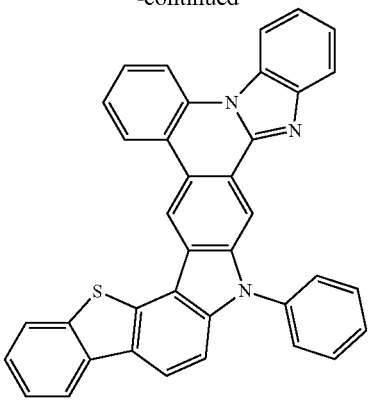
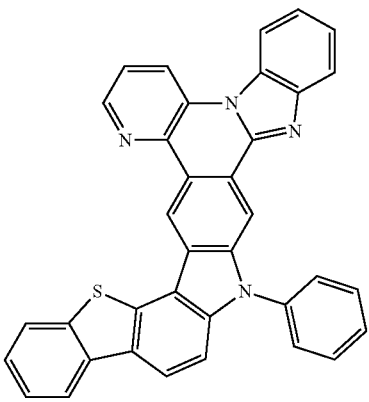
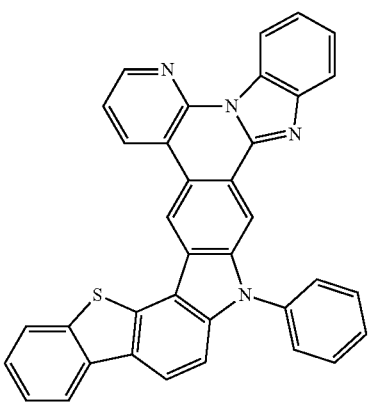
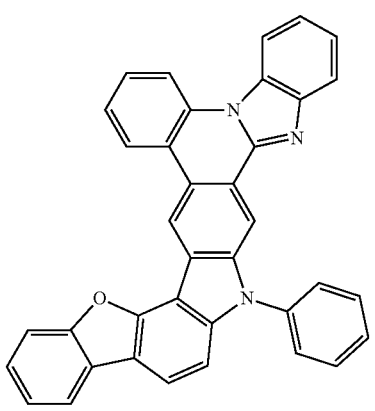

-continued
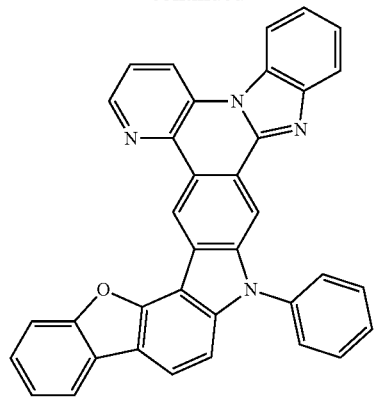
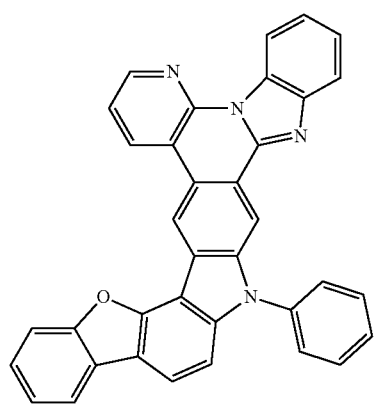
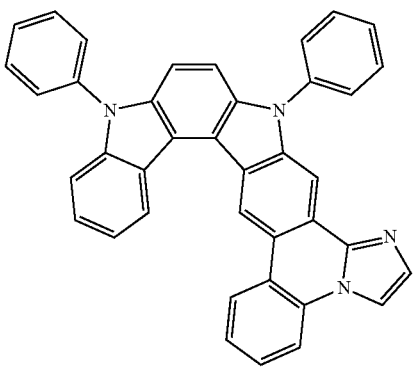
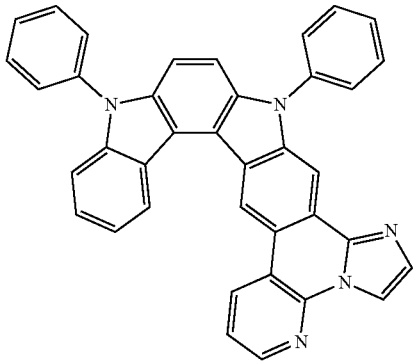
-continued
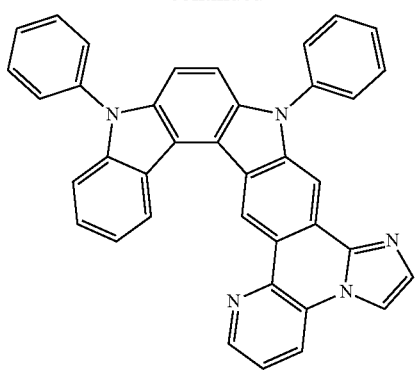
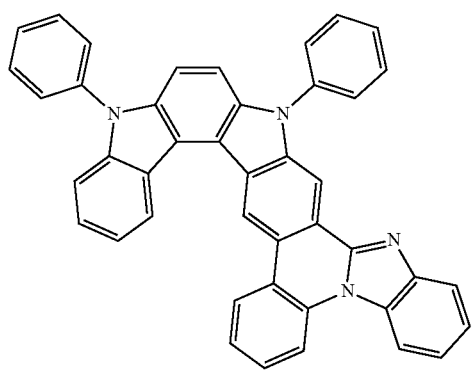
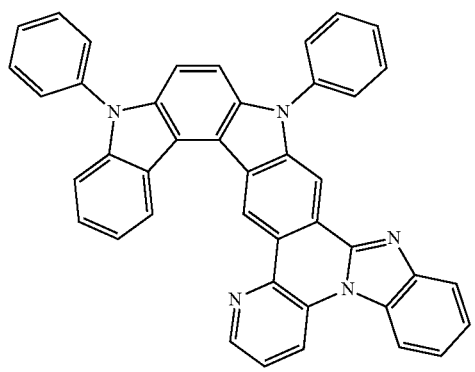
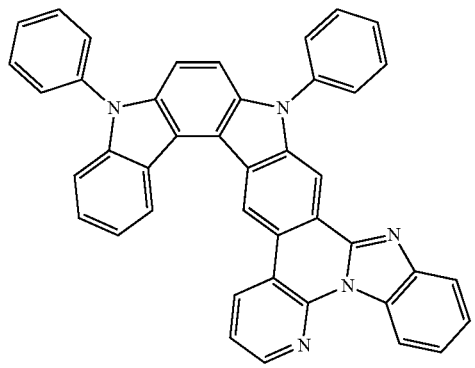

85
-continued
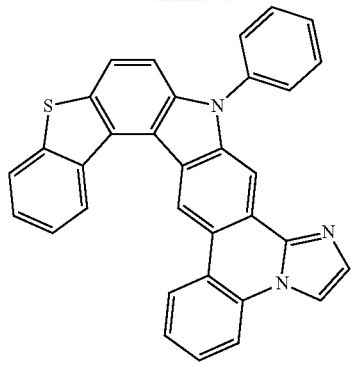
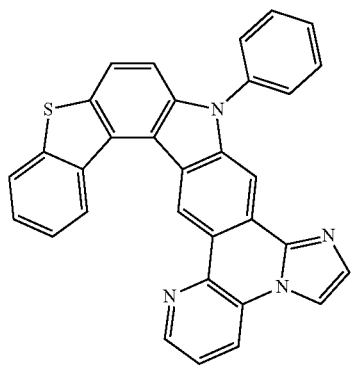
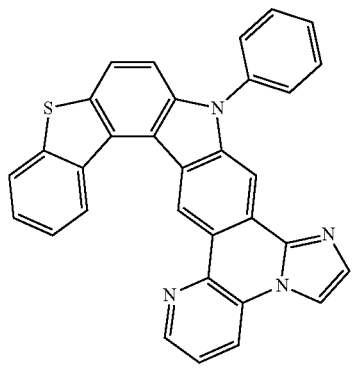
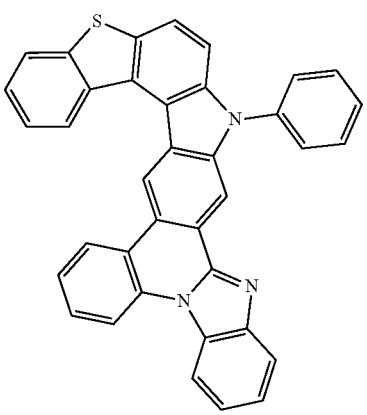
86
-continued
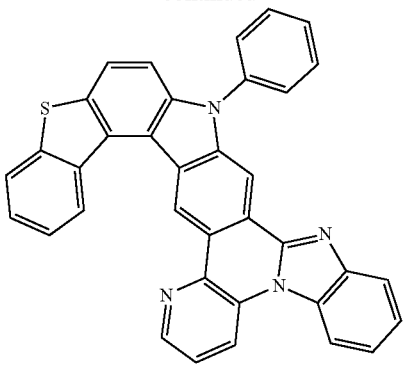
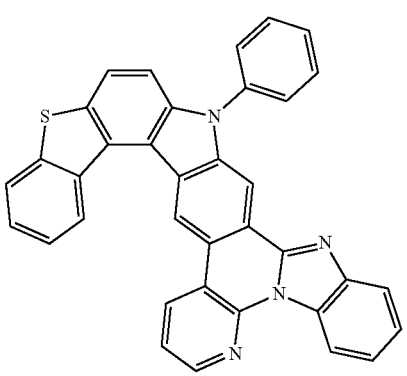
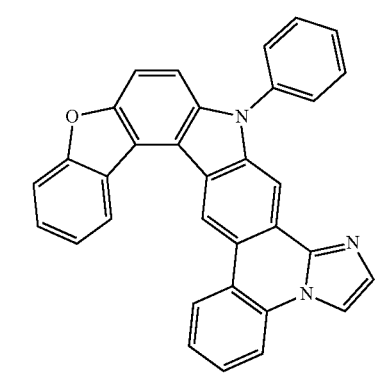
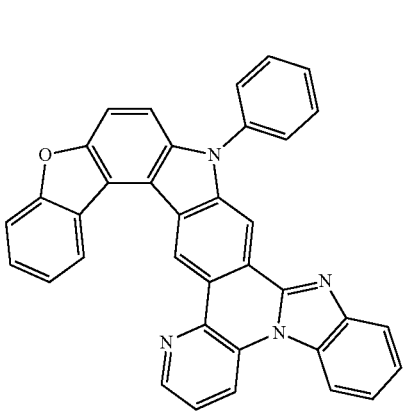

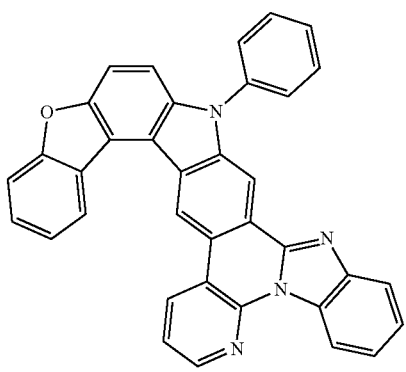
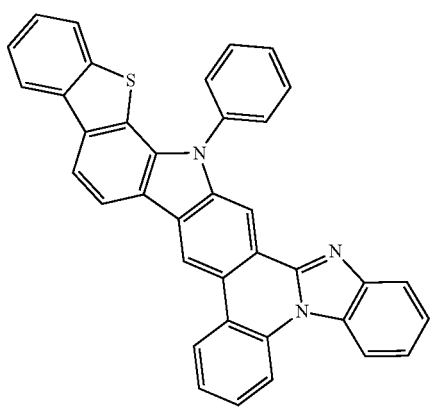
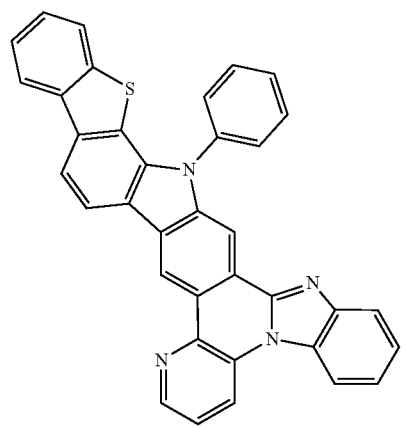
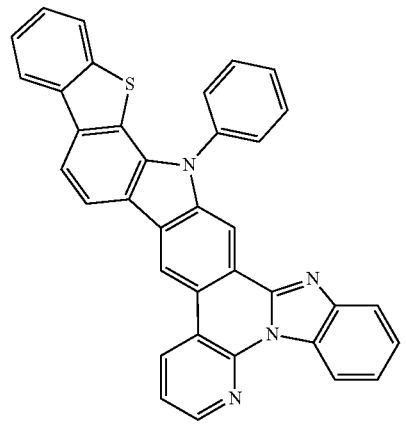
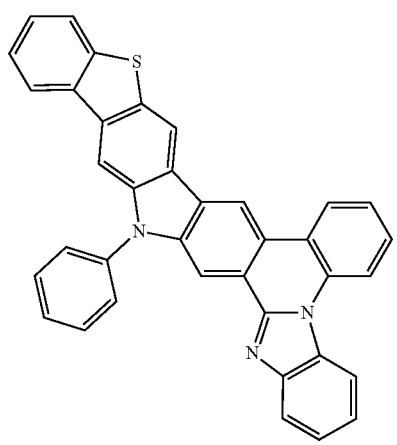
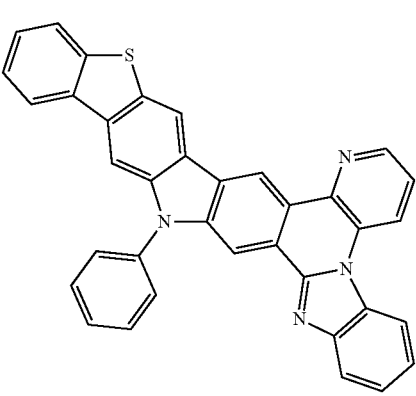
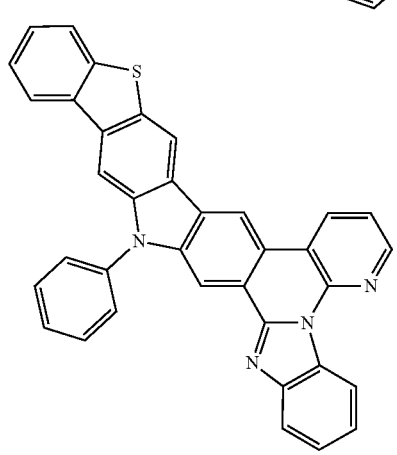
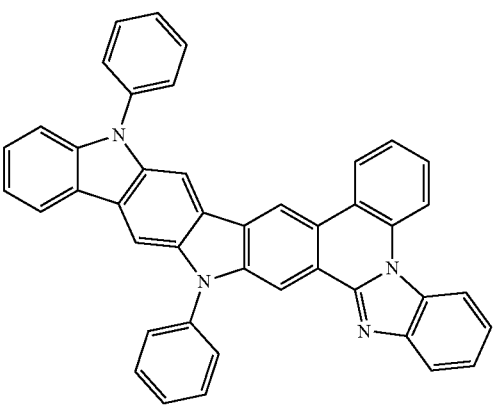

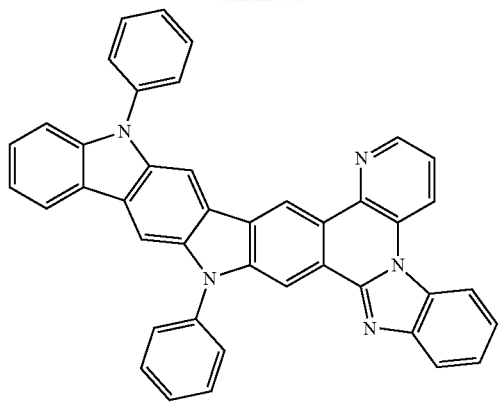
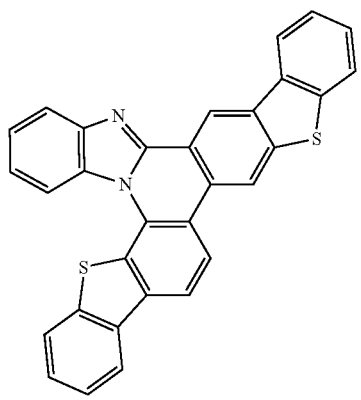
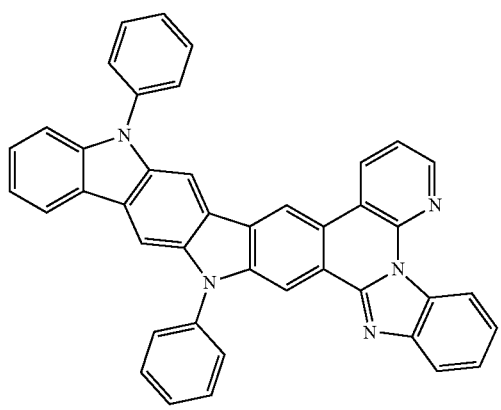
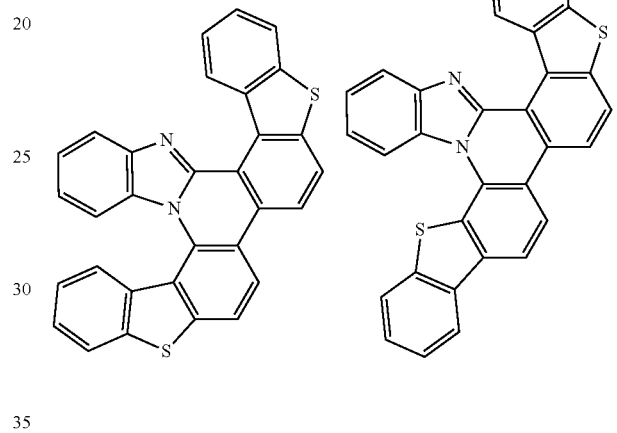
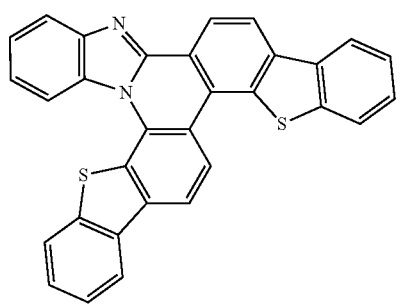
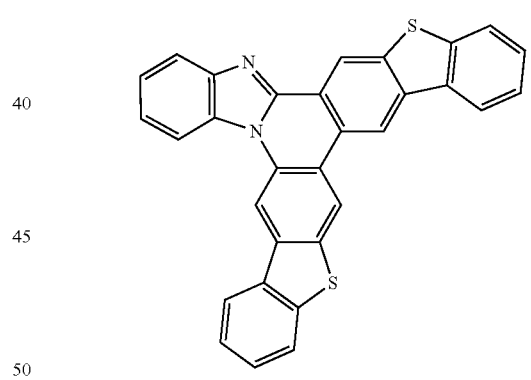
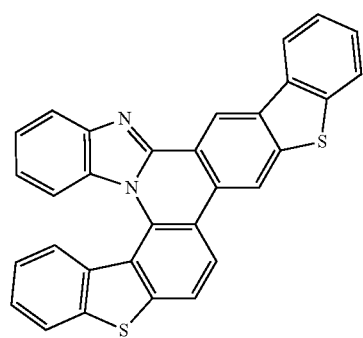
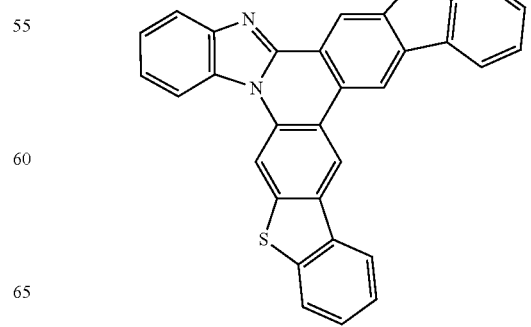

91
-continued
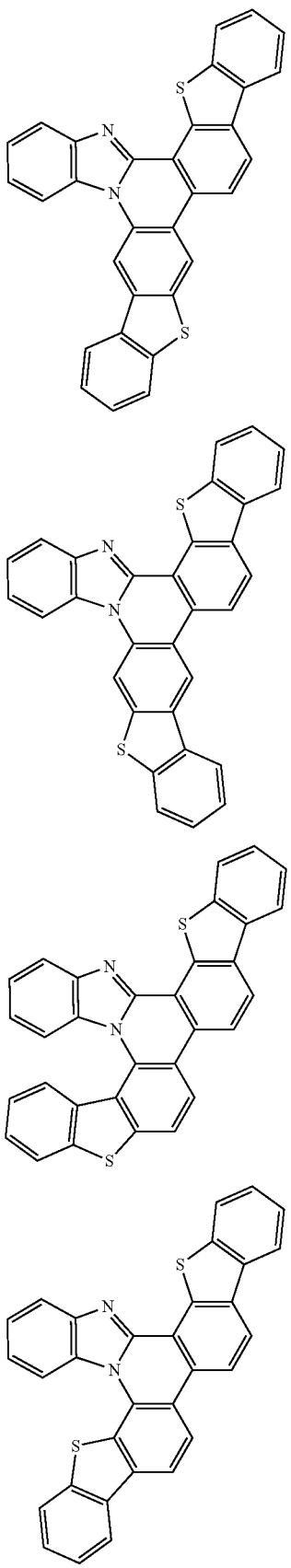
92
-continued
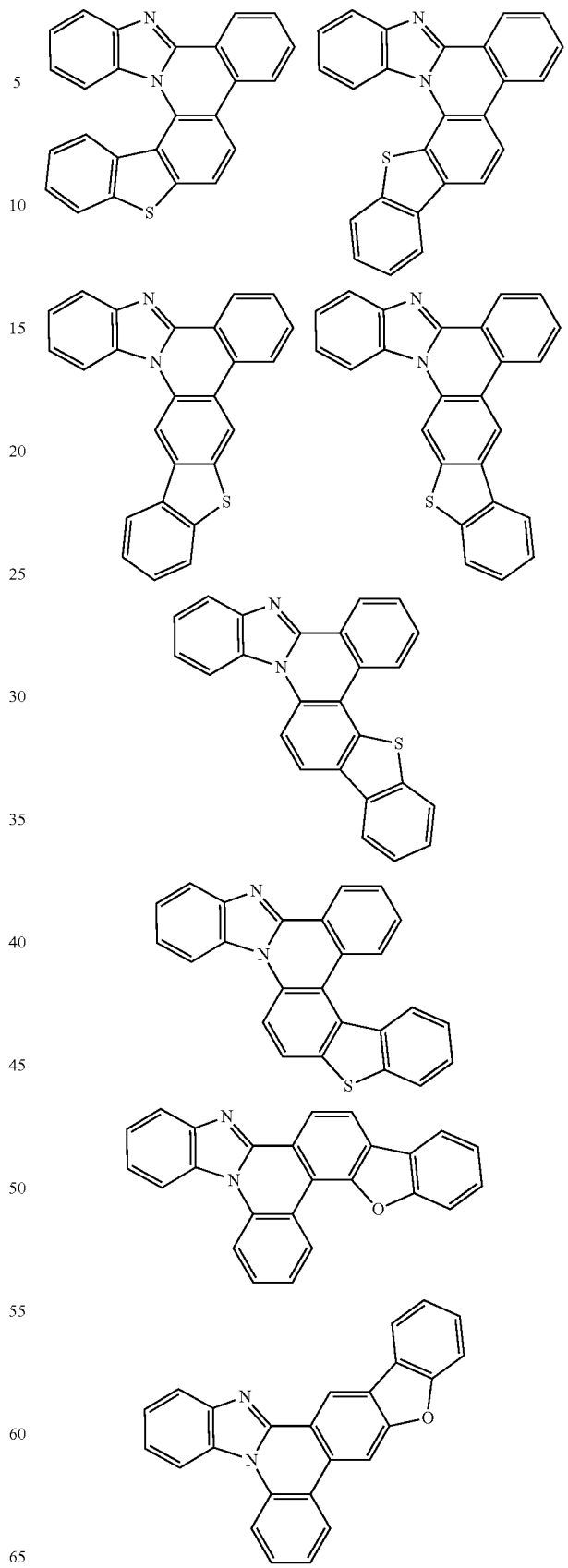

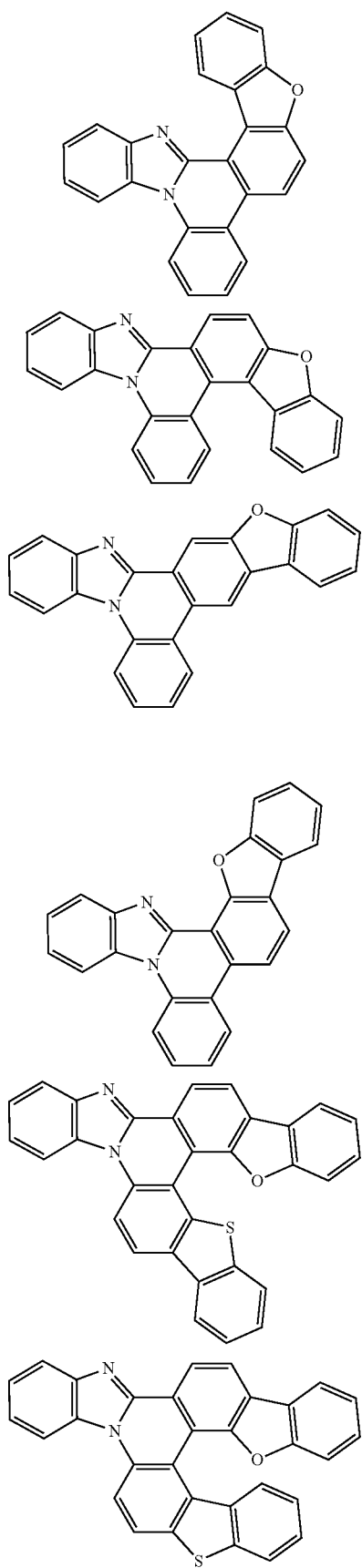
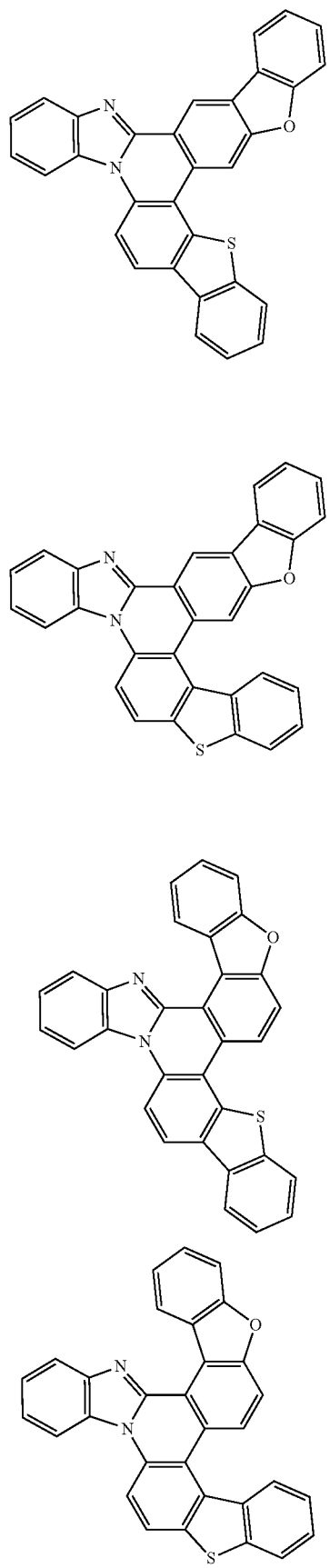

-continued
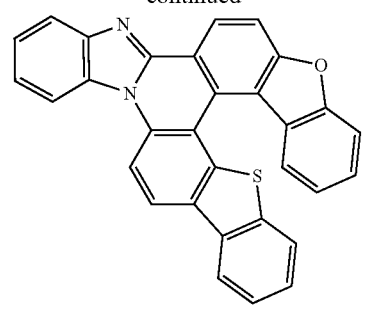
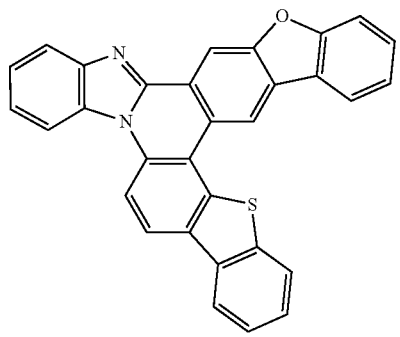
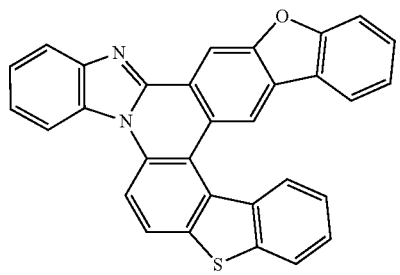
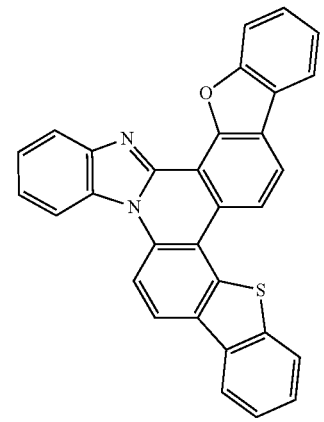
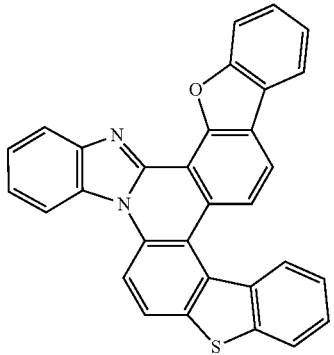
-continued
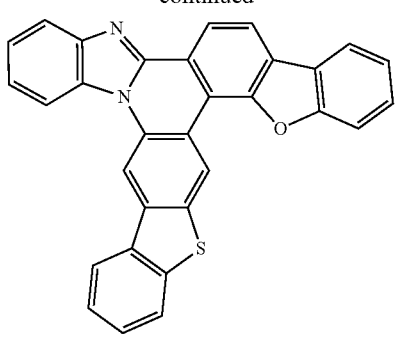
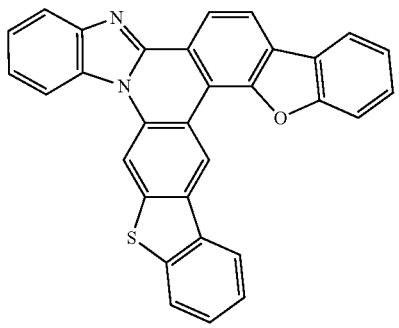
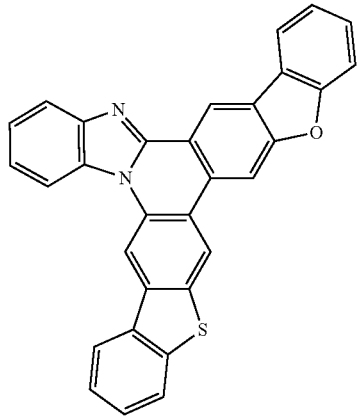
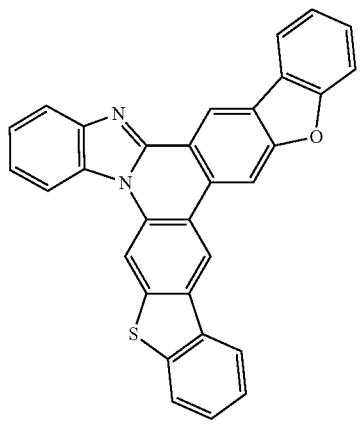

97
-continued
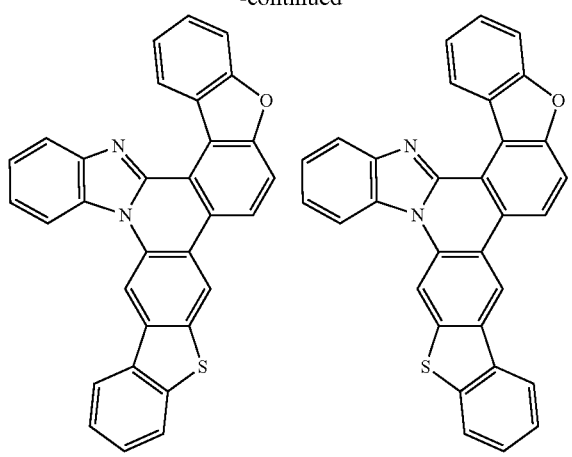
98
-continued
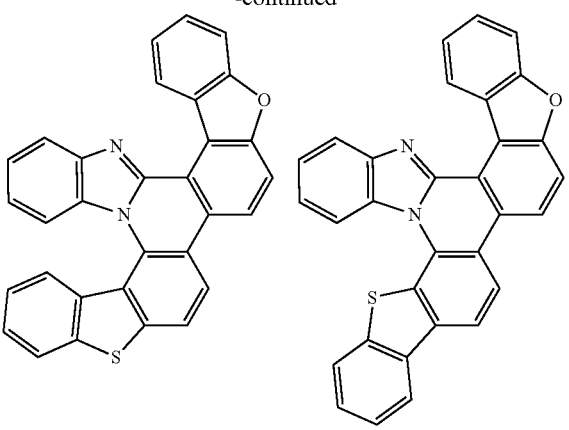
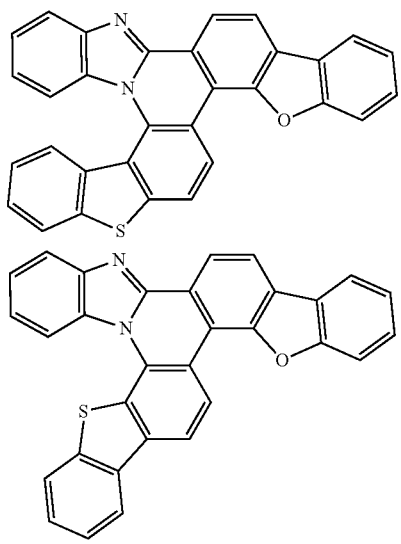
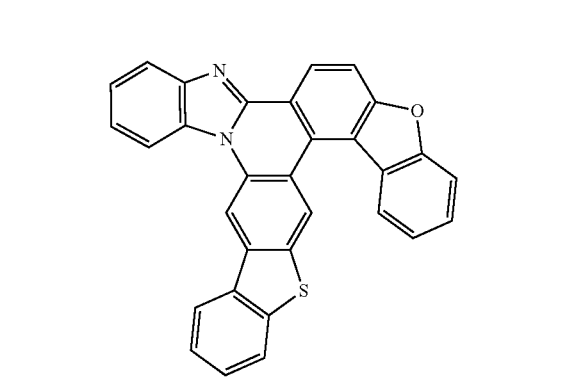
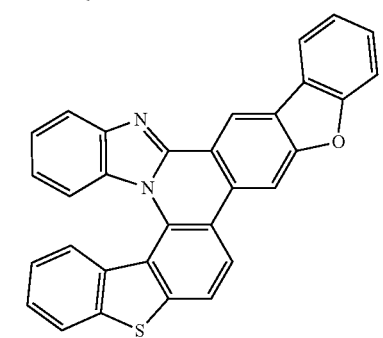
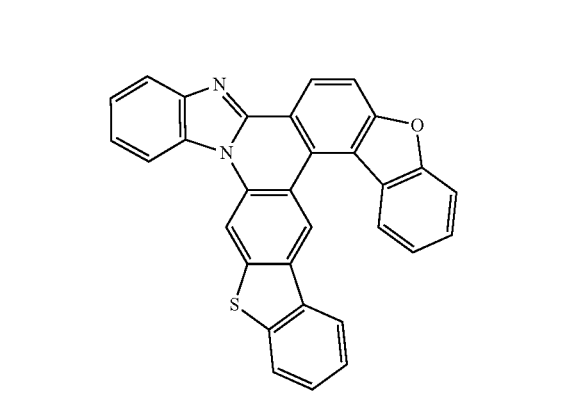
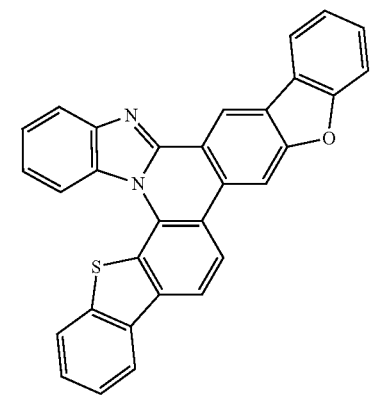
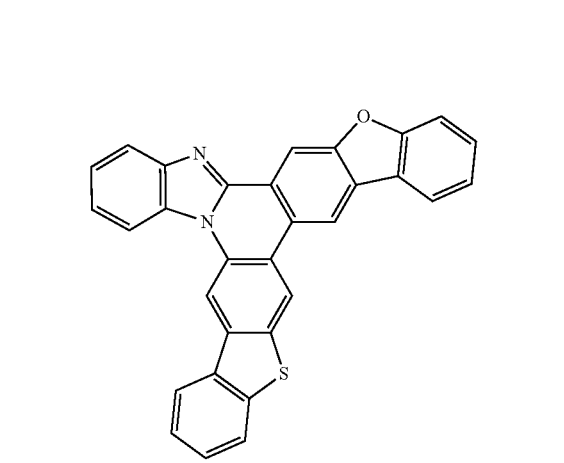

99
-continued
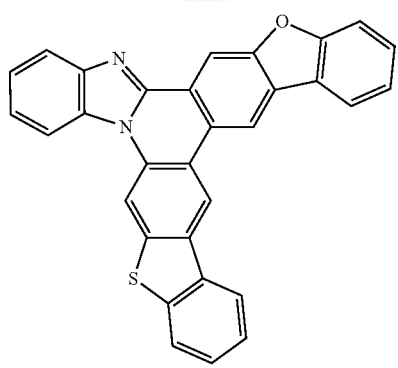
100
-continued
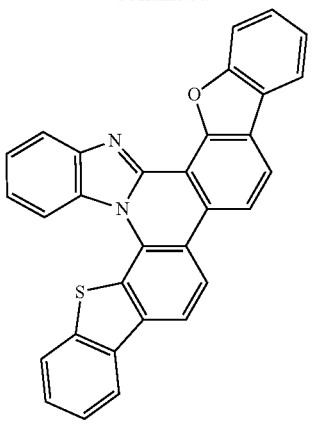
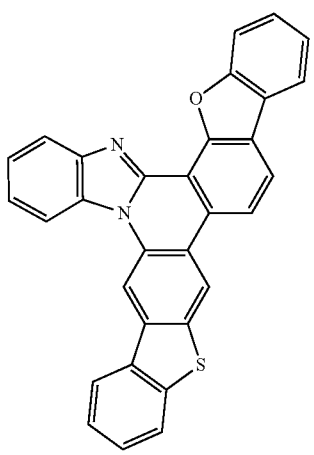
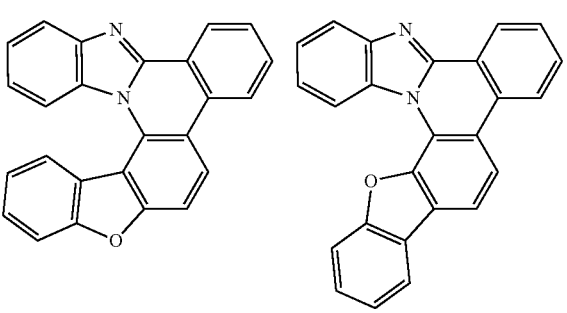
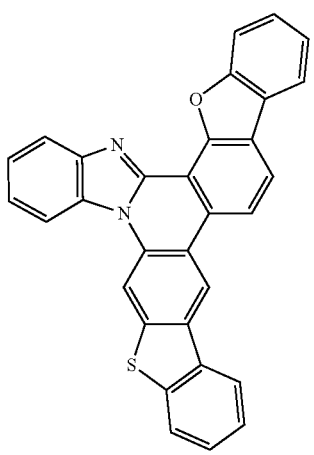
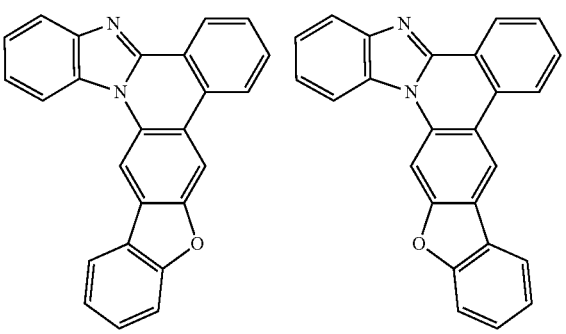
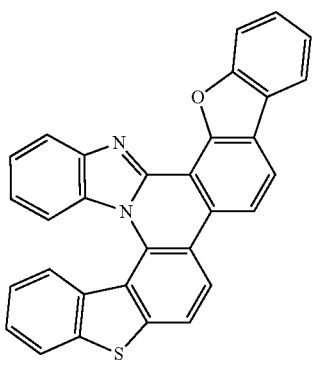
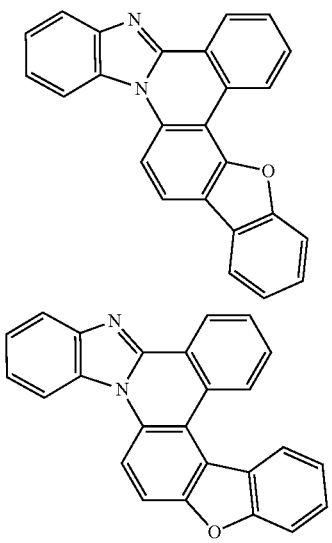

101
-continued
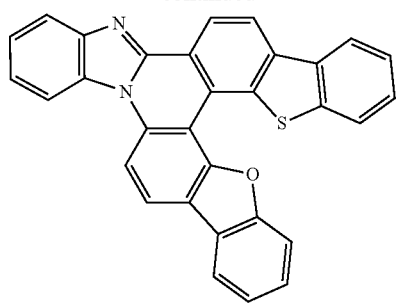
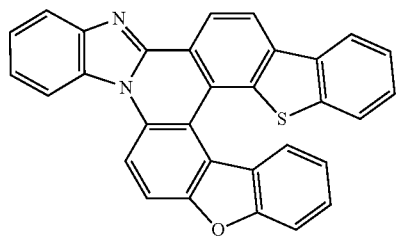
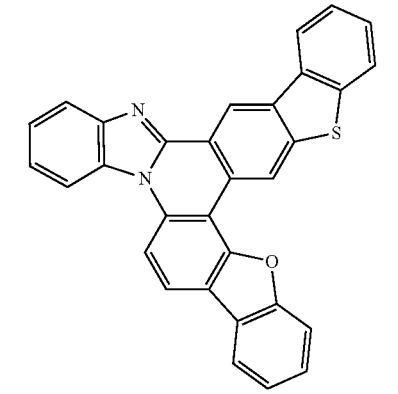
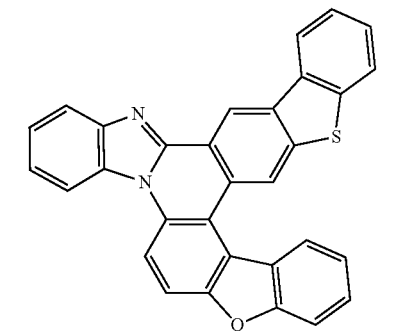
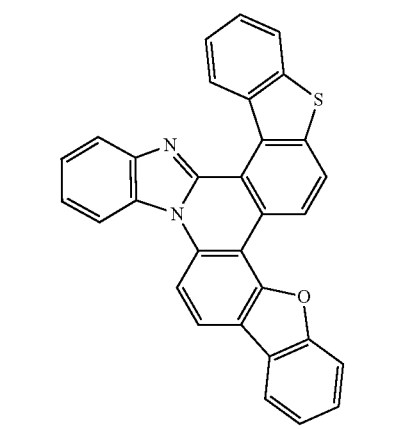
102
-continued
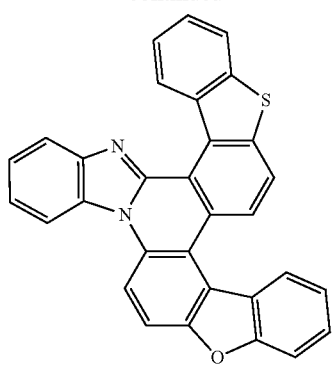
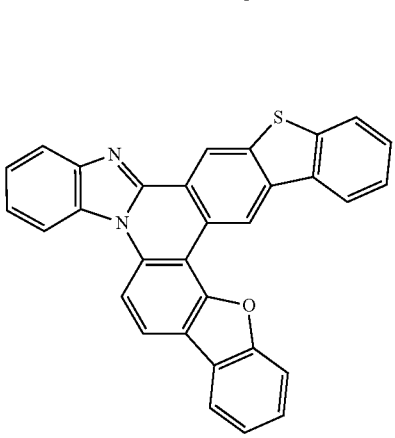
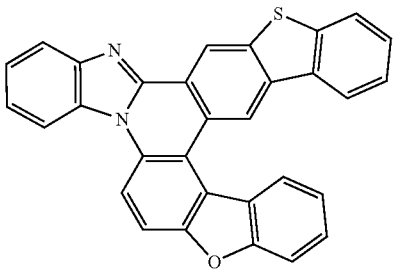
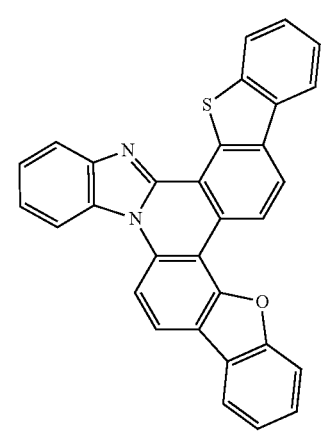

103
-continued
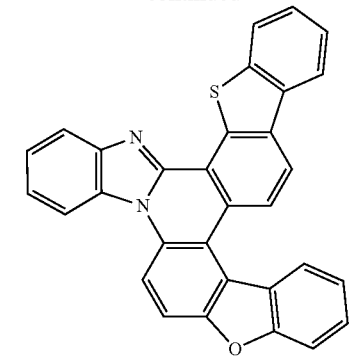
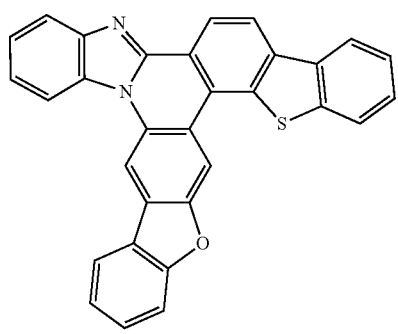
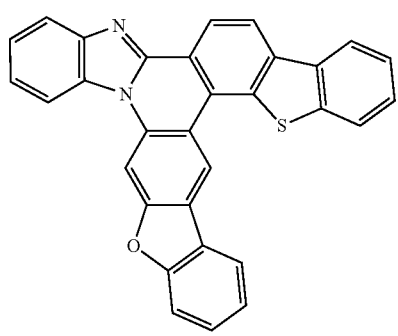
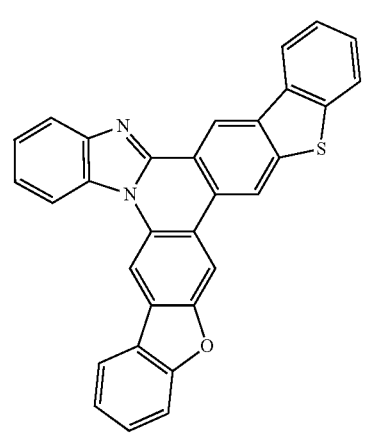
104
-continued
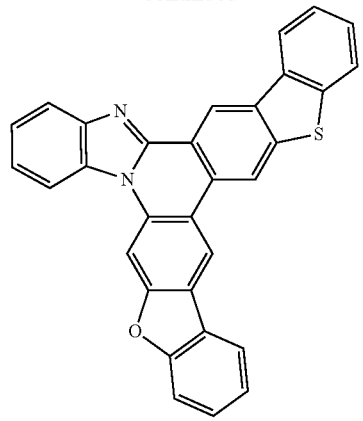
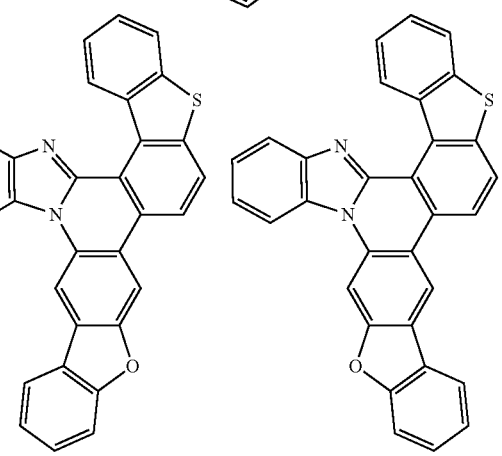
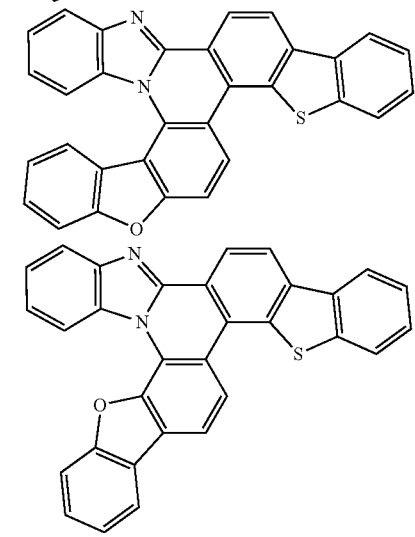
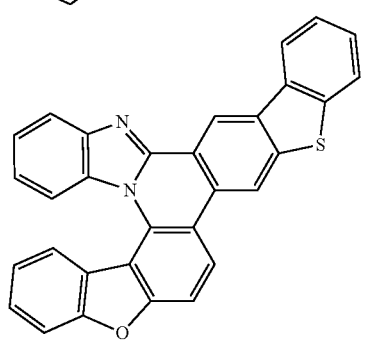

105
-continued
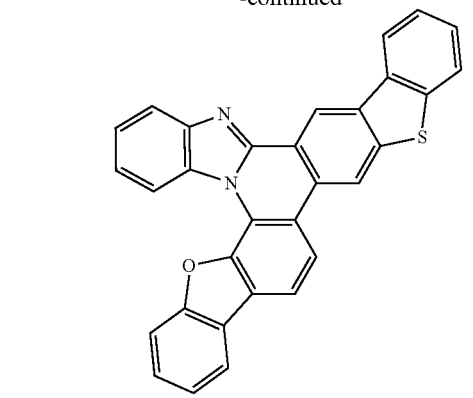
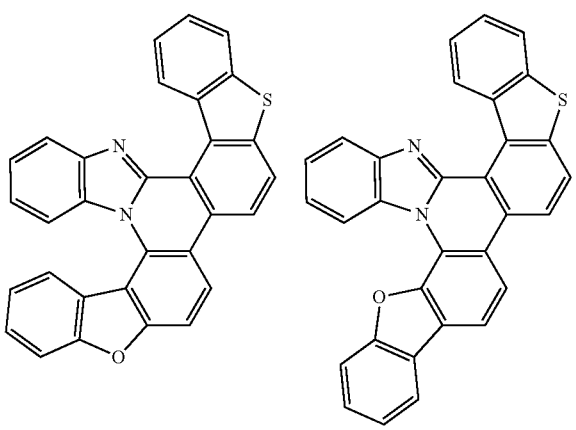
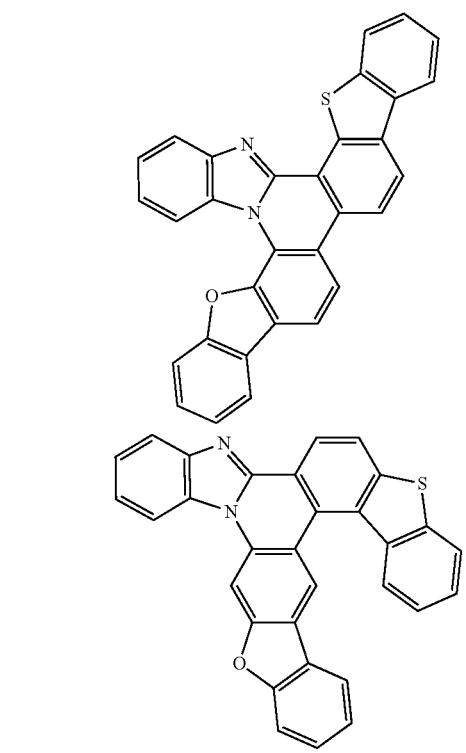
106
-continued
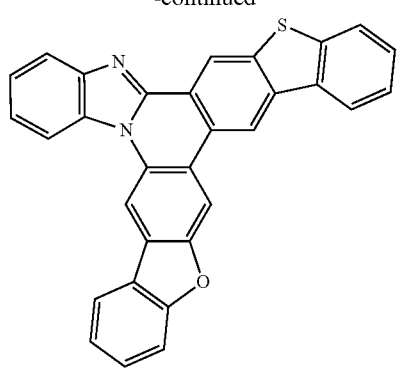
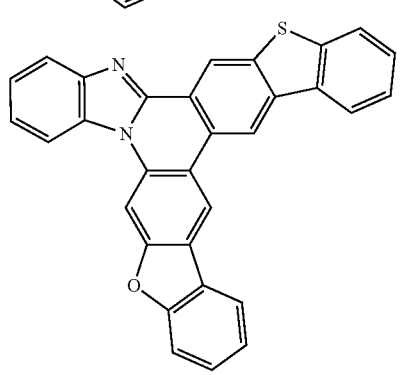
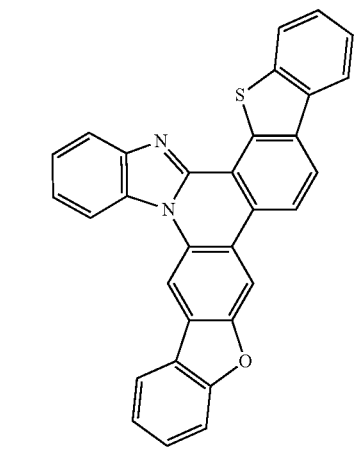
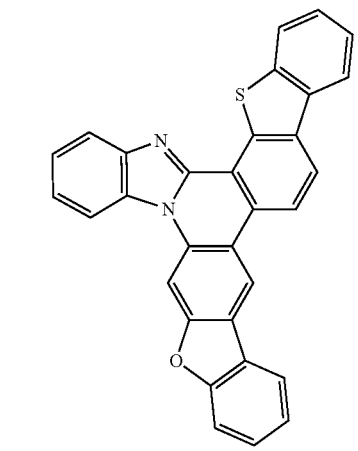

107
-continued
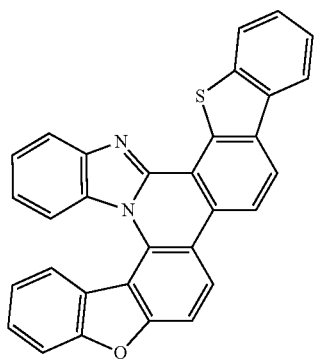
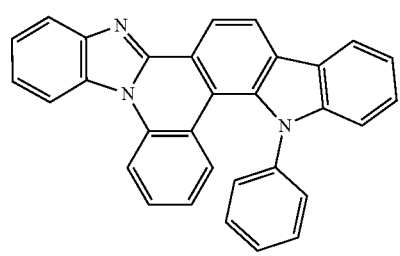
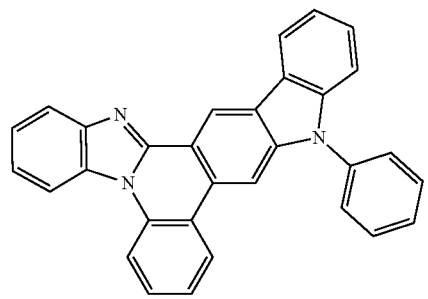
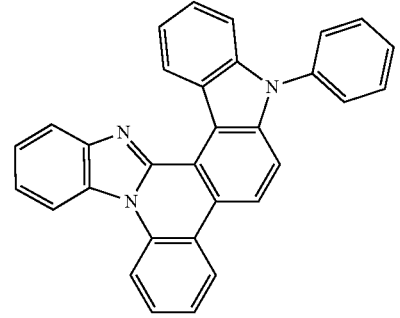
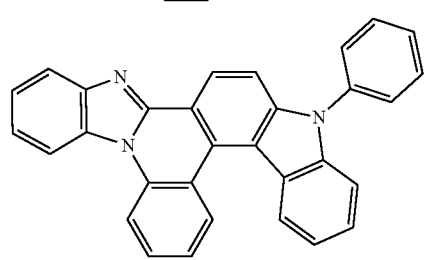
108
-continued
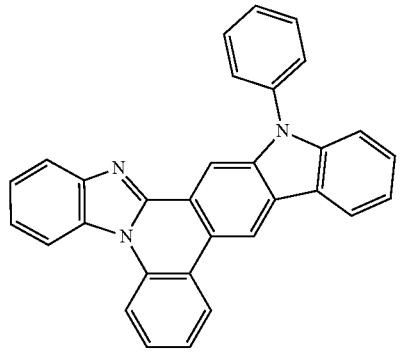
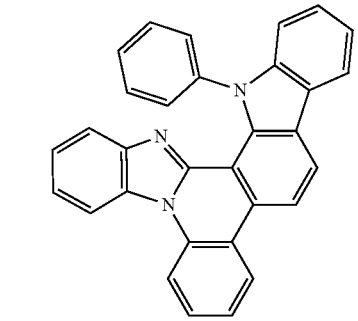
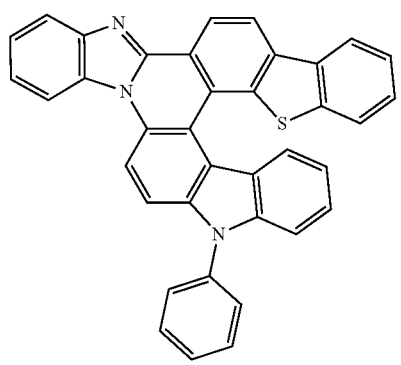
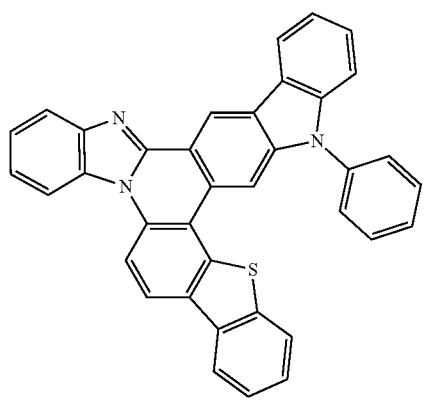

109
-continued
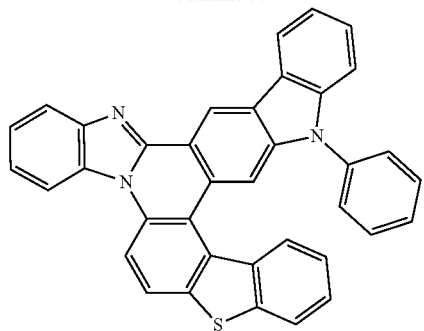
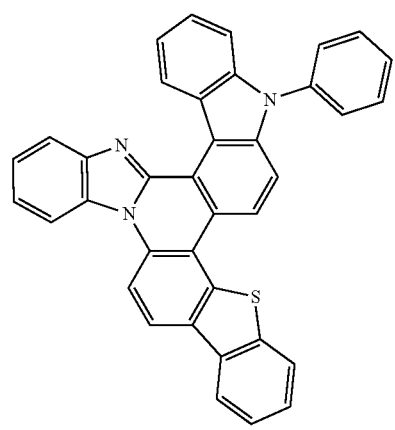
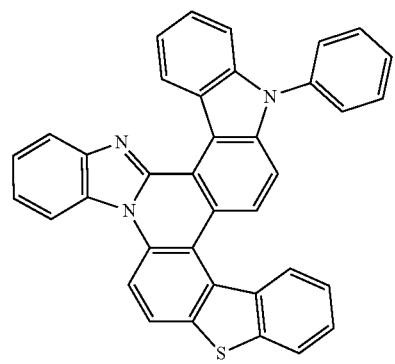
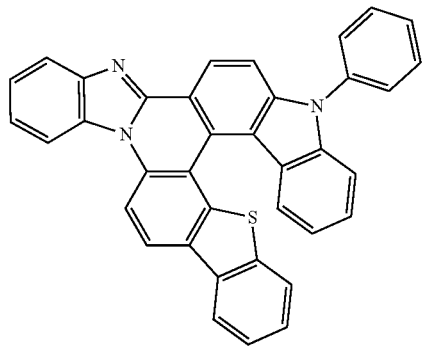
110
-continued
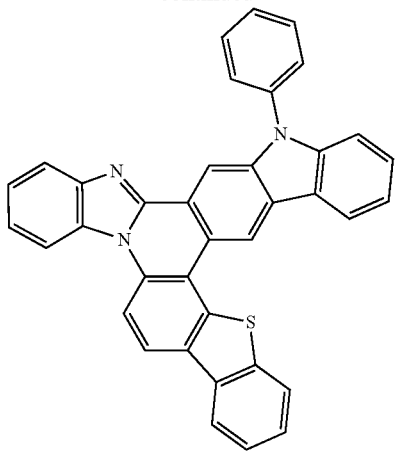
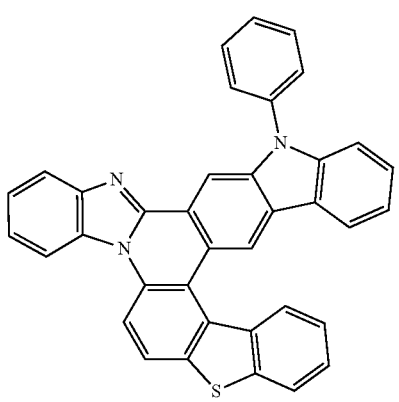
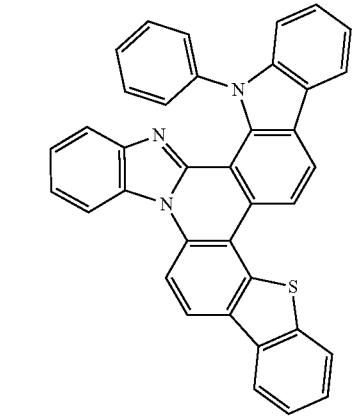
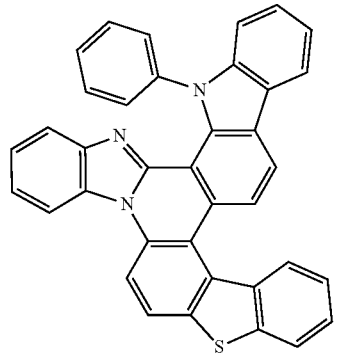

111
-continued
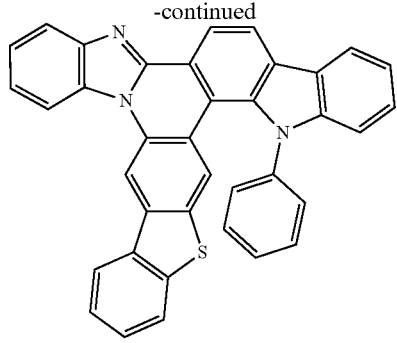
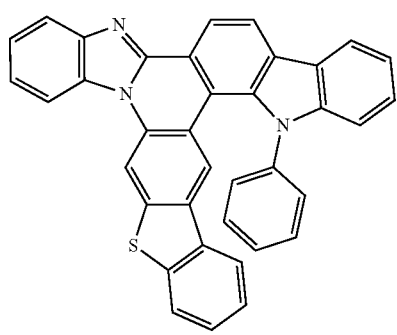
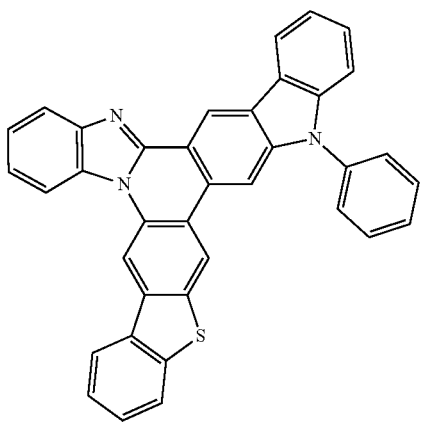
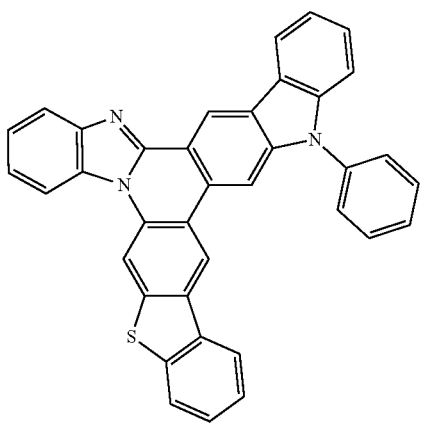
112
-continued
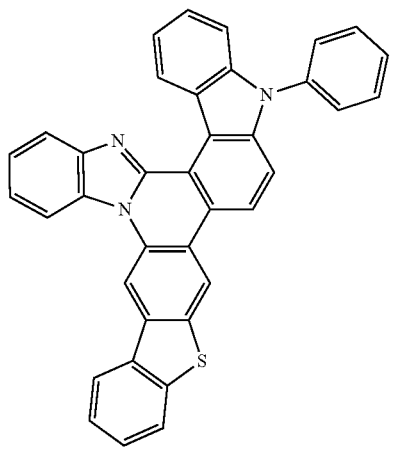
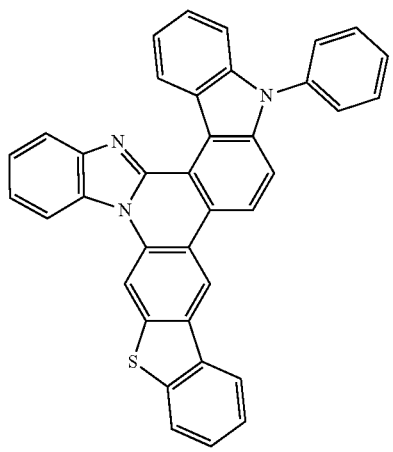
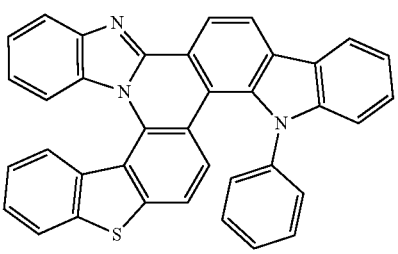
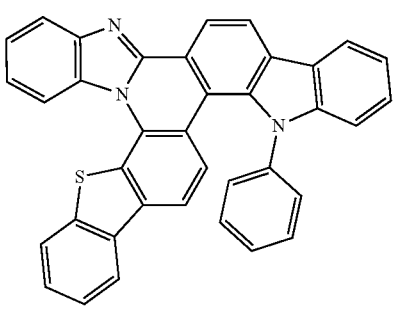

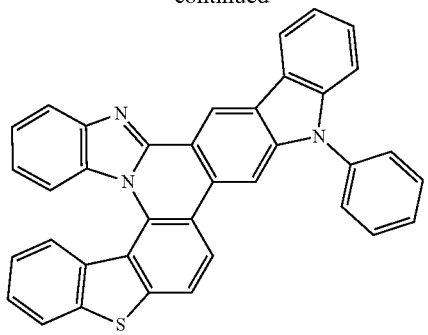
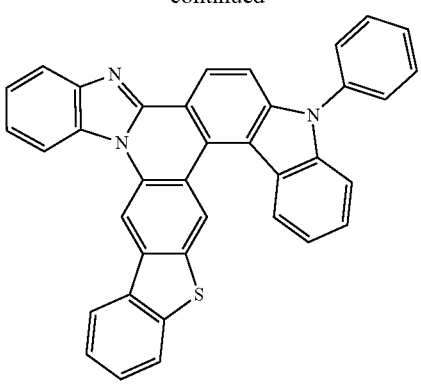
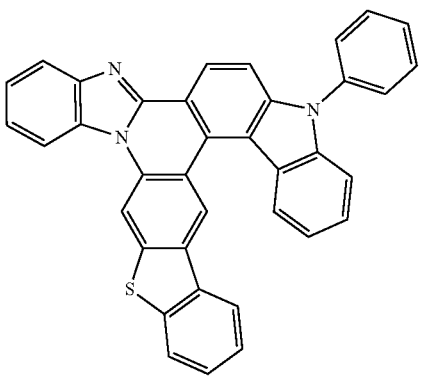
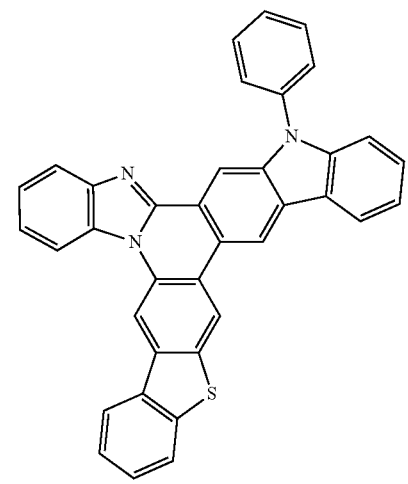
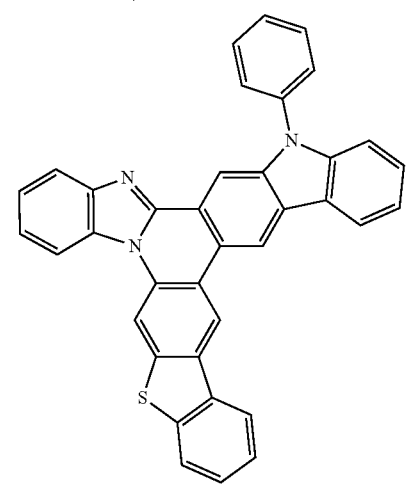

115
-continued
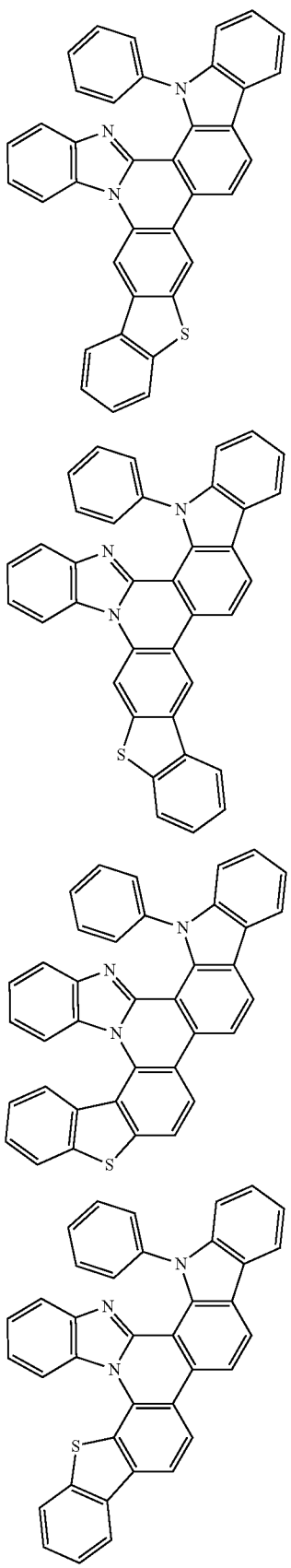
116
-continued
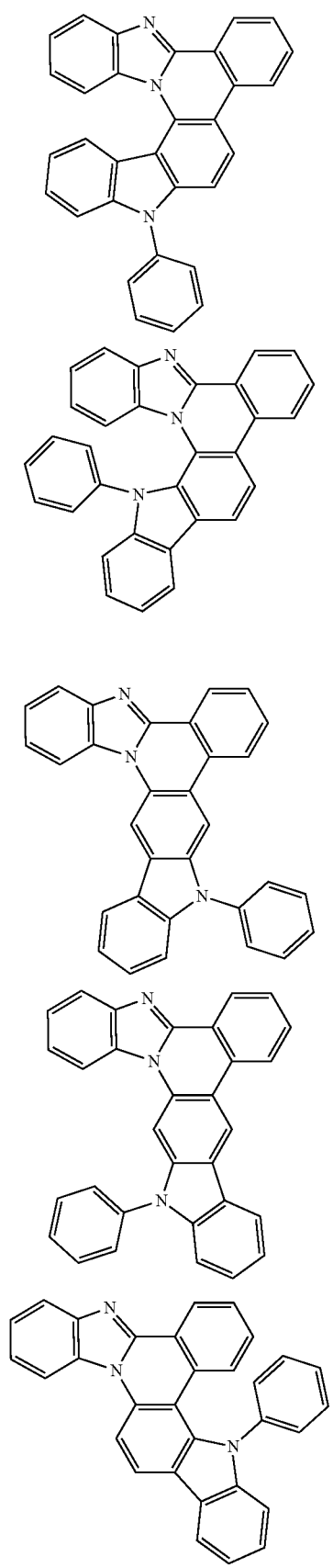

117
-continued
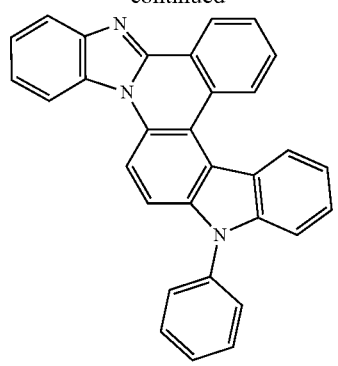
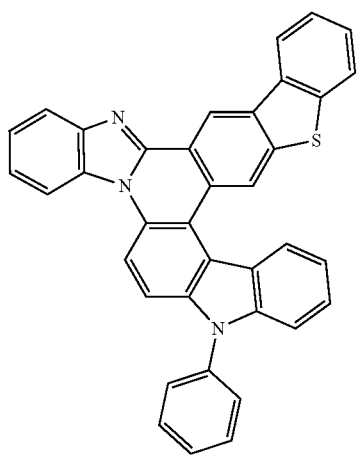
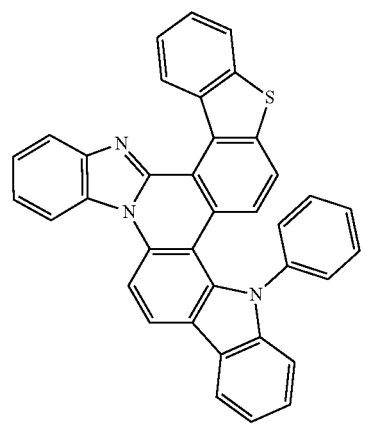
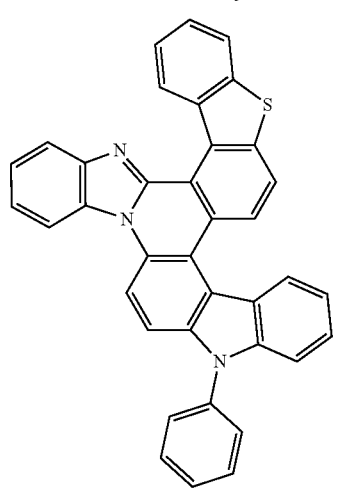
118
-continued
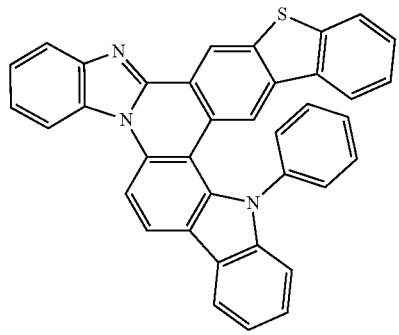
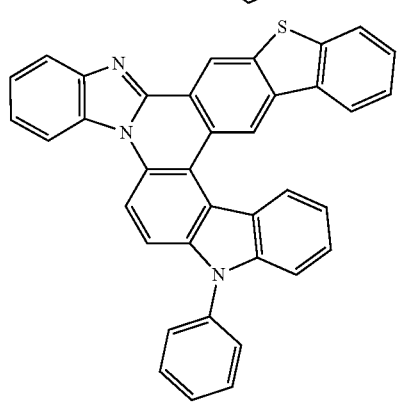
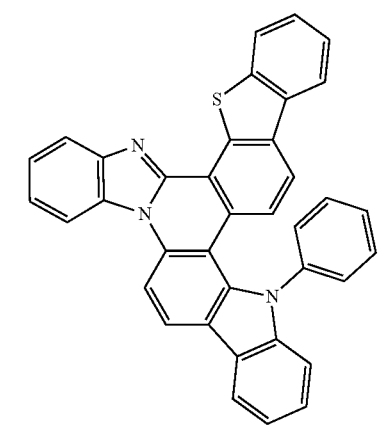
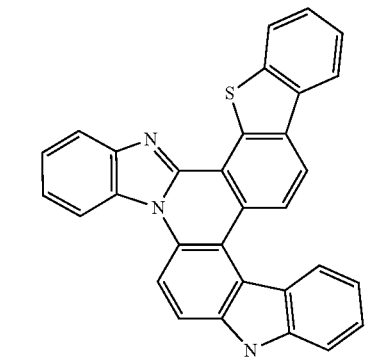

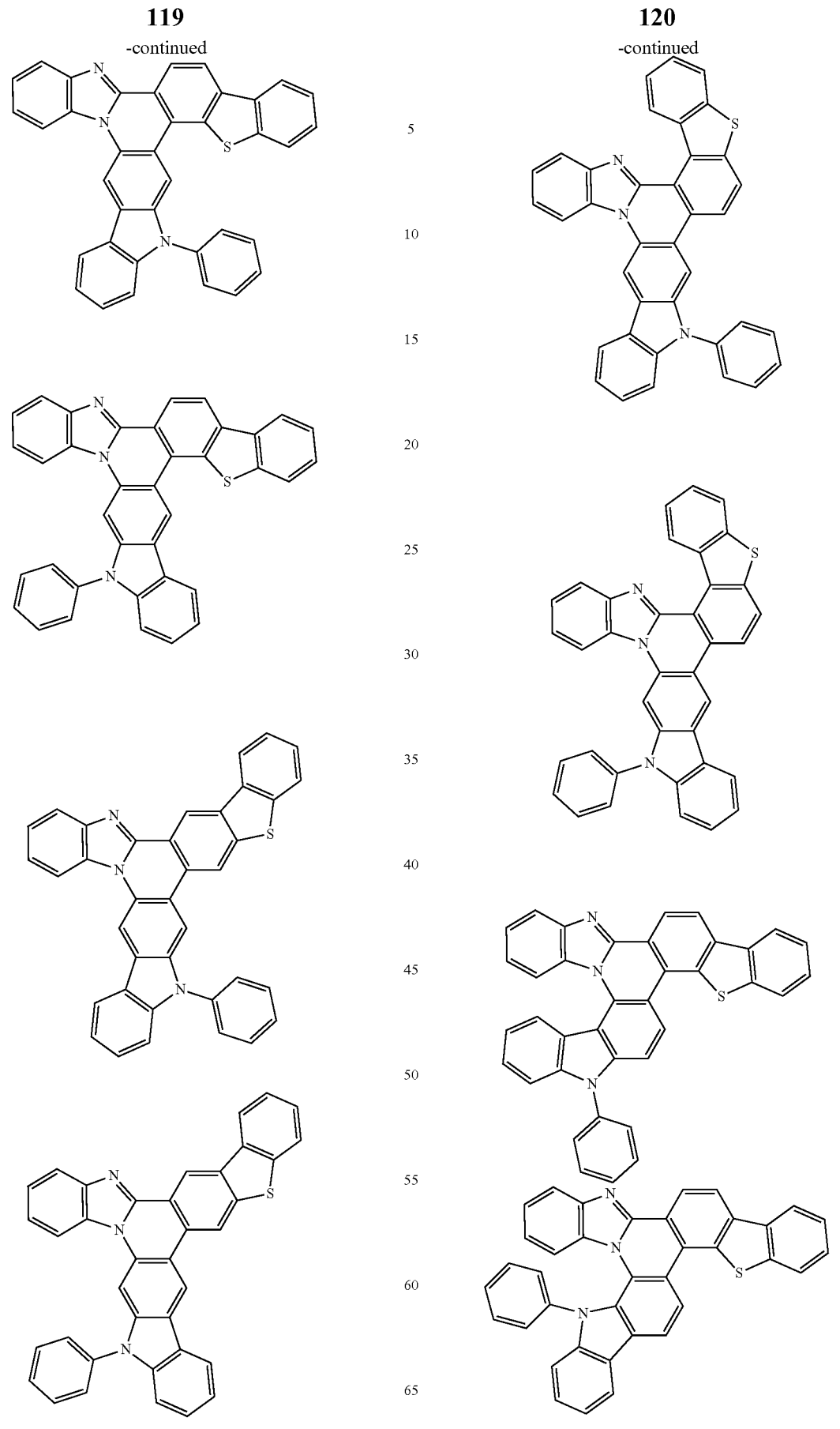

119
-continued

120
-continued

121
-continued
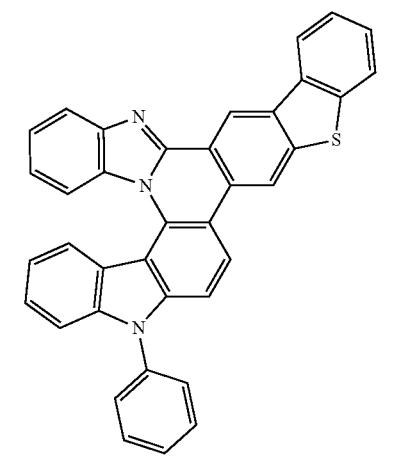
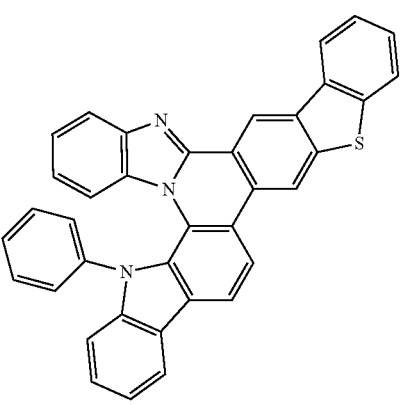
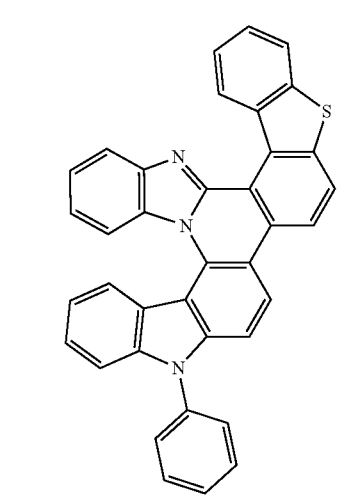
122
-continued
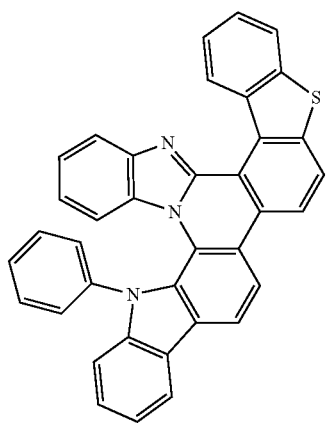
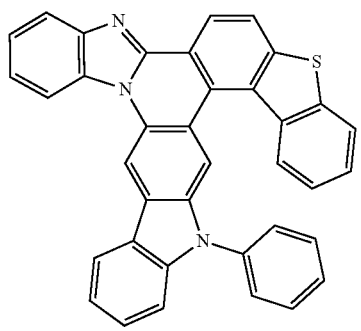
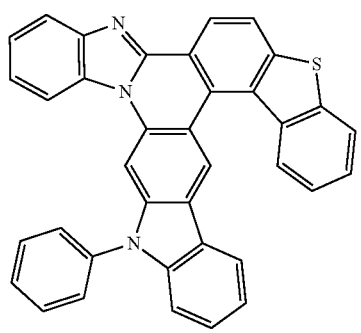
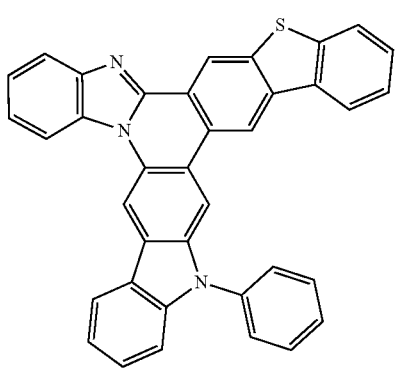

123
-continued
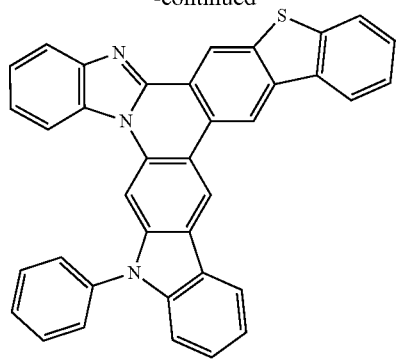
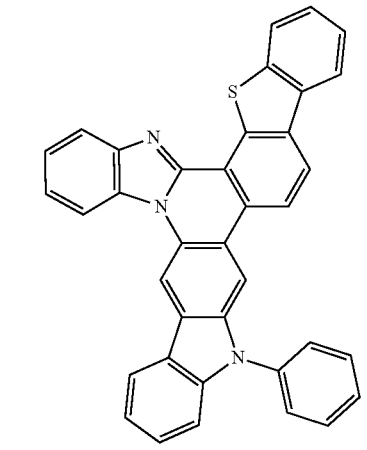
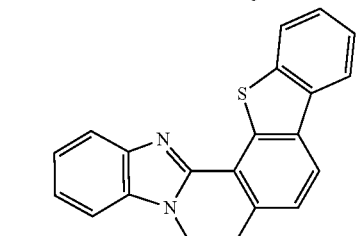
124
-continued
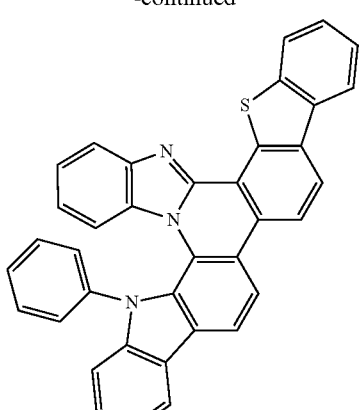
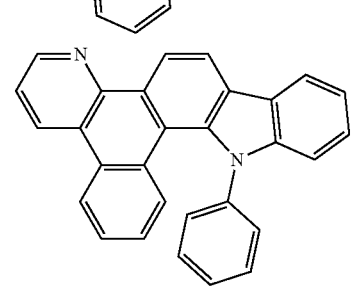
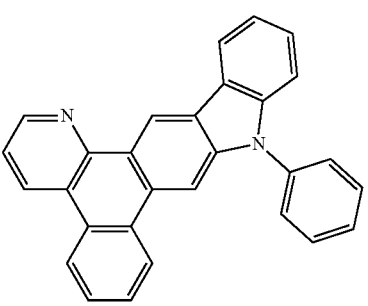
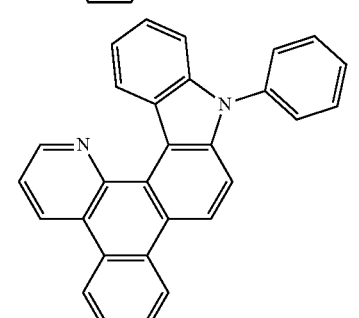
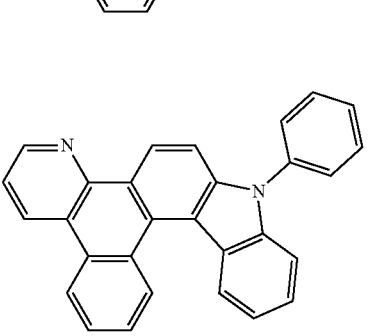

125
-continued
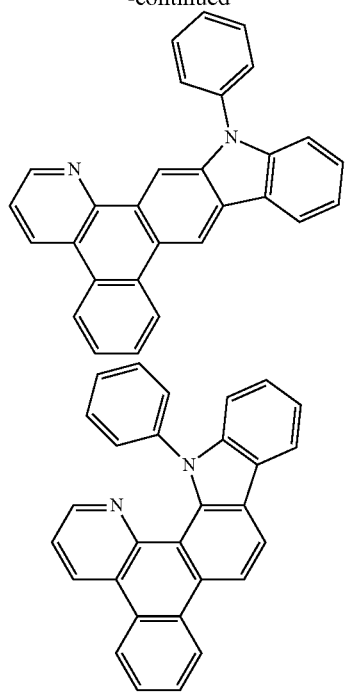
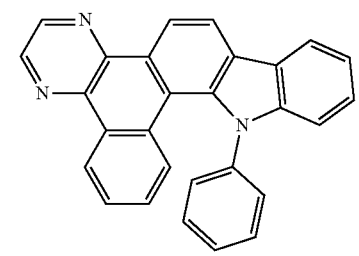
126
-continued
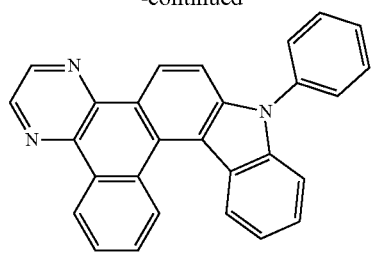
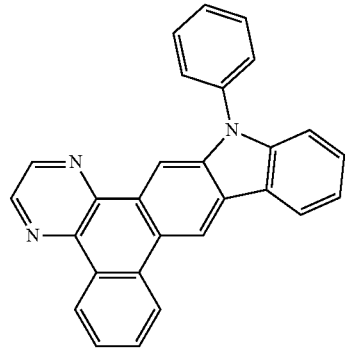
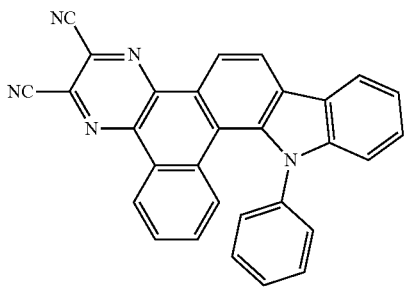
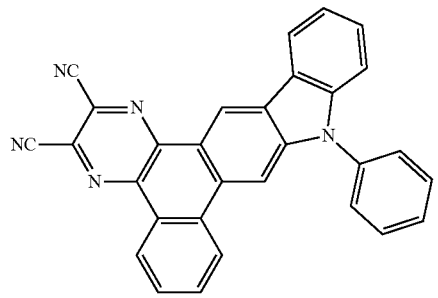

127
-continued
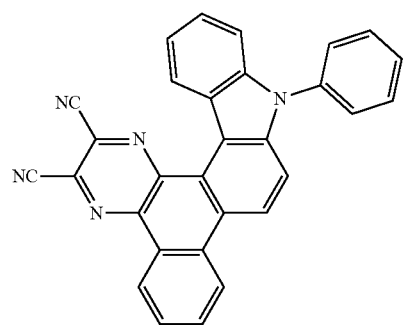
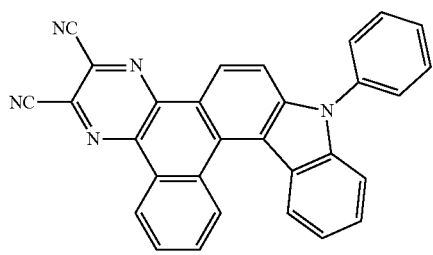
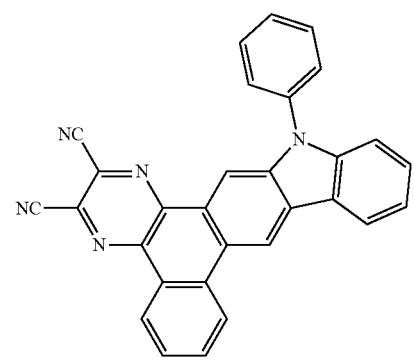
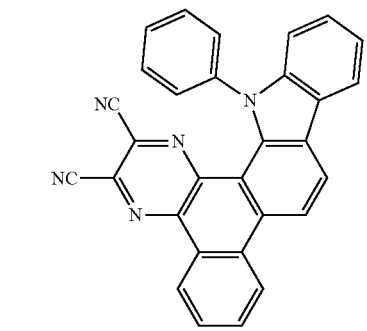
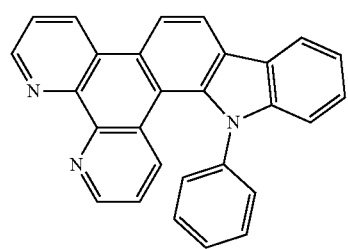
128
-continued
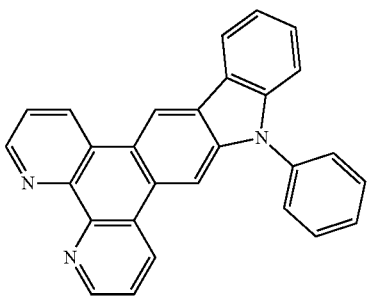
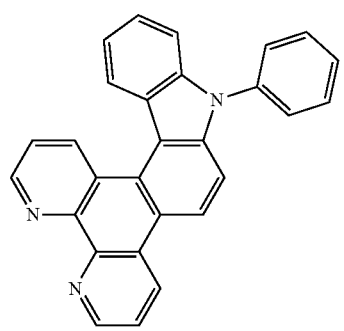
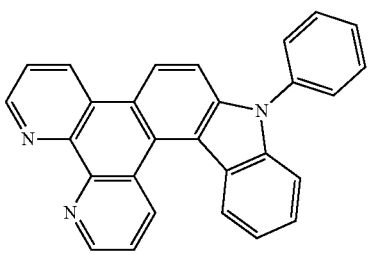
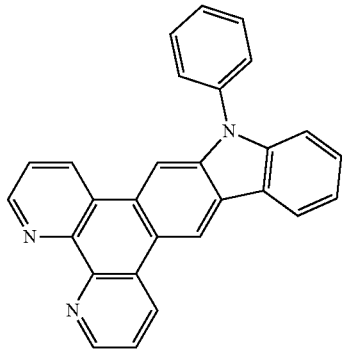
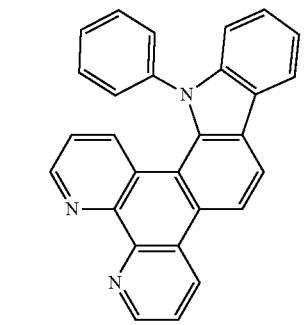

129
-continued
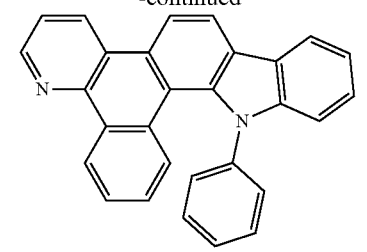
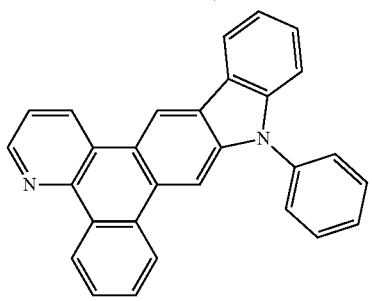
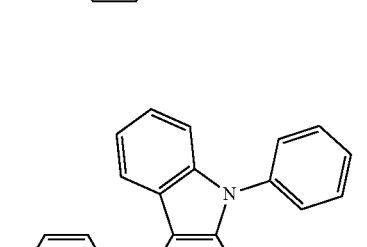
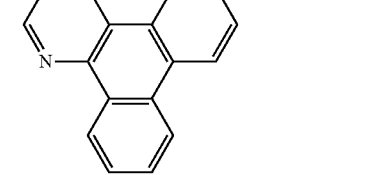
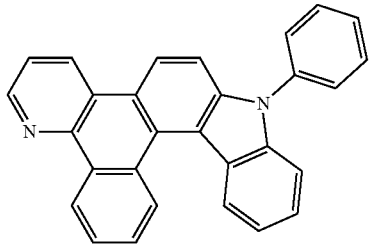
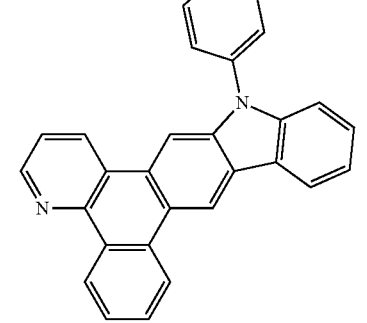
130
-continued
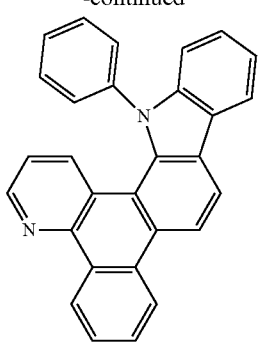
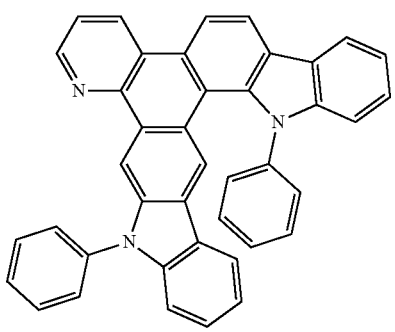
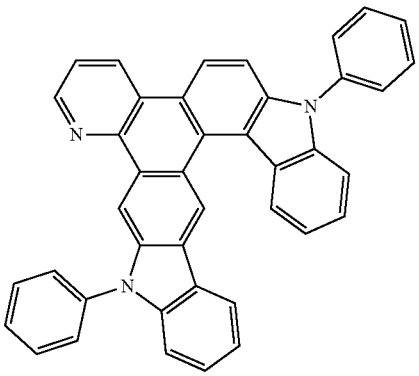
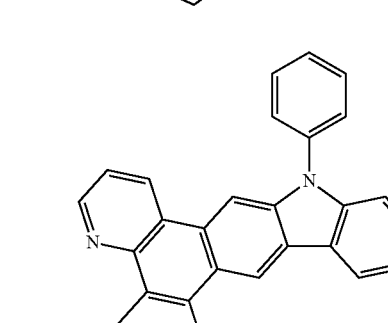
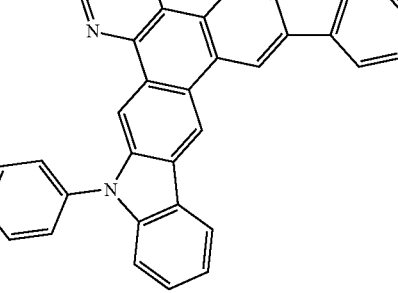

131
-continued
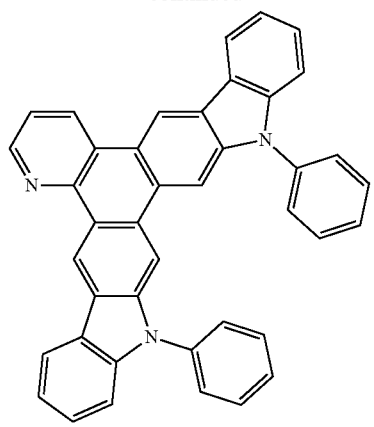
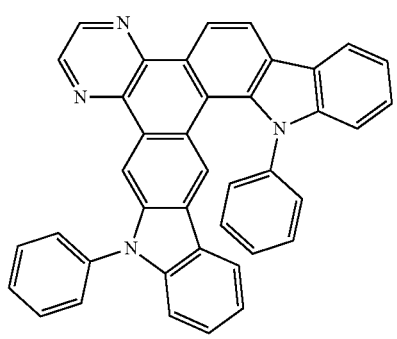
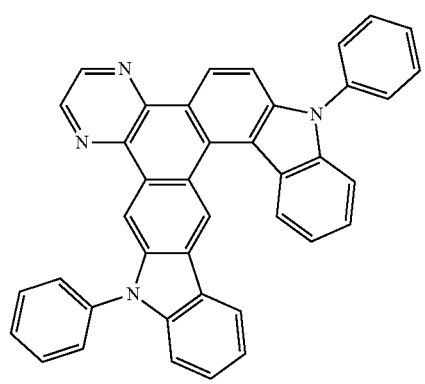
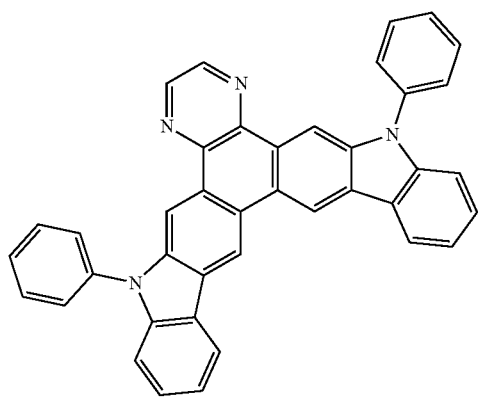
132
-continued
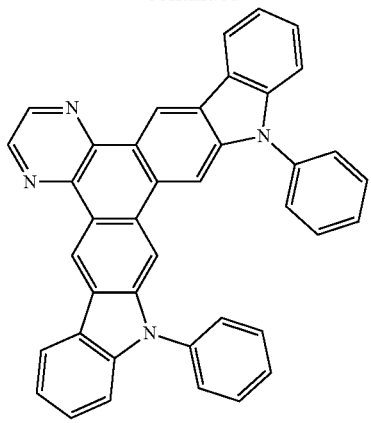
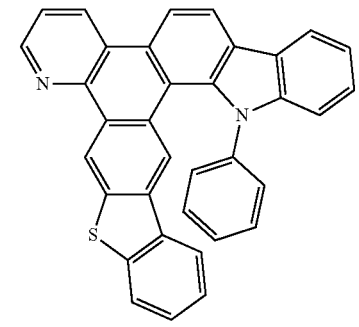
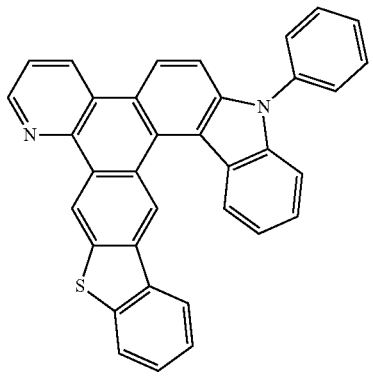
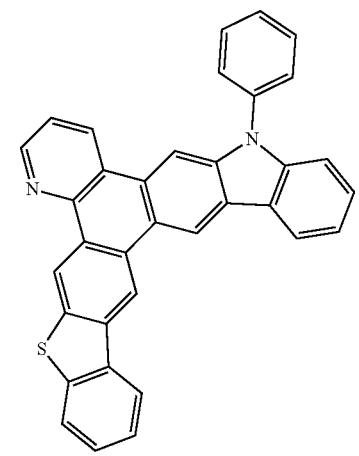

133
-continued
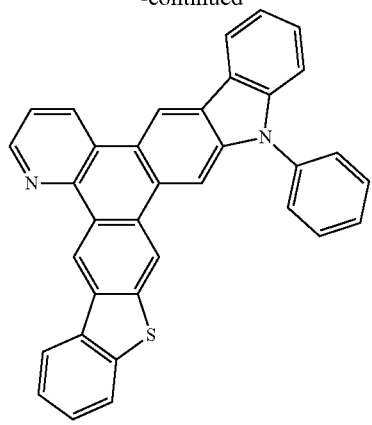
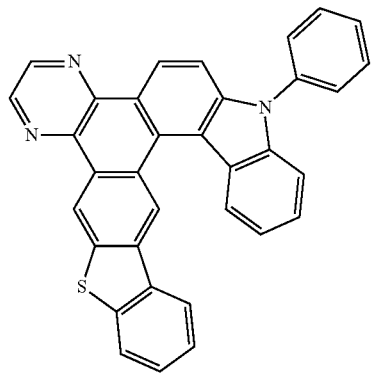
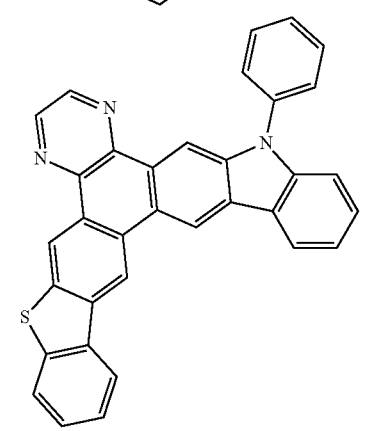
134
-continued
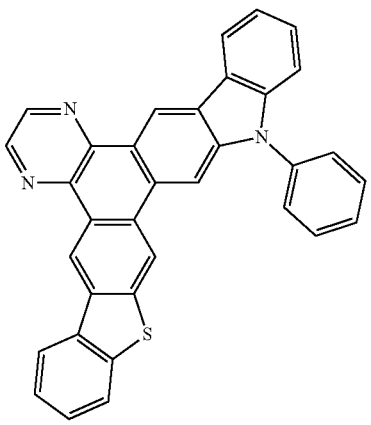
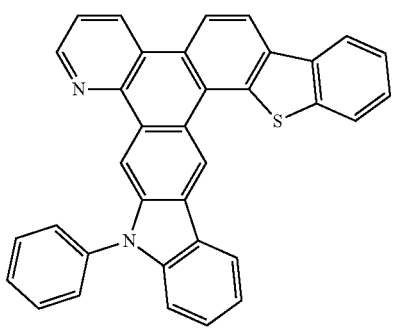
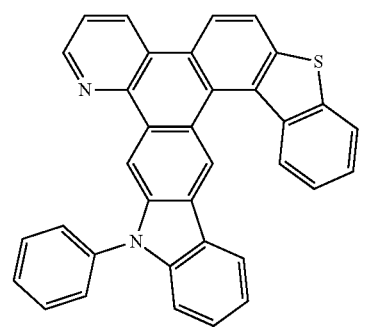
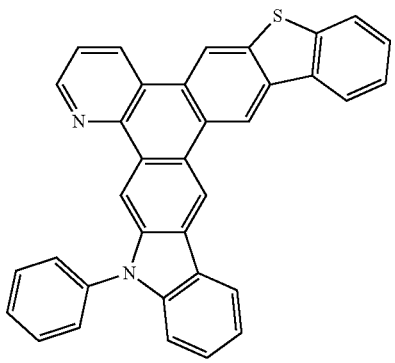

135
-continued
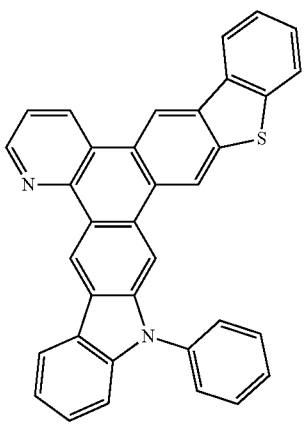
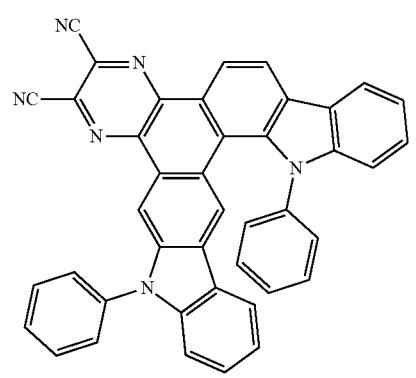
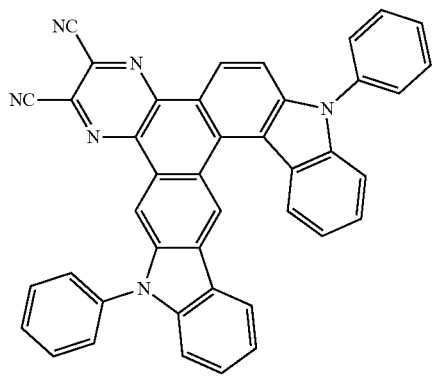
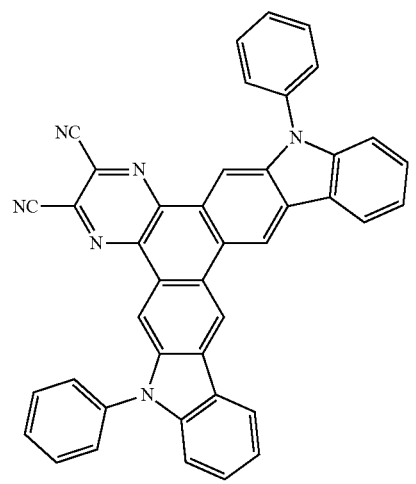
136
-continued
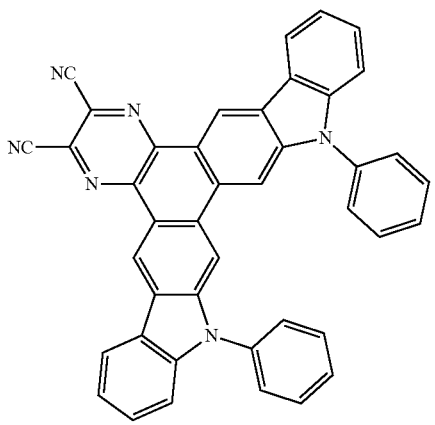
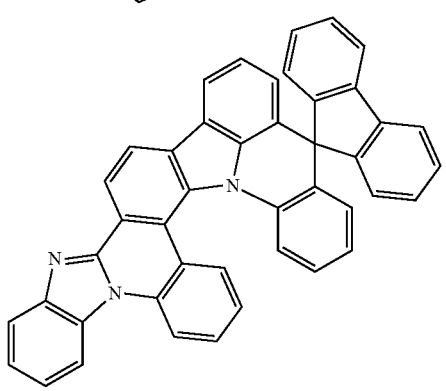
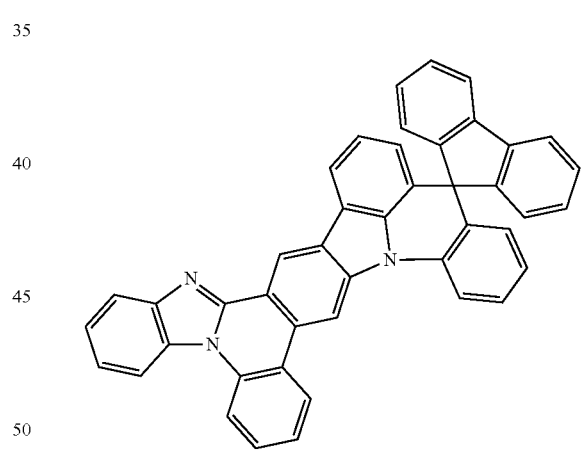
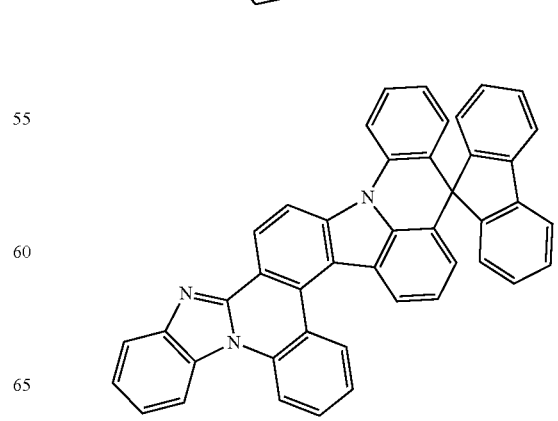

137
-continued
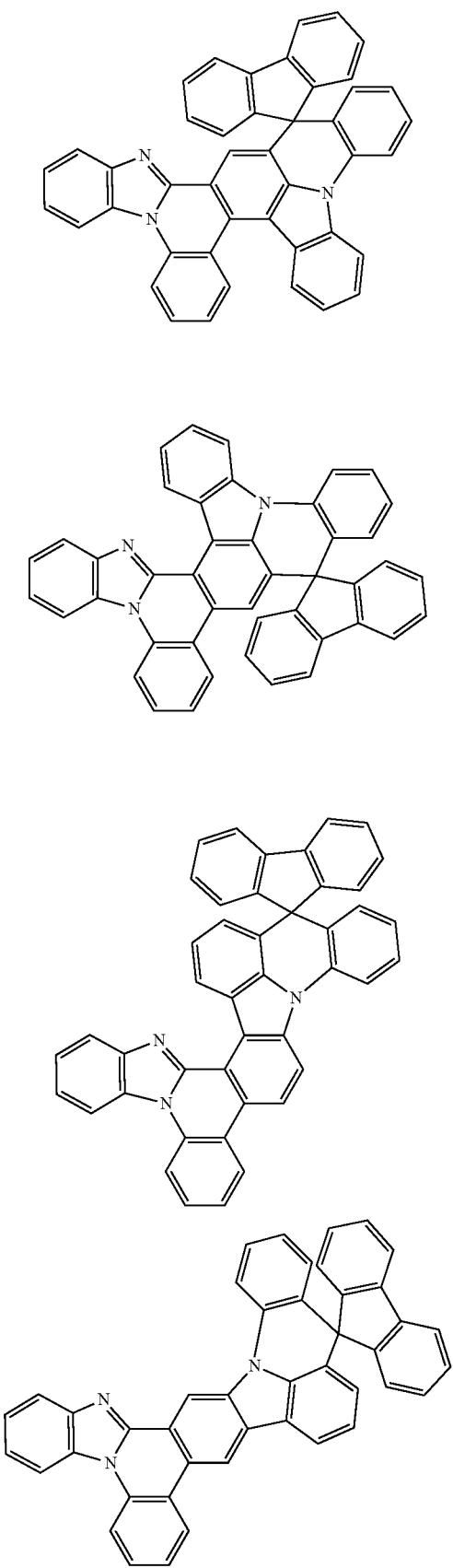
138
-continued
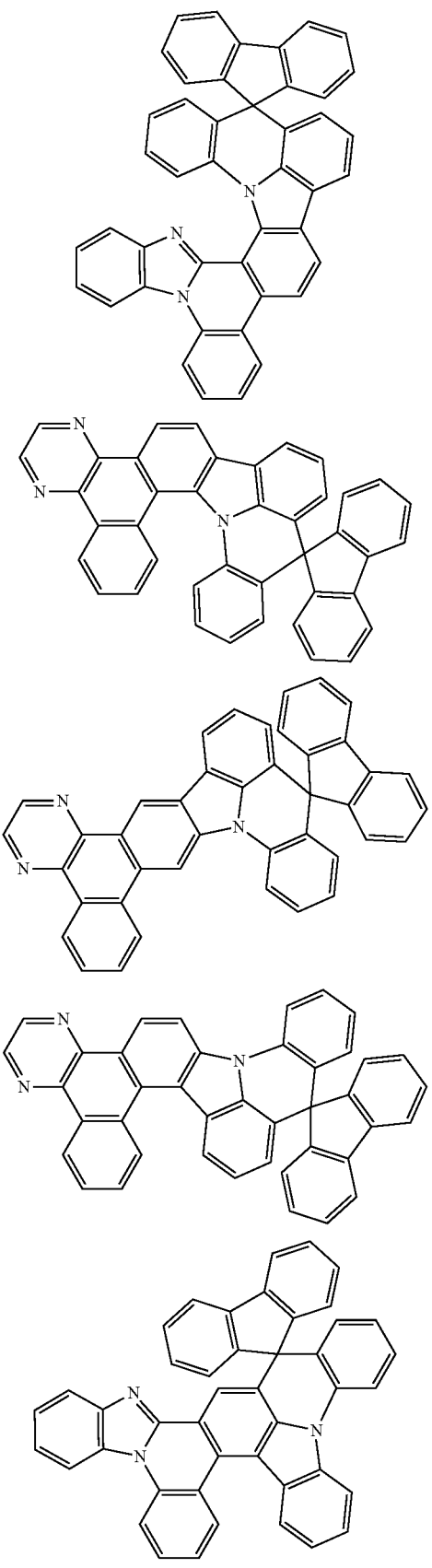

139
-continued
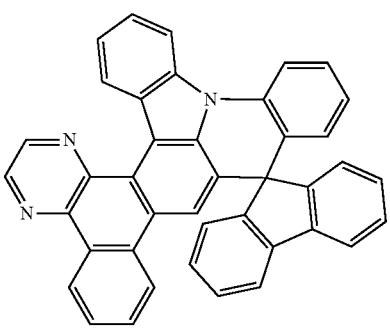
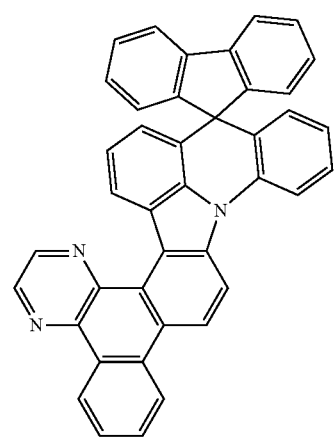
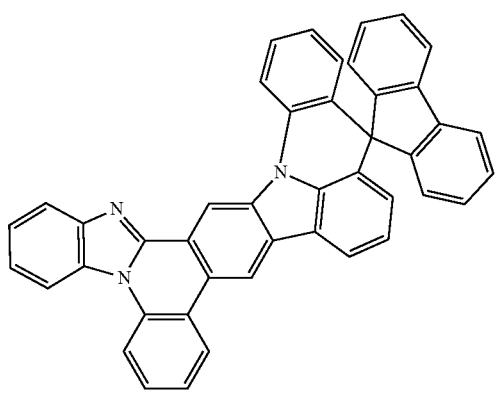
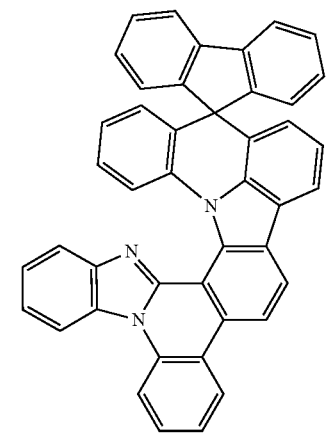
140
-continued
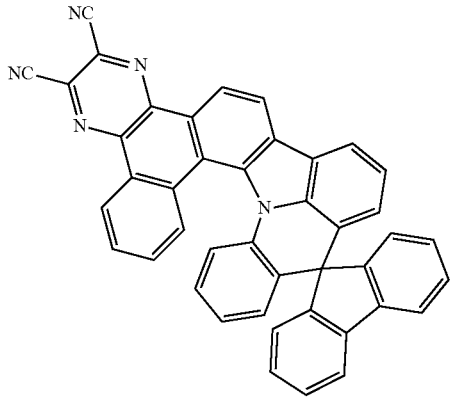
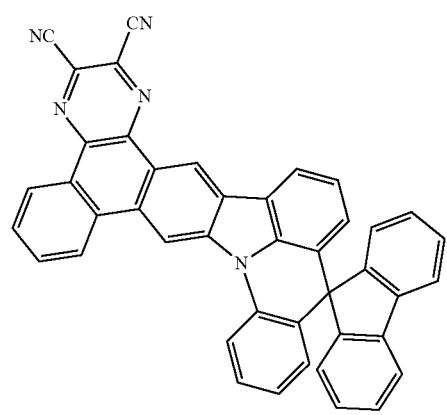
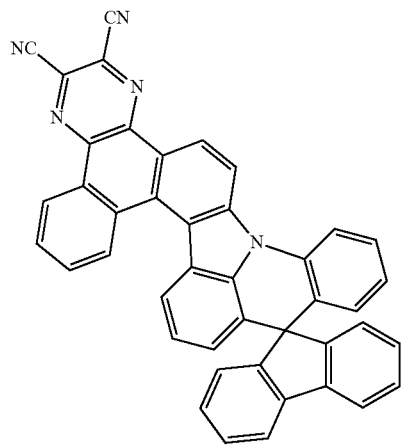
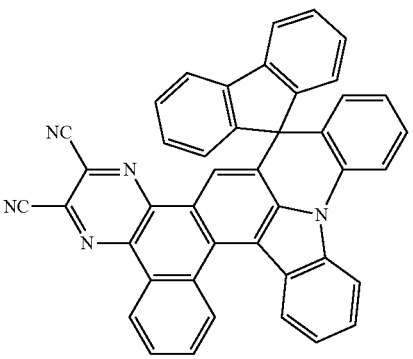

141
-continued
142
-continued
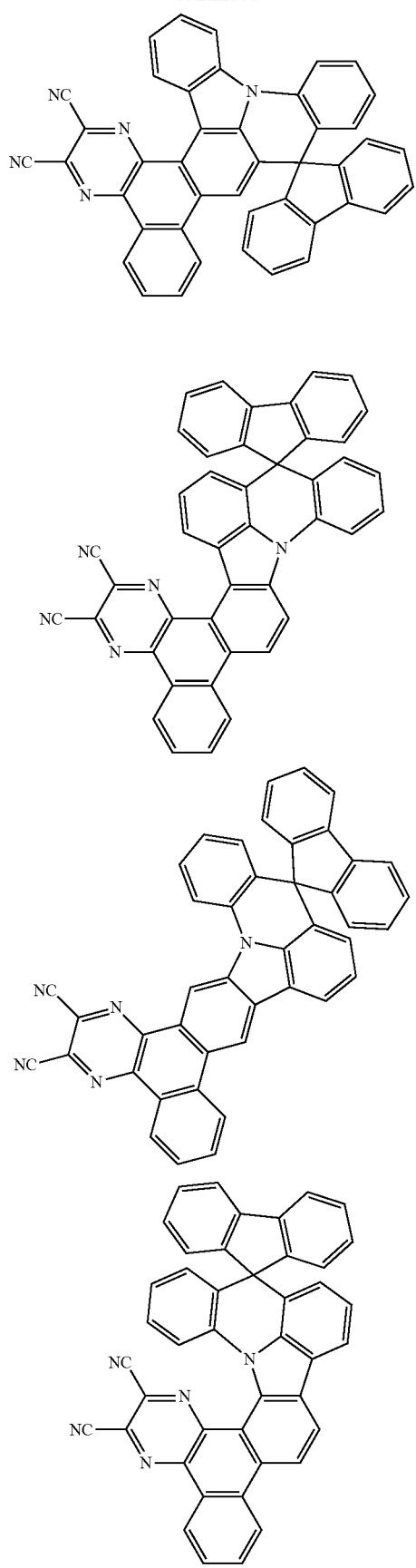
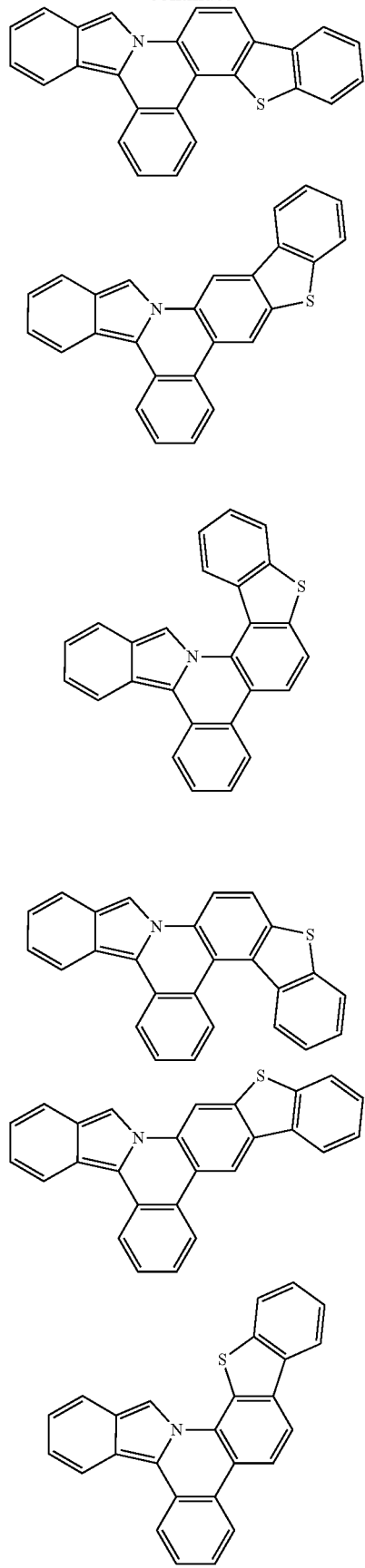

143
-continued
144
-continued
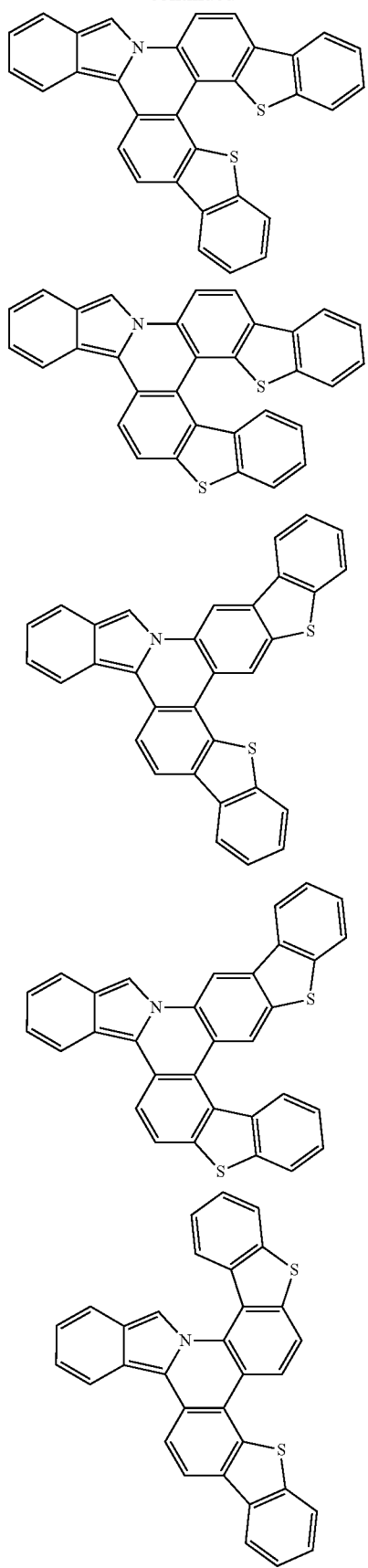
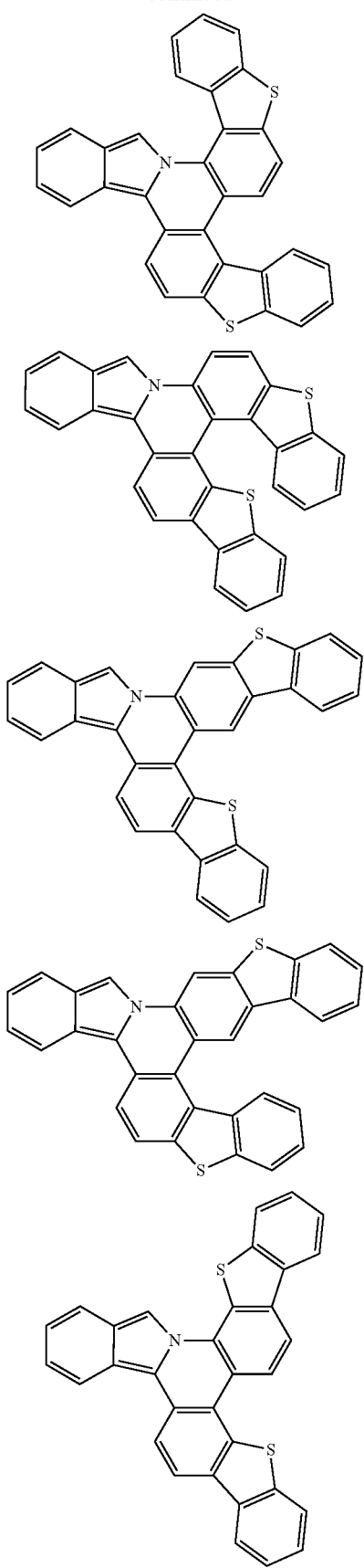

-continued
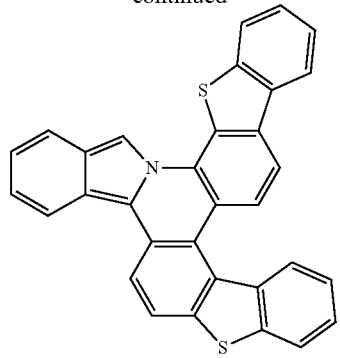
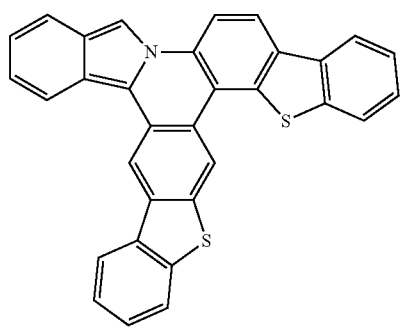
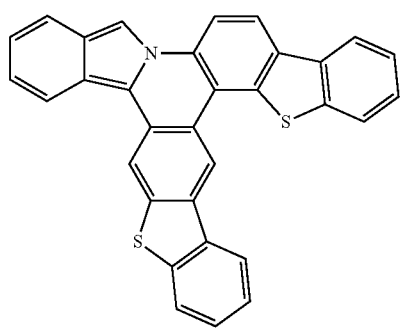
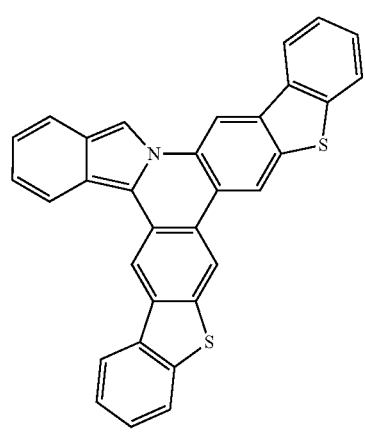
-continued
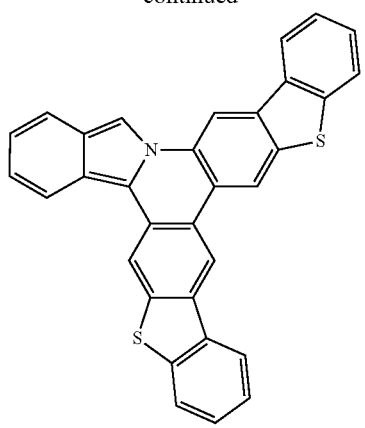
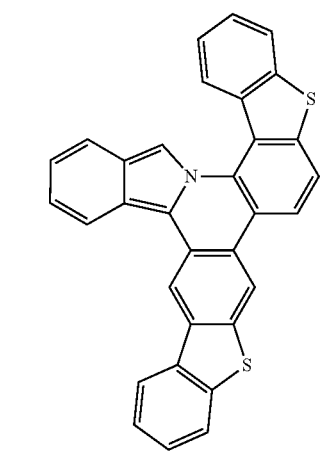
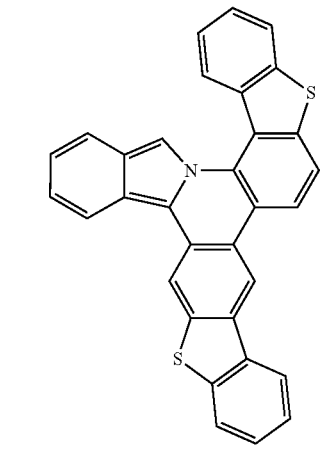
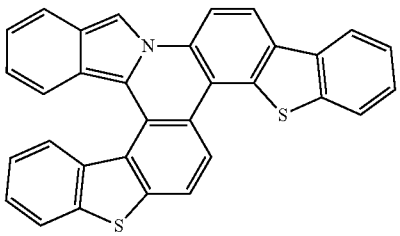

-continued
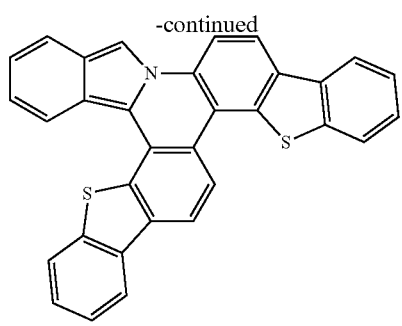
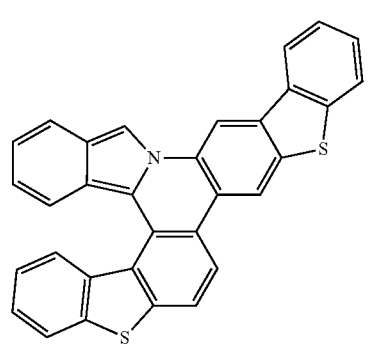
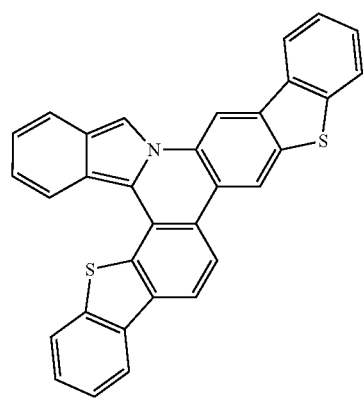
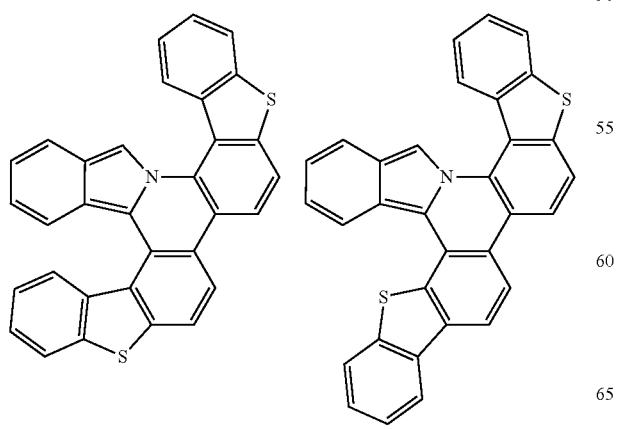
-continued
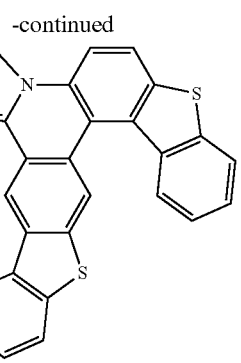
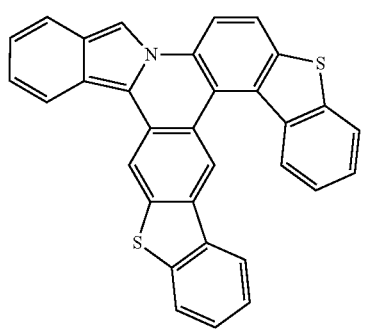
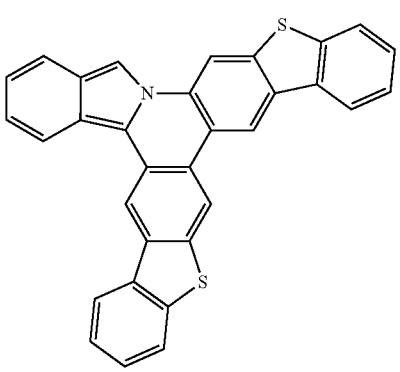
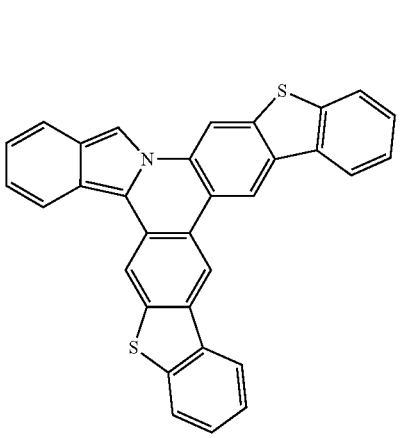

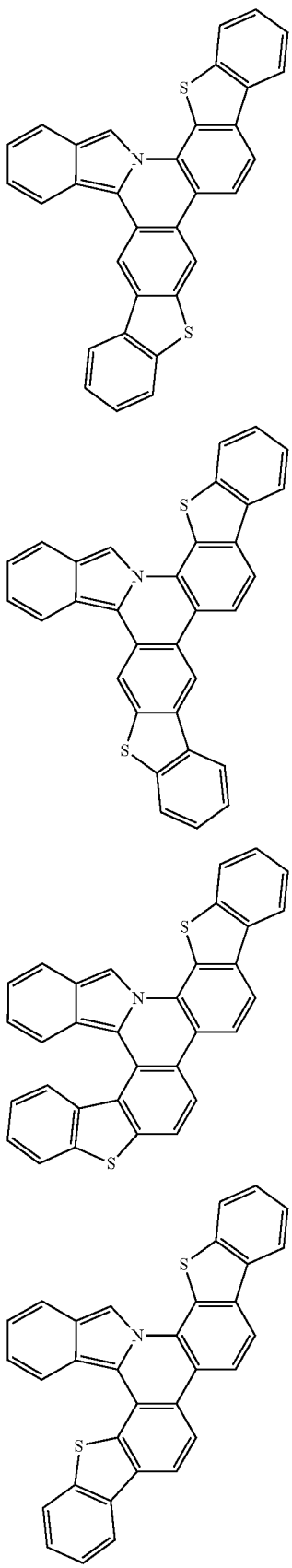
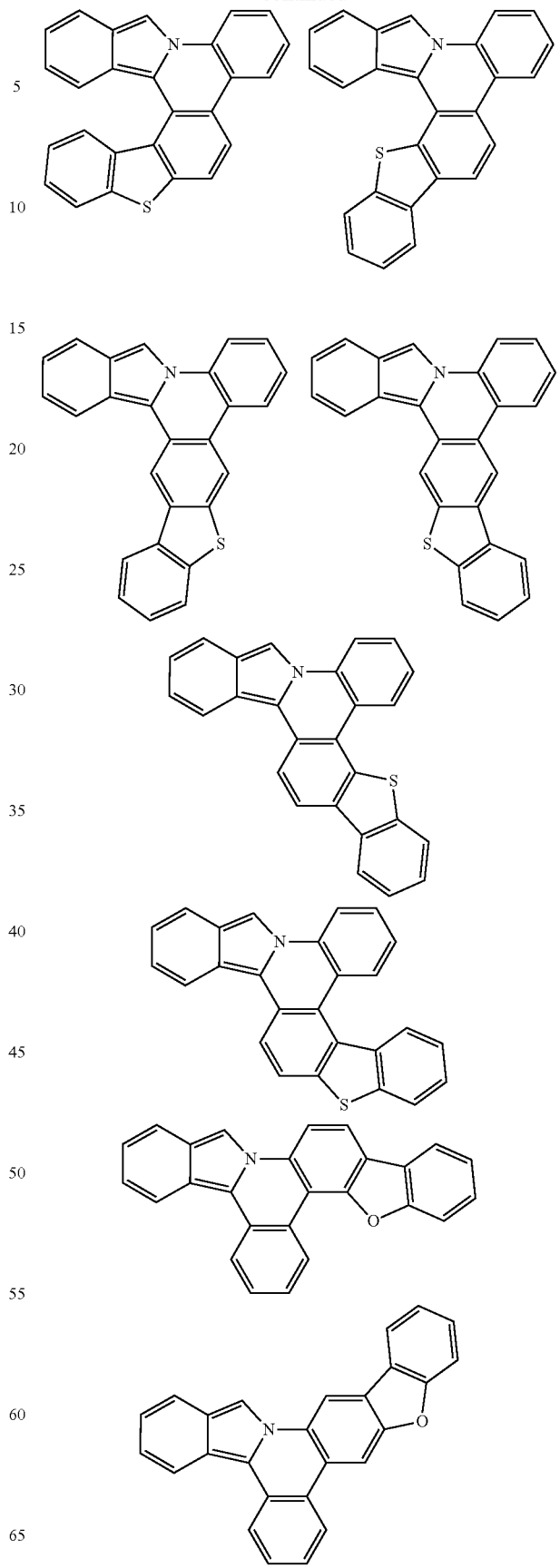

151
-continued
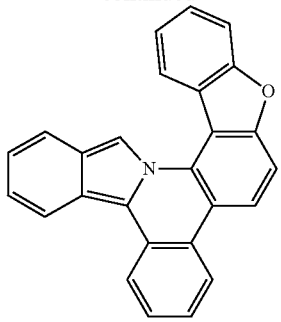
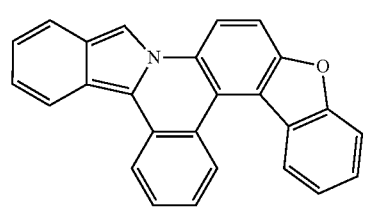
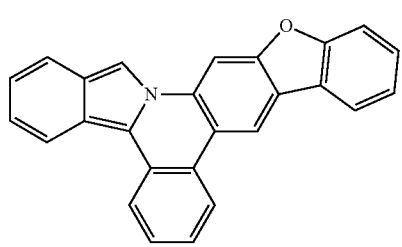
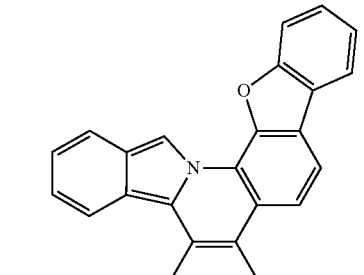
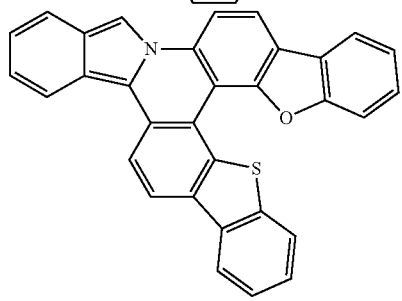
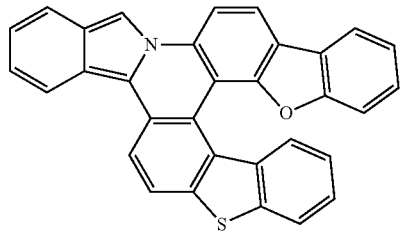
152
-continued
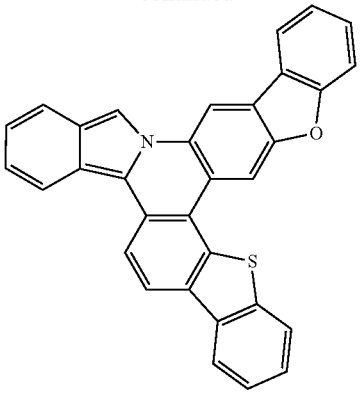
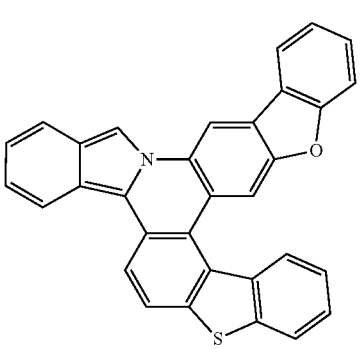
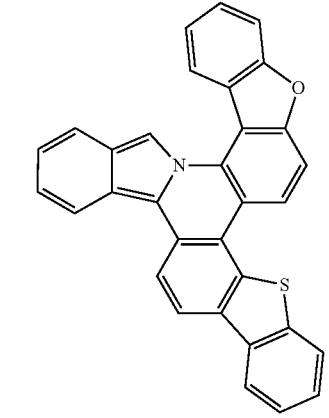
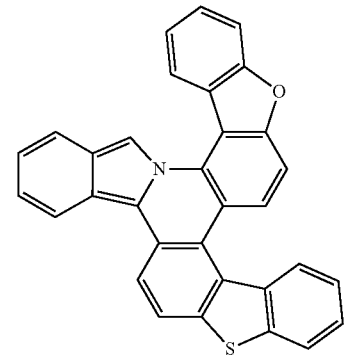

153
-continued
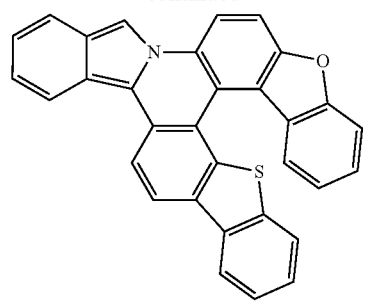
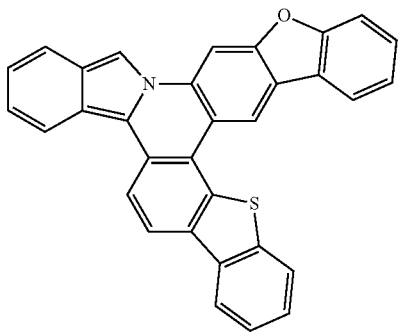
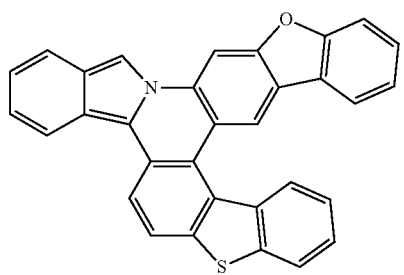
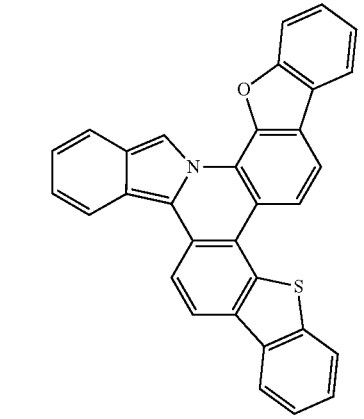
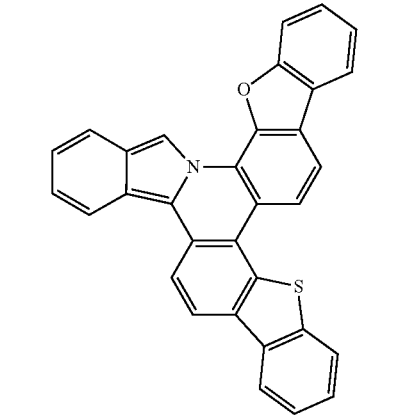
154
-continued
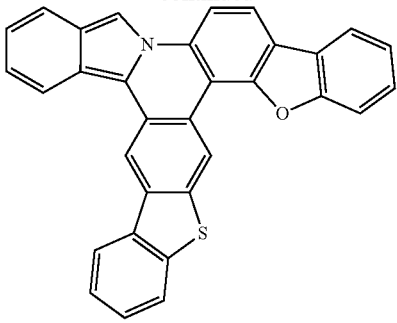
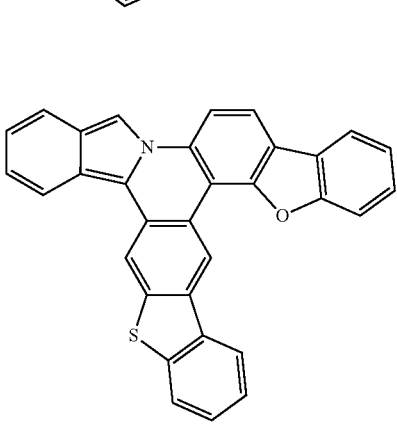
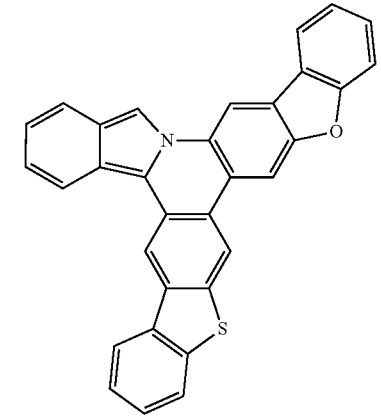
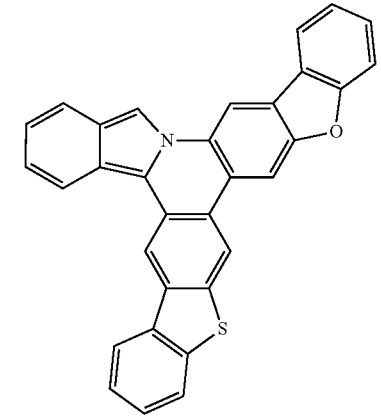

155
-continued
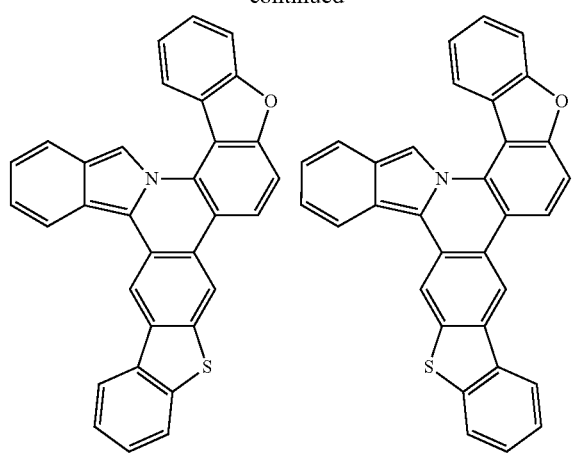
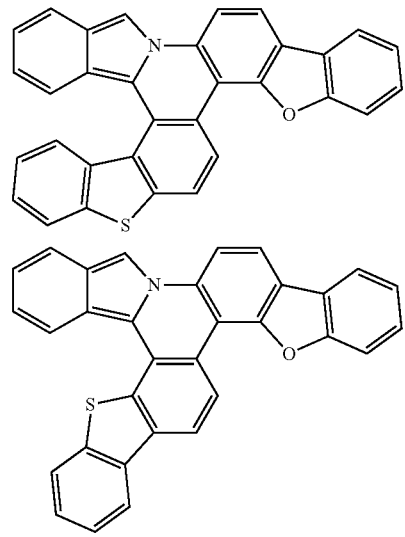
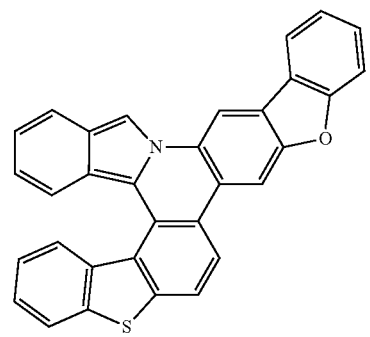
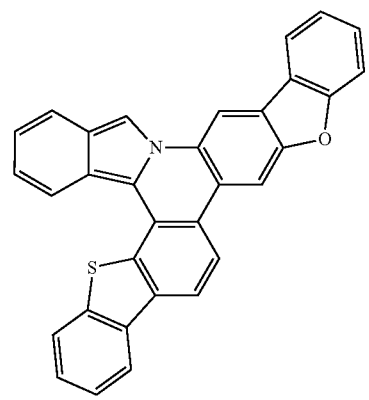
156
-continued
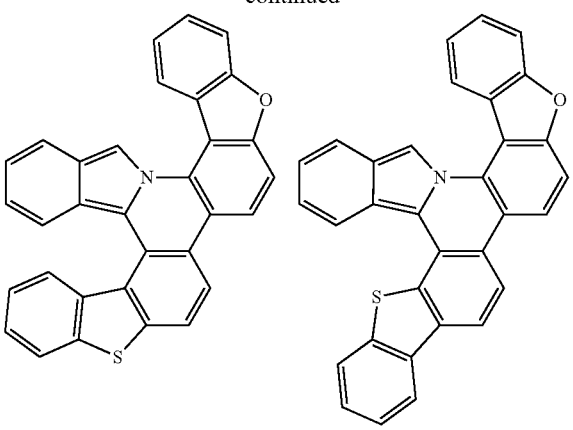
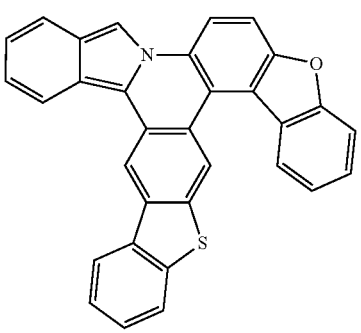
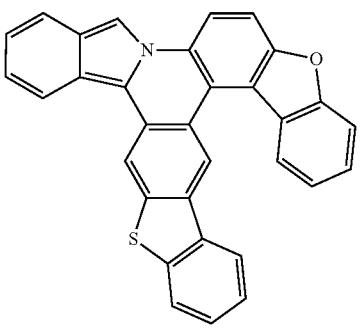
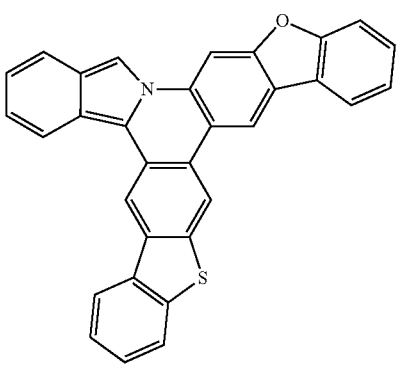

157
-continued
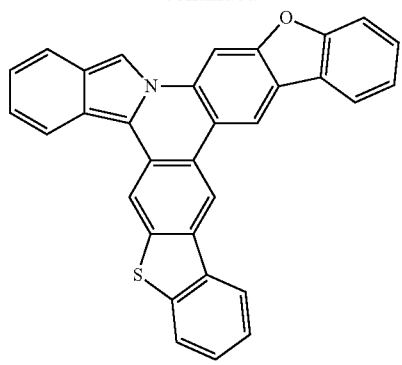
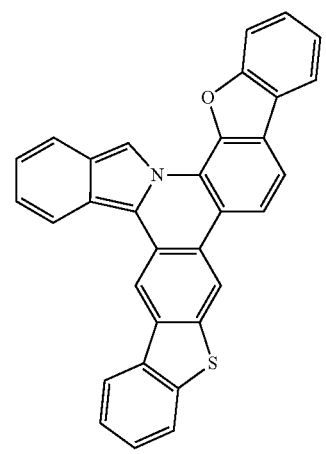
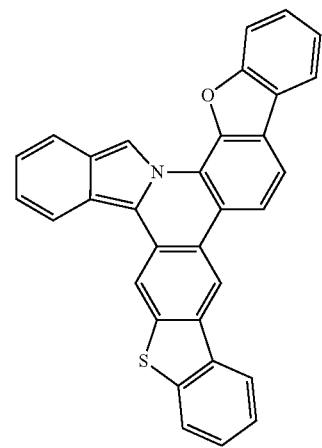
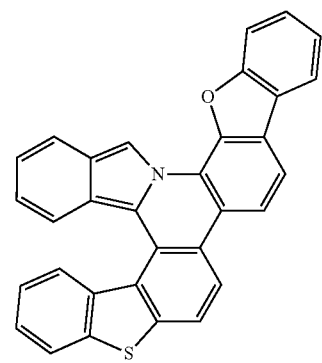
158
-continued
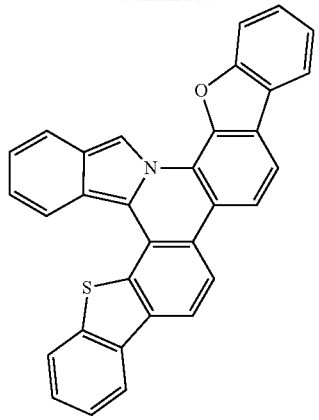
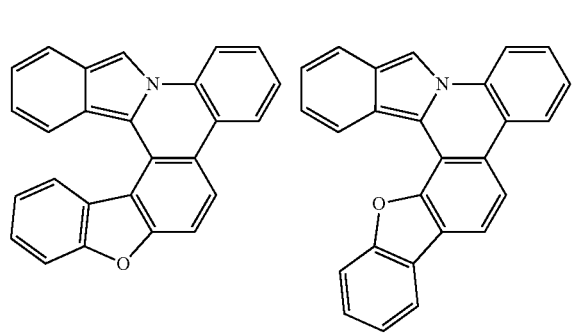
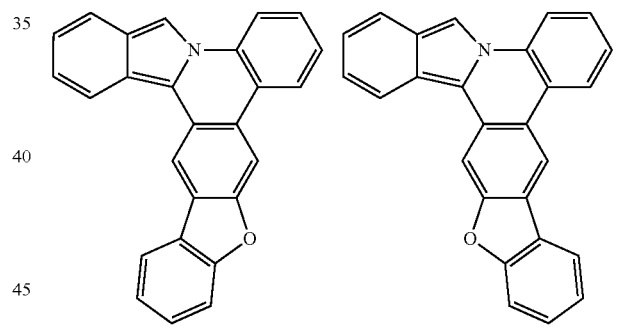
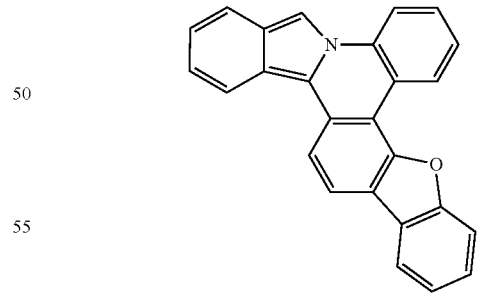
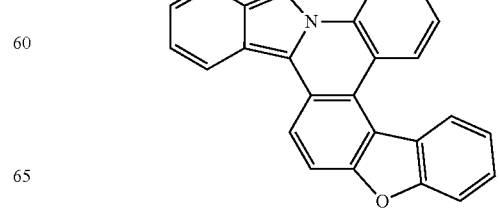

159
-continued
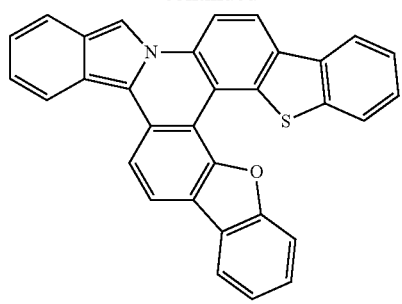
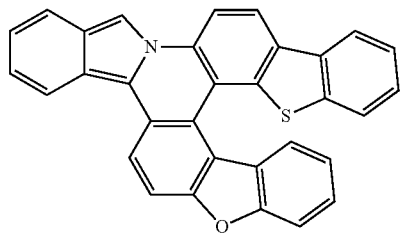
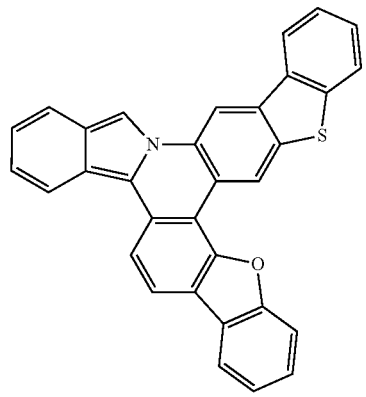
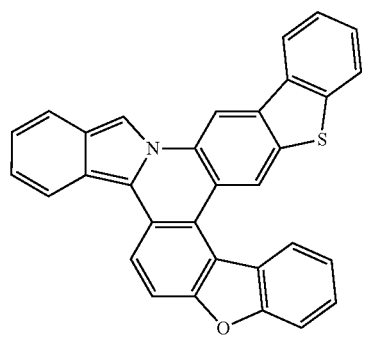
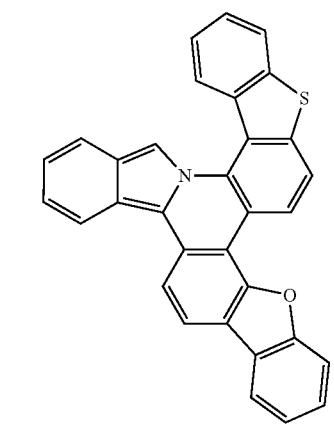
160
-continued
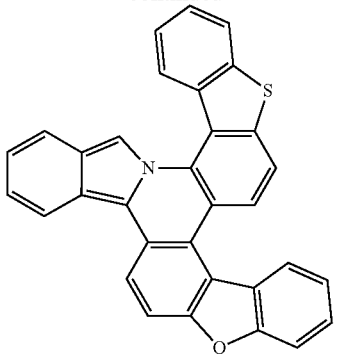
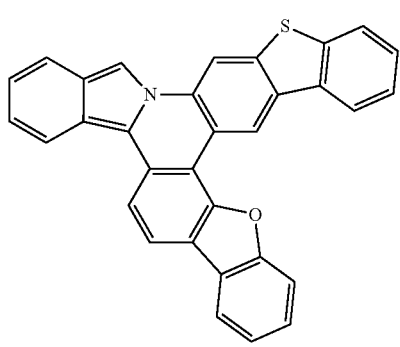
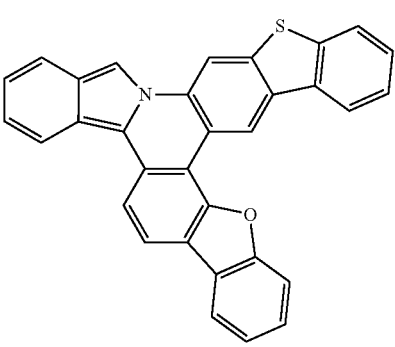
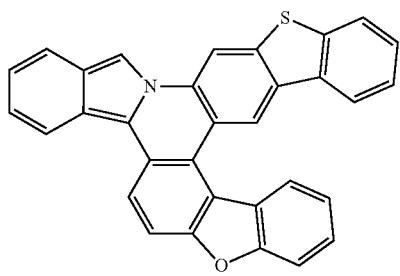
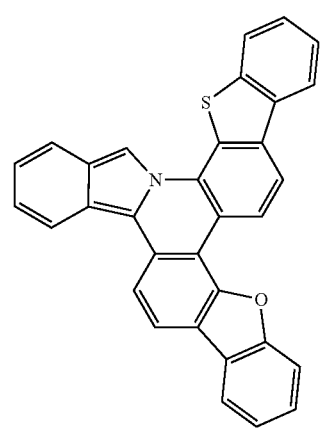

161
-continued
162
-continued
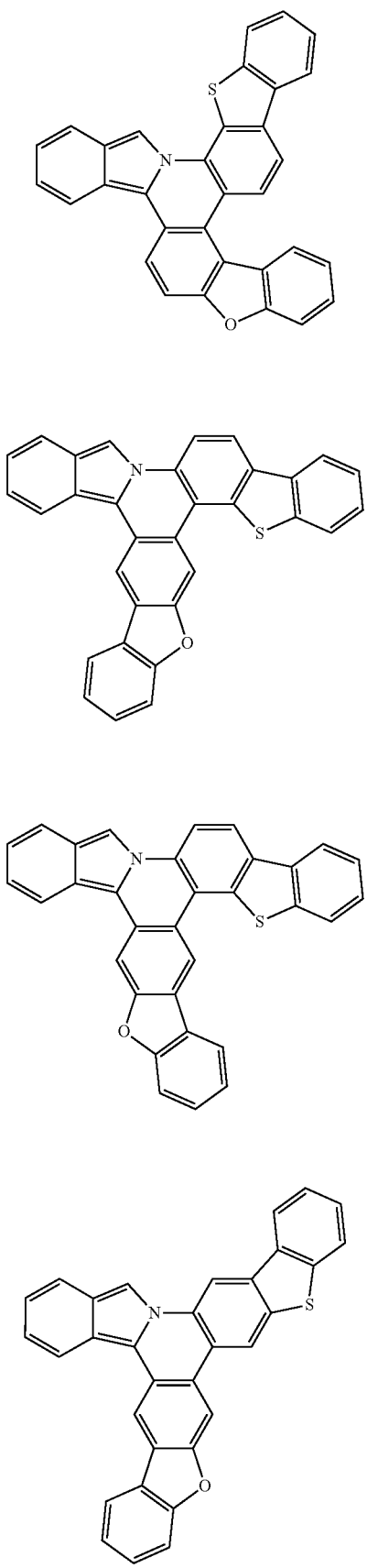
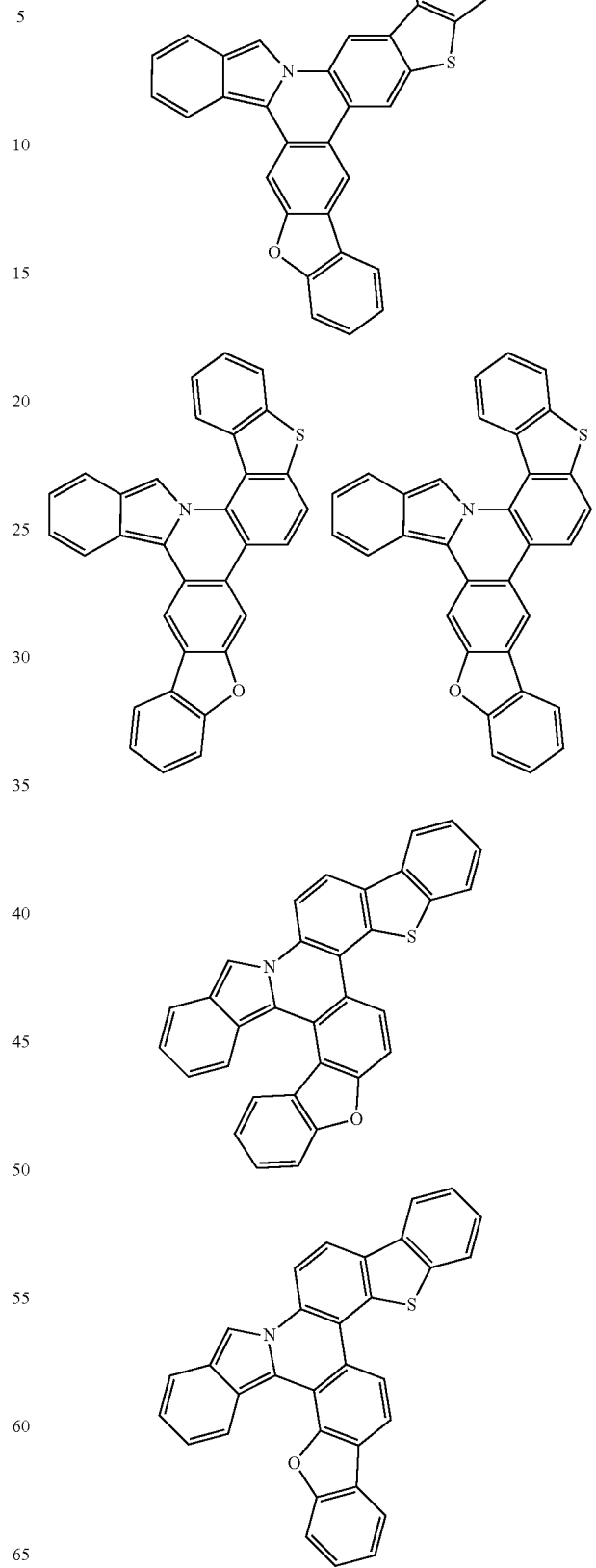

-continued
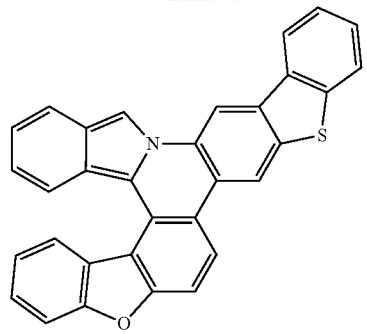
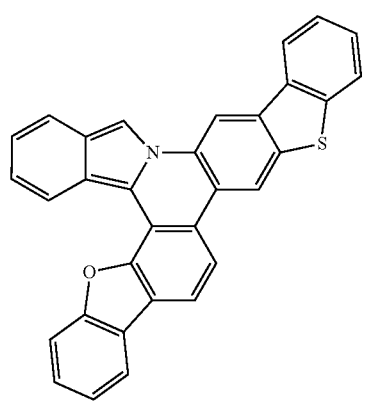
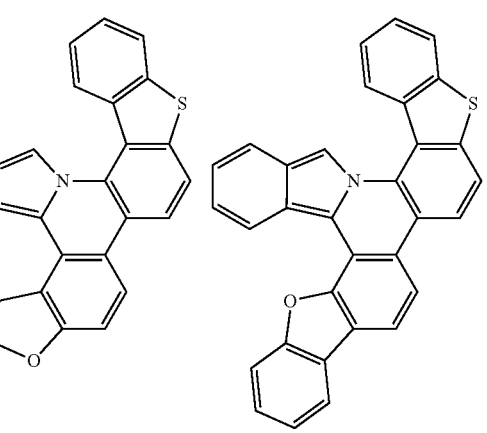
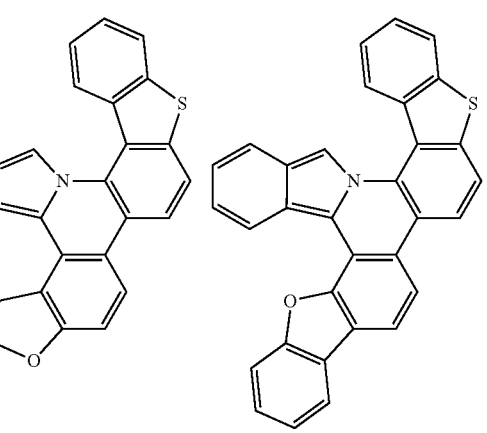
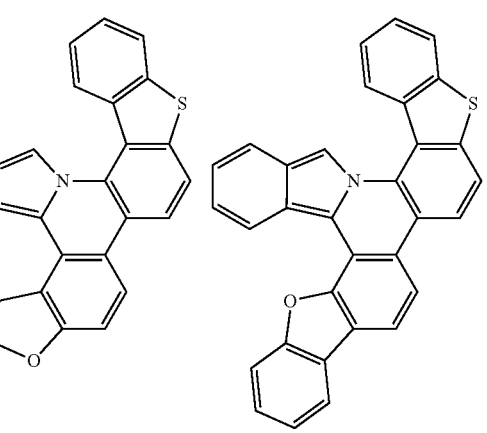
-continued
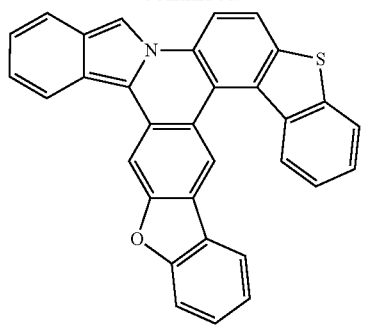
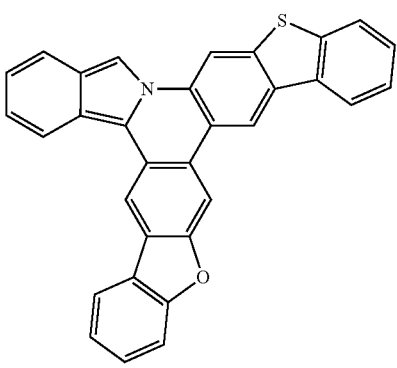
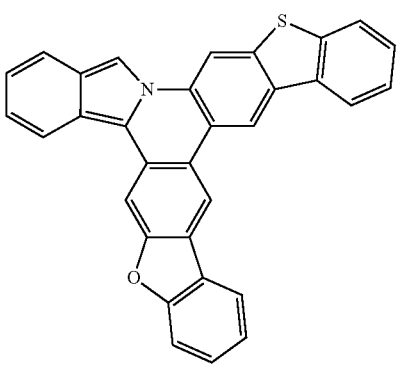
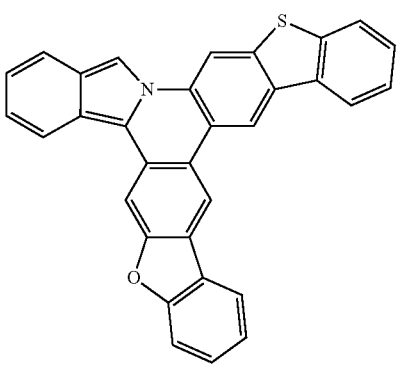

-continued
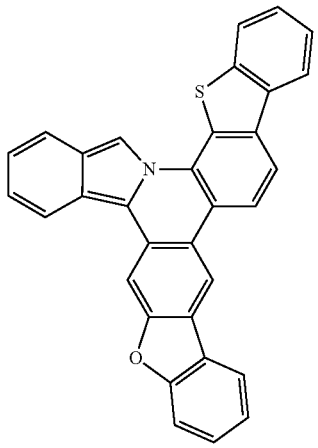
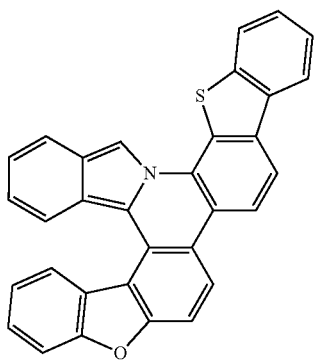
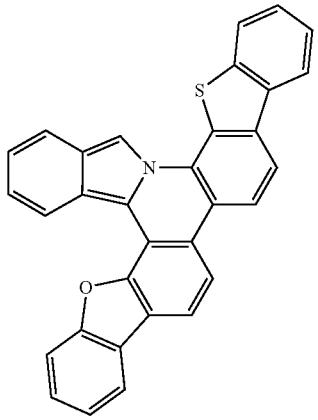
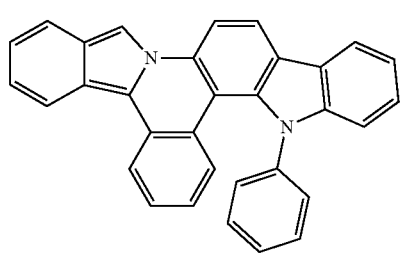
-continued
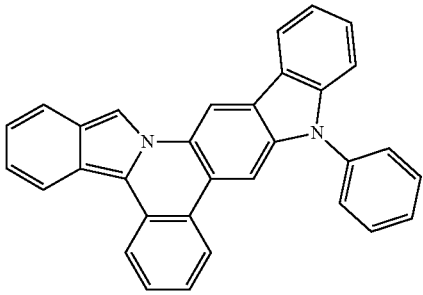
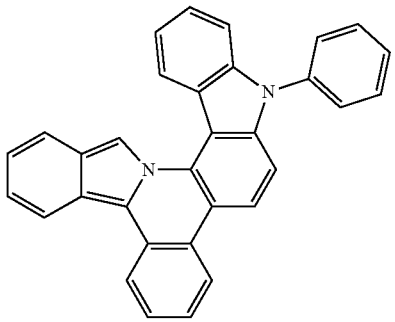
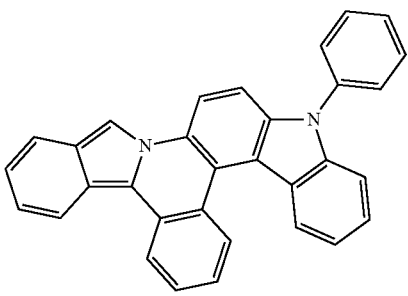
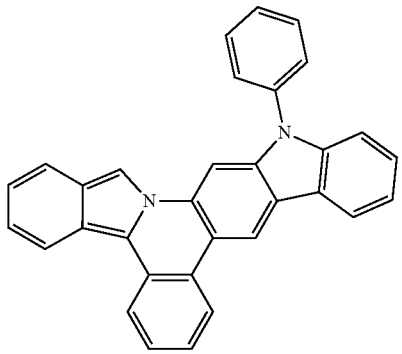
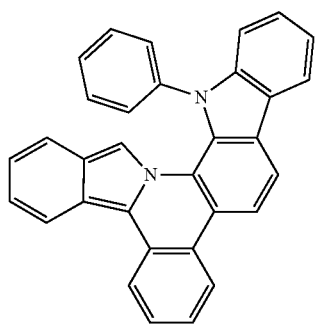

US 10,615,349 B2
167
-continued
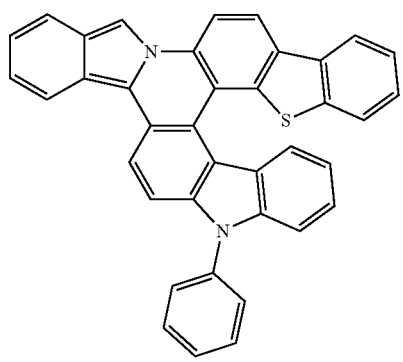
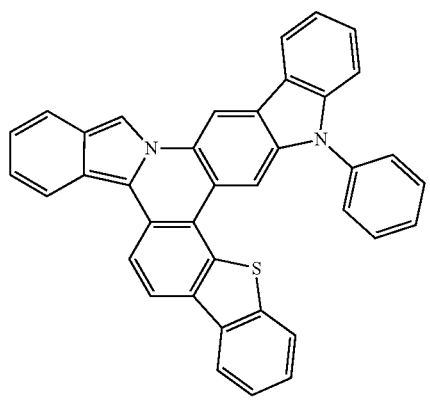
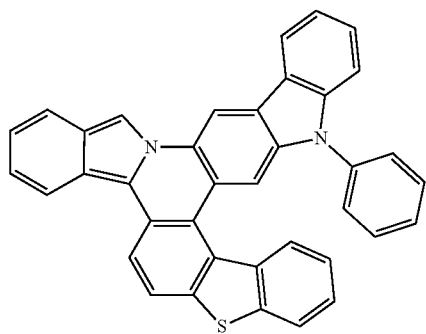
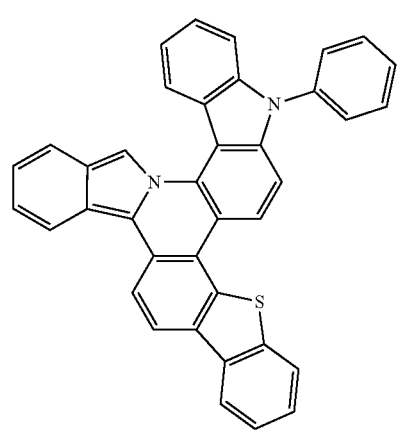
168
-continued
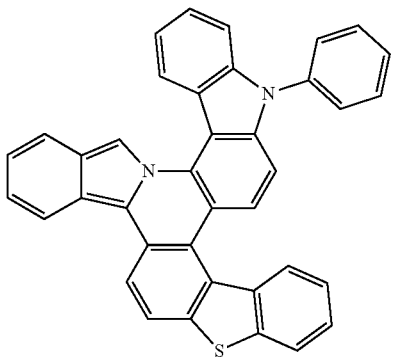
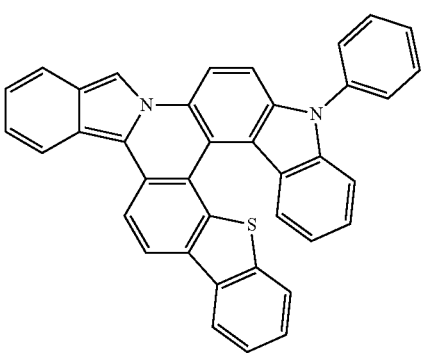
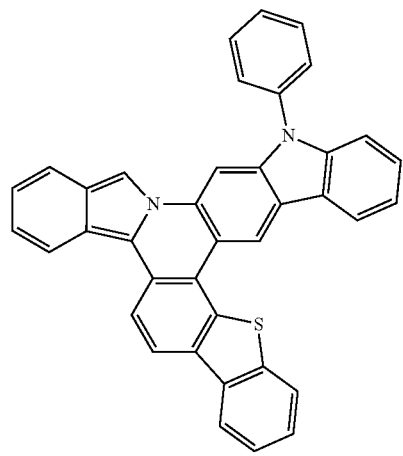
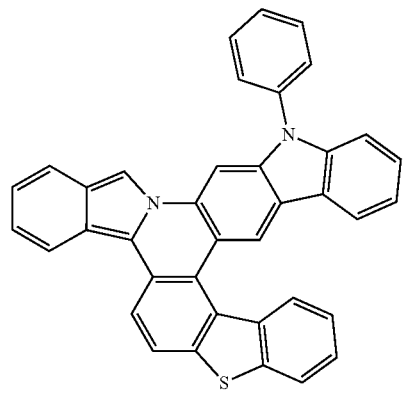

169
-continued
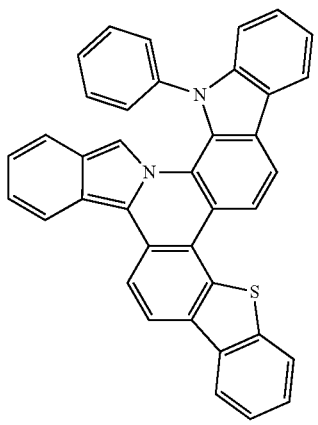
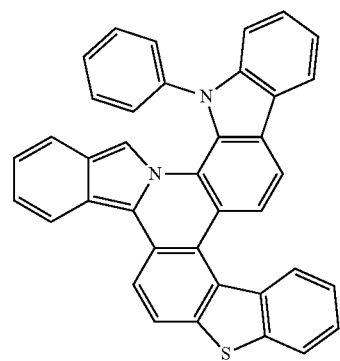
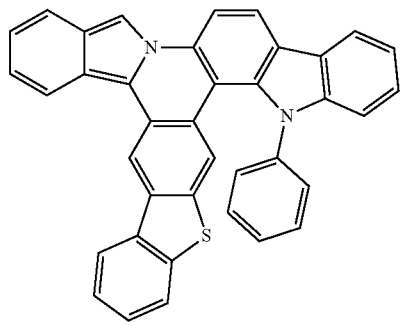
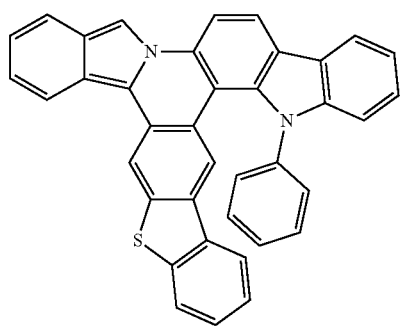
170
-continued
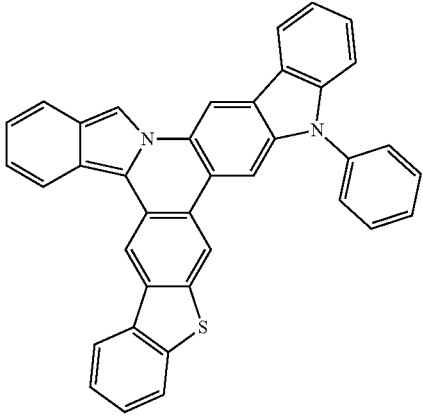
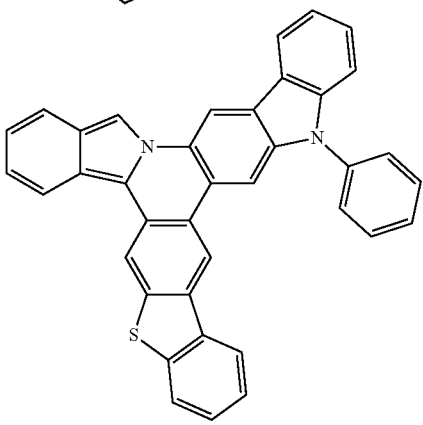
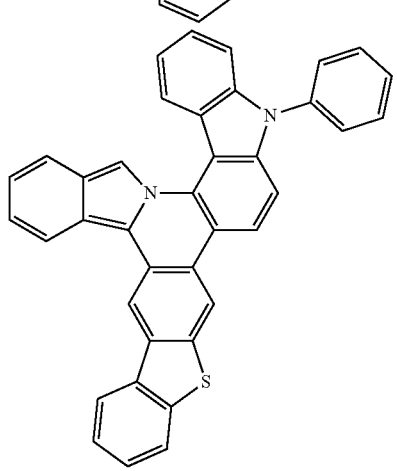
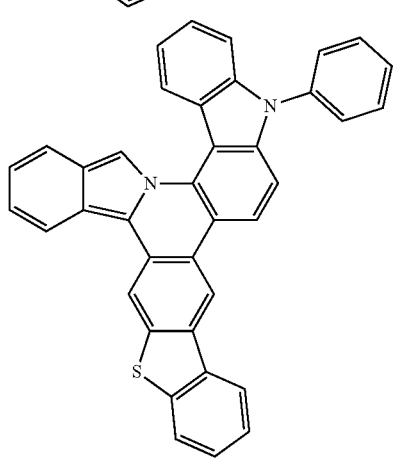

-continued
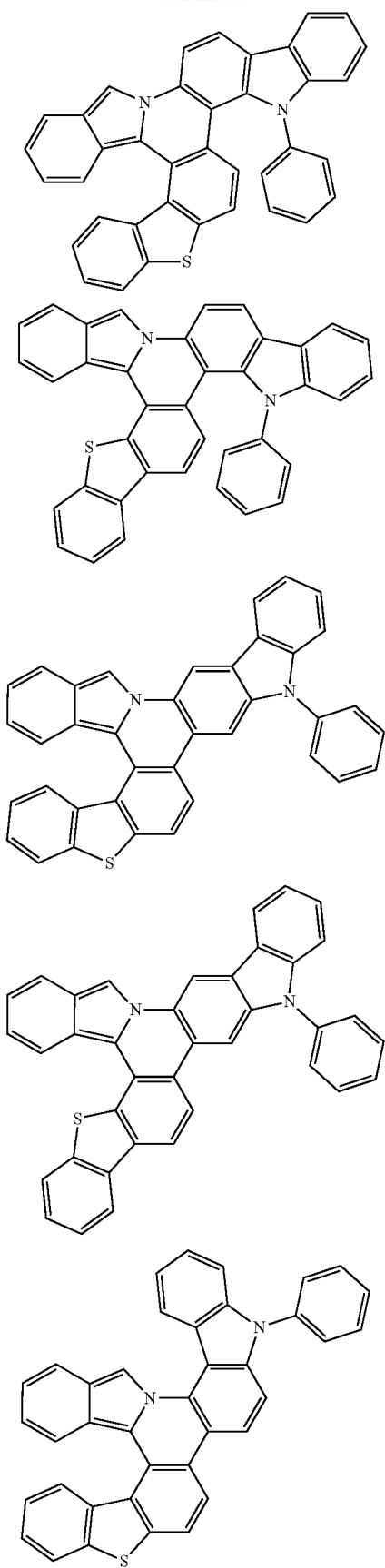
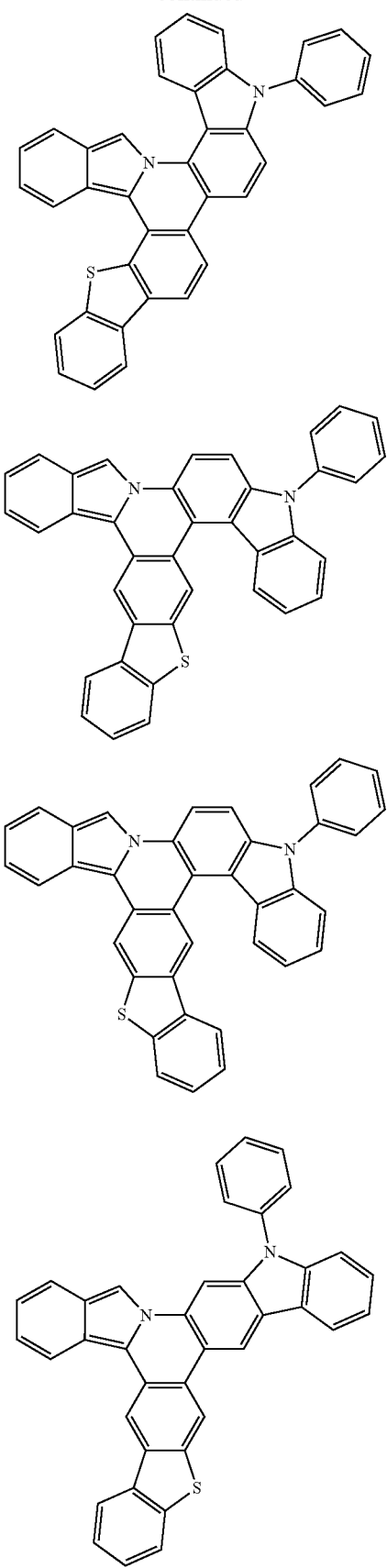

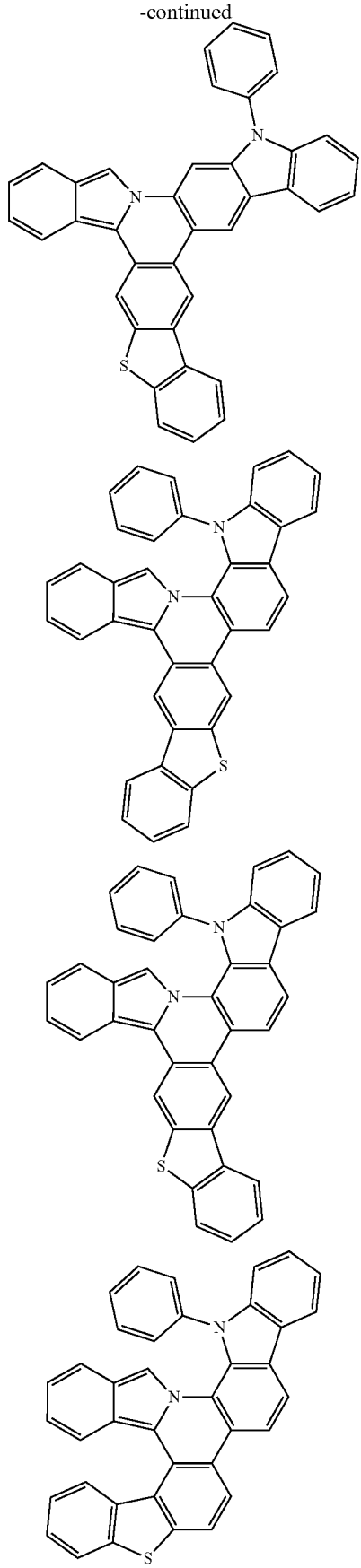
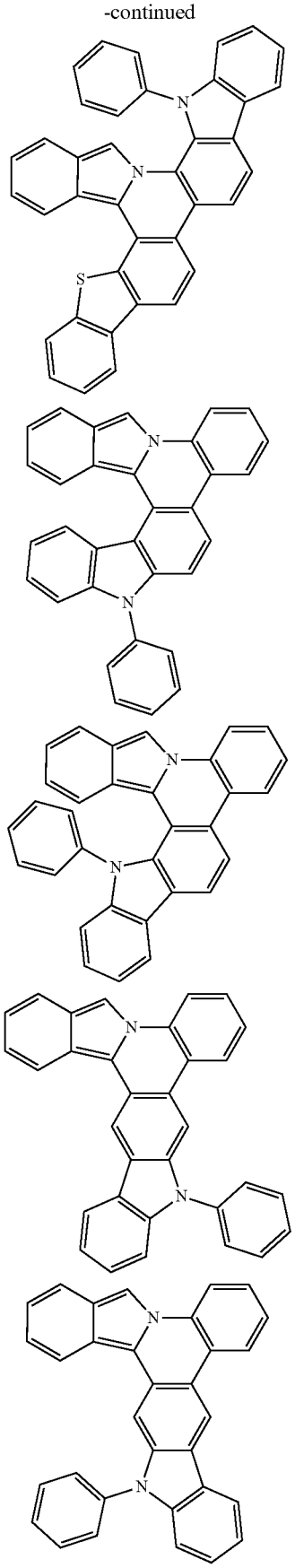

-continued
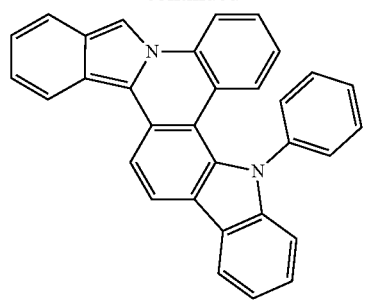
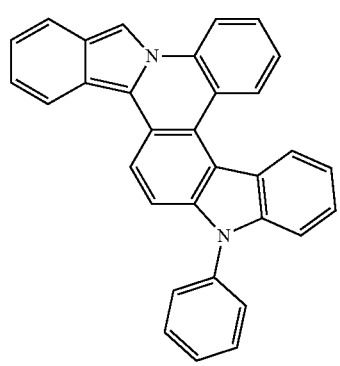
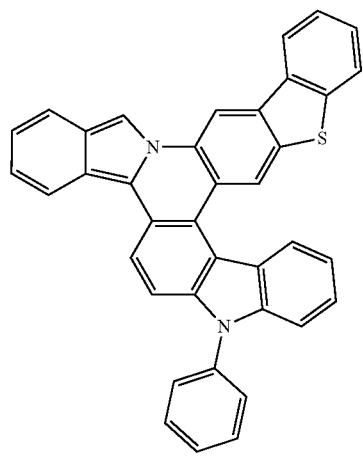
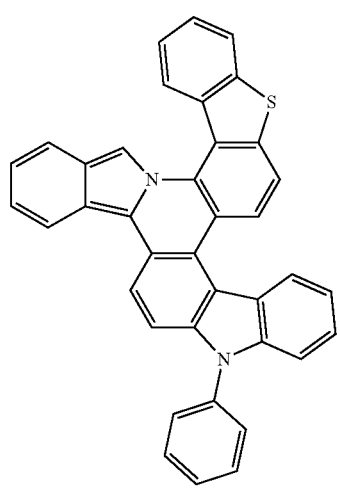
-continued
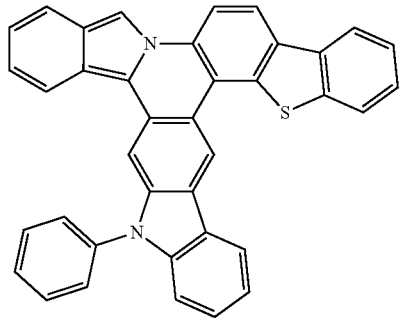
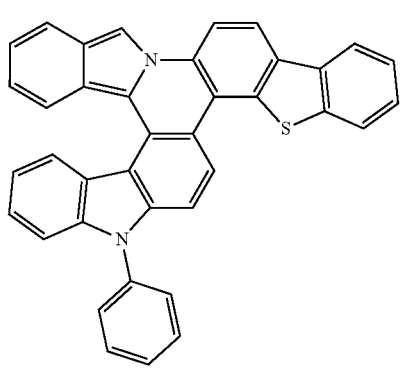
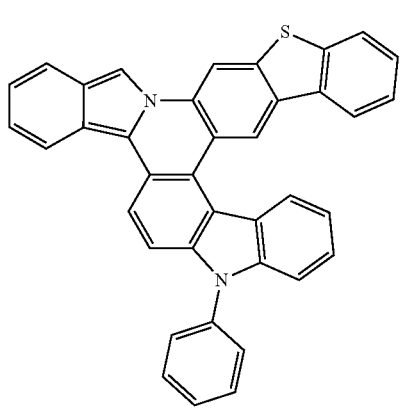
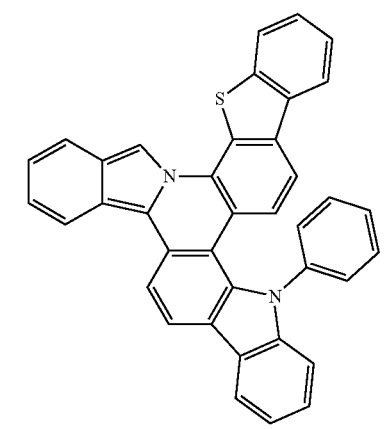

177
-continued
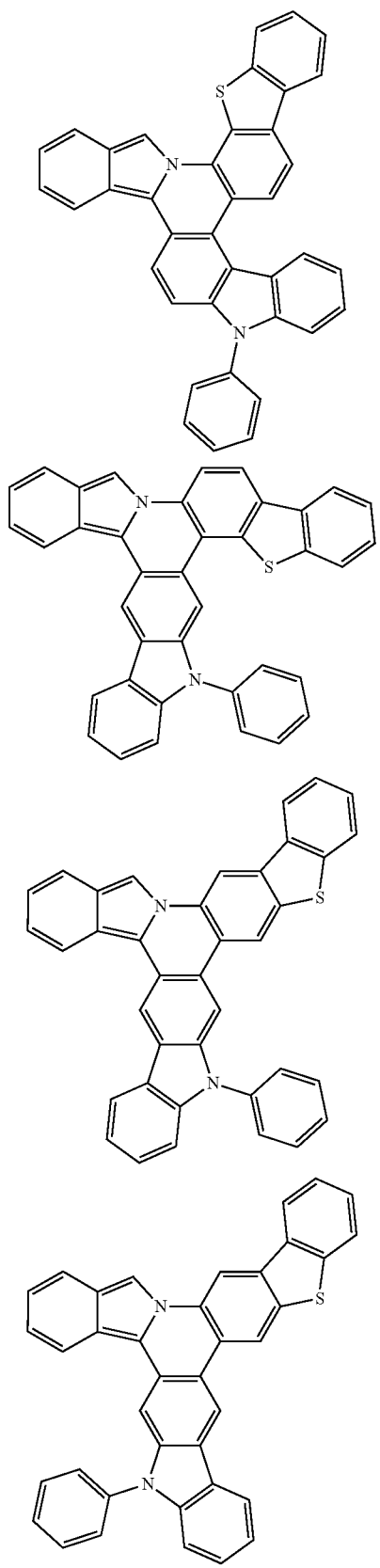
178
-continued
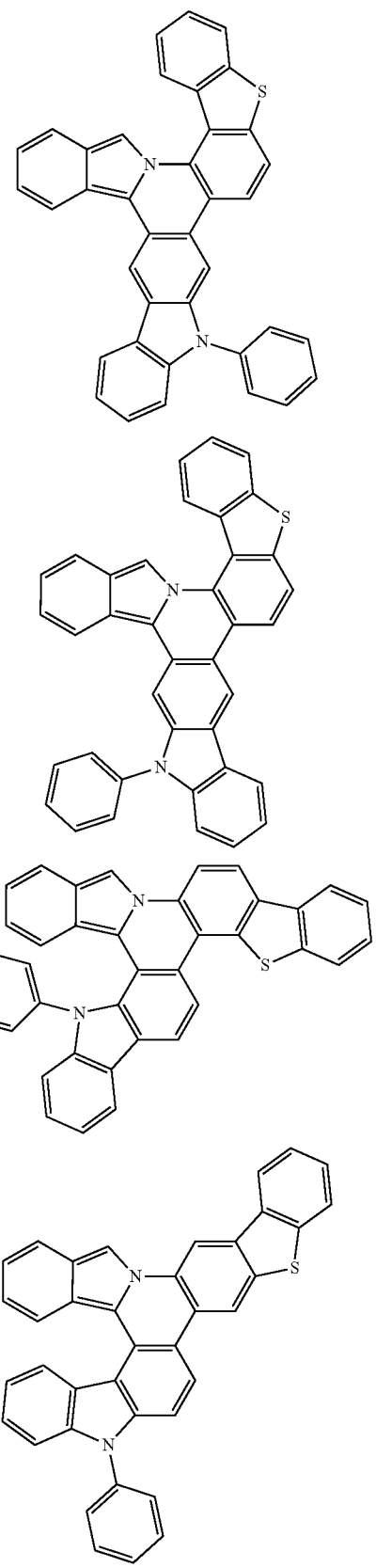

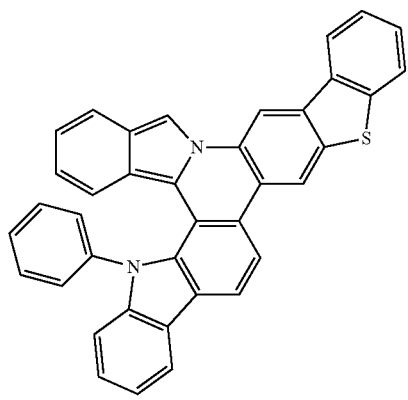
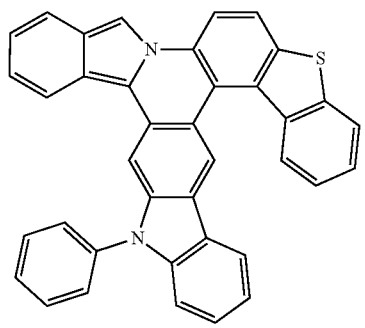
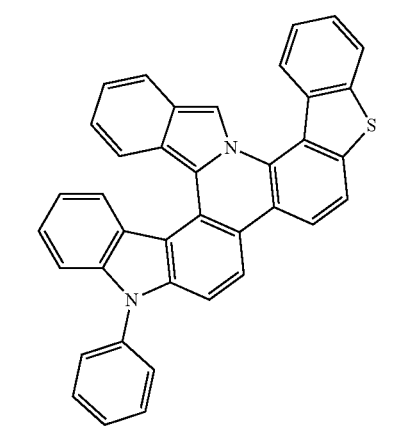
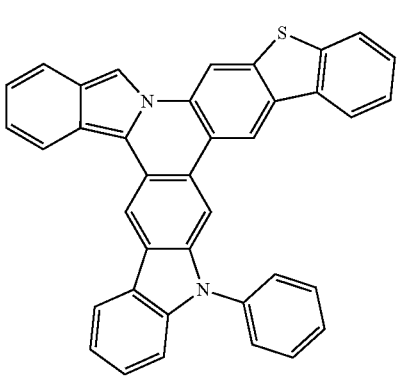
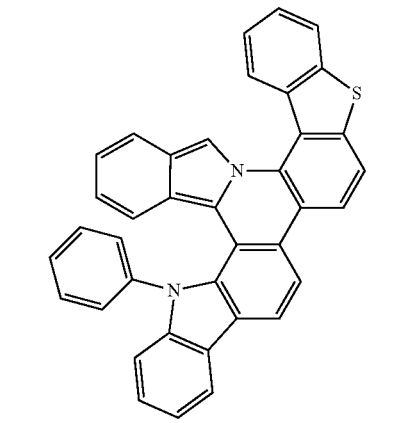
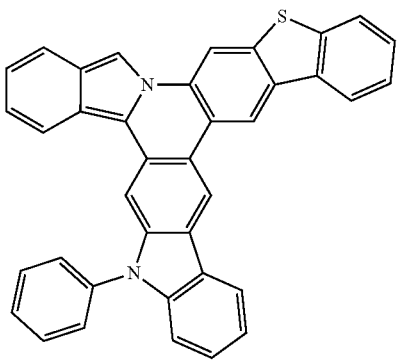
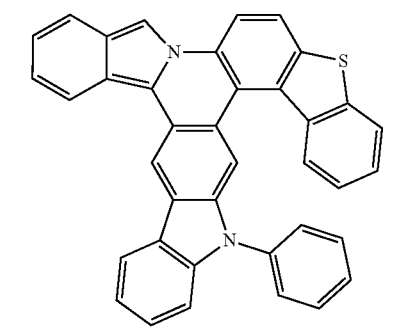
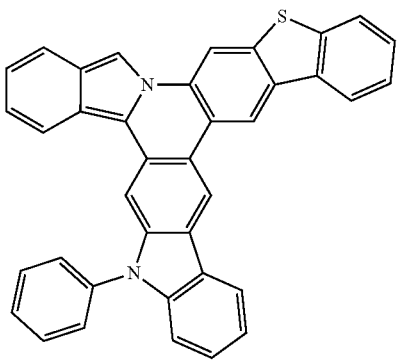

-continued

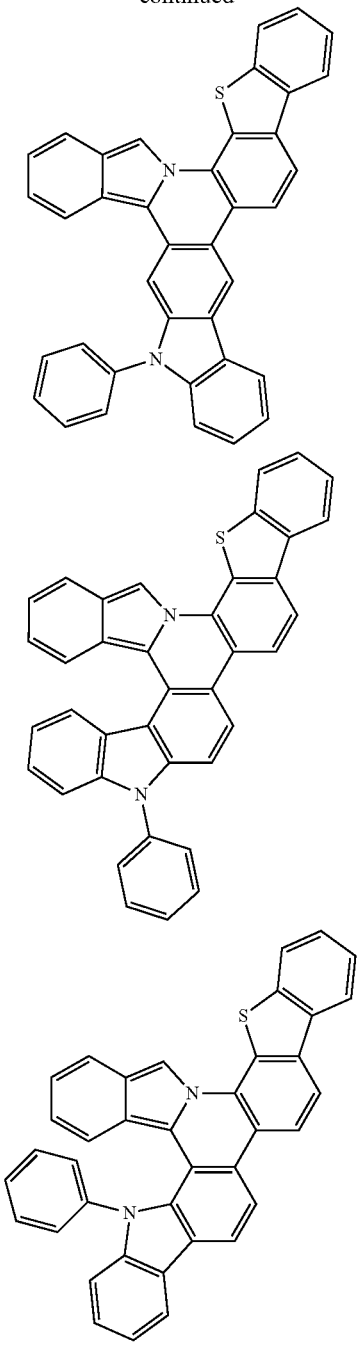

As referred to herein, a linking atom or group connects two atoms such as, for example, an N atom and a C atom. A linking atom or group is in one aspect disclosed as $L^1$, $L^2$, $L^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties. The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —$N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula —(A$^1$O(O)C-A$^2$-C(O)O)$_a$— or —(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an interger from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula —(A$^1$O-A$^2$O)—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" or "halo" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "cyanide" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group." the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

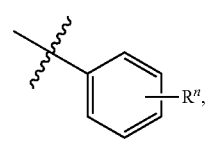

which is understood to be equivalent to a formula:

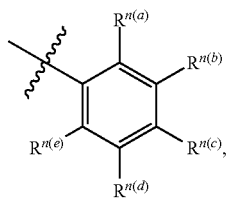

wherein n is typically an integer. That is, R″ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. In a case where there is a single R″ (e.g., only $R^{n(a)}$, R″ is referred to as a "single substituent." In a case where there are two or more R″ (e.g., at least $R^{n(a)}$ and $R^{n(b)}$) R″ is referred to as a "multiple substituents."

Several references to R. $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

The compounds disclosed herein are suited for use in a wide variety of devices, including, for example, organic light emitting diodes (OLEDs) for full color displays and lighting applications.

Also disclosed herein are compositions including one or more compounds disclosed herein. The present disclosure provides light emitting device that include one or more compositions described herein. The present disclosure also provides a photovoltaic device comprising one or more complexes or compositions described herein. Further, the present disclosure also provides a luminescent display device comprising one or more compounds described herein.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Some of these synthetic examples have been performed. Others are based on an understanding of related synthetic procedures and are predictive in nature. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

Example 1

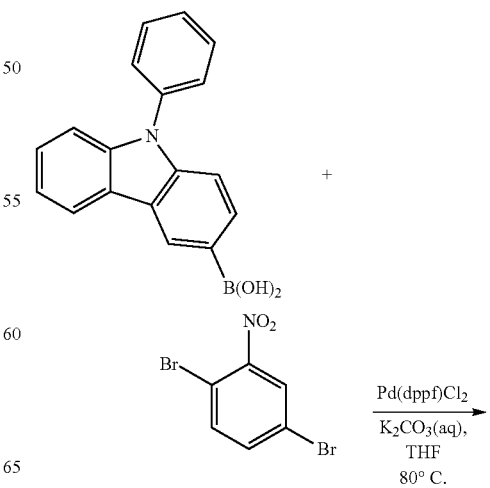

189
-continued

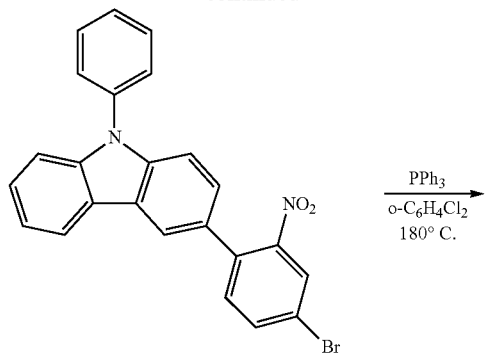

190
-continued

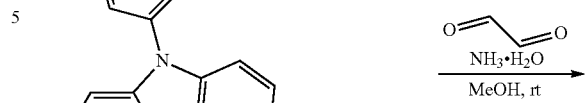

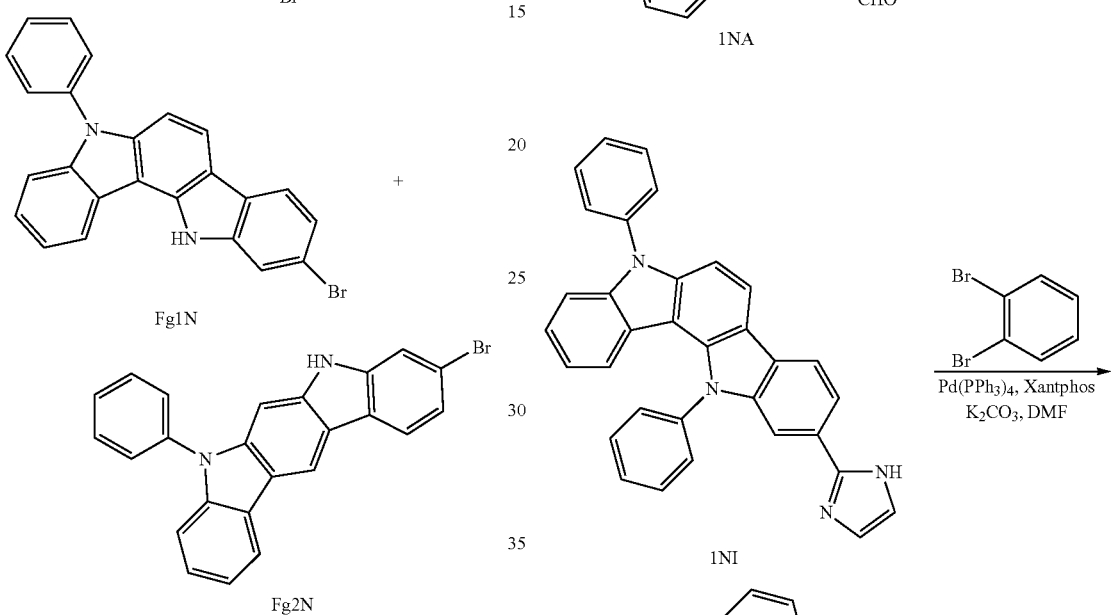

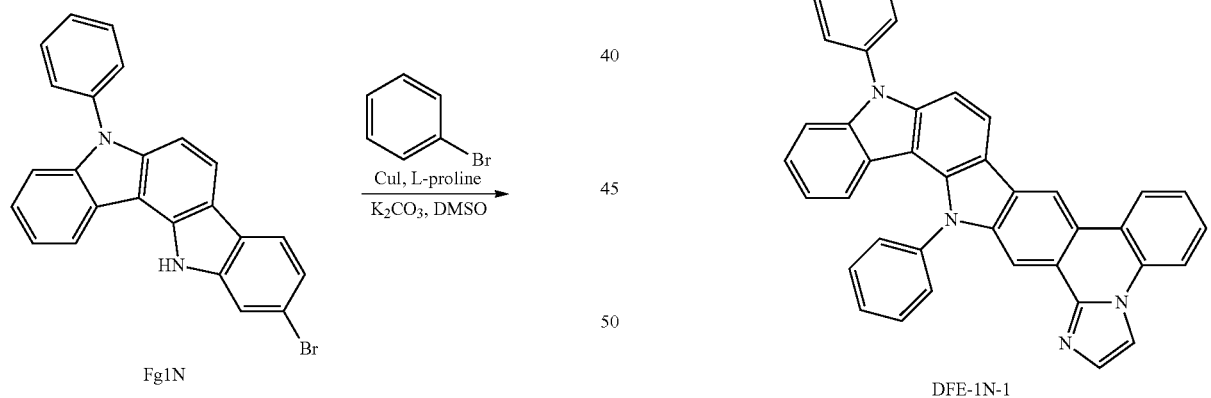

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 1NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1N-1 in 61% yield.

Example 2

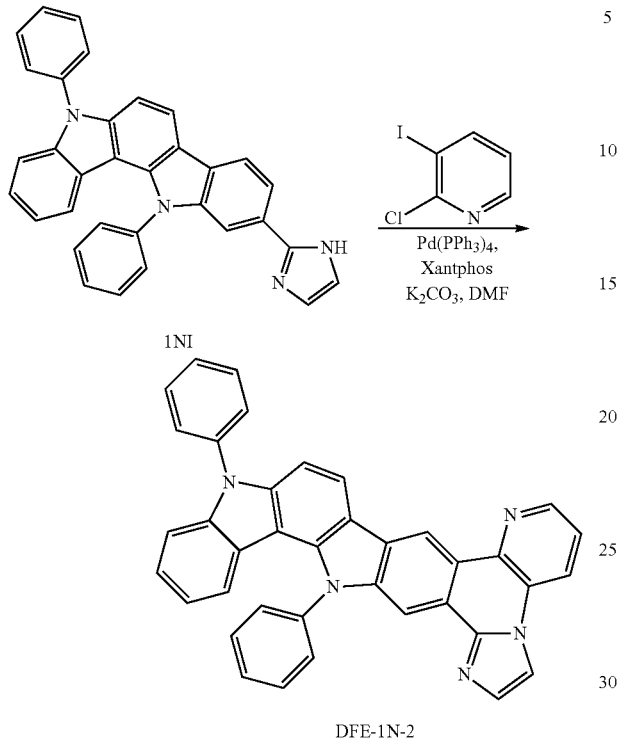

DFE-1N-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 1NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1N-2 in 53% yield.

Example 3

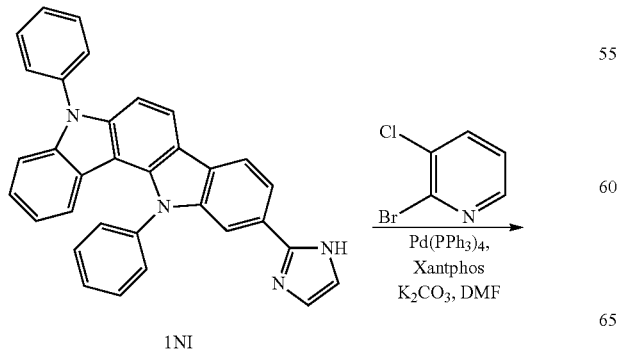

1NI

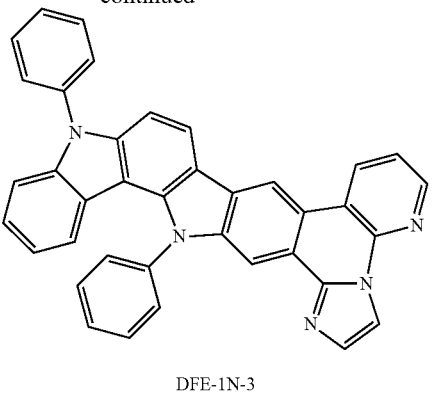

DFE-1N-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 1NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1N-3 in 22% yield.

Example 4

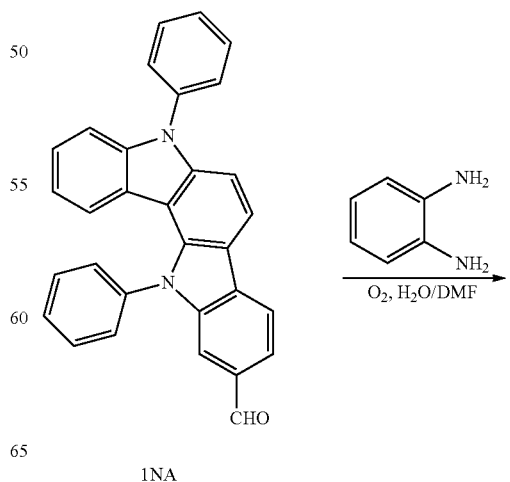

1NA

-continued

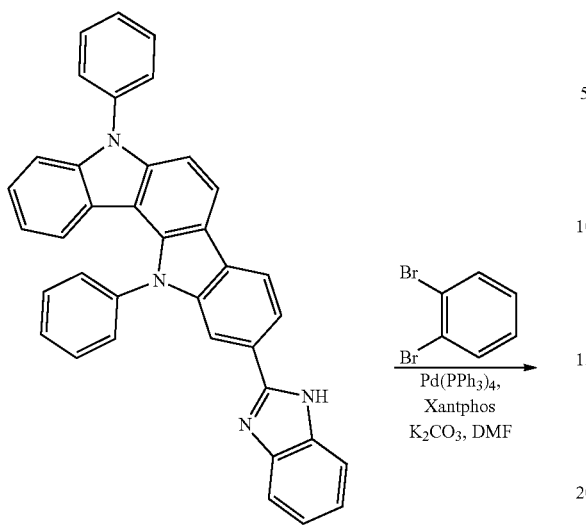

1NB

Example 5

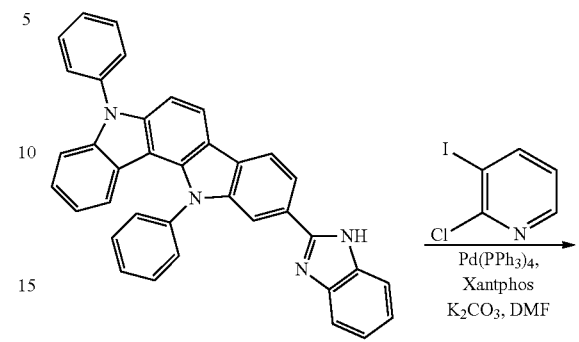

1NB

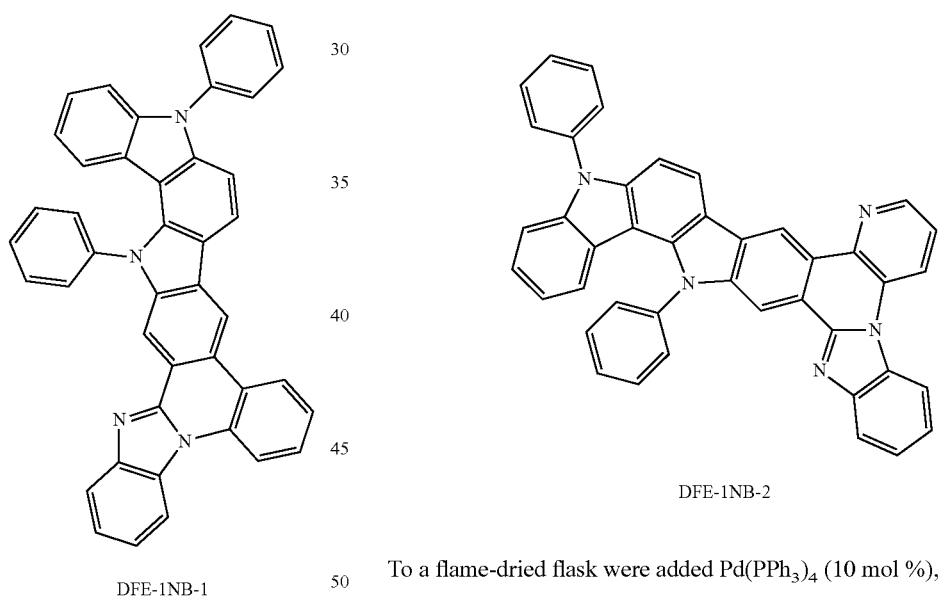

DFE-1NB-1

DFE-1NB-2

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 1NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1NB-1 in 55% yield.

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 1NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1NB-2 in 42% yield.

Example 6

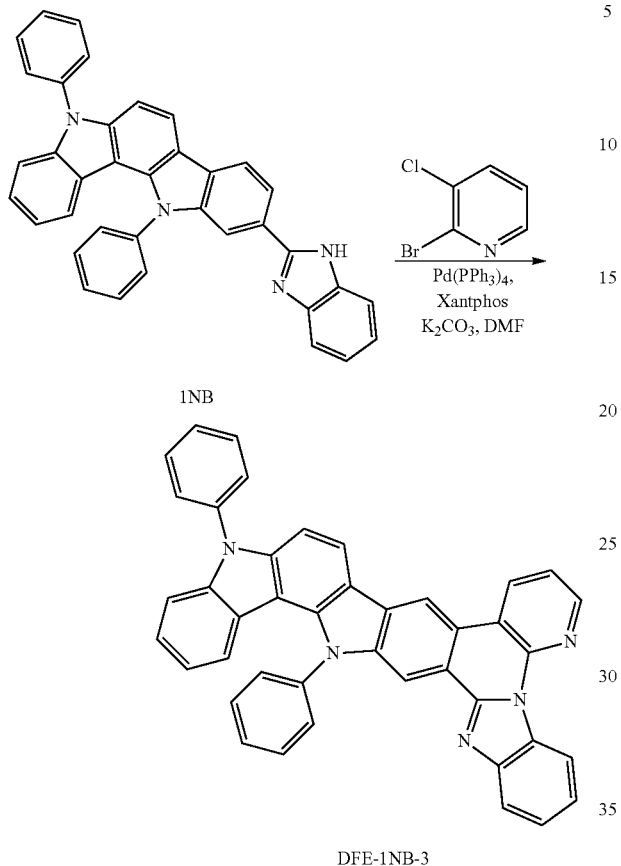

To a flame-dried flask were added Pd(PPh₃)₄ (10 mol %), Xantphos (10 mol %), Cs₂CO₃ (3 eq) and 2-bromo-3-chloropyridine (1.2 eq). Then, 1NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1NB-3 in 35% yield.

Example 7

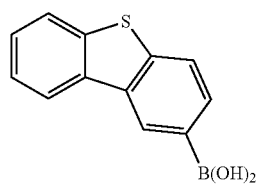

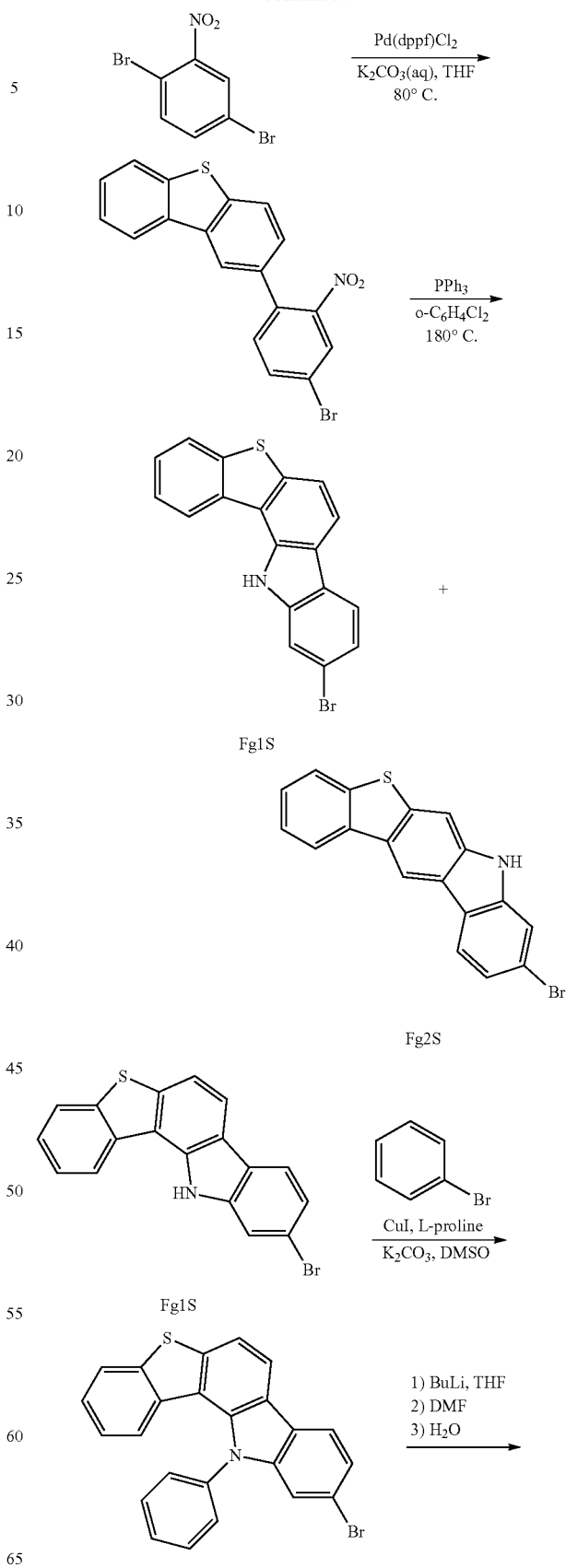

-continued

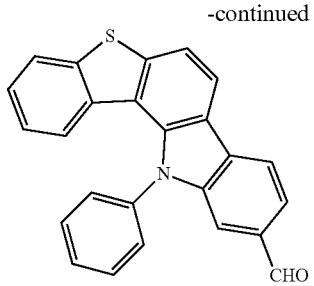 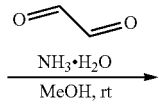

NH$_3$·H$_2$O
MeOH, rt

1SA

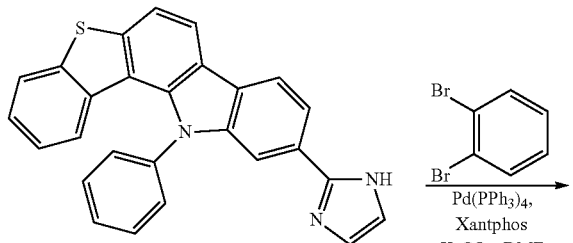 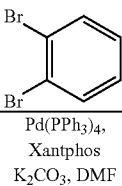

Pd(PPh$_3$)$_4$,
Xantphos
K$_2$CO$_3$, DMF

1SI

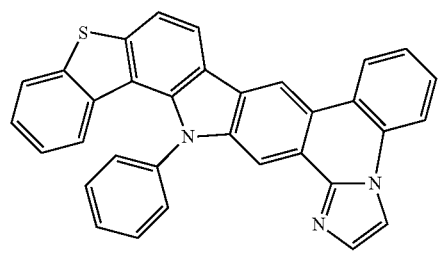

DFE-1S-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 1SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1S-1 in 64% yield.

Example 8

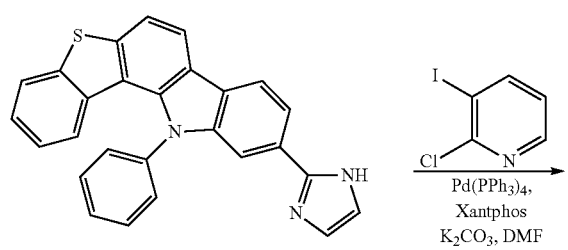 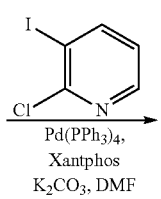

Pd(PPh$_3$)$_4$,
Xantphos
K$_2$CO$_3$, DMF

1SI

-continued

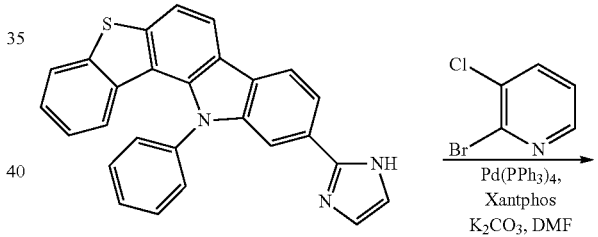

DFE-1S-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 1SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1S-2 in 67% yield.

Example 9

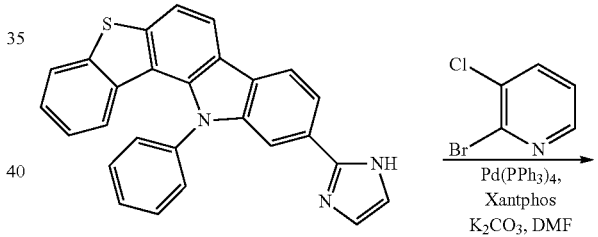 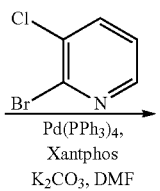

Pd(PPh$_3$)$_4$,
Xantphos
K$_2$CO$_3$, DMF

1SI

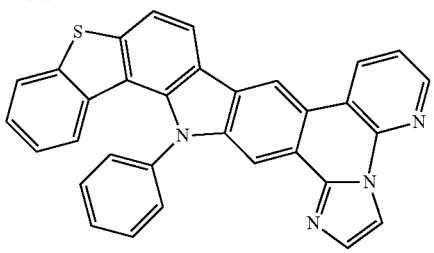

DFE-1S-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 1SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1S-3 in 22% yield.

Example 10

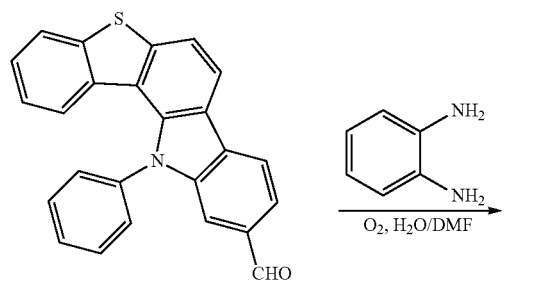

1SA

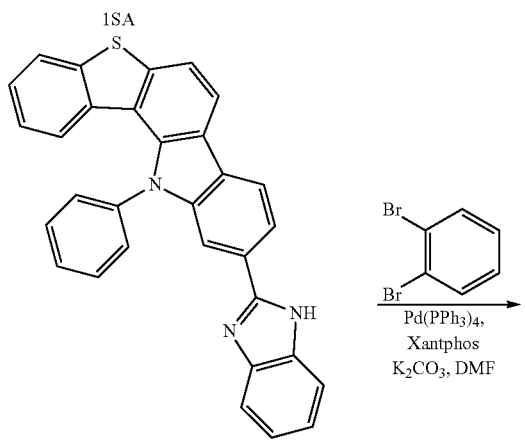

1SB

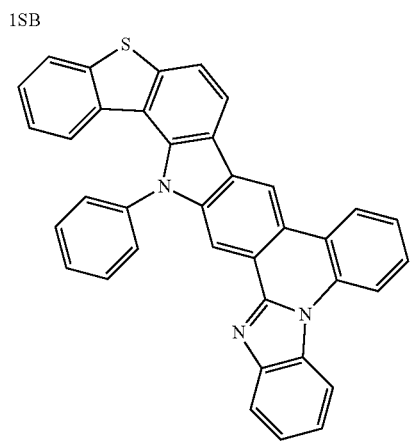

DFE-1SB-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 1SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1SB-1 in 66% yield.

Example 11

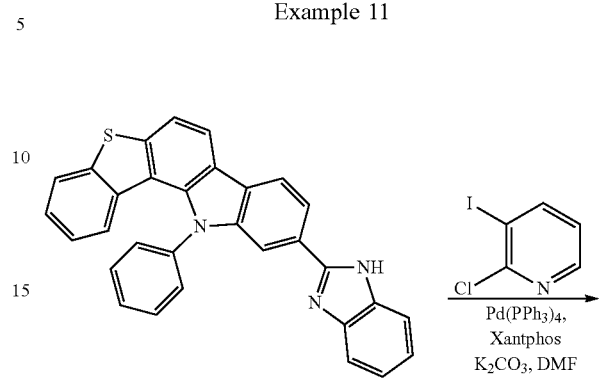

1SB

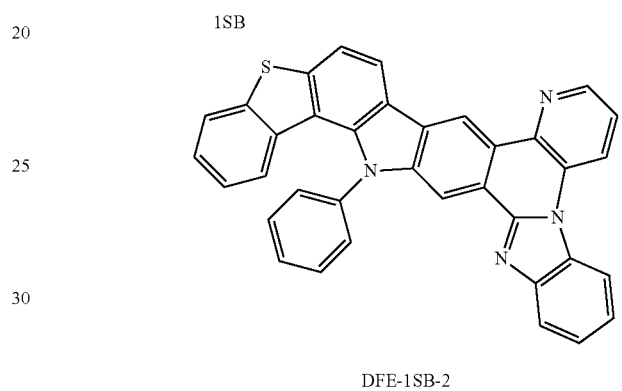

DFE-1SB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 1SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1SB-2 in 45% yield.

Example 12

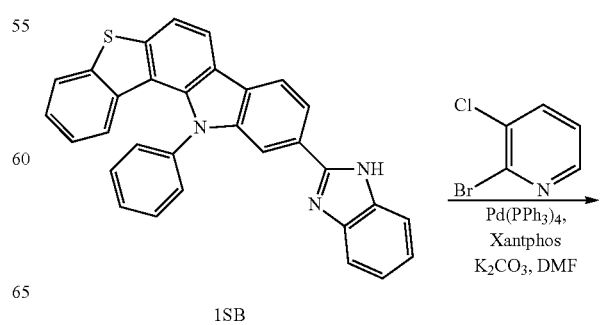

1SB

201

-continued

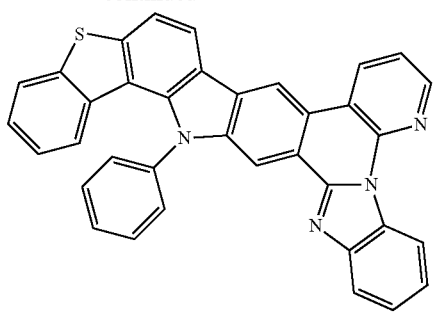

DFE-1SB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 1SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1SB-3 in 39% yield.

Example 13

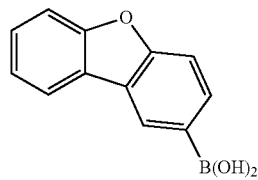

+

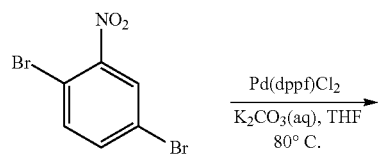

$\xrightarrow{\text{Pd(dppf)Cl}_2}_{\text{K}_2\text{CO}_3\text{(aq), THF}}$
80° C.

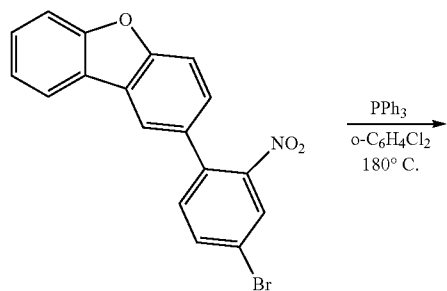

$\xrightarrow{\text{PPh}_3}_{\text{o-C}_6\text{H}_4\text{Cl}_2}$
180° C.

202

-continued

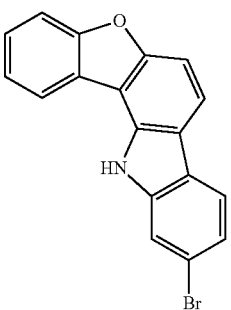

Fg1O  Fg2O

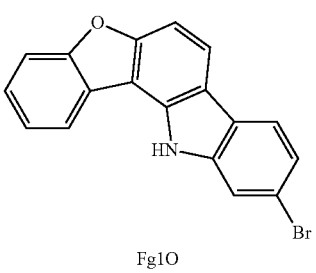

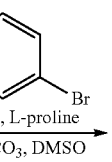

$\xrightarrow{\text{CuI, L-proline}}_{\text{K}_2\text{CO}_3\text{, DMSO}}$

Fg1O

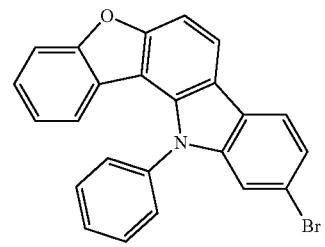

1) BuLi, THF
2) DMF
3) H$_2$O

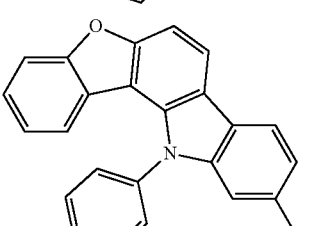

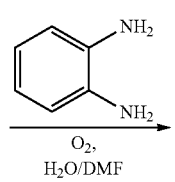

$\xrightarrow{\text{O}_2,\text{H}_2\text{O/DMF}}$

1OA

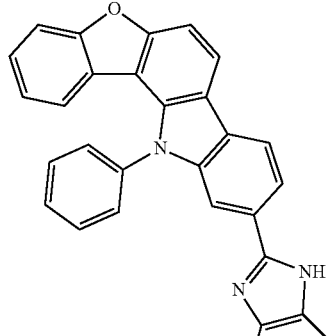

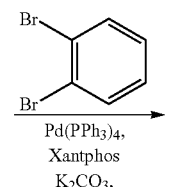

$\xrightarrow{\text{Pd(PPh}_3\text{)}_4,\text{Xantphos}\\\text{K}_2\text{CO}_3,\\\text{DMF}}$

1OB

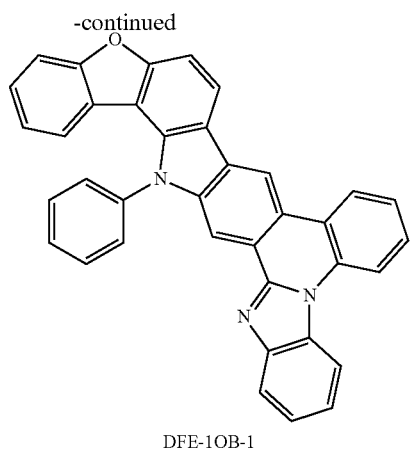

DFE-1OB-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 1OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1OB-1 in 61% yield.

Example 14

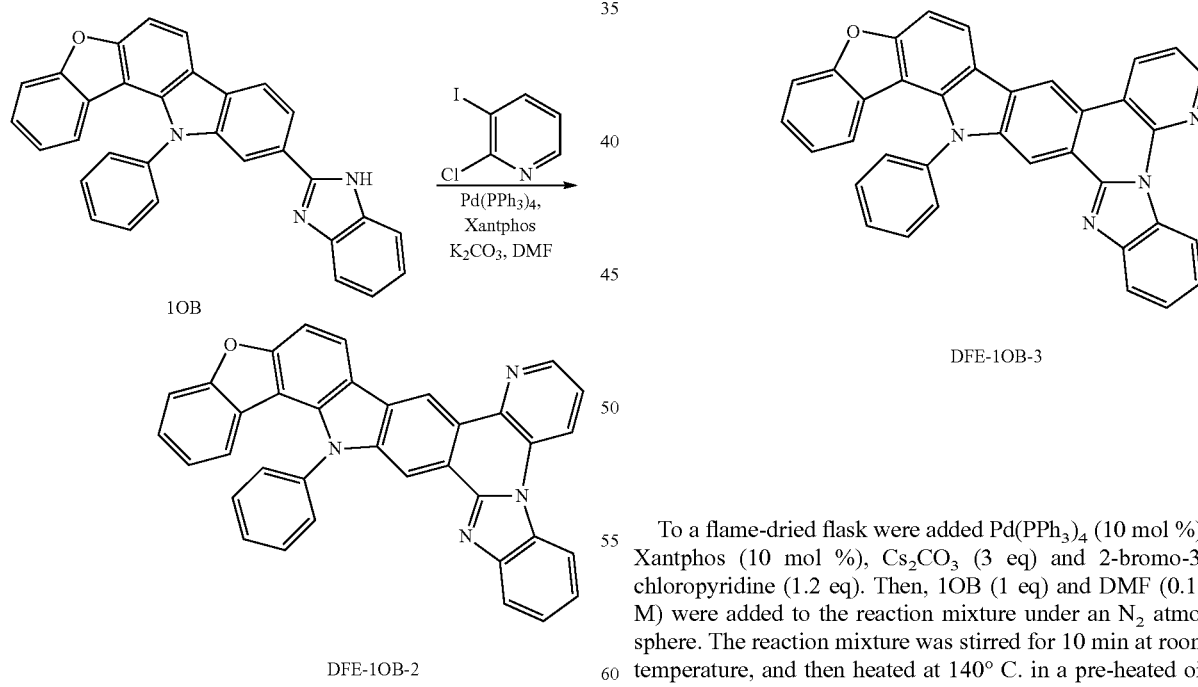

DFE-1OB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 1OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1OB-2 in 41% yield.

Example 15

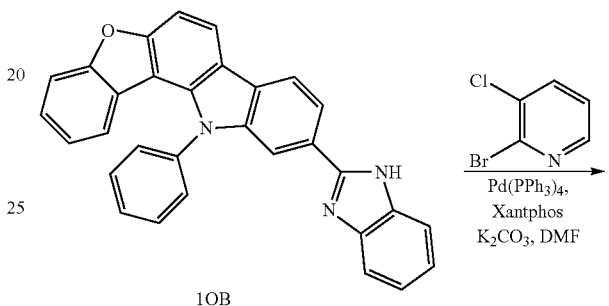

1OB

DFE-1OB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 1OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1OB-3 in 36% yield.

Example 16

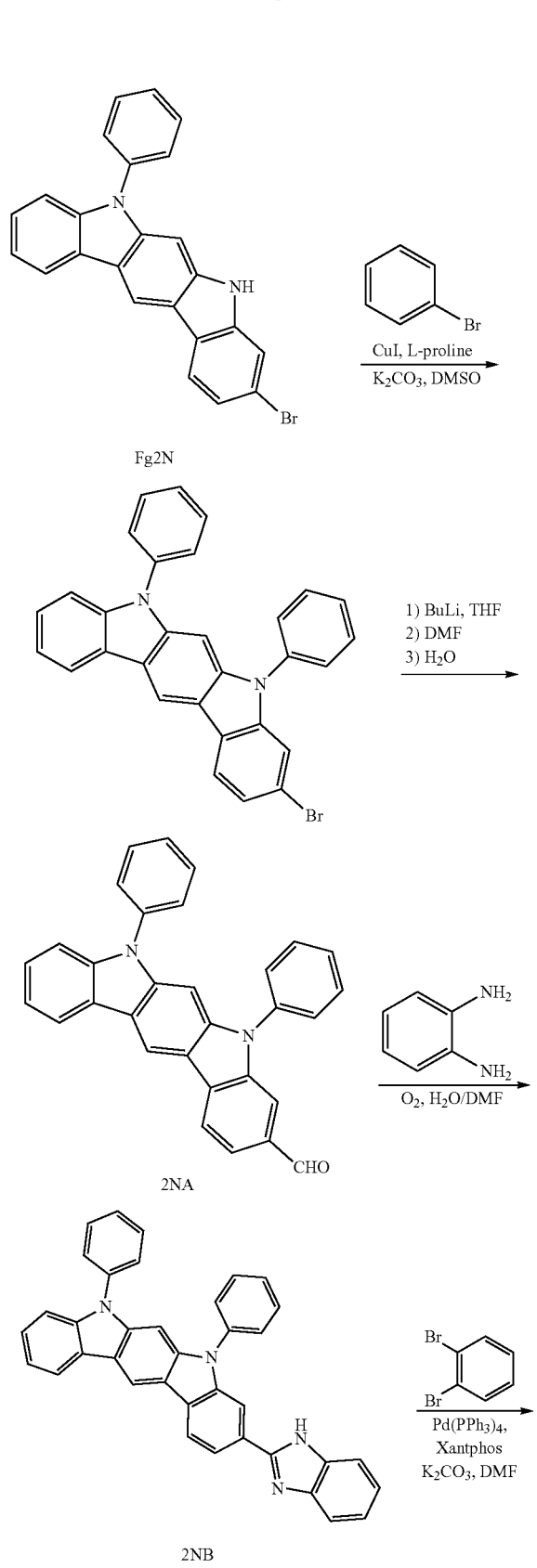

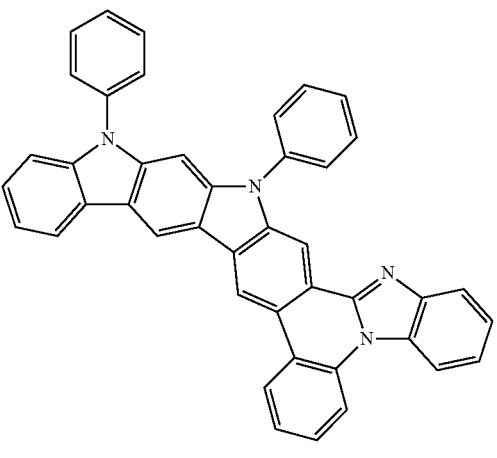

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 2NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-2NB-1 in 55% yield.

Example 17

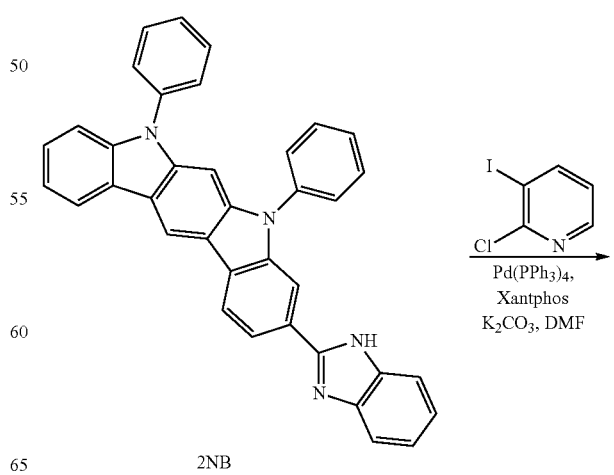

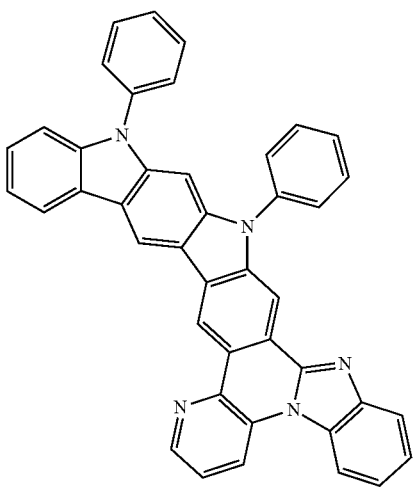

DFE-2NB-2

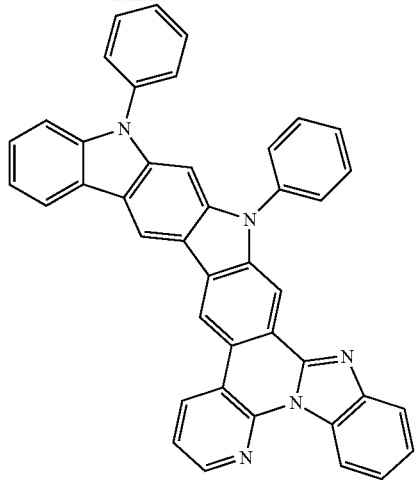

DFE-2NB-3

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 2NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-2NB-2 in 37% yield.

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 2NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-2NB-3 in 33% yield.

Example 18

Example 19

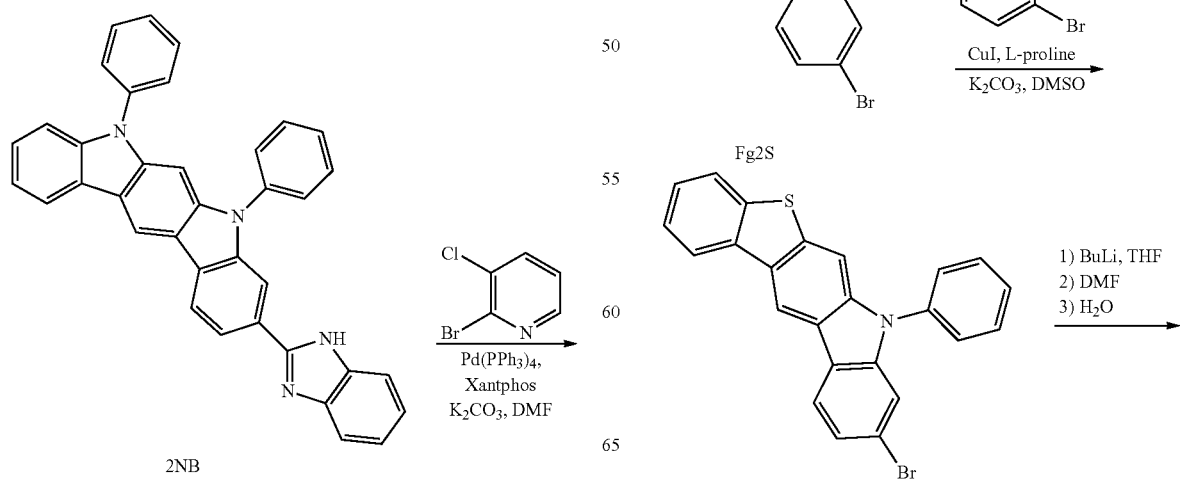

-continued

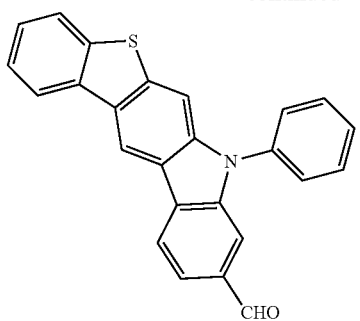 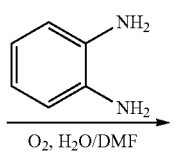

2SA

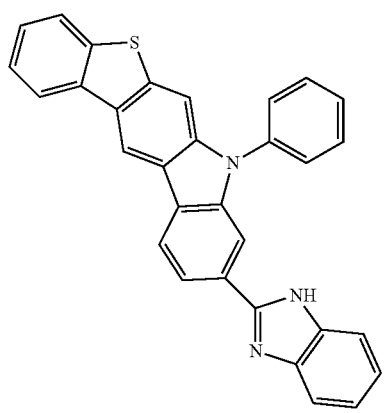 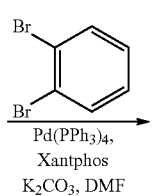

2SB

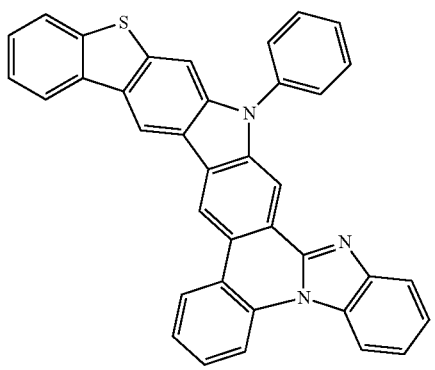

DFE-2SB-1

To a flame-dried flask were added Pd(PPh₃)₄ (10 mol %), Xantphos (10 mol %), Cs₂CO₃ (3 eq) and 1,2-dibromobenzene (1.2 eq). Then, 2SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2SB-1 in 73% yield.

Example 20

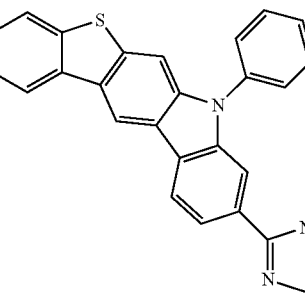 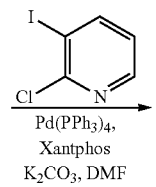

2SB

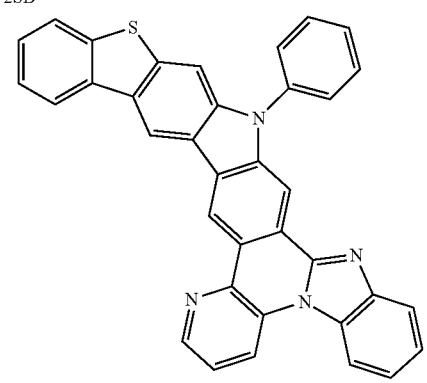

DFE-2SB-2

To a flame-dried flask were added Pd(PPh₃)₄ (10 mol %), Xantphos (10 mol %), Cs₂CO₃ (3 eq) and 2-chloro-3-iodopyridine (1.2 eq). Then, 2SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2SB-2 in 42% yield.

Example 21

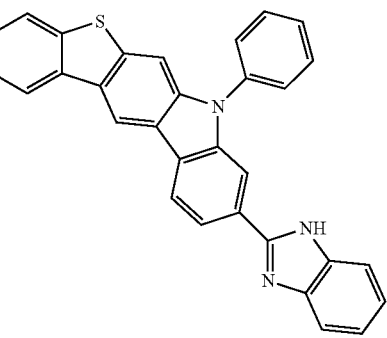 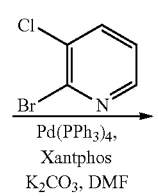

2SB

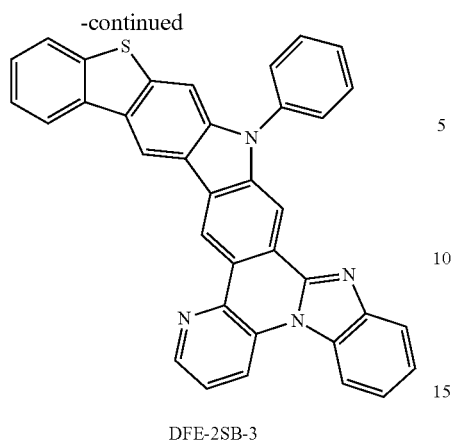

DFE-2SB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 2SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-2SB-3 in 38% yield.

Example 22

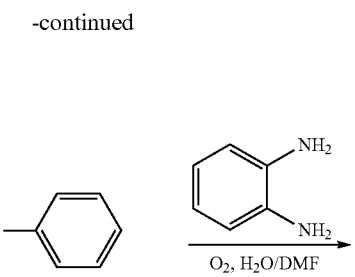

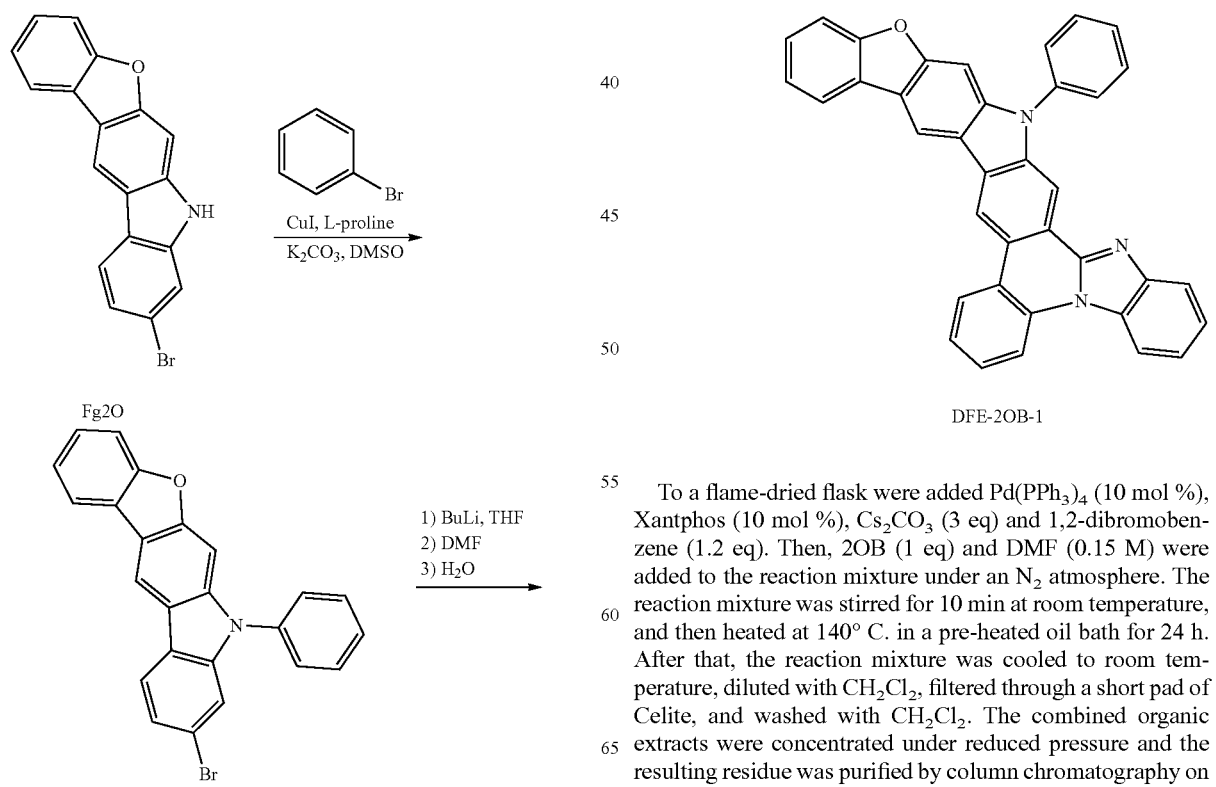

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 2OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-2OB-1 in 68% yield.

Example 23

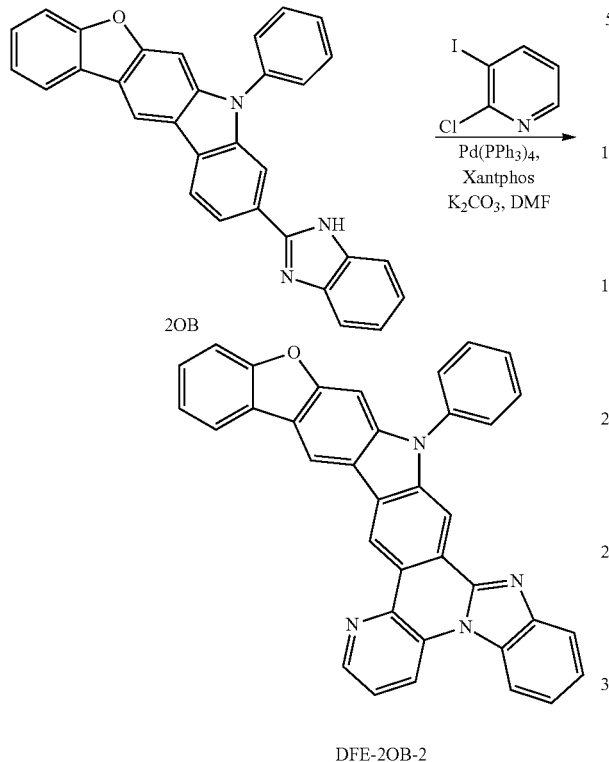

2OB

DFE-2OB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 2OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-2OB-2 in 34% yield.

Example 24

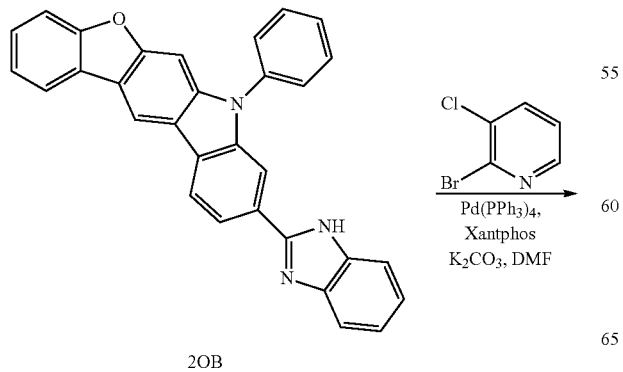

2OB

-continued

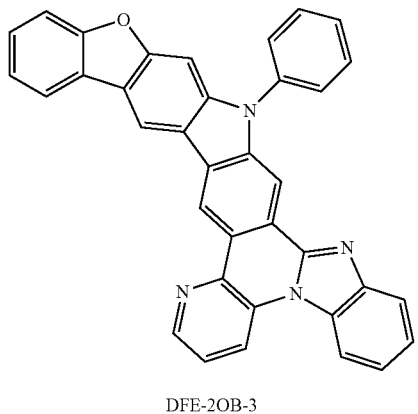

DFE-2OB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 2OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-2OB-3 in 32% yield.

Example 25

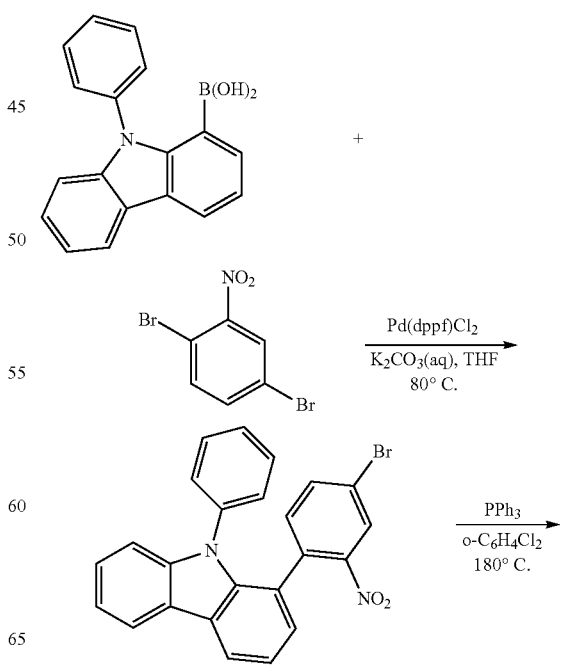

-continued

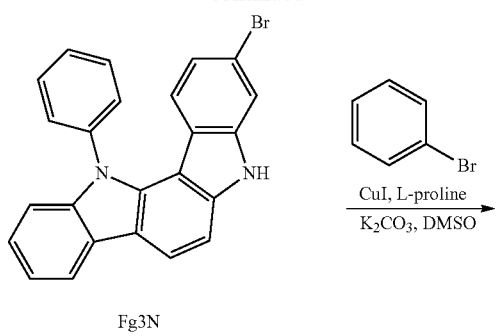

Fg3N

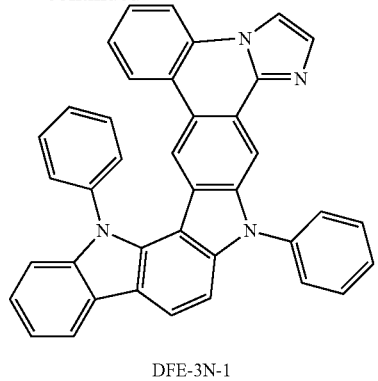

DFE-3N-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 3NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3N-1 in 71% yield.

Example 26

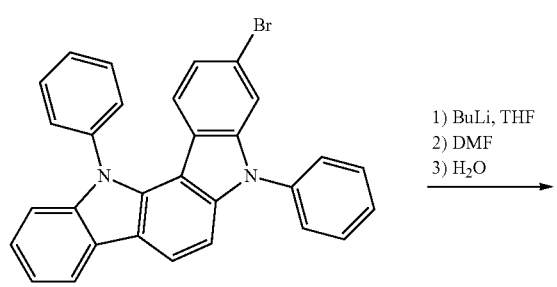

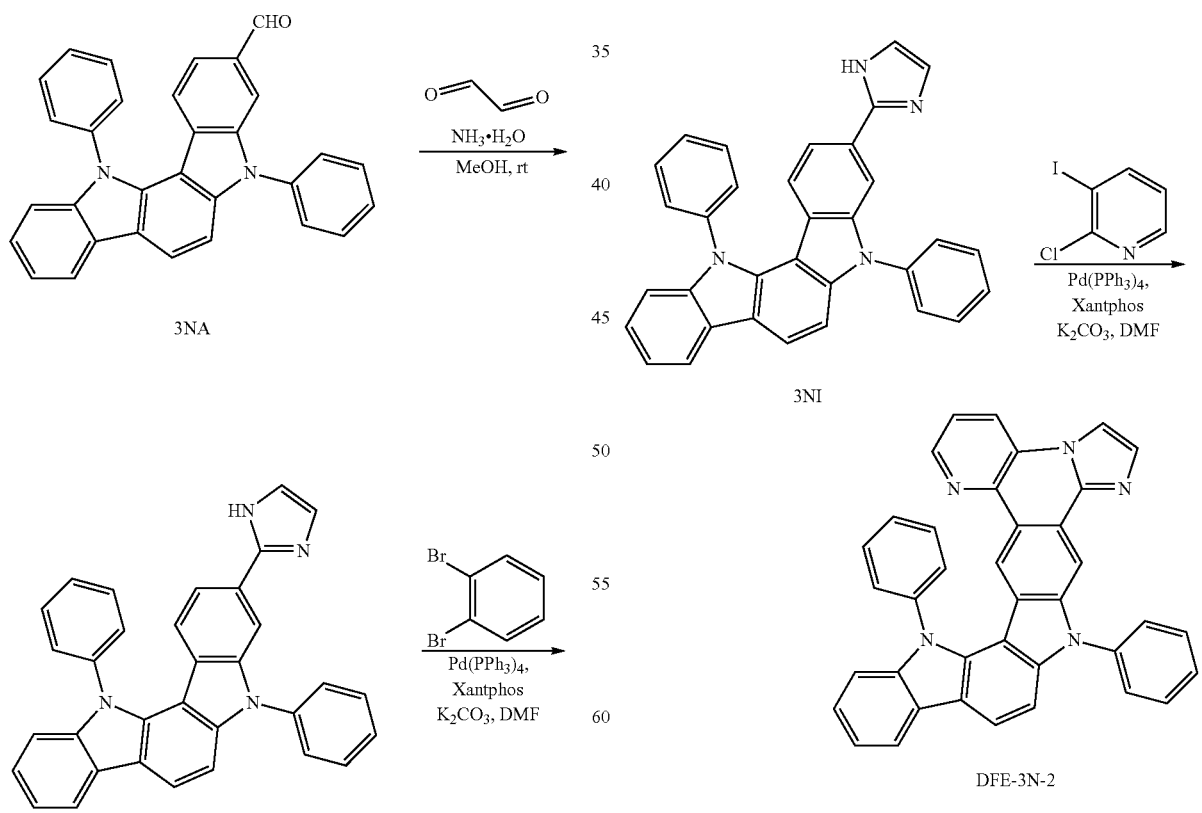

DFE-3N-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 3NI (1 eq) and DMF (0.15 M)

were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3N-2 in 30% yield.

Example 27

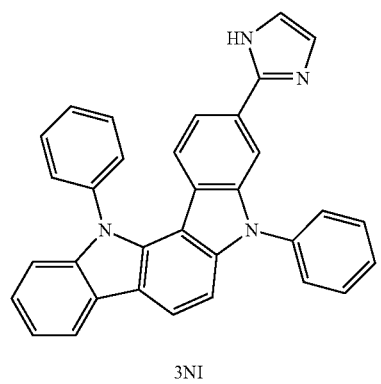

3NI

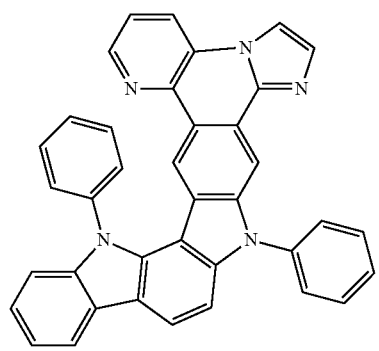

DFE-3N-3

To a flame-dried flask were added Pd(PPh₃)₄ (10 mol %), Xantphos (10 mol %), Cs₂CO₃ (3 eq) and 2-bromo-3-chloropyridine (1.2 eq). Then, 3NI (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3N-3 in 24% yield.

Example 28

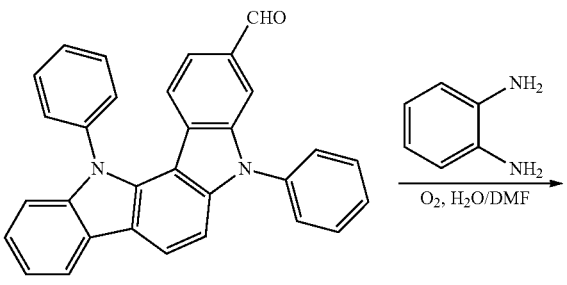

3NA

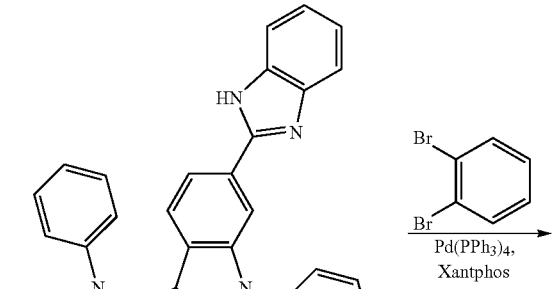

3NB

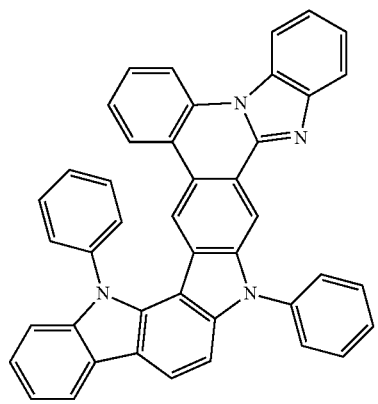

DFE-3NB-1

To a flame-dried flask were added Pd(PPh₃)₄ (10 mol %), Xantphos (10 mol %), Cs₂CO₃ (3 eq) and 1,2-dibromobenzene (1.2 eq). Then, 3NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3NB-1 in 66% yield.

Example 29

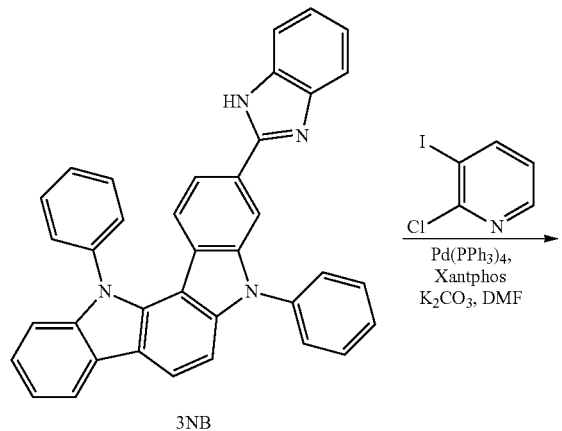

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 3NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3N-2 in 44% yield.

Example 30

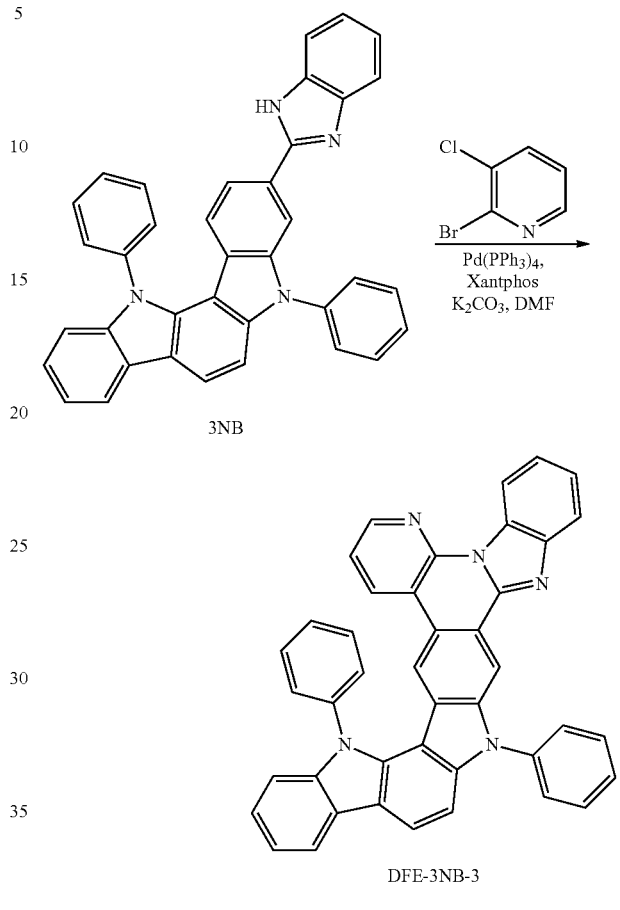

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 3NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3NB-3 in 21% yield.

Example 31

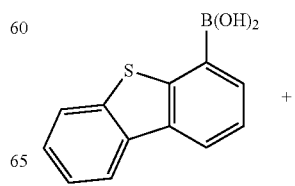

-continued

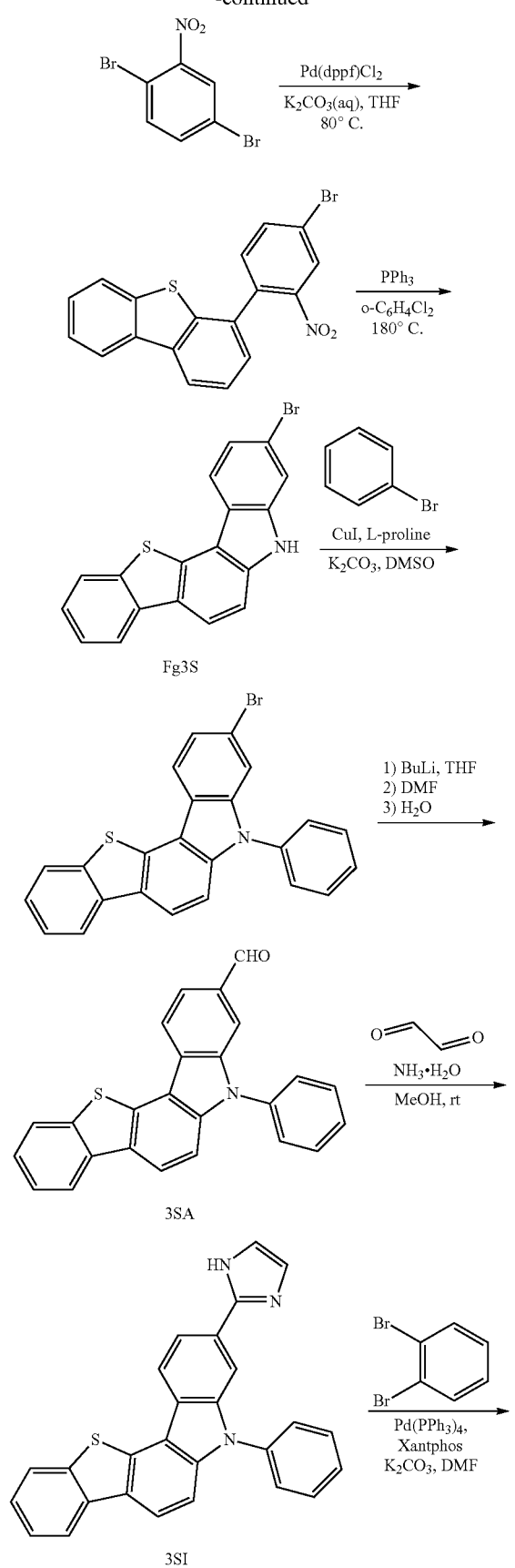

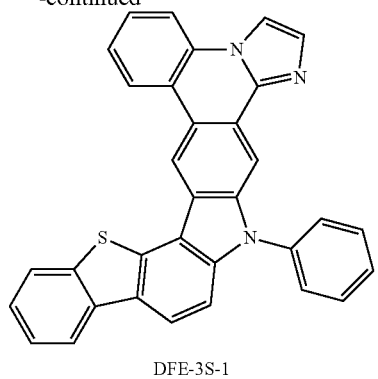

DFE-3S-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 3SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3S-1 in 75% yield.

Example 32

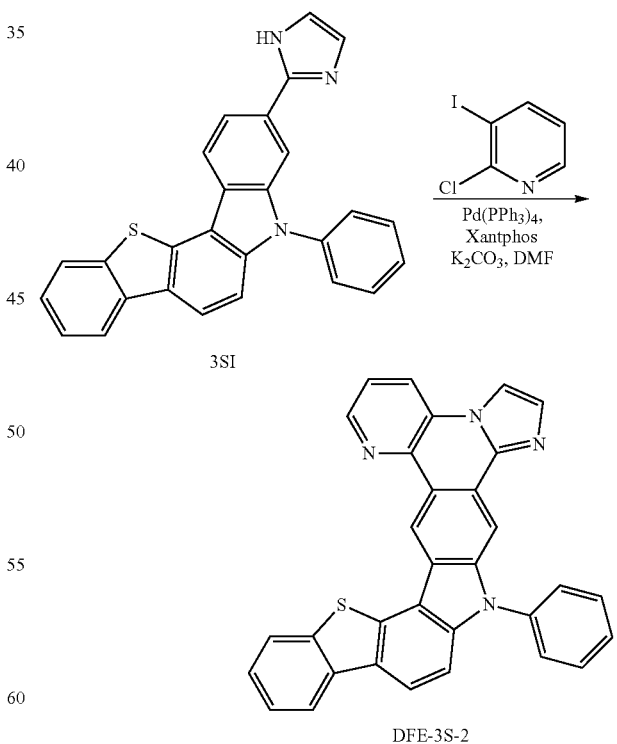

DFE-3S-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 3SI (1 eq) and DMF (0.15 M) were added to the reaction mixture under an N$_2$ atmosphere.

The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3S-2 in 64% yield.

Example 33

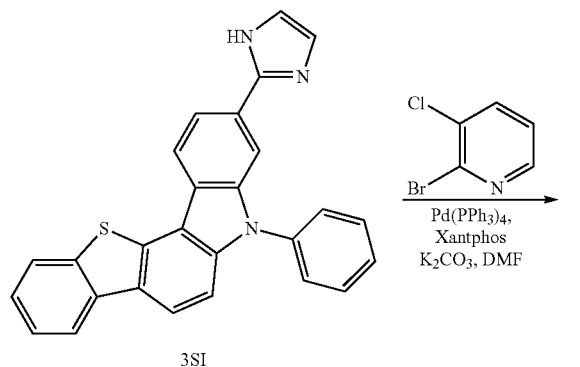

Example 34

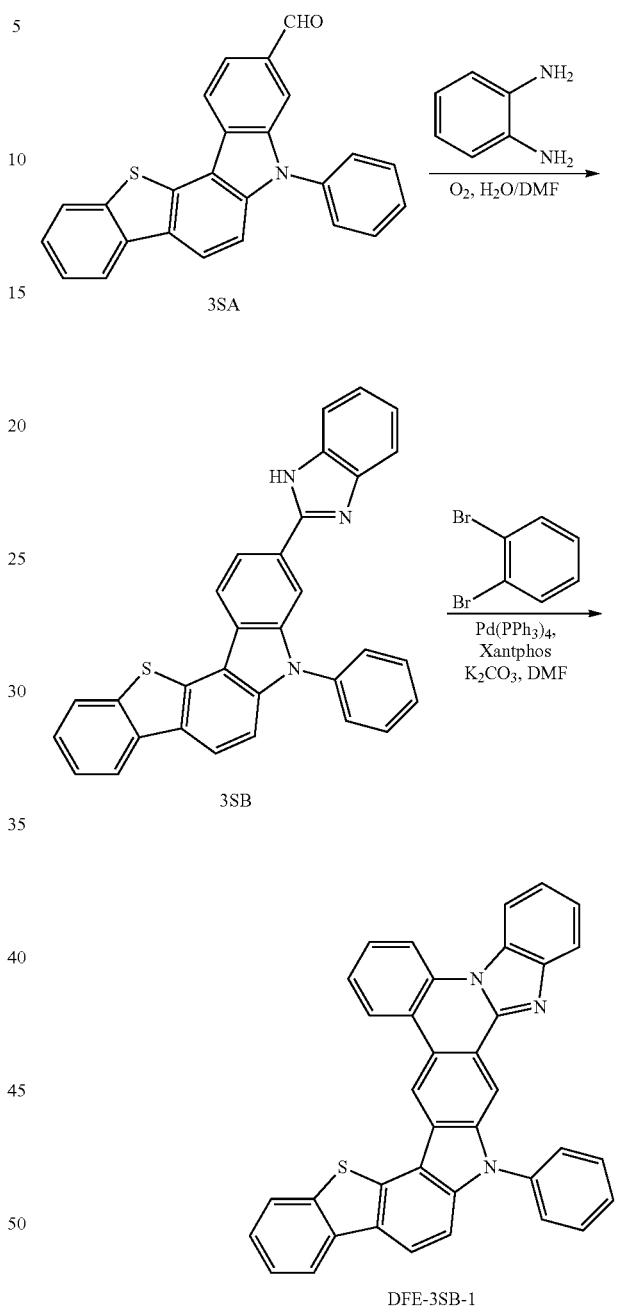

To a flame-dried flask were added Pd(PPh₃)₄ (10 mol %), Xantphos (10 mol %), Cs₂CO₃ (3 eq) and 2-bromo-3-chloropyridine (1.2 eq). Then, 3SI (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3S-3 in 29% yield.

To a flame-dried flask were added Pd(PPh₃)₄ (10 mol %), Xantphos (10 mol %), Cs₂CO₃ (3 eq) and 1,2-dibromobenzene (1.2 eq). Then, 3SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3SB-1 in 72% yield.

Example 35

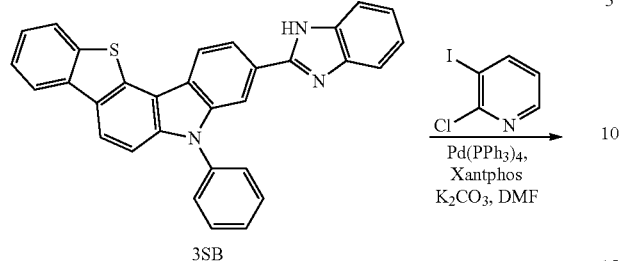

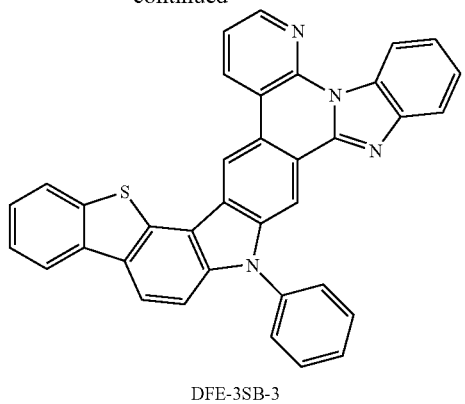

To a flame-dried flask were added Pd(PPh₃)₄ (10 mol %), Xantphos (10 mol %), Cs₂CO₃ (3 eq) and 2-bromo-3-chloropyridine (1.2 eq). Then, 3SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3SB-3 in 24% yield.

Example 37

To a flame-dried flask were added Pd(PPh₃)₄ (10 mol %), Xantphos (10 mol %), Cs₂CO₃ (3 eq) and 2-chloro-3-iodopyridine (1.2 eq). Then, 3SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3SB-2 in 59% yield.

Example 36

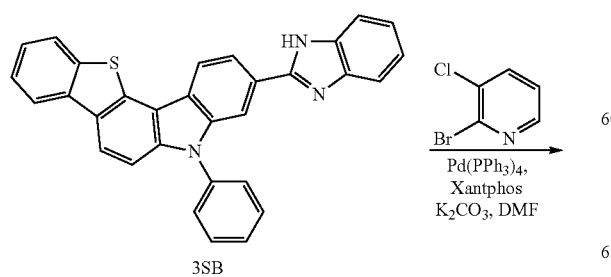

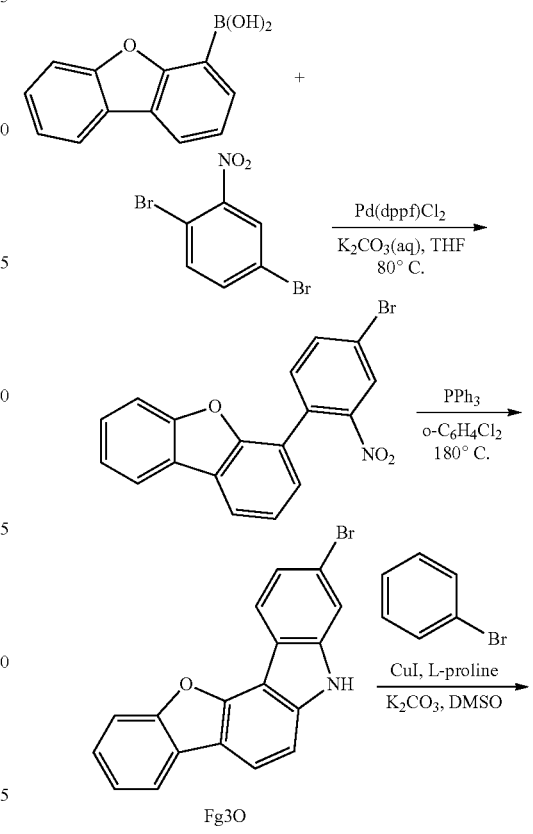

227
-continued

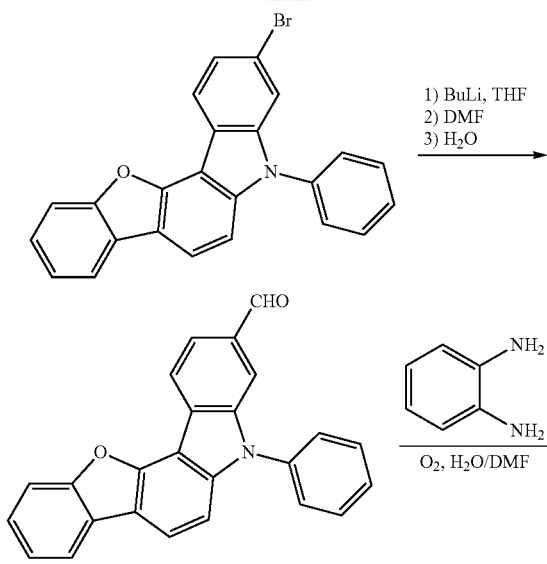

3OA

Example 38

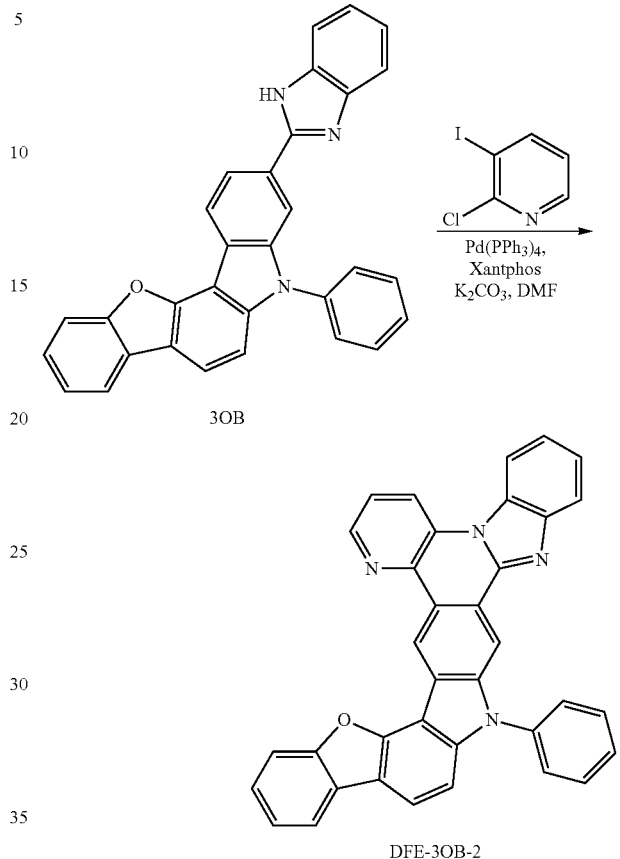

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 3OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3OB-2 in 62% yield.

Example 39

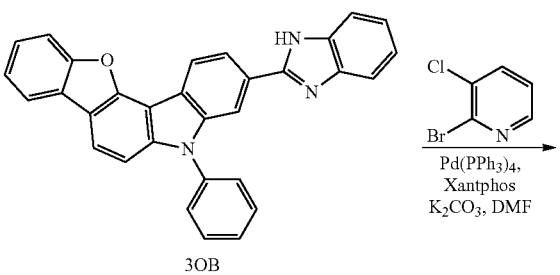

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 3OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3OB-1 in 68% yield.

229
-continued

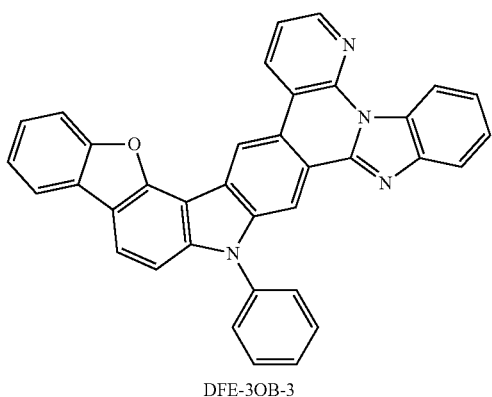

DFE-3OB-3

230
-continued

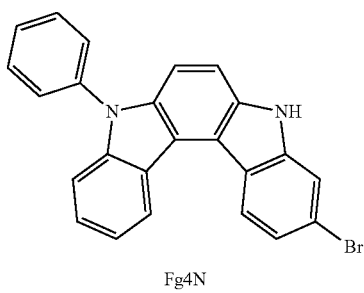 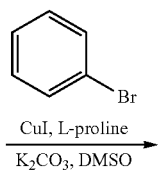

Fg4N

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 3OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3OB-3 in 32% yield.

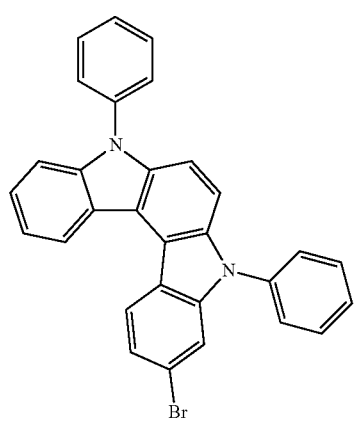 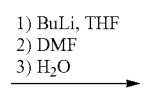

1) BuLi, THF
2) DMF
3) H$_2$O

Example 40

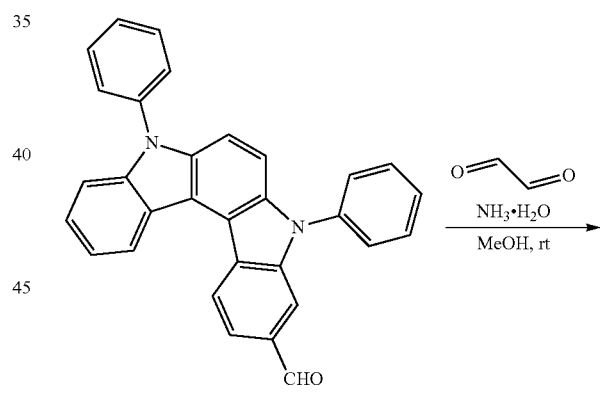

4NA

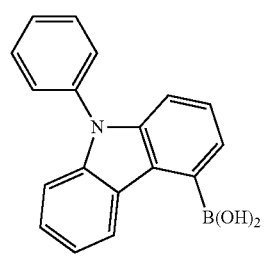

+

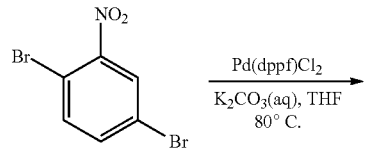

Pd(dppf)Cl$_2$
K$_2$CO$_3$(aq), THF
80° C.

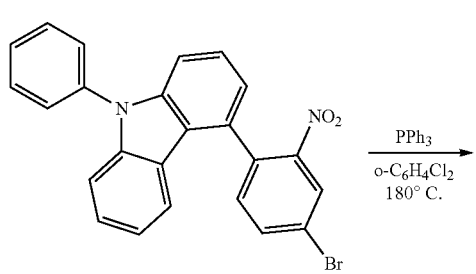

PPh$_3$
o-C$_6$H$_4$Cl$_2$
180° C.

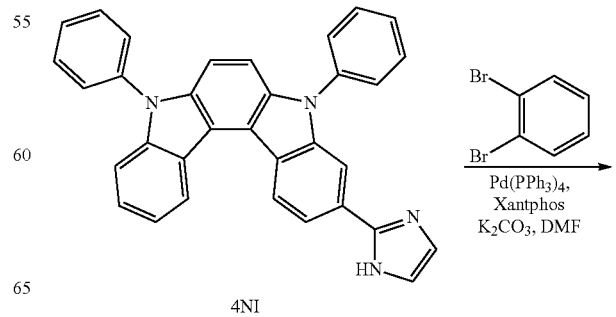

4NI

Pd(PPh$_3$)$_4$,
Xantphos
K$_2$CO$_3$, DMF

-continued

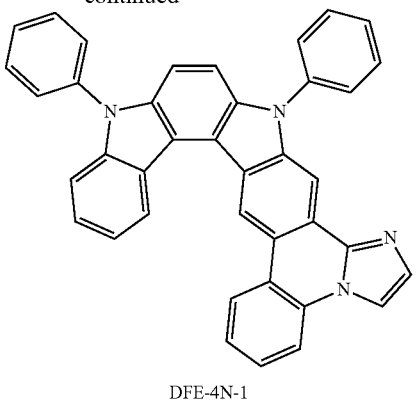

DFE-4N-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 4NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4N-1 in 61% yield.

Example 41

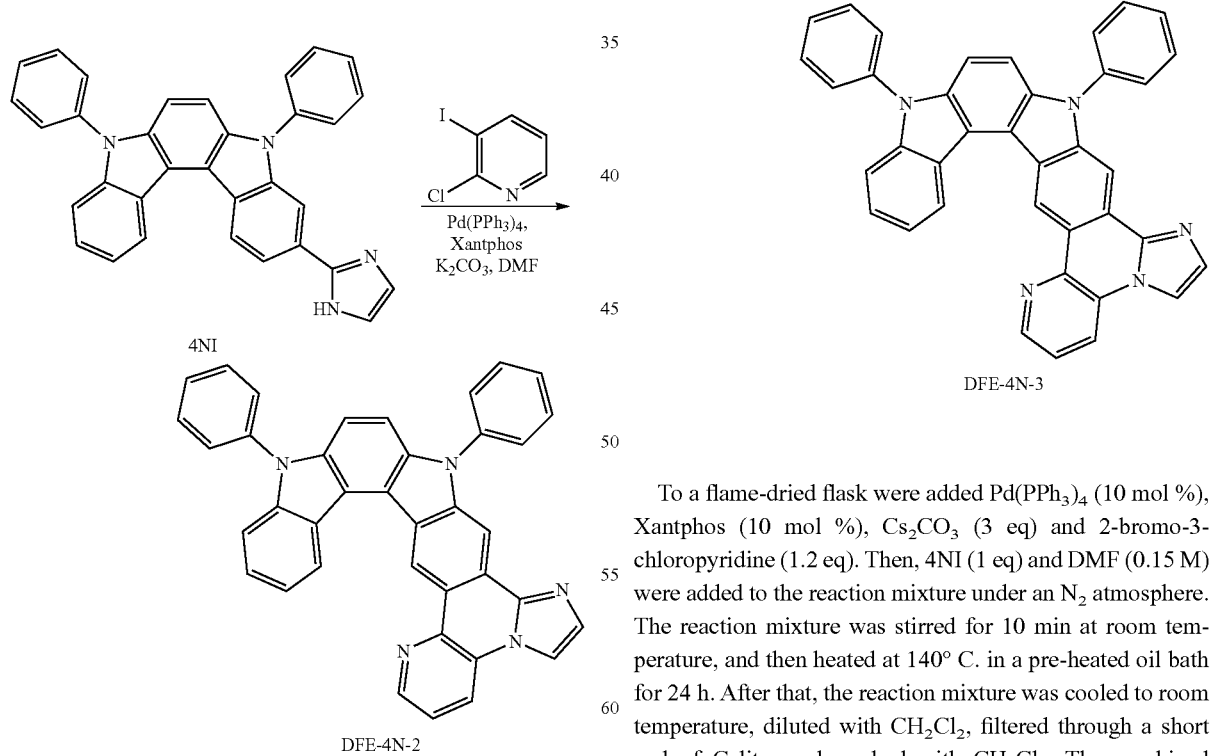

DFE-4N-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 4NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4N-2 in 51% yield.

Example 42

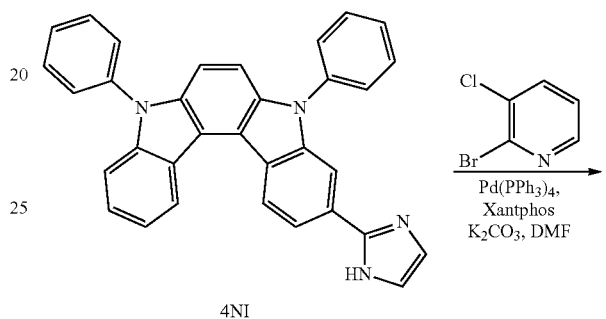

DFE-4N-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 4NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4N-3 in 27% yield.

Example 43

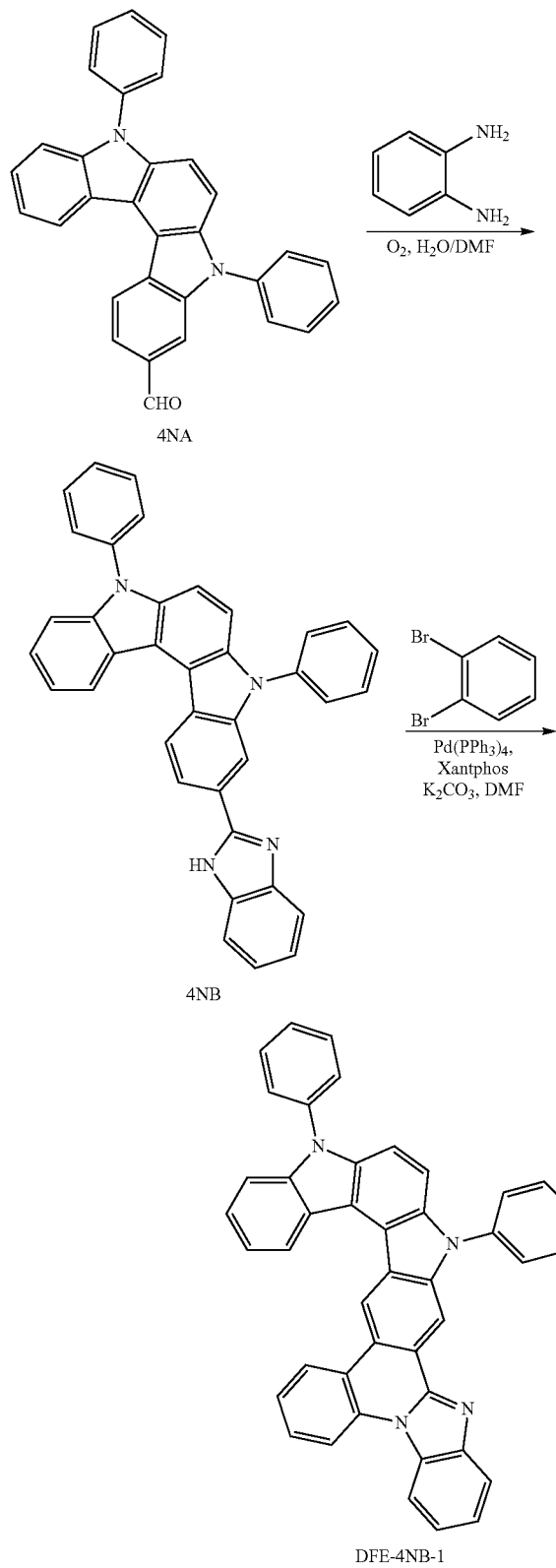

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 4NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4NB-1 in 57% yield.

Example 44

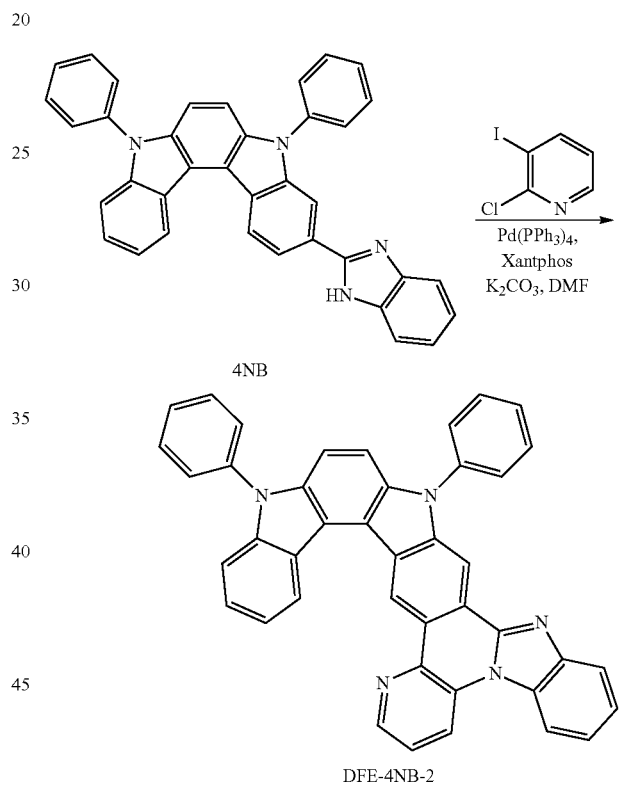

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 4NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4NB-2 in 43% yield.

Example 45

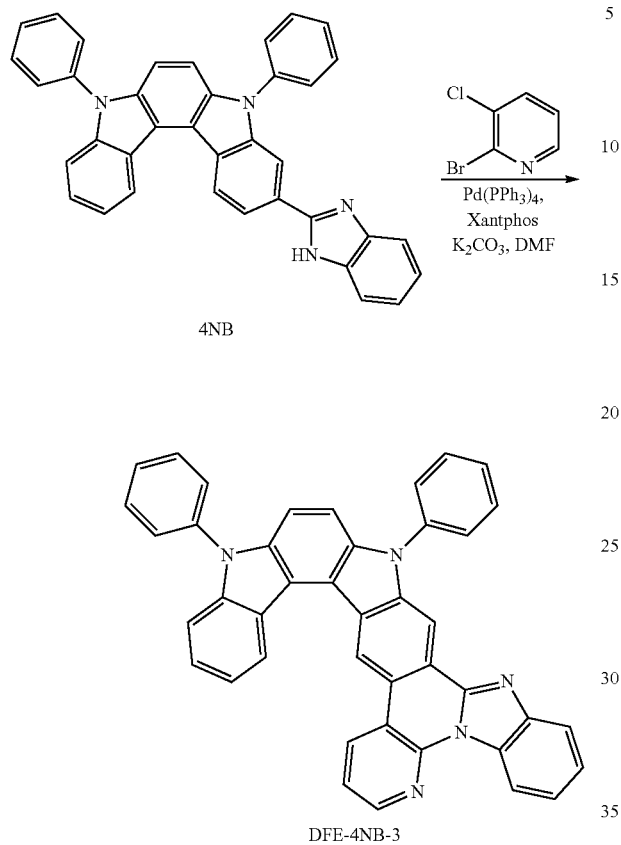

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 4NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4NB-3 in 22% yield.

Example 46

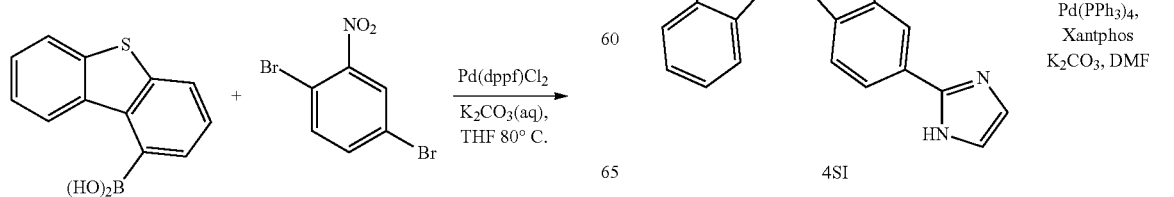

-continued

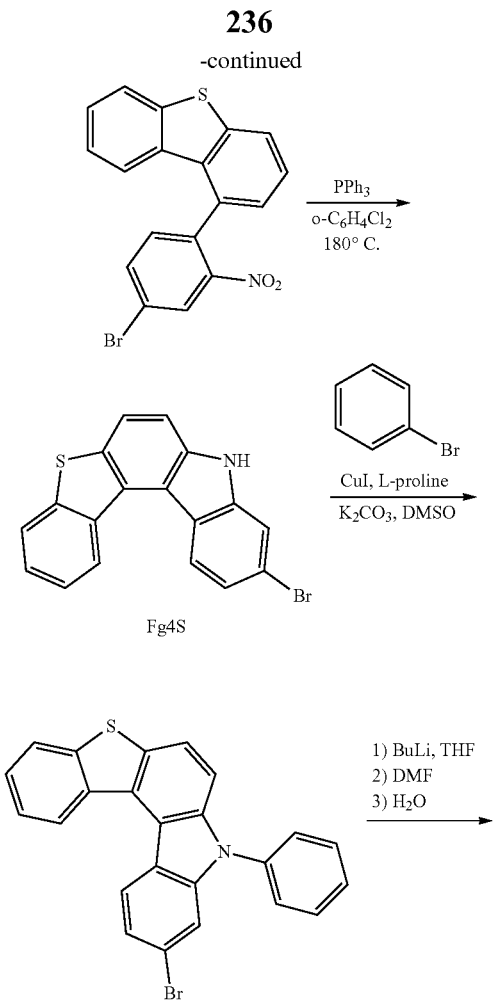

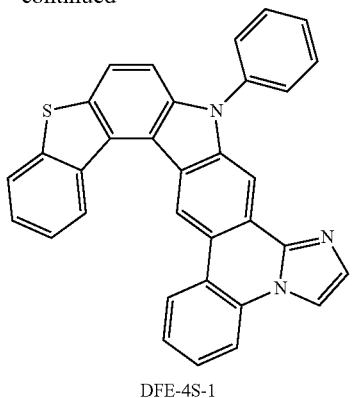

DFE-4S-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 4SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4S-1 in 57% yield.

Example 47

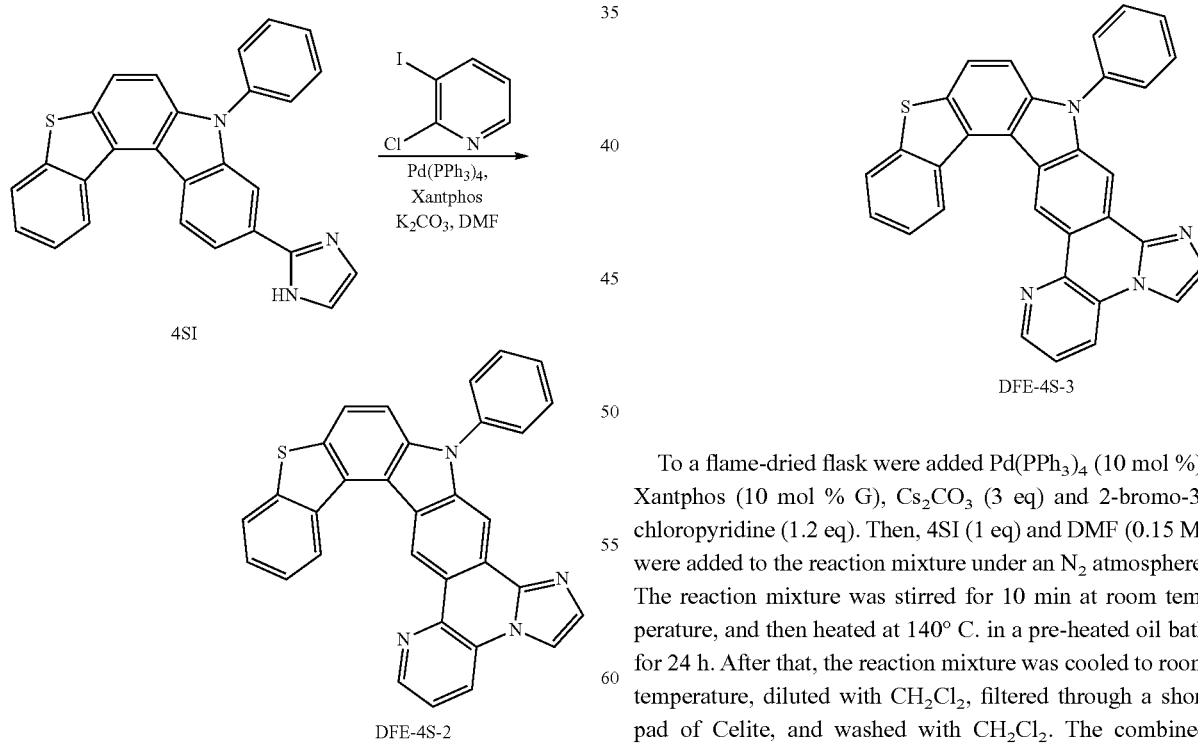

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 4SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4S-2 in 44% yield.

Example 48

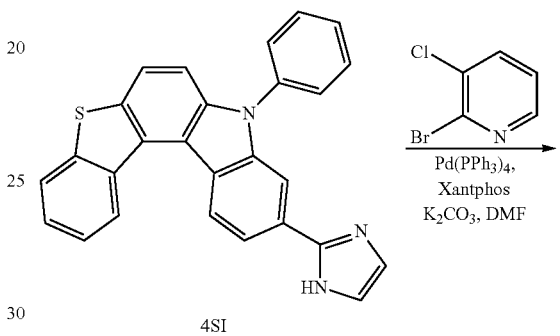

4SI

To a flame-dried flask were added Pd(PPh$_3$)$_4$ (10 mol %), Xantphos (10 mol % G), Cs$_2$CO$_3$ (3 eq) and 2-bromo-3-chloropyridine (1.2 eq). Then, 4SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4S-3 in 23% yield.

Example 49

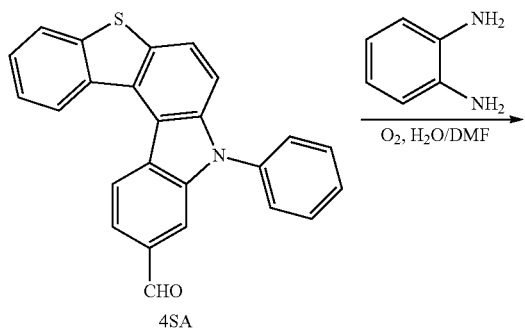

4SA

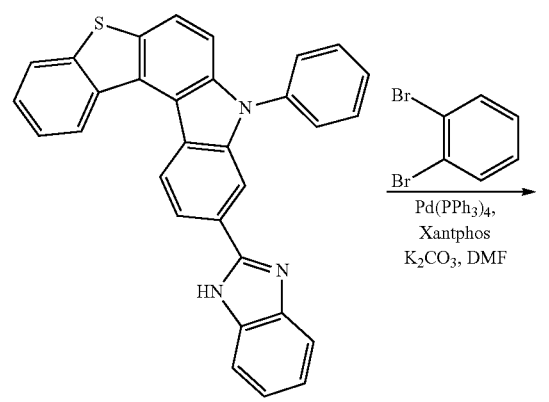

4SB

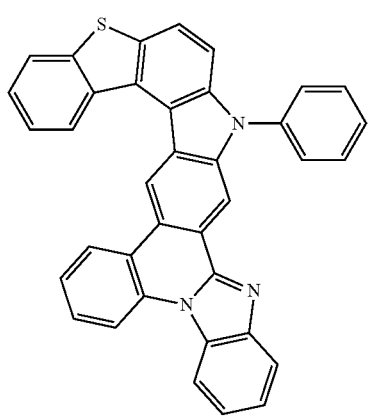

DFE-4SB-1

To a flame-dried flask were added Pd(PPh₃)₄ (10 mol %), Xantphos (10 mol %), Cs₂CO₃ (3 eq) and 1,2-dibromobenzene (1.2 eq). Then, 4SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-4SB-1 in 51% yield.

Example 50

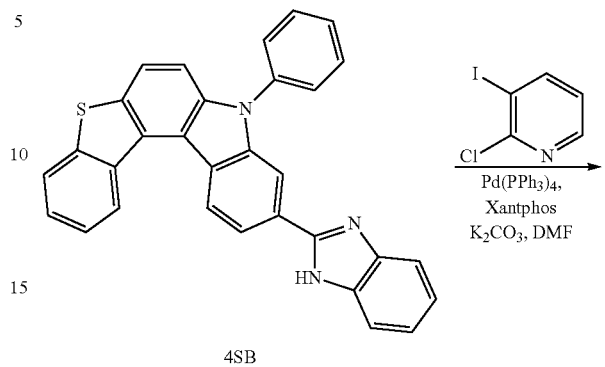

4SB

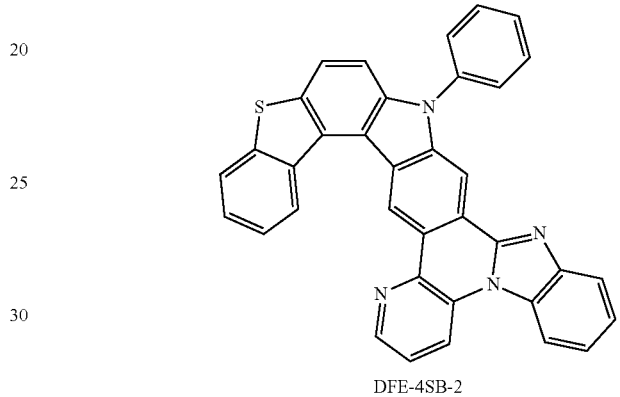

DFE-4SB-2

To a flame-dried flask were added Pd(PPh₃)₄ (10 mol %), Xantphos (10 mol %), Cs₂CO₃ (3 eq) and 2-chloro-3-iodopyridine (1.2 eq). Then, 4SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-4SB-2 in 39% yield.

Example 51

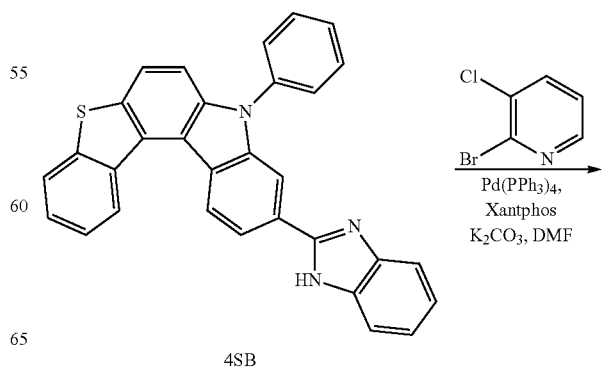

4SB

-continued

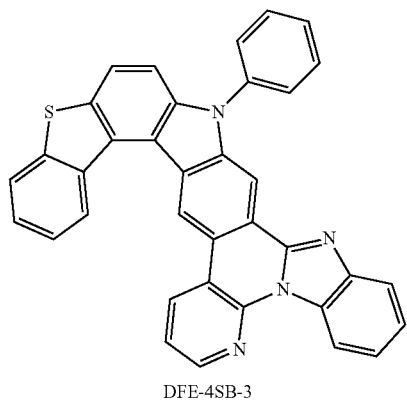

DFE-4SB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 4SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4SB-3 in 31% yield.

Example 52

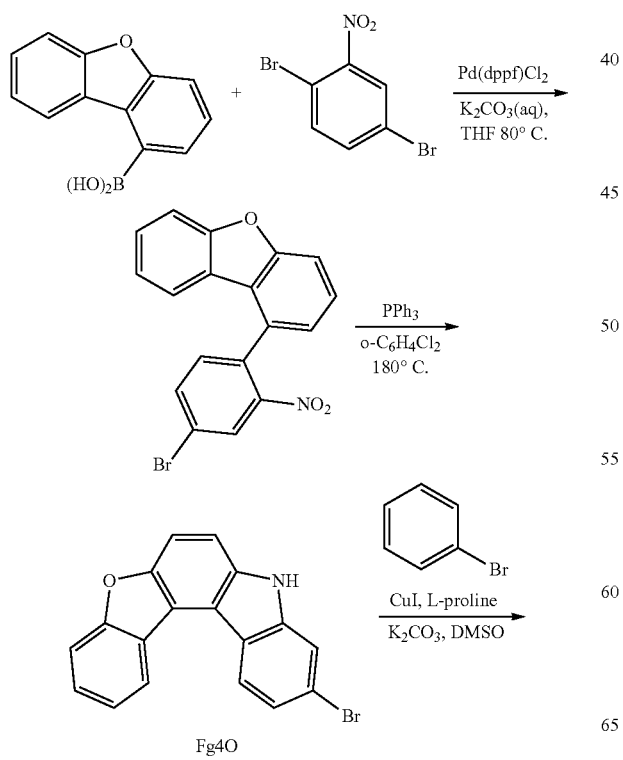

-continued

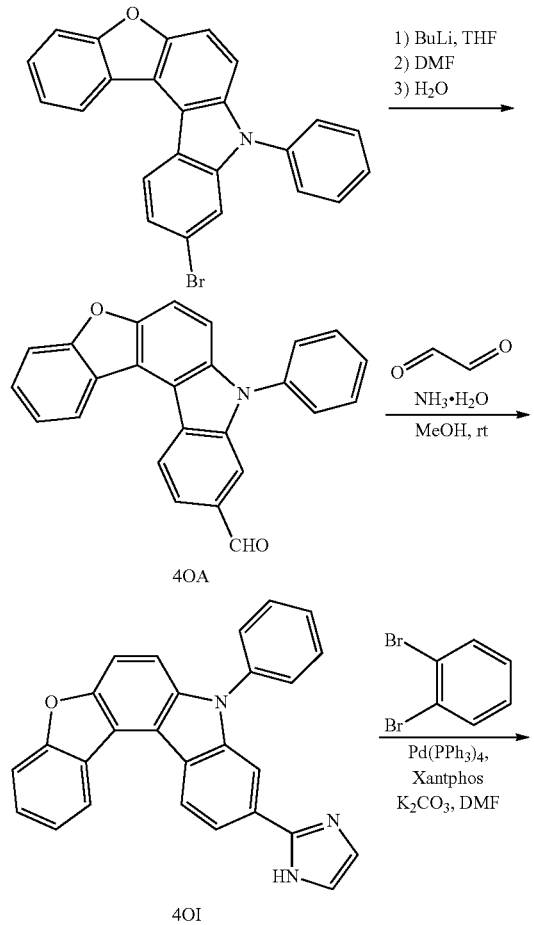

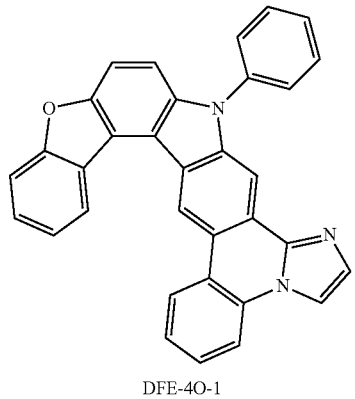 [SMILES: c1ccc(-n2c3cc4c(cc3c3c5c(ccc32)oc2ccccc25)c2ccccc2n2ccnc42)cc1]

DFE-4O-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 4OI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4O-1 in 64% yield.

Example 53

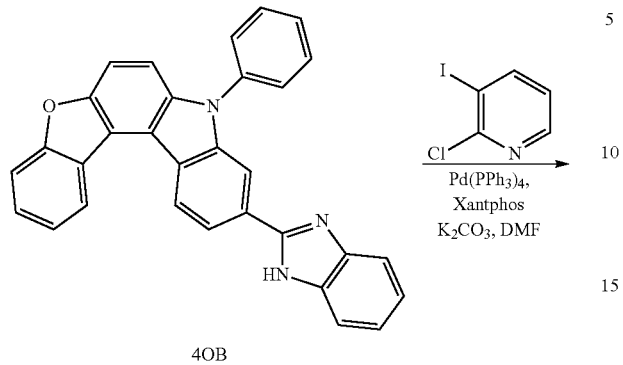

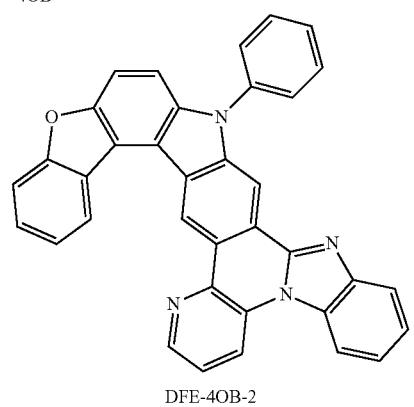

DFE-4OB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 4OI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4O-2 in 37% yield.

Example 54

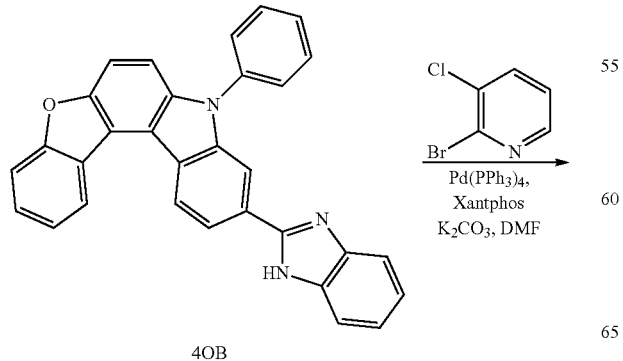

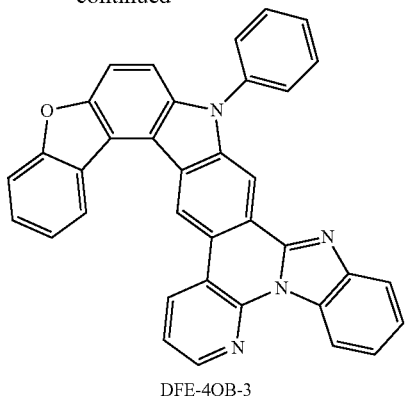

DFE-4OB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 4OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4OB-3 in 26% yield.

Example 55

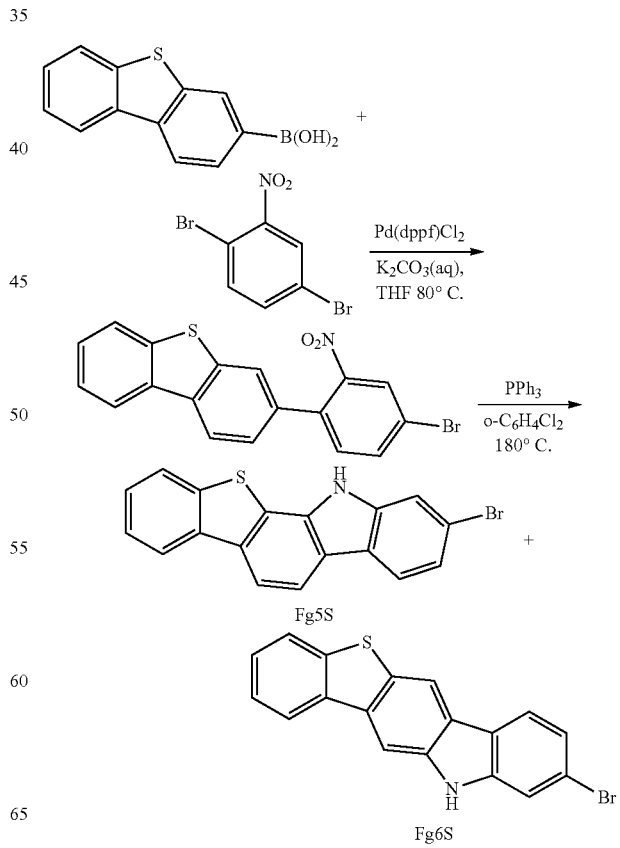

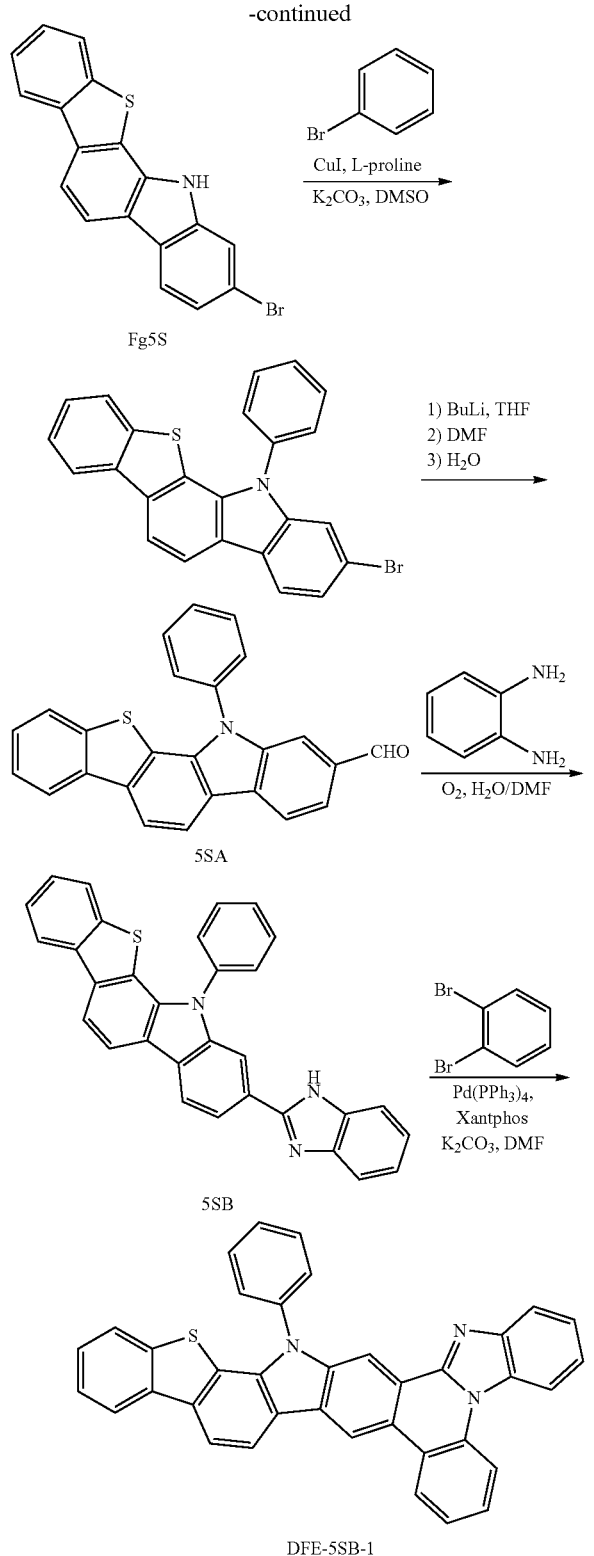

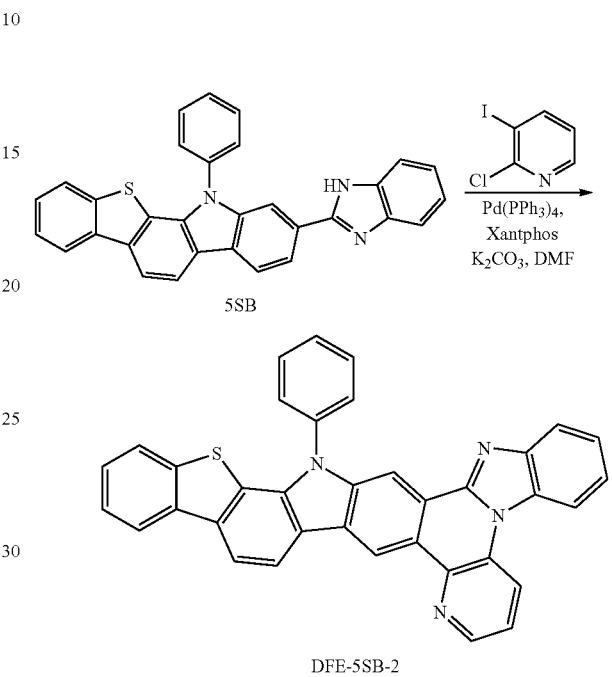

After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-5SB-1 in 56% yield.

Example 56

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 5SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-5SB-2 in 33% yield.

Example 57

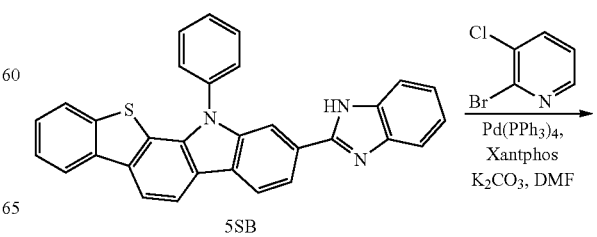

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 5SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h.

247

-continued

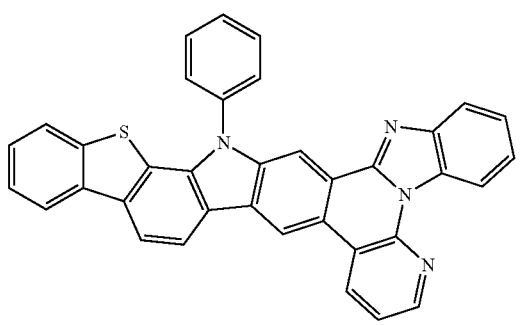

DFE-5SB-3

To a flame-dried flask were added Pd(PPh₃)₄ (10 mol %), Xantphos (10 mol %), Cs₂CO₃ (3 eq) and 2-bromo-3-chloropyridine (1.2 eq). Then, 5SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-5SB-3 in 35% yield.

Example 58

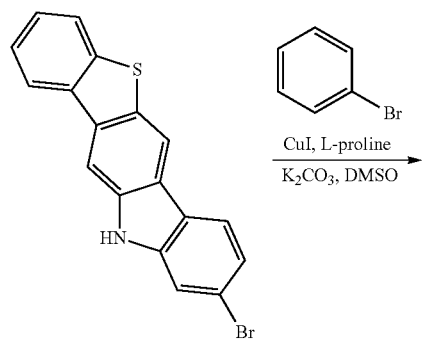

Fg6S

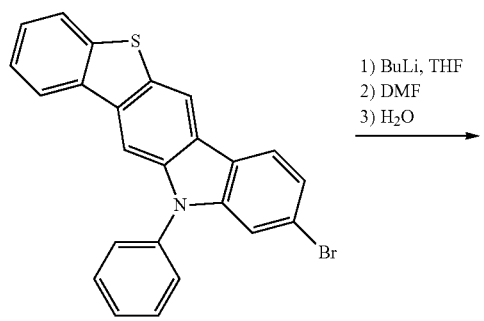

248

-continued

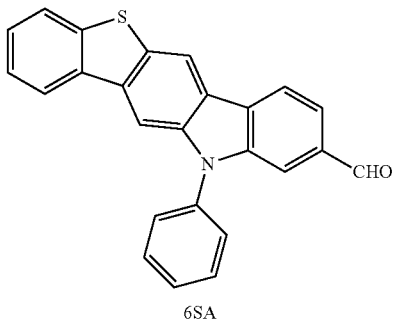 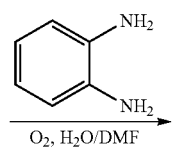

6SA

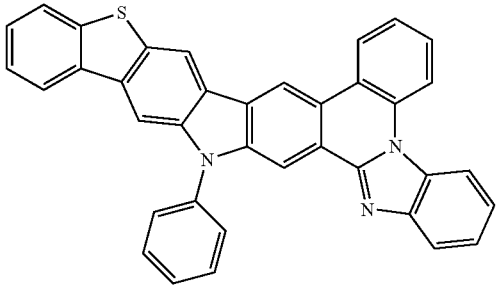

6SB

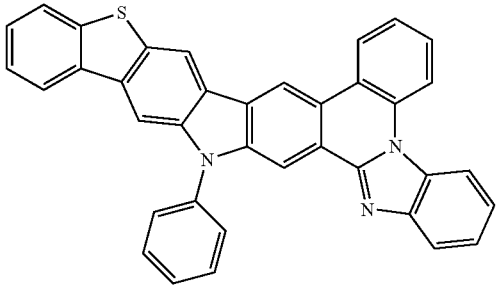

DFE-6SB-1

To a flame-dried flask were added Pd(PPh₃)₄ (10 mol %), Xantphos (10 mol %), Cs₂CO₃ (3 eq) and 1,2-dibromobenzene (1.2 eq). Then, 6SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-6SB-1 in 59% yield.

Example 59

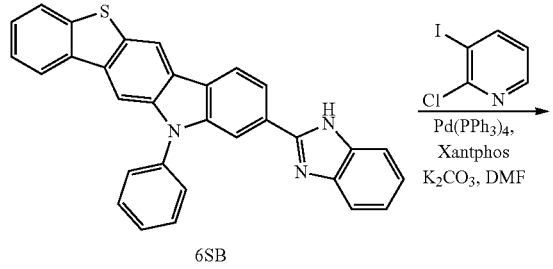

6SB

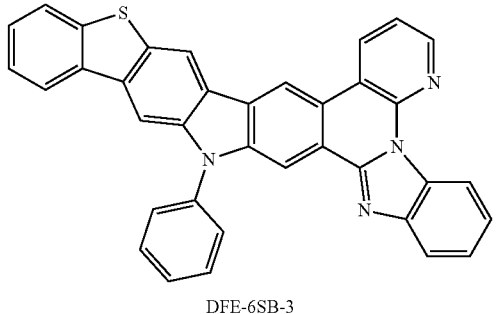

DFE-6SB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 6SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-6SB-3 in 28% yield.

Example 61

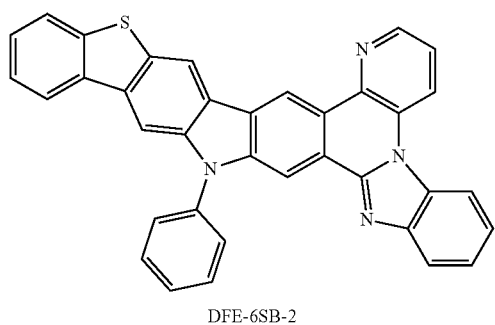

DFE-6SB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 6SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-6SB-2 in 39% yield.

Example 60

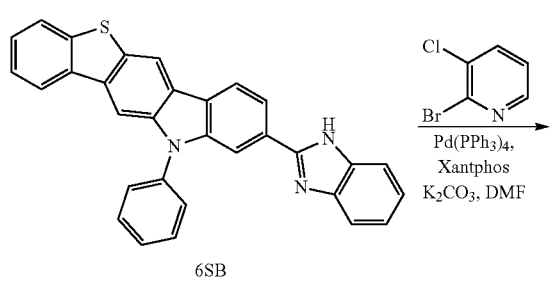

6SB

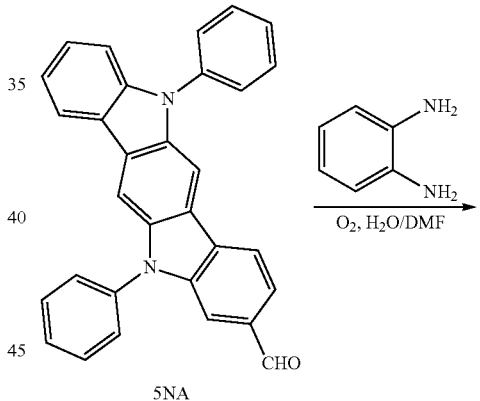

5NA

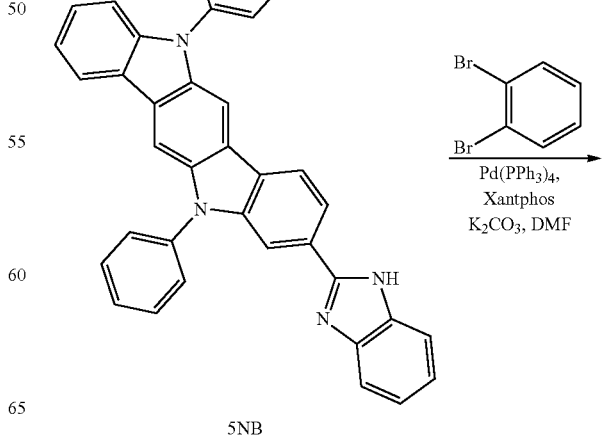

5NB

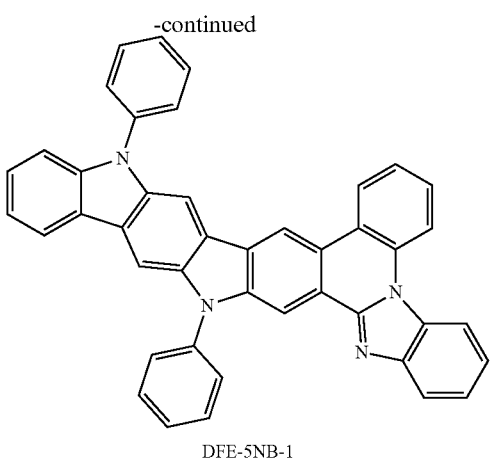

DFE-5NB-1

To a flame-dried flask were added Pd(PPh$_3$)$_4$ (10 mol %), Xantphos (10 mol %), Cs$_2$CO$_3$ (3 eq) and 1,2-dibromobenzene (1.2 eq). Then, 5NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-5NB-1 in 54% yield.

Example 62

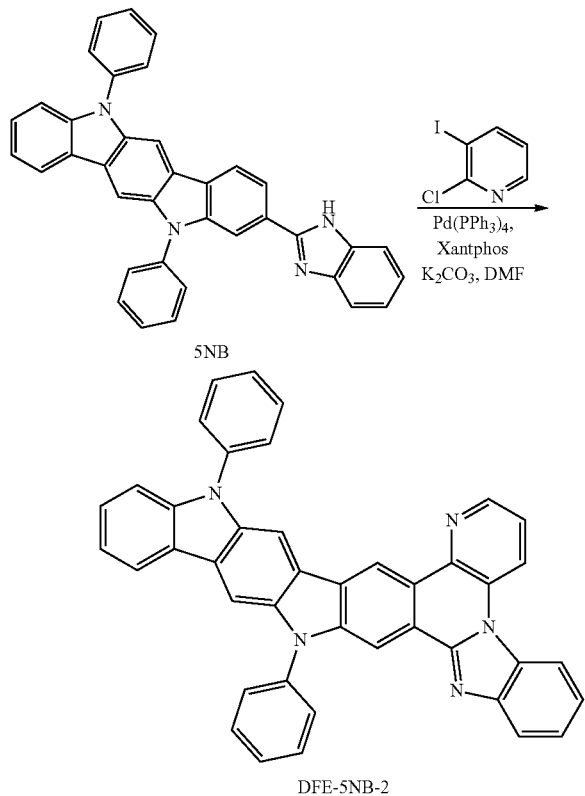

DFE-5NB-2

To a flame-dried flask were added Pd(PPh$_3$)$_4$ (10 mol %), Xantphos (10 mol %), Cs$_2$CO$_3$ (3 eq) and 2-chloro-3-iodopyridine (1.2 eq). Then, 5NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-5NB-2 in 43% yield.

Example 63

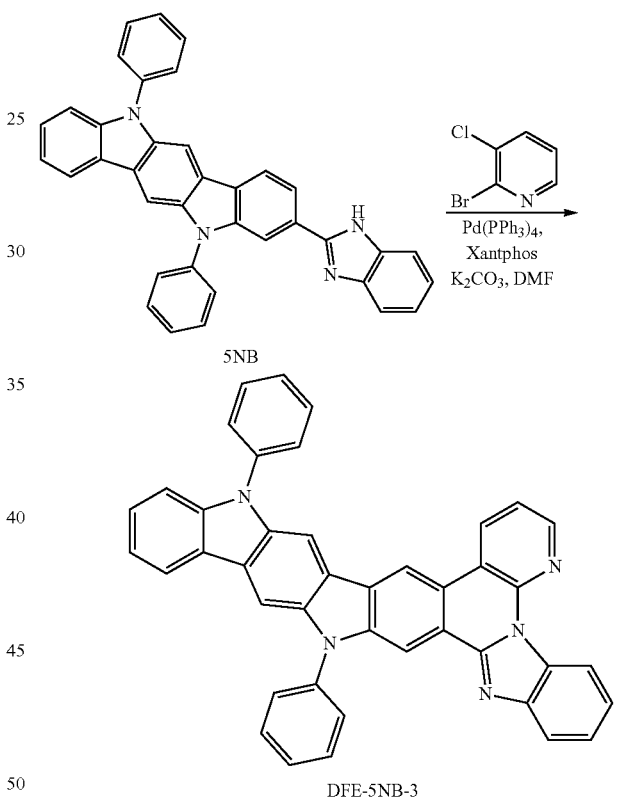

DFE-5NB-3

To a flame-dried flask were added Pd(PPh$_3$)$_4$ (10 mol %), Xantphos (10 mol %), Cs$_2$CO$_3$ (3 eq) and 2-bromo-3-chloropyridine (1.2 eq). Then, 5NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-5NB-3 in 25% yield.

Example 64

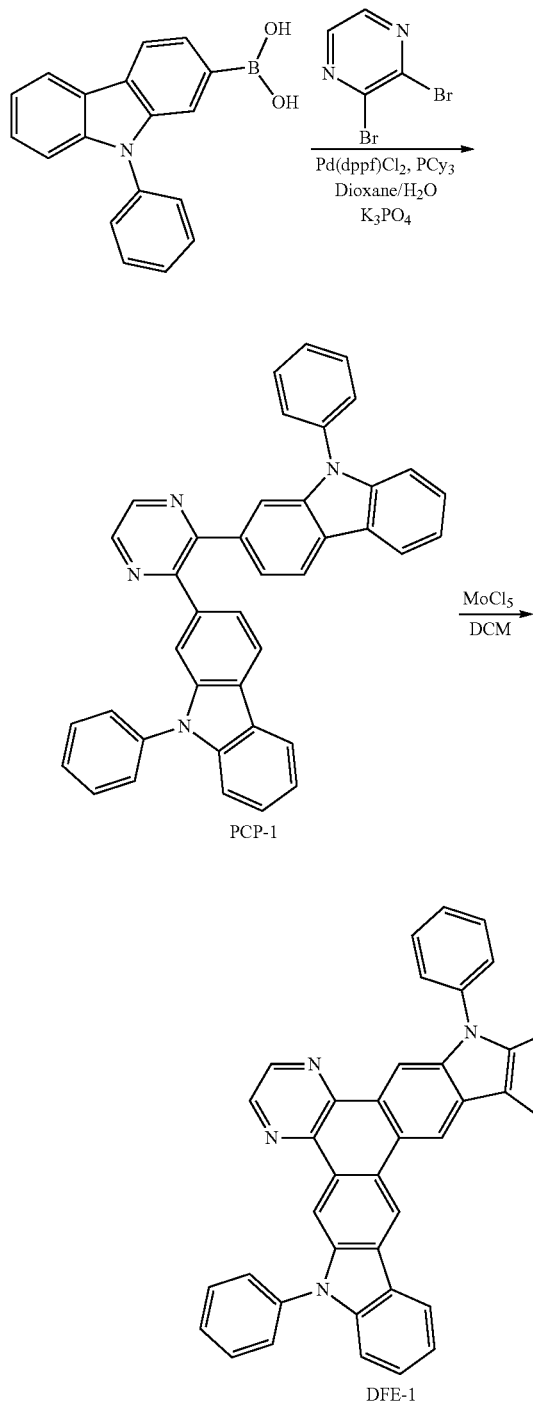

Example 65

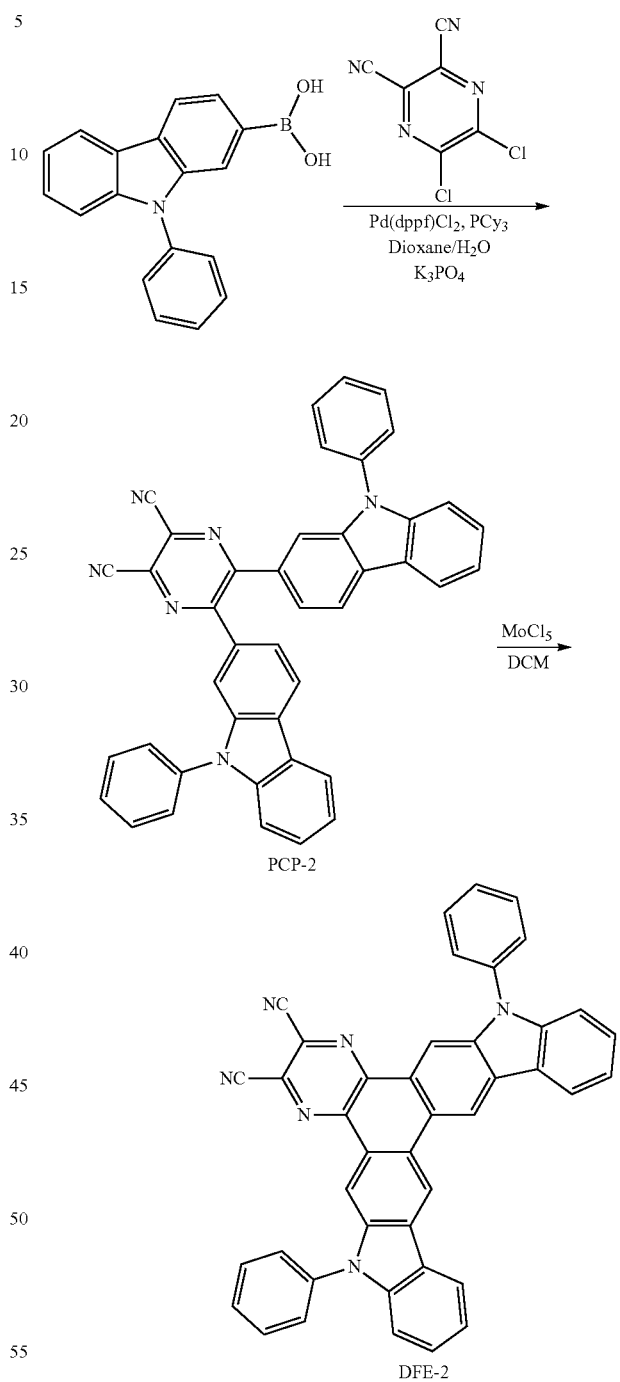

MoCl$_5$ (1.0 equiv) was added quickly to a solution of PCP-1 (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-1 in 45% yield.

MoCl$_5$ (1.0 equiv) was added quickly to a solution of PCP-2 (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-2 in 41% yield.

Example 66

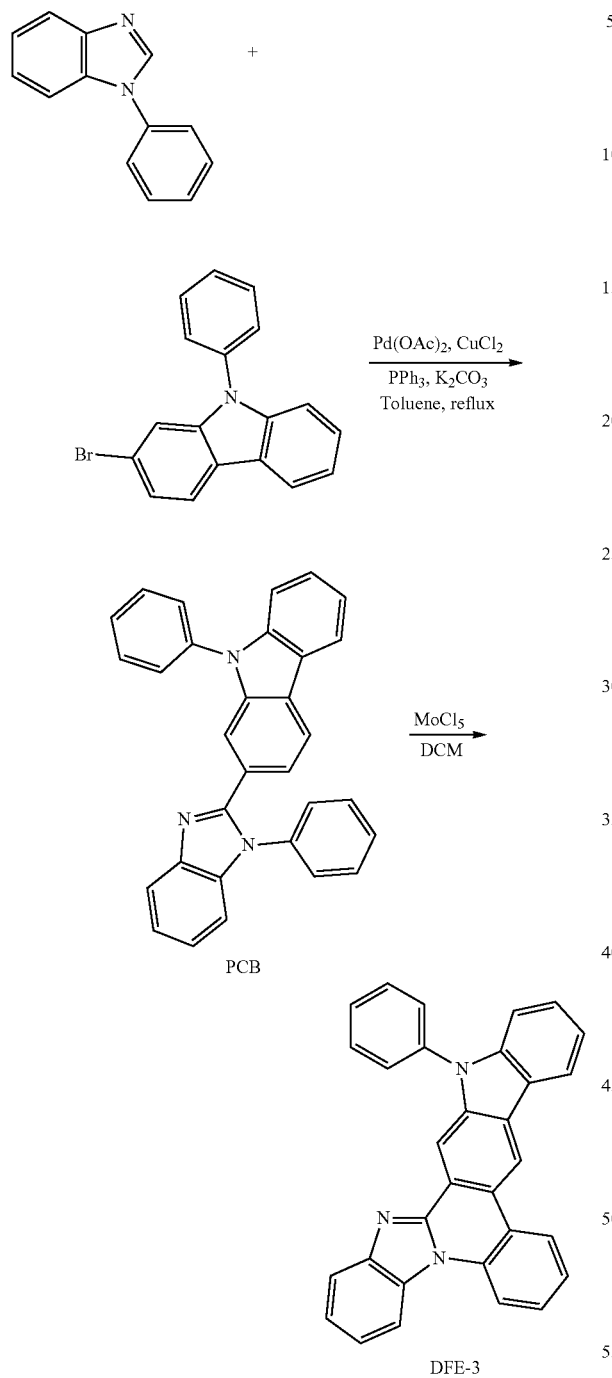

MoCl₅ (1.0 equiv) was added quickly to a solution of PCB (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-3 in 38% yield.

Example 67

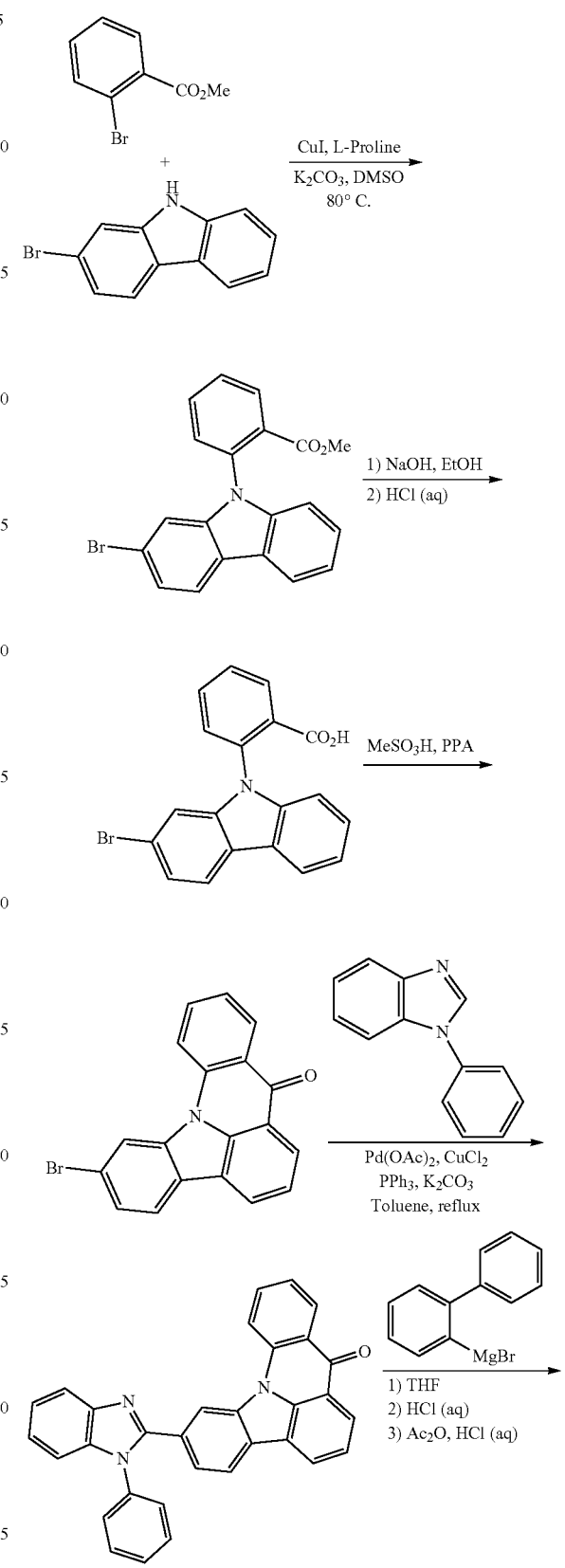

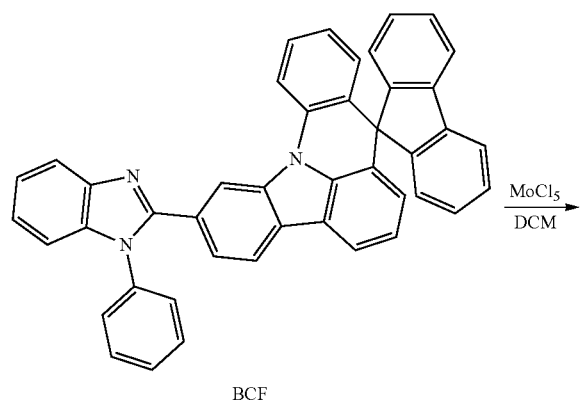

BCF

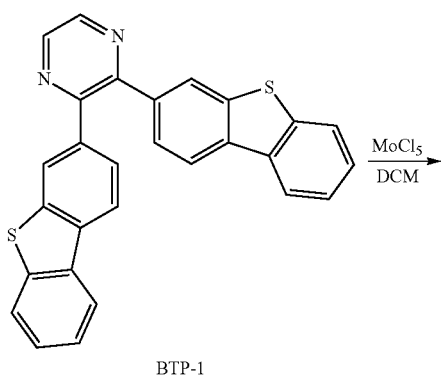

BTP-1

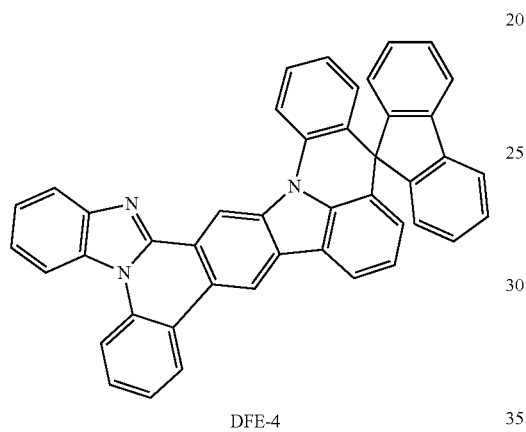

DFE-4

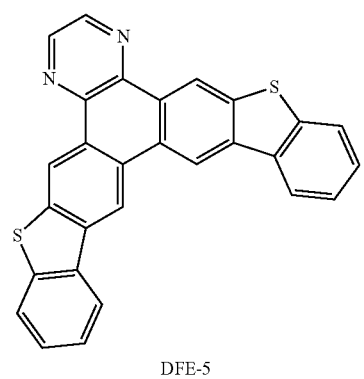

DFE-5

MoCl$_5$ (1.0 equiv) was added quickly to a solution of BCF (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-4 in 42% yield.

Example 68

MoCl$_5$ (1.0 equiv) was added quickly to a solution of BTP-1 (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-5 in 49% yield.

Example 69

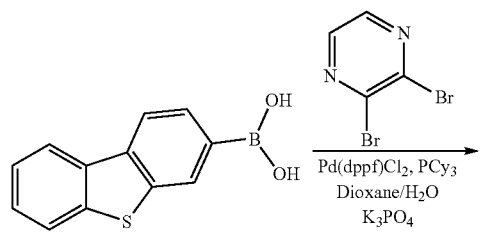

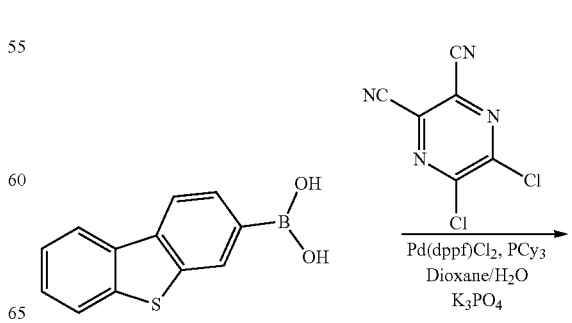

-continued

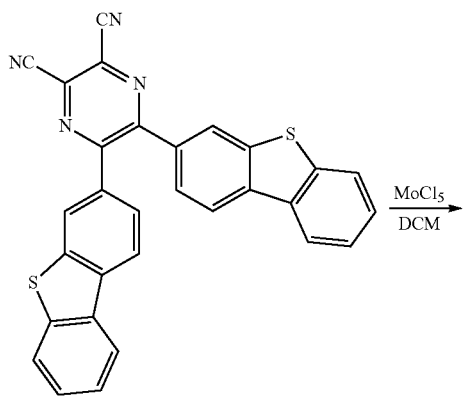

BTP-2

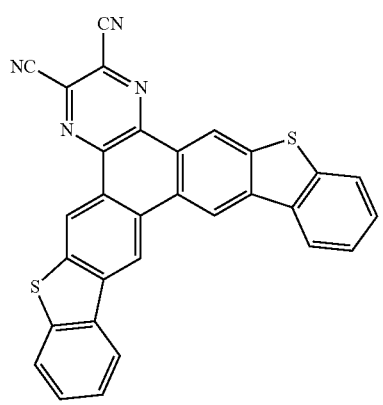

DFE-6

MoCl₅ (1.0 equiv) was added quickly to a solution of BTP-2 (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-6 in 38% yield.

Example 70

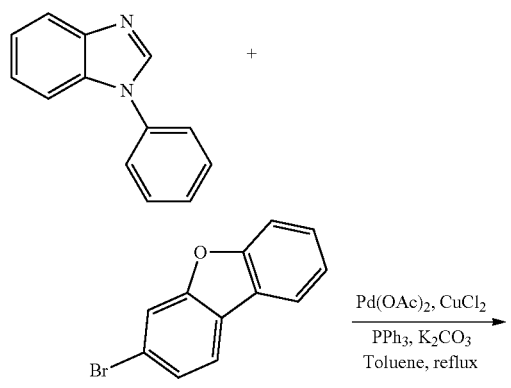

-continued

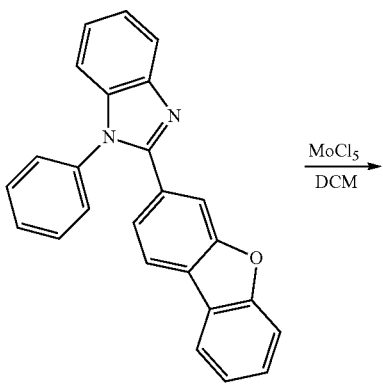

BFB

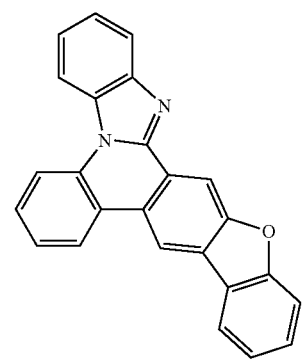

DFE-7

MoCl₅ (1.0 equiv) was added quickly to a solution of BFB (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-7 in 34% yield.

Example 71

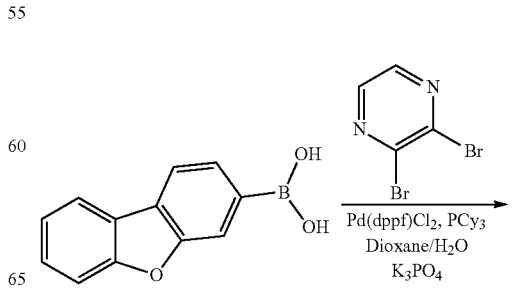

-continued

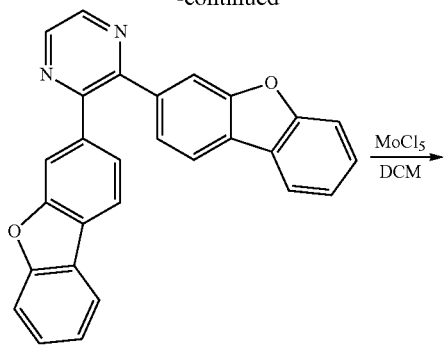

BFP

MoCl₅ / DCM →

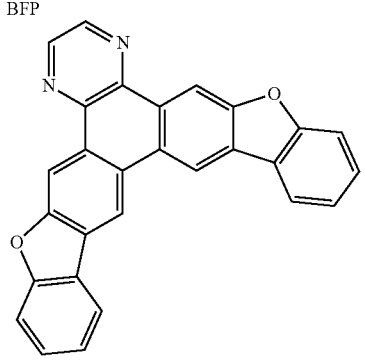

DFE-8

MoCl₅ (1.0 equiv) was added quickly to a solution of BFP (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-8 in 52% yield.

Example 72

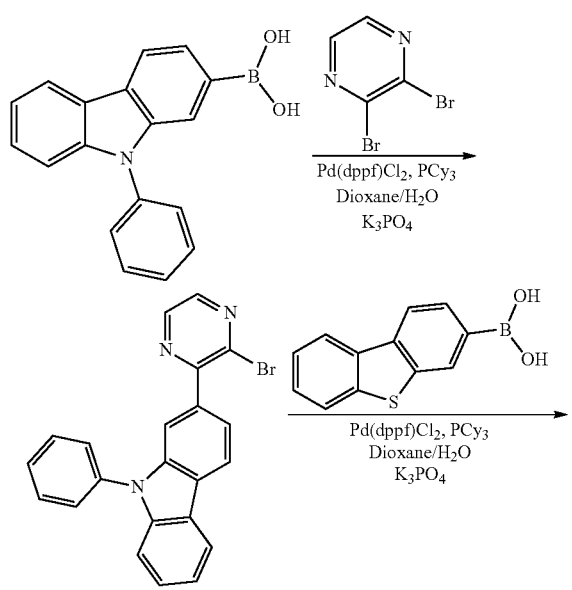

-continued

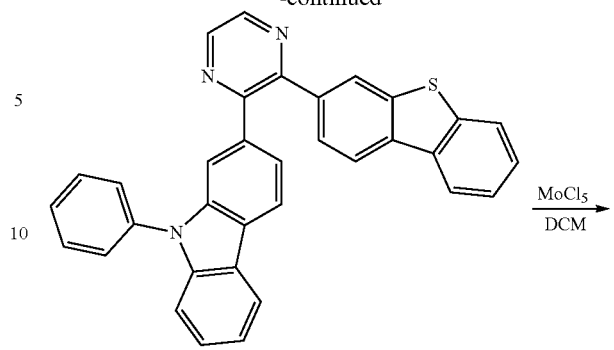

PCBTP

MoCl₅ / DCM →

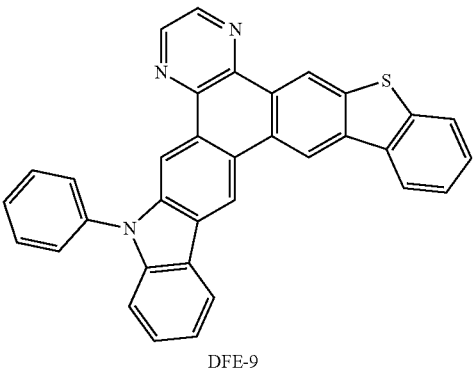

DFE-9

MoCl₅ (1.0 equiv) was added quickly to a solution of PCBTP (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-8 in 49% yield.

Example 73

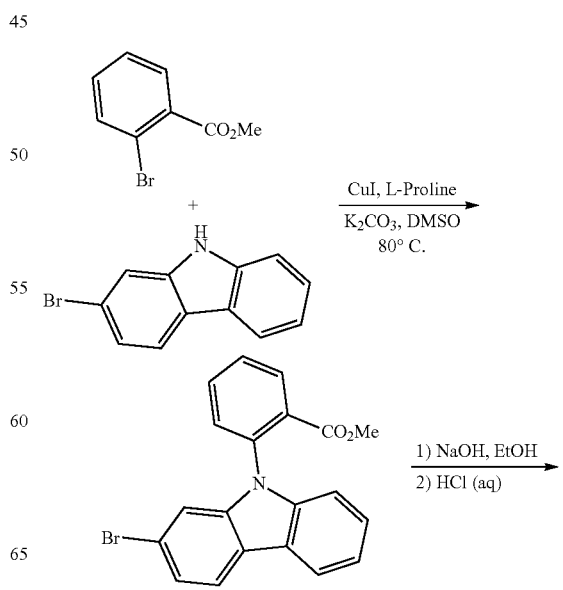

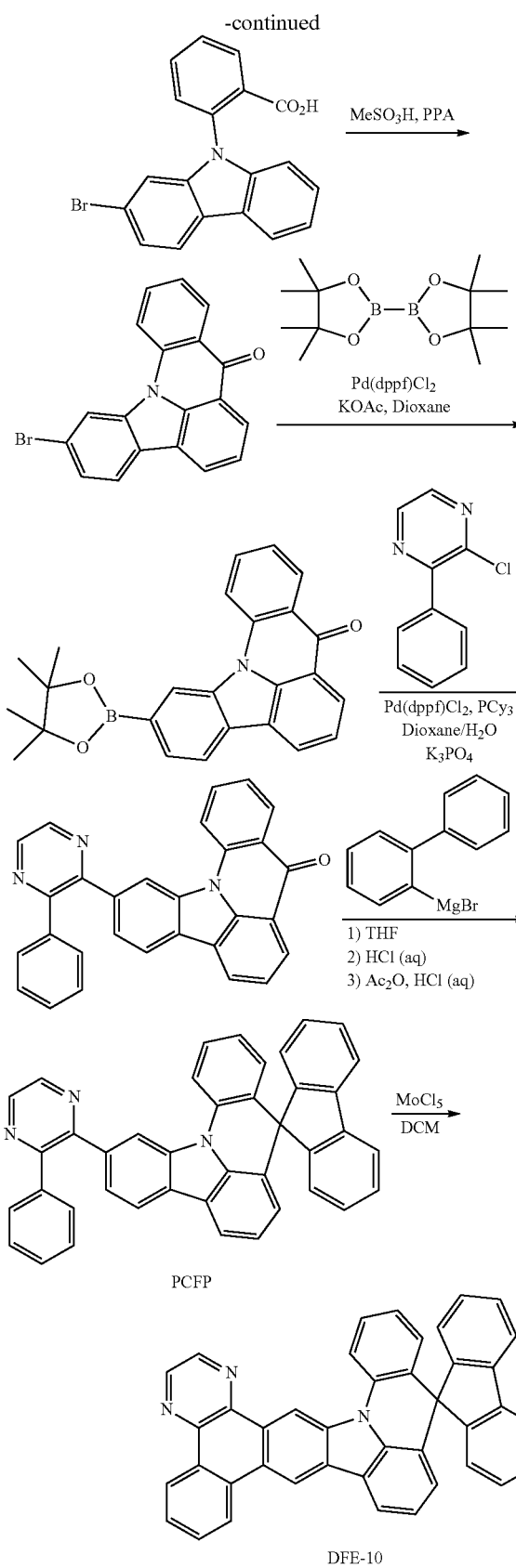

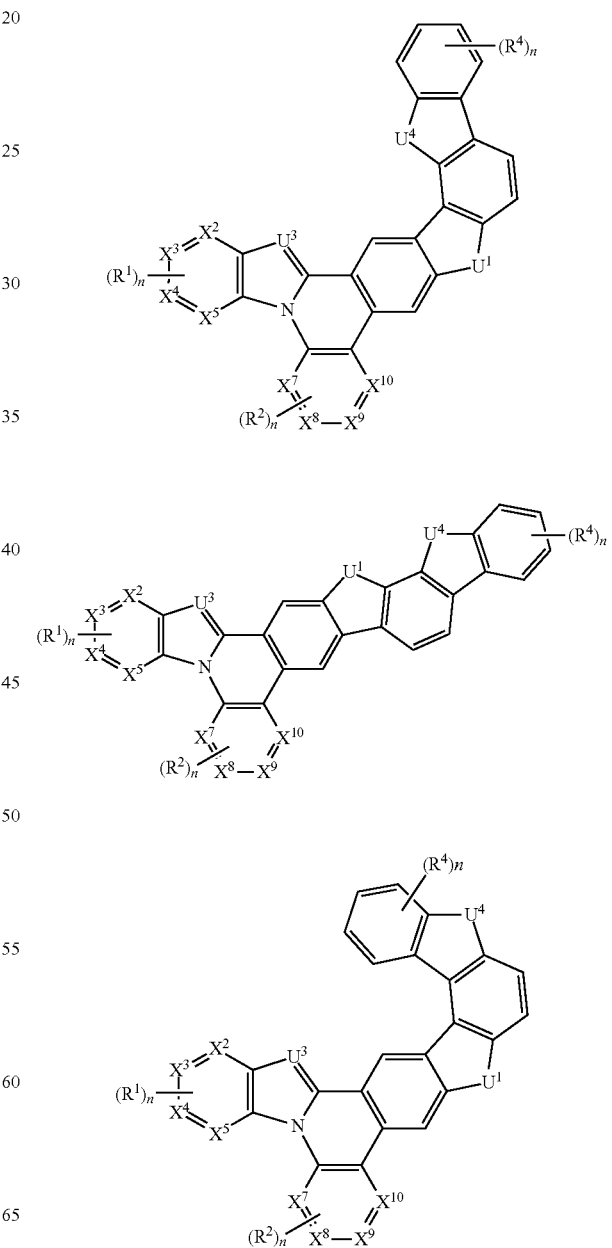

mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂C₂. The filtrate was concentrated, and the residue was purified through column chromatography on silica gel to afford the product DFE-10 in 33% yield.

Only a few implementations are described and illustrated. Variations, enhancements and improvements of the described implementations and other implementations can be made based on what is described and illustrated in this document.

What is claimed is:

1. A compound represented by one of the following structures:

MoCl₅ (1.0 equiv) was added quickly to a solution of PCFP (1.00 equiv) in CH₂Cl₂ (0.05 M) under nitrogen. The -continued
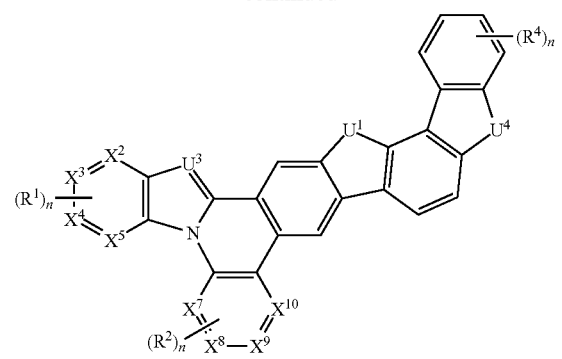
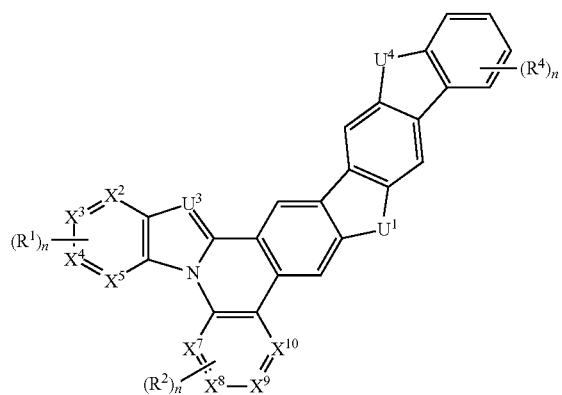
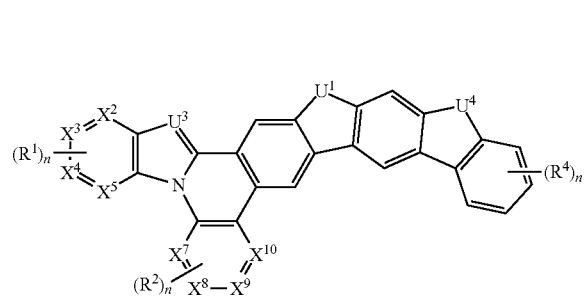
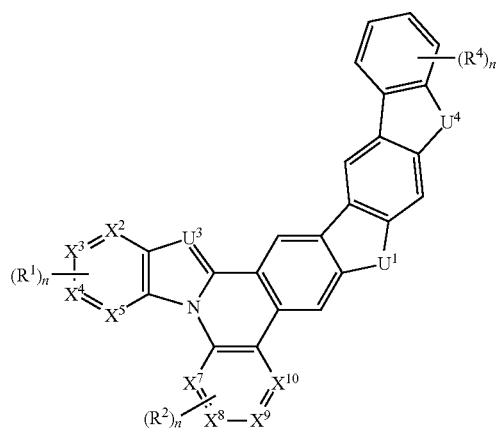
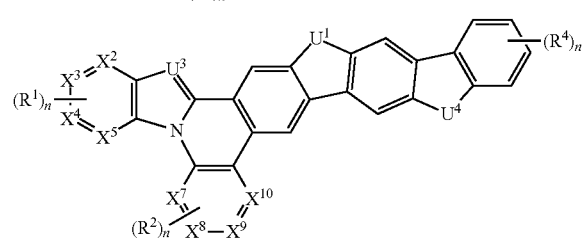
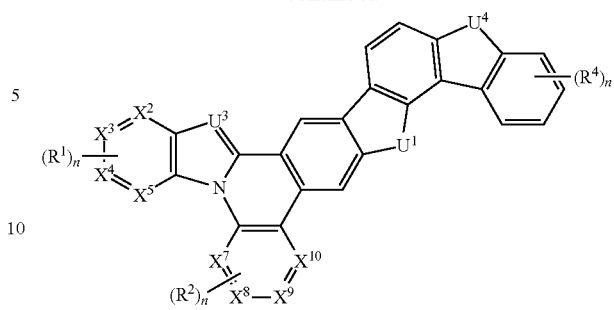
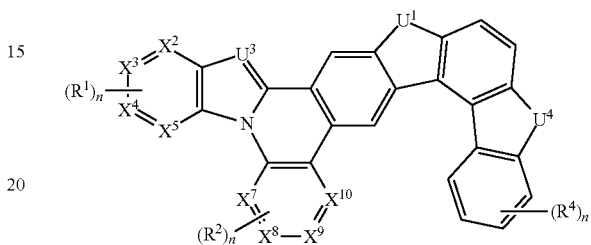
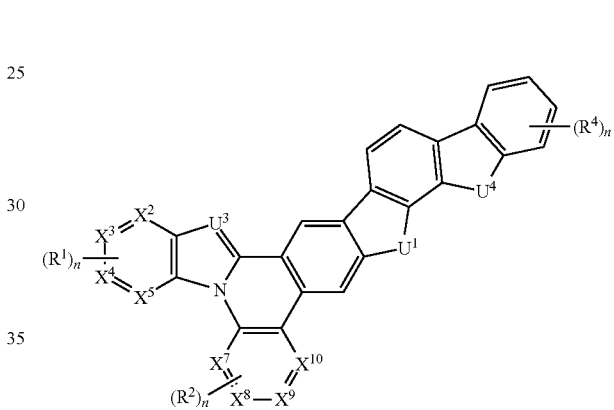
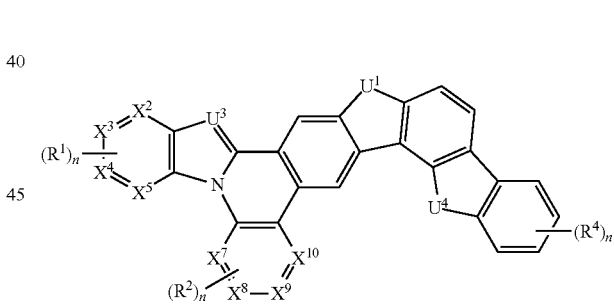
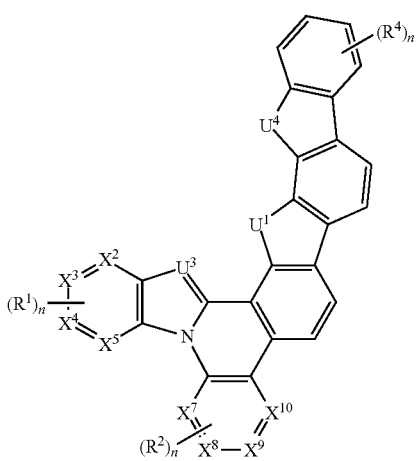

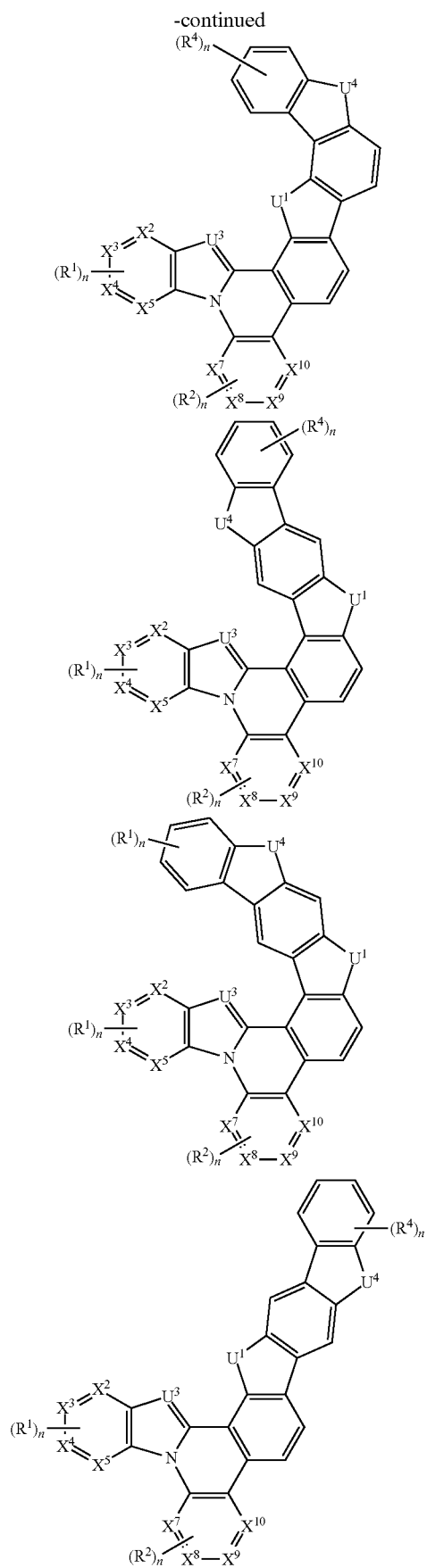
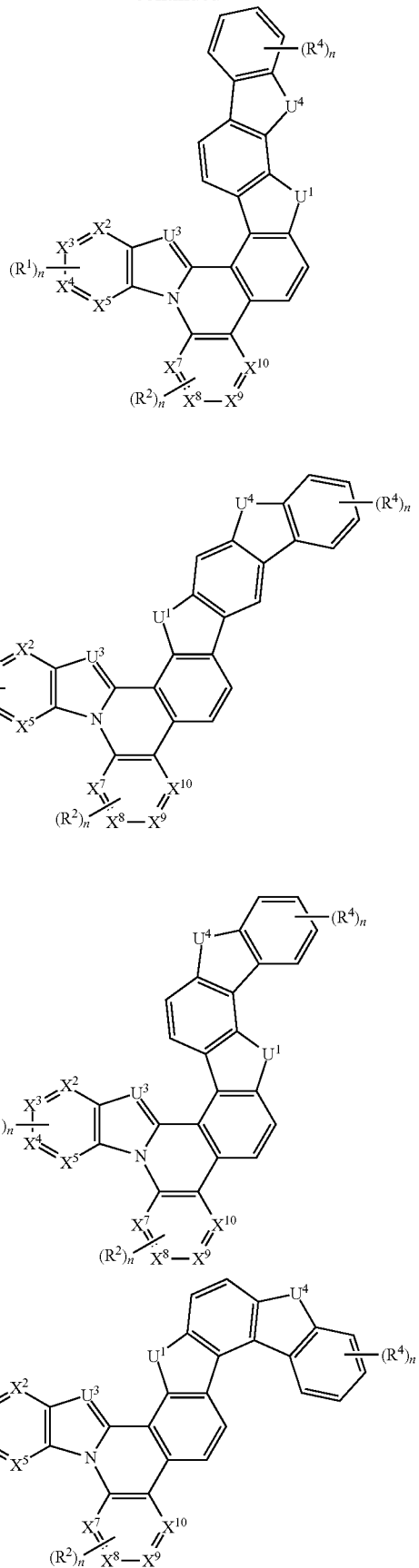

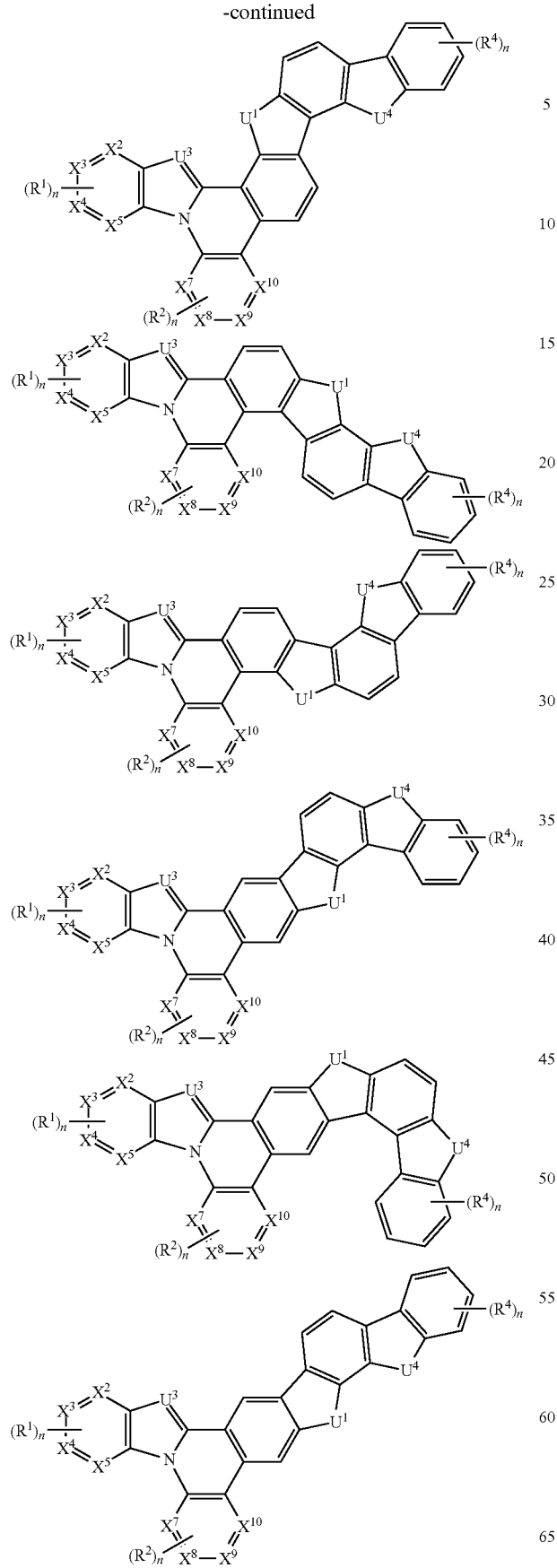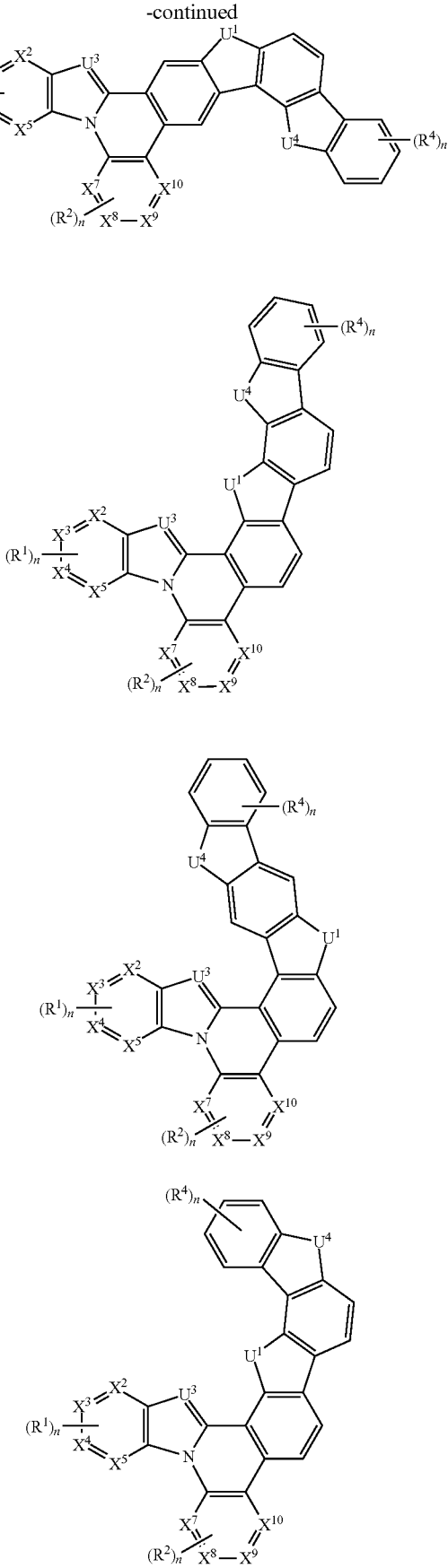

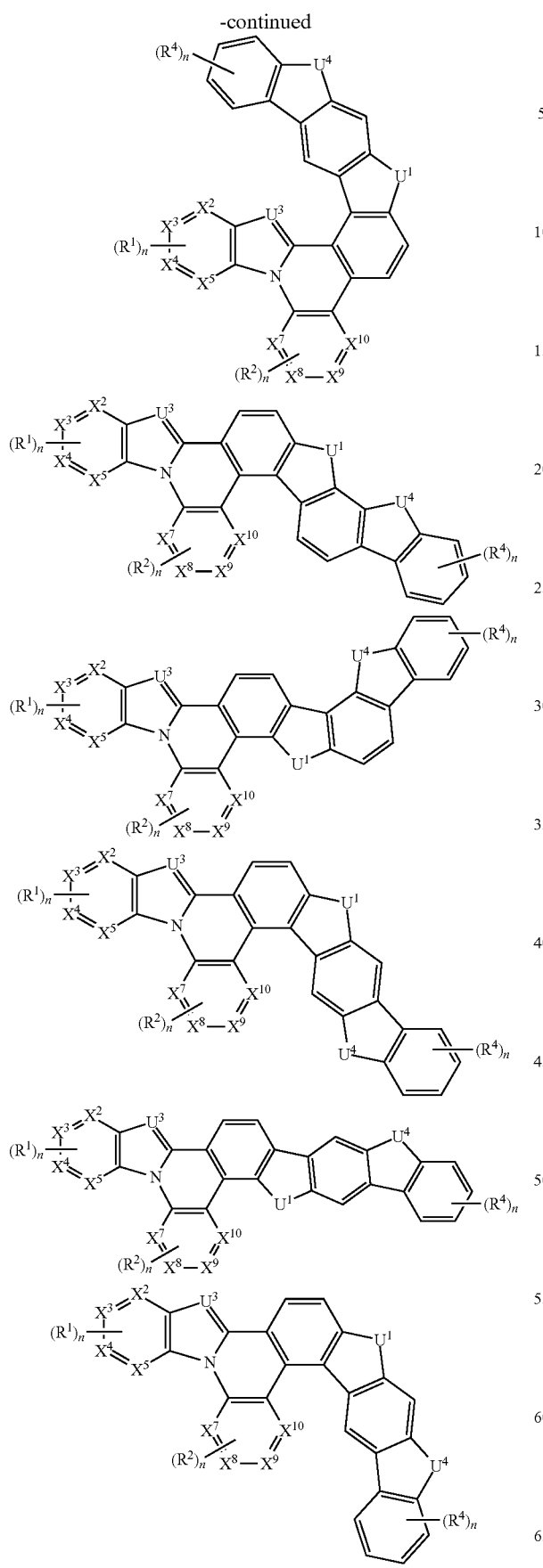
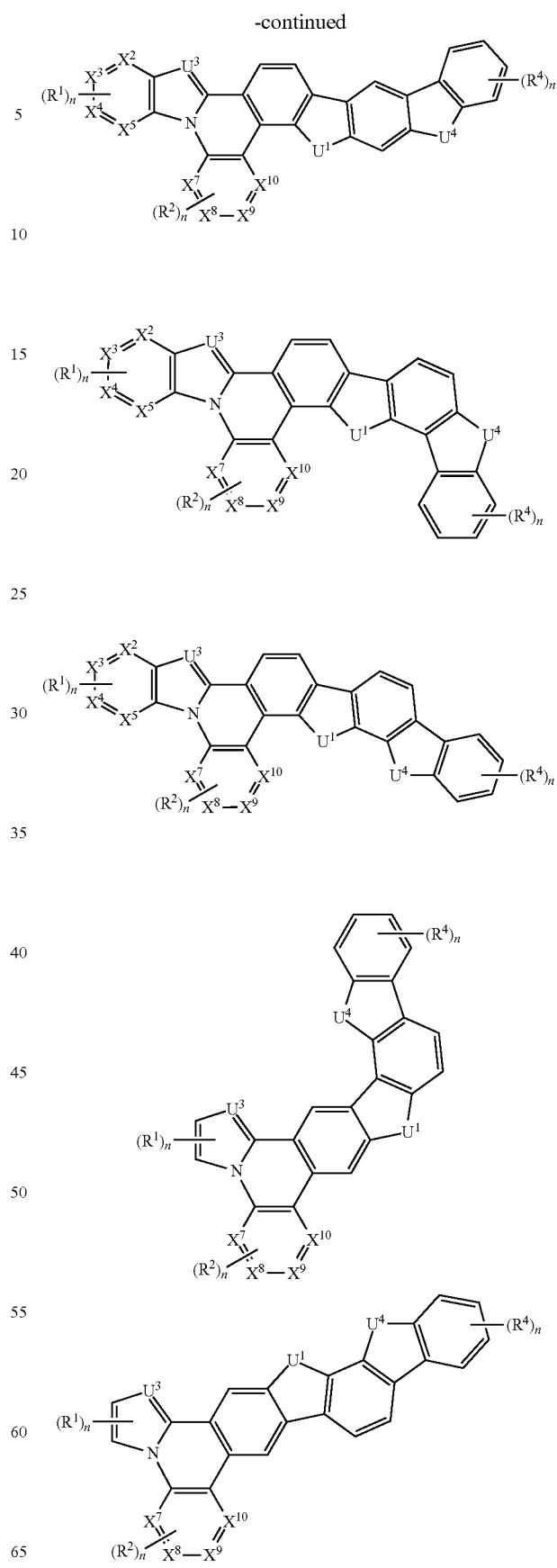

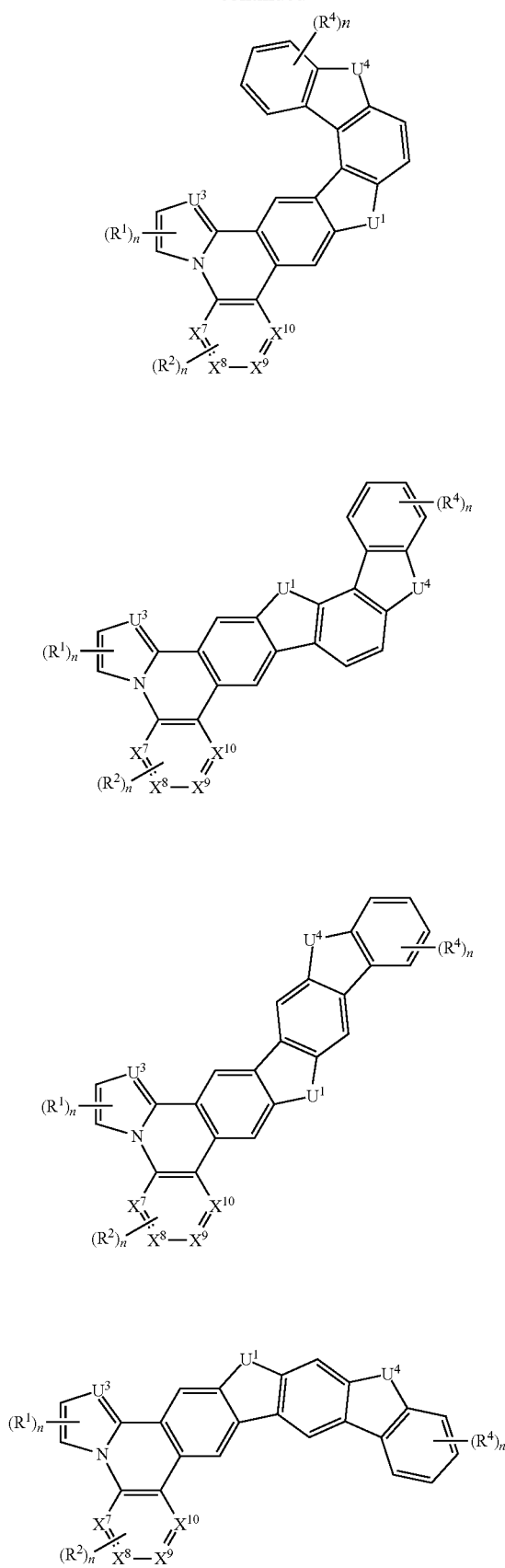
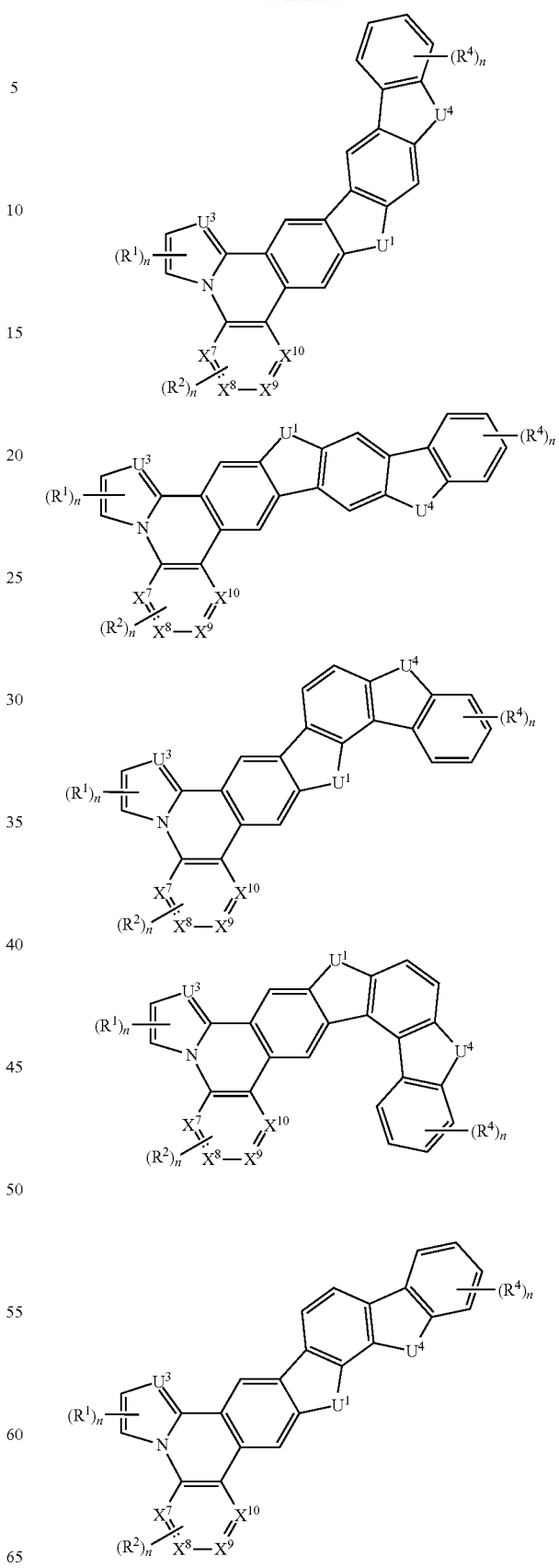

275
-continued
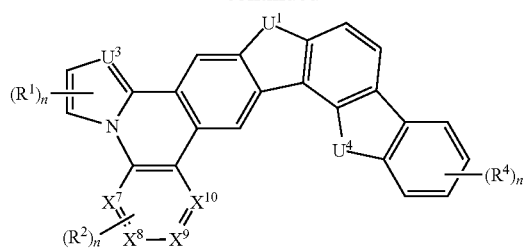
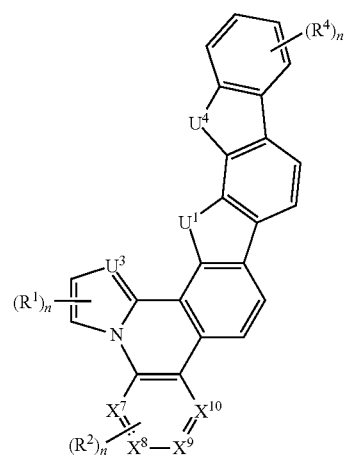
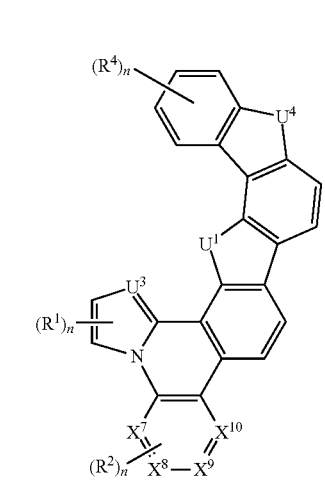
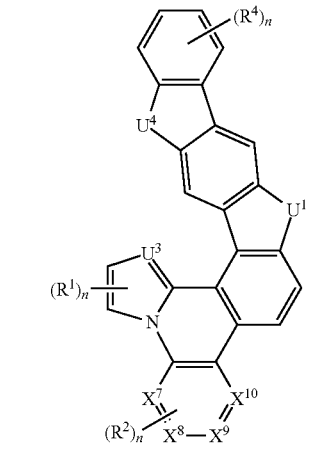
276
-continued
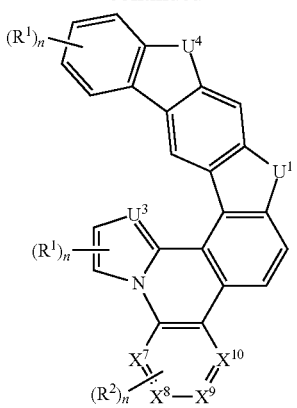
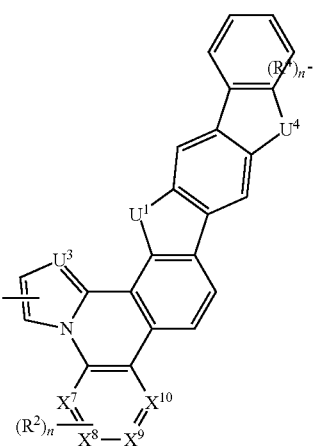
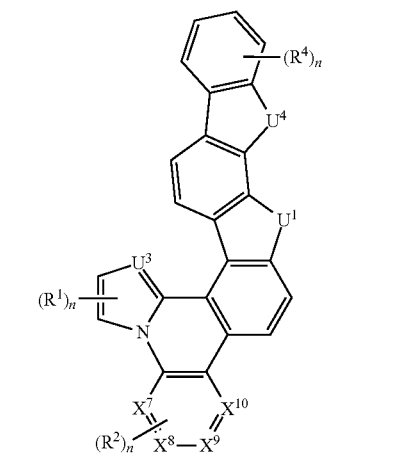
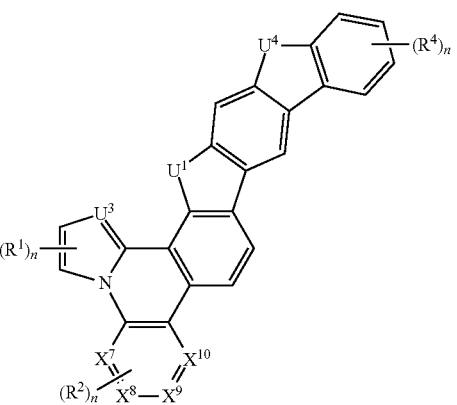

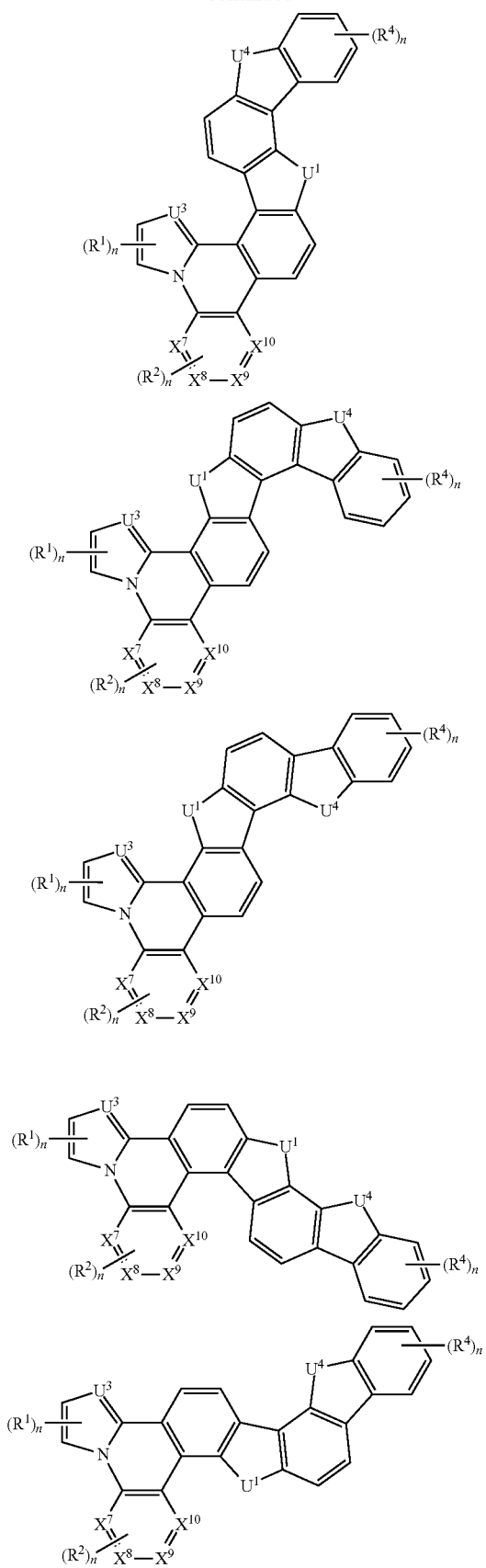
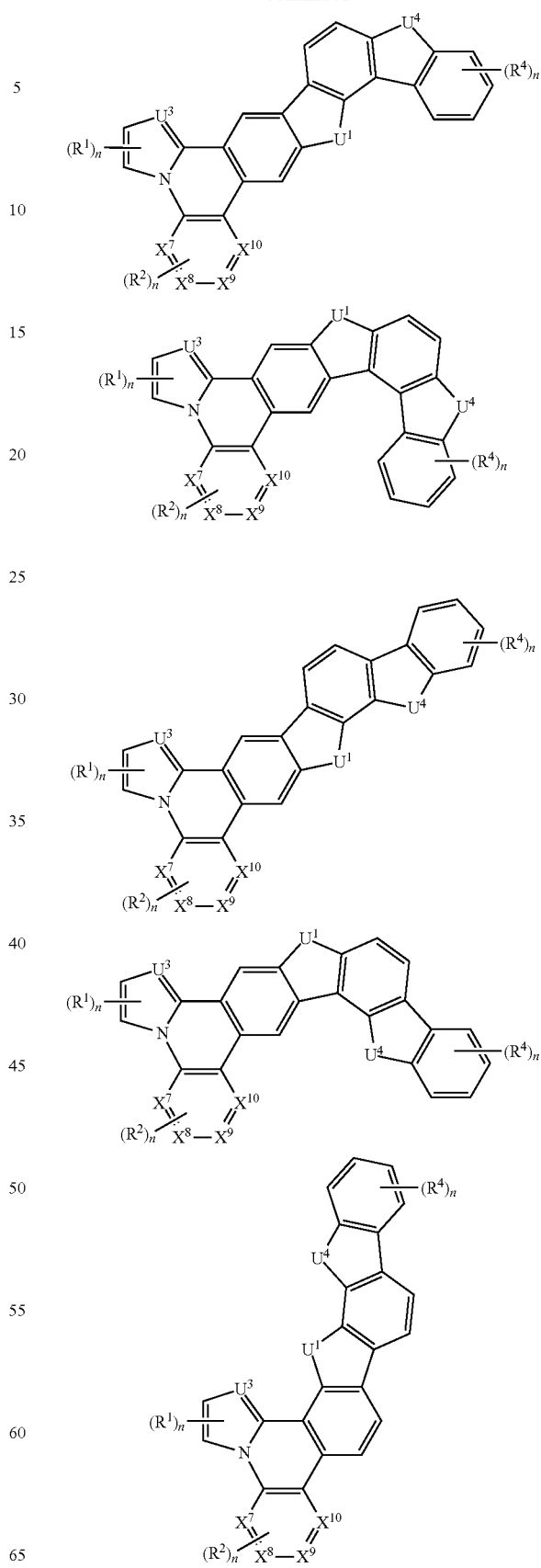

-continued
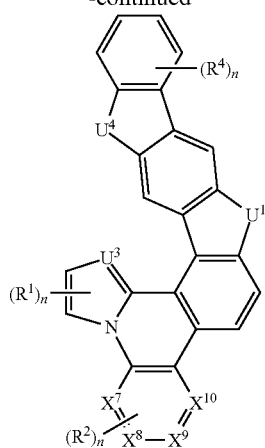
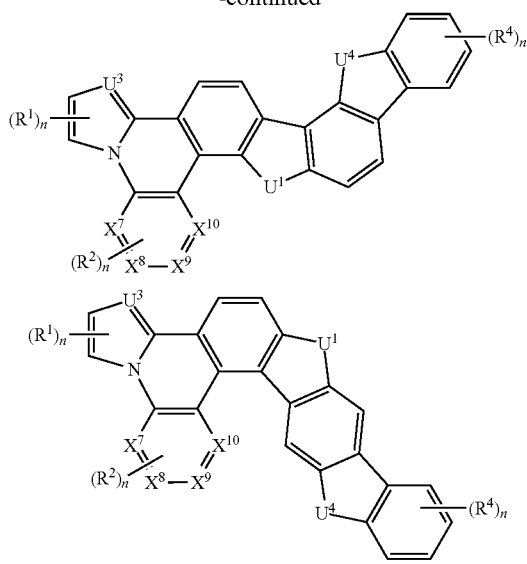
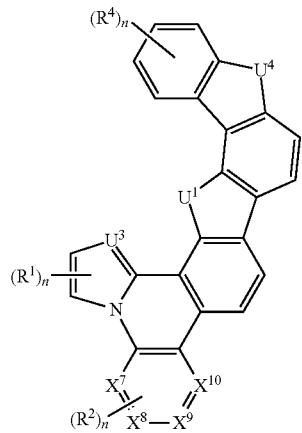
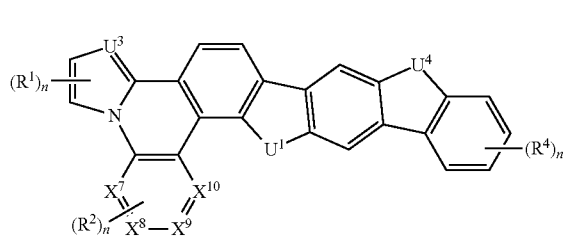
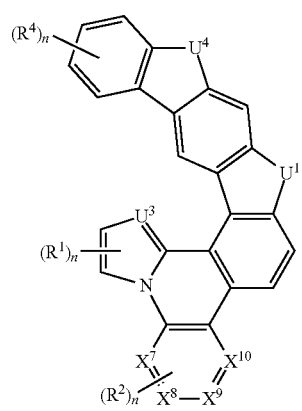
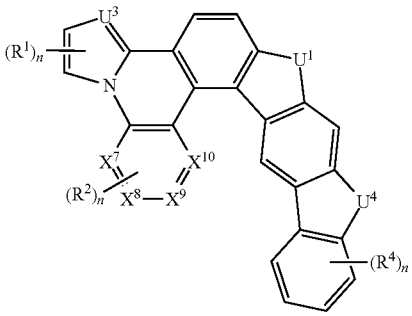
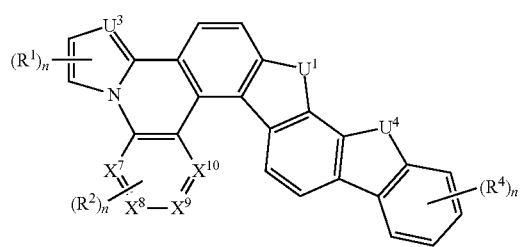
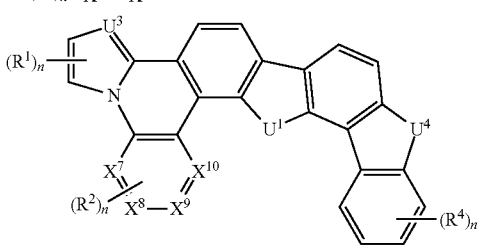

-continued
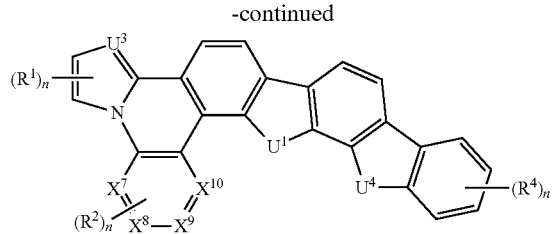
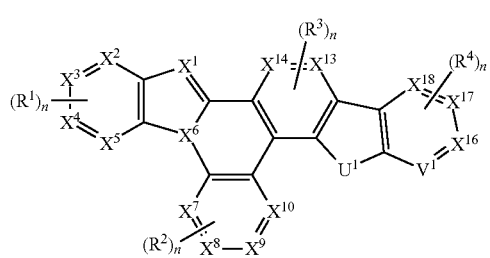
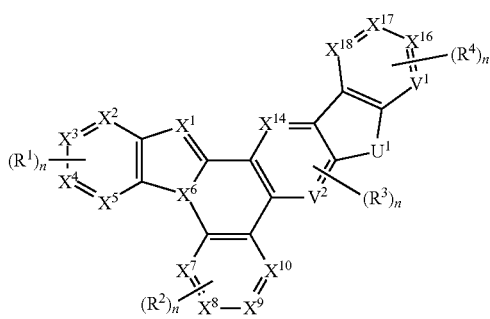
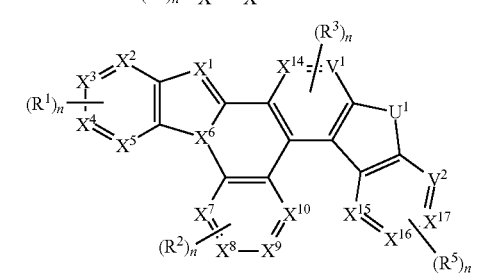
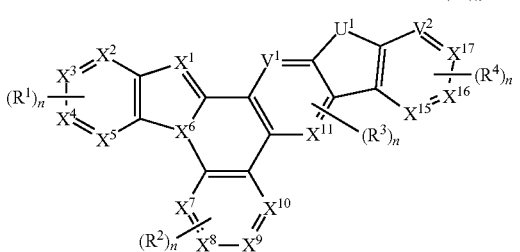
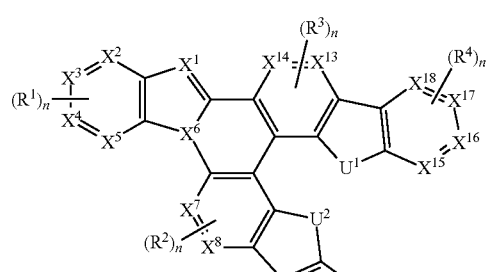
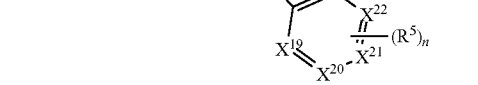
-continued
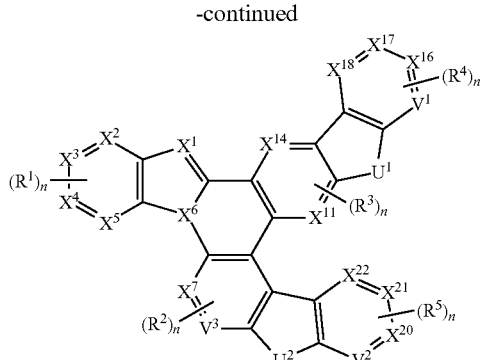
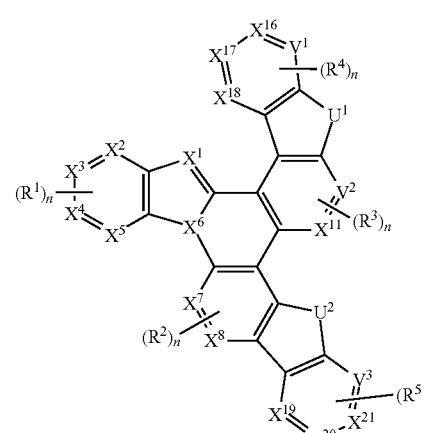
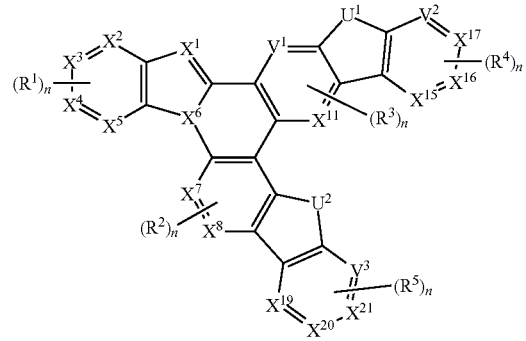
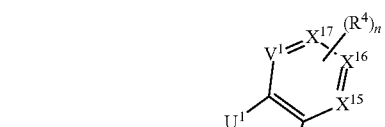
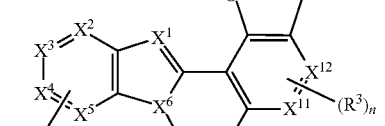
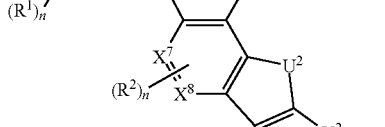

-continued
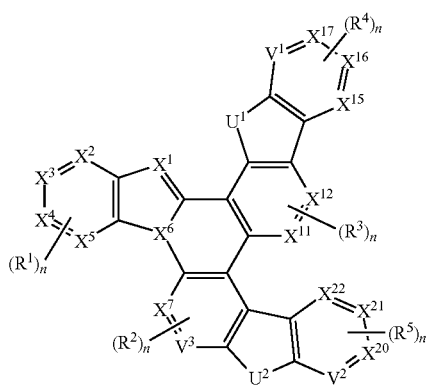
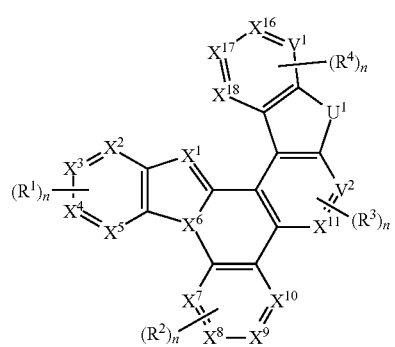
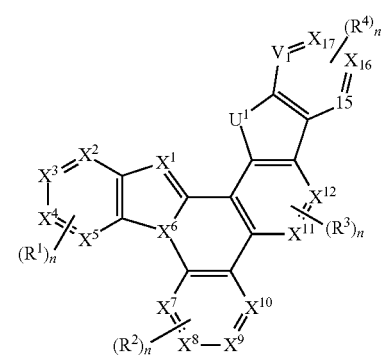
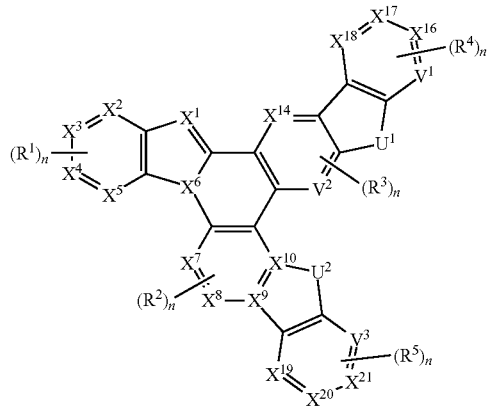
-continued
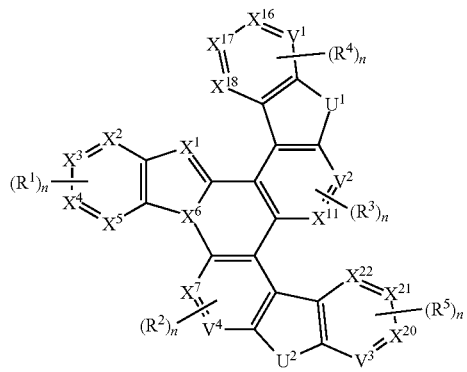
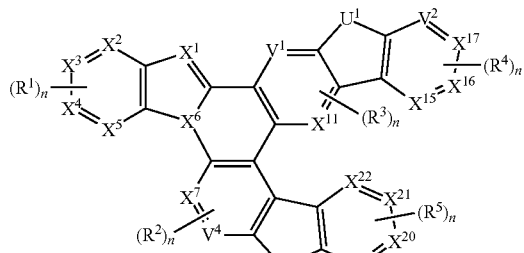
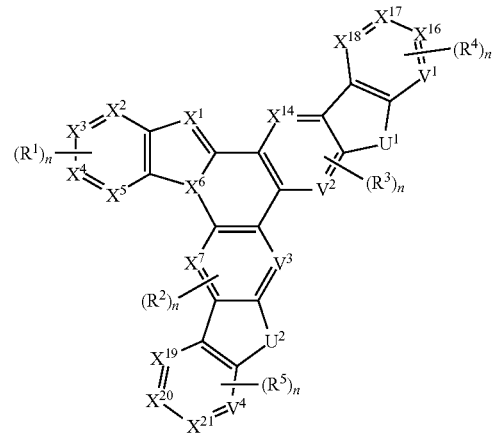
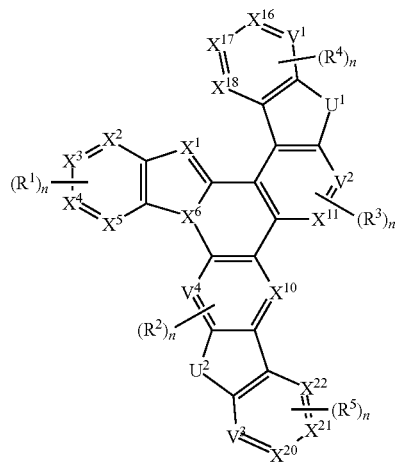

-continued
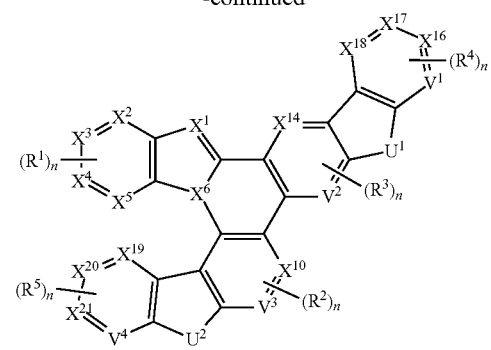
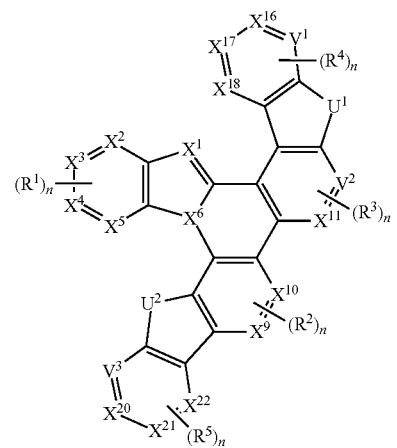
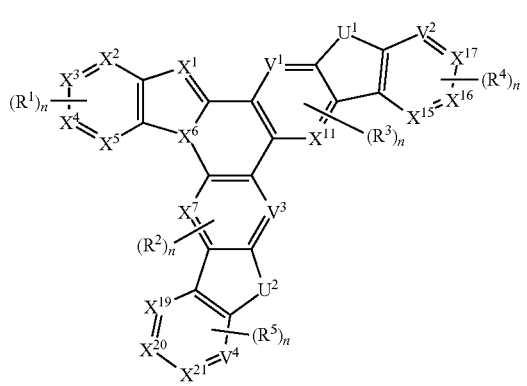
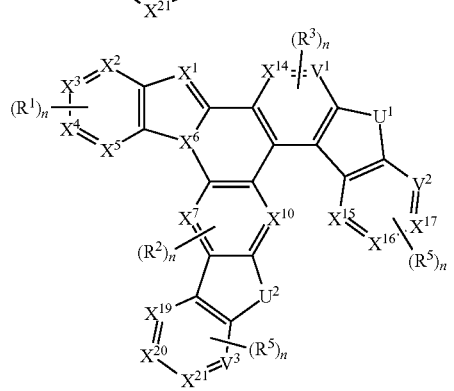
-continued
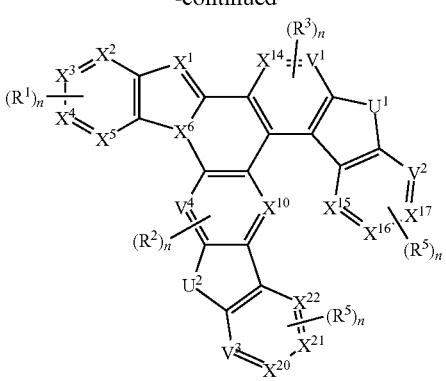
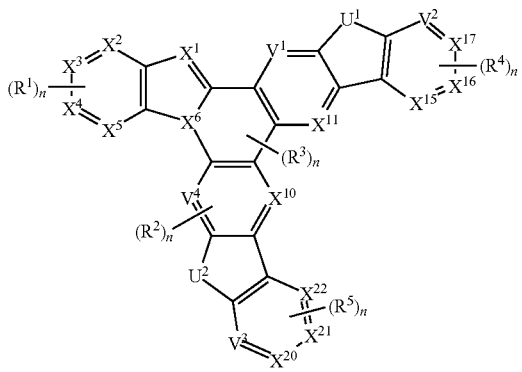
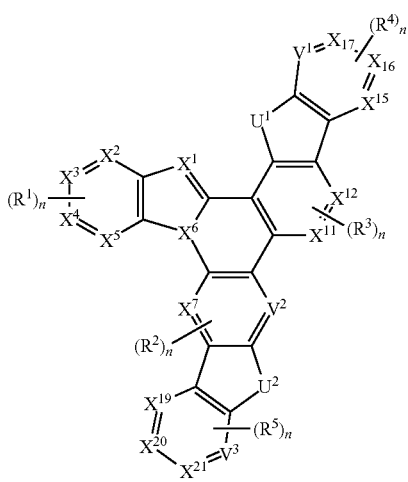
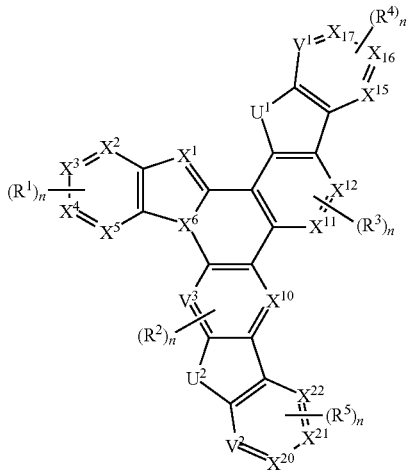

-continued
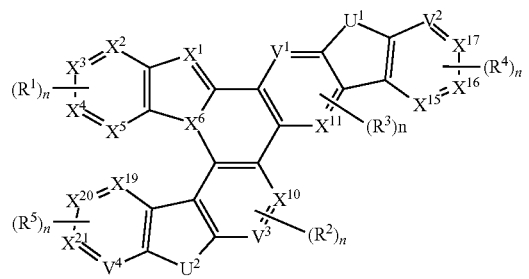
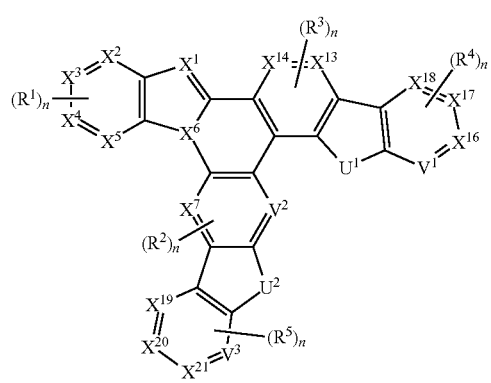
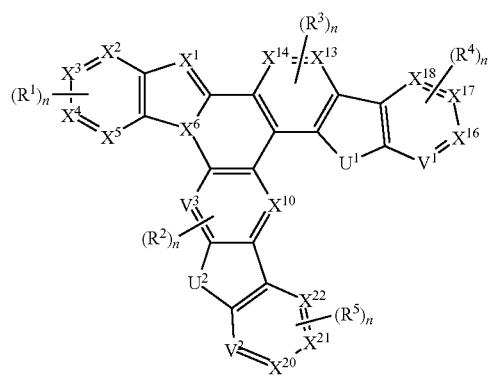
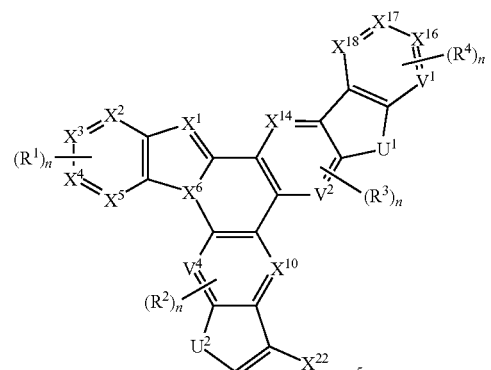
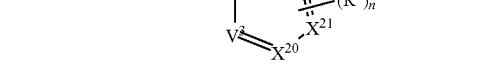
-continued
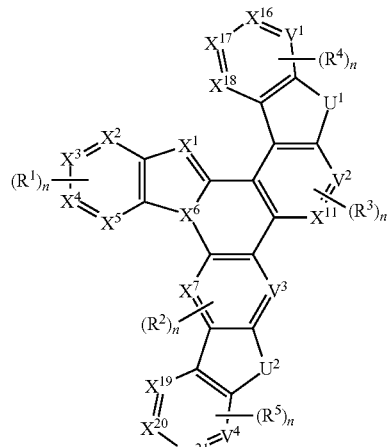
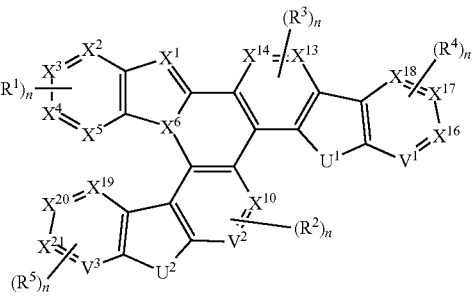
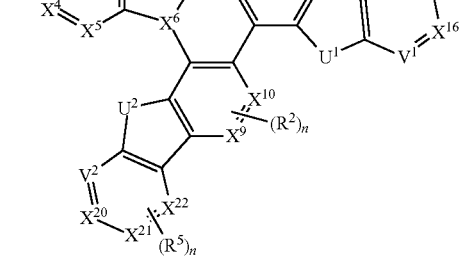
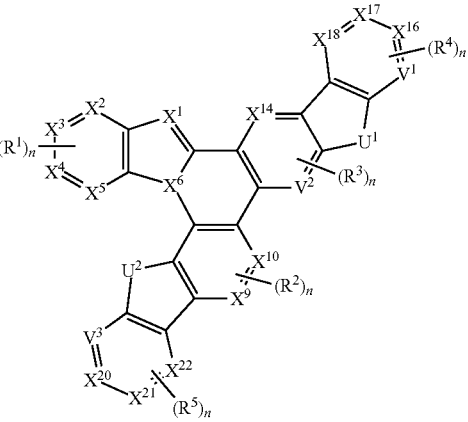

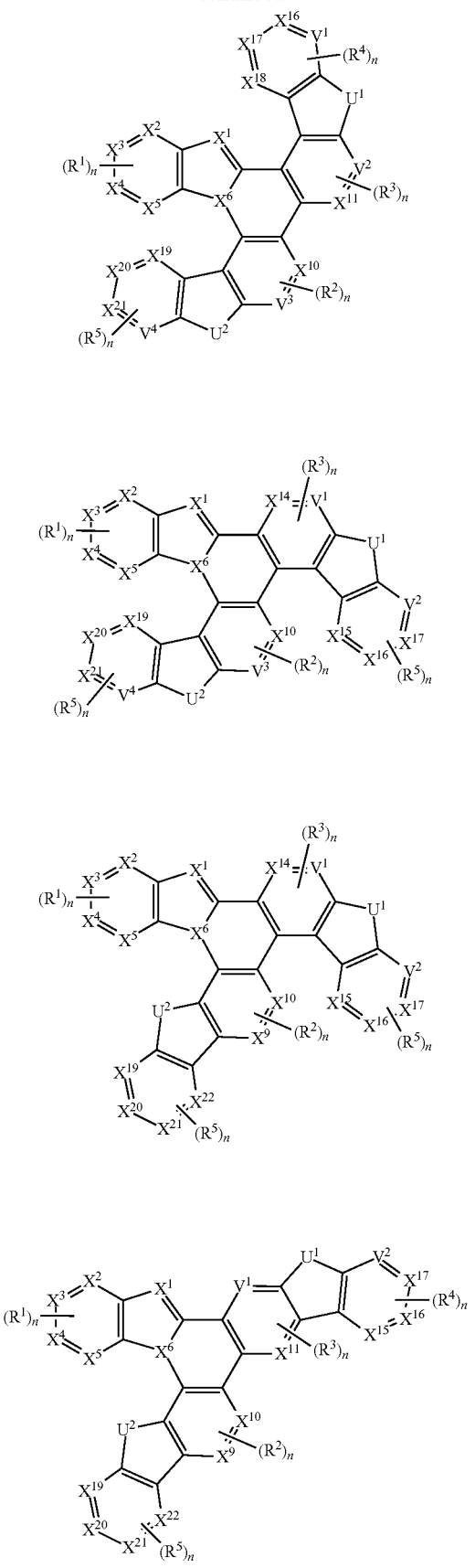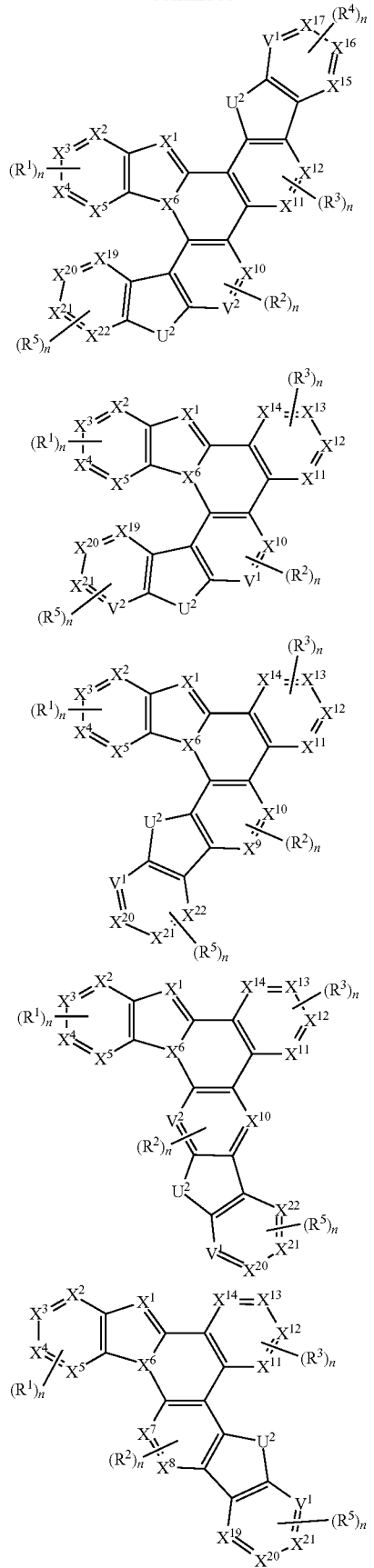

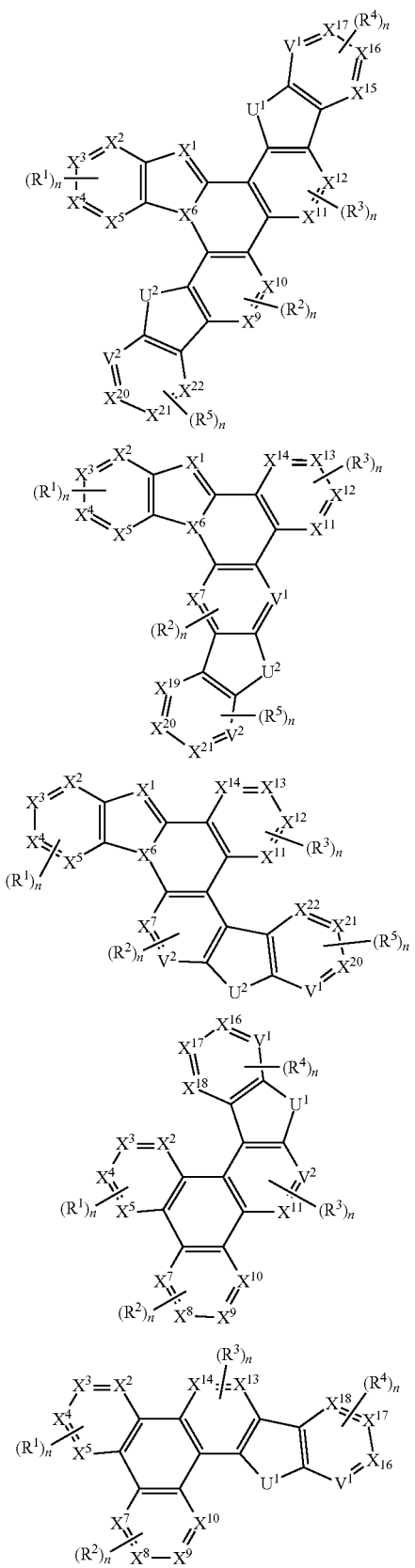
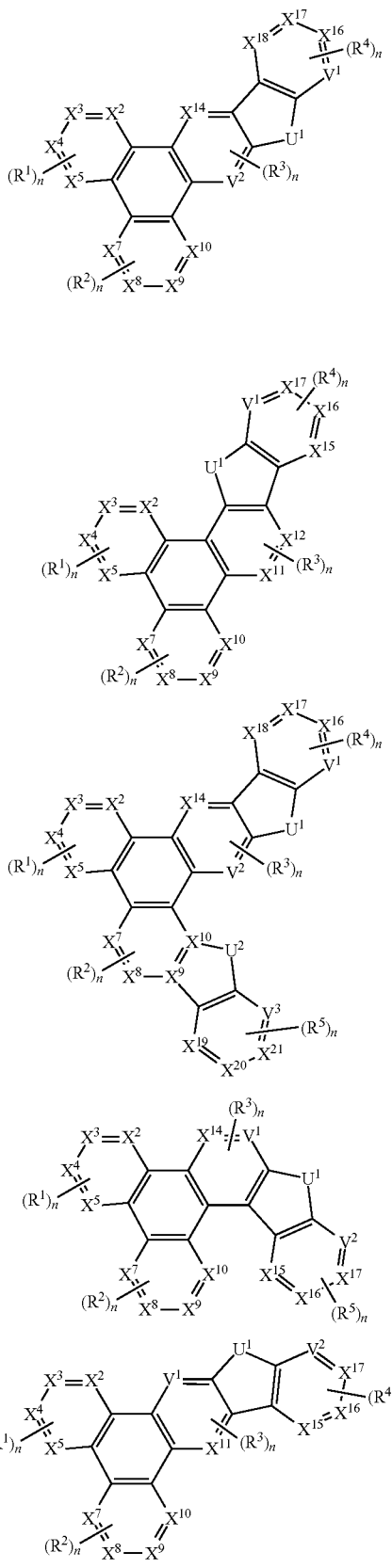

-continued
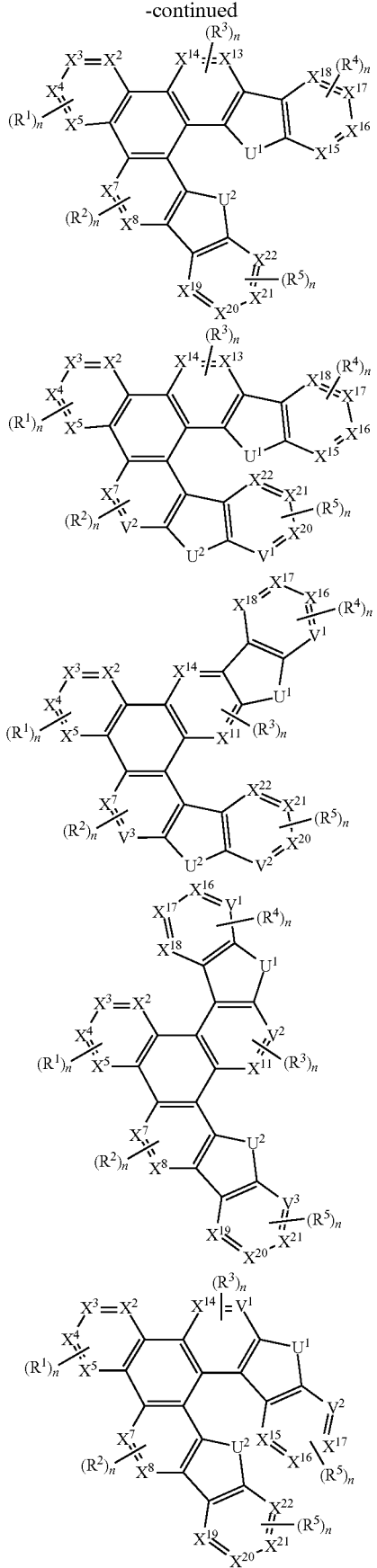
-continued
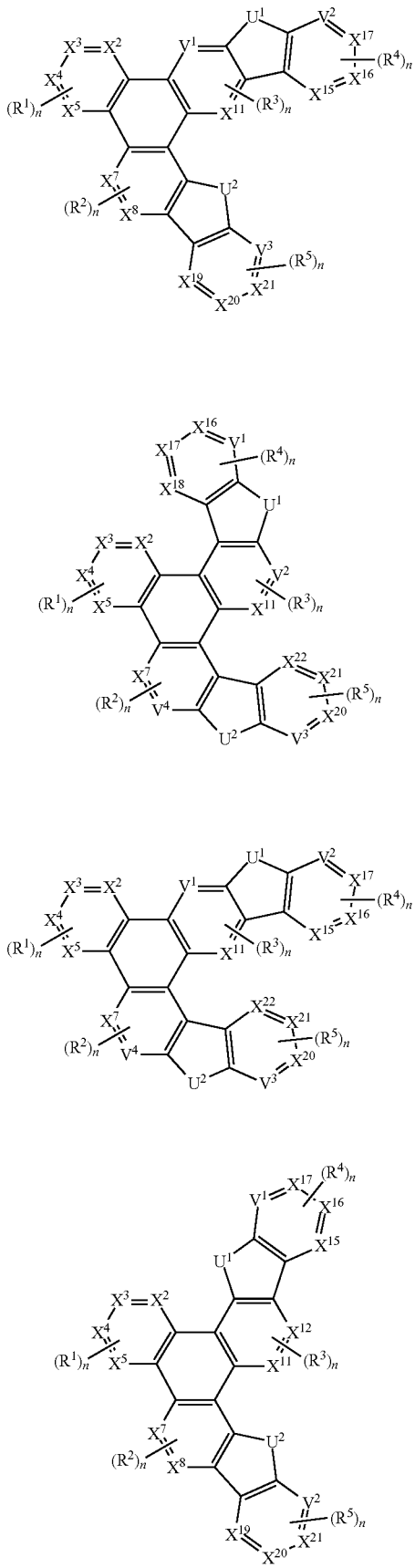

-continued
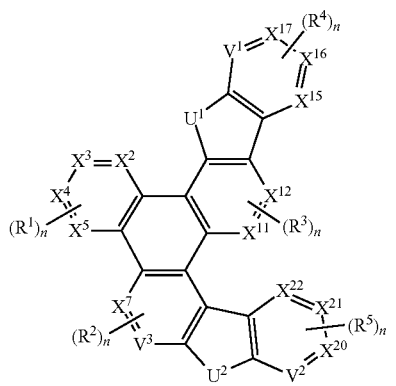
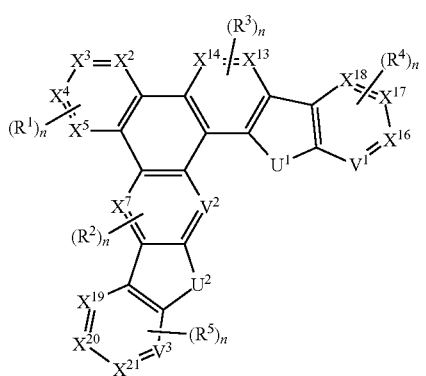
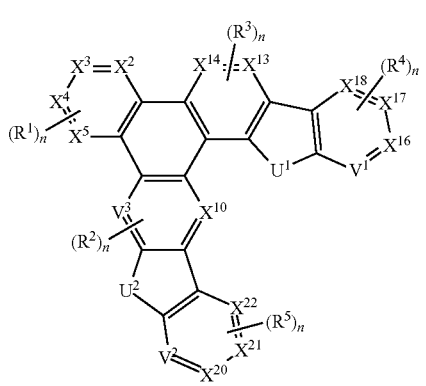
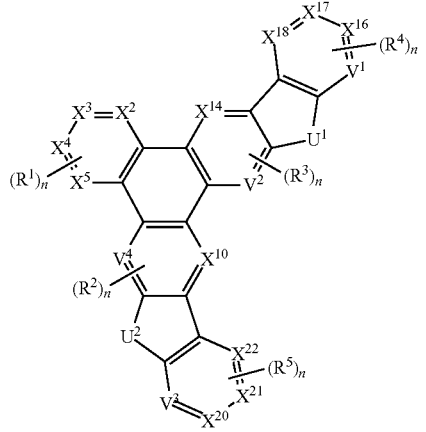
-continued
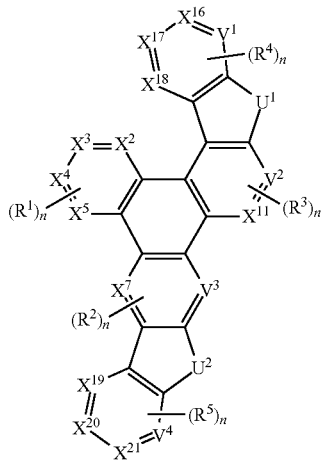
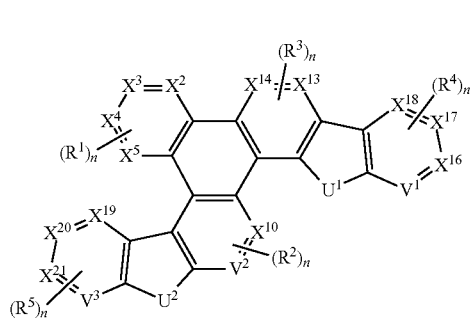
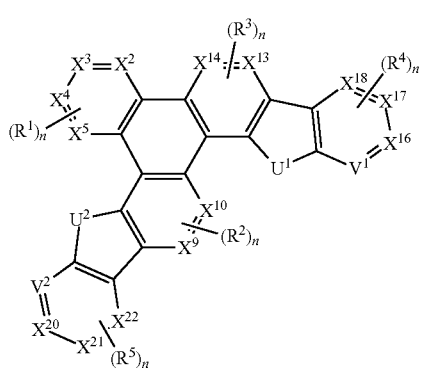
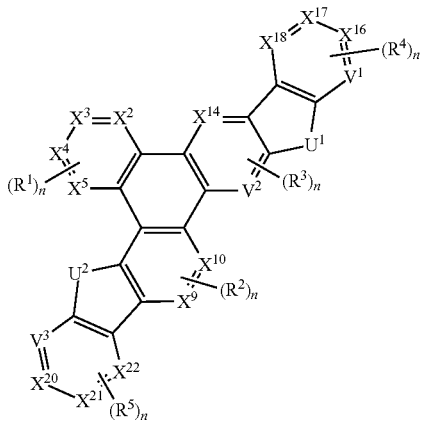

297
-continued
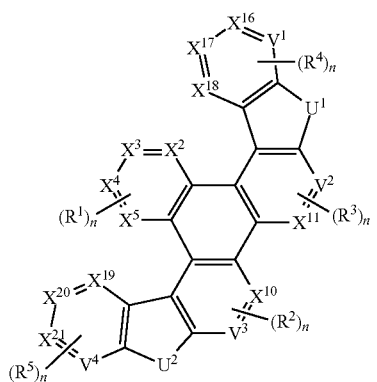
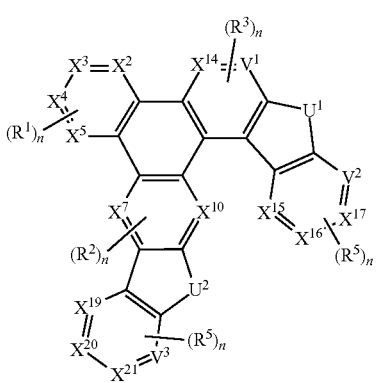
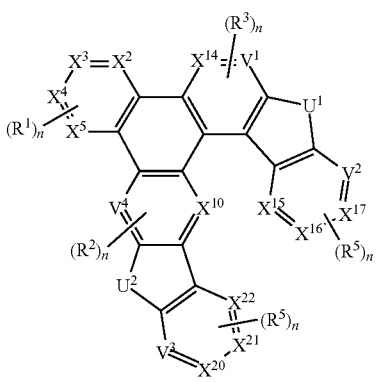
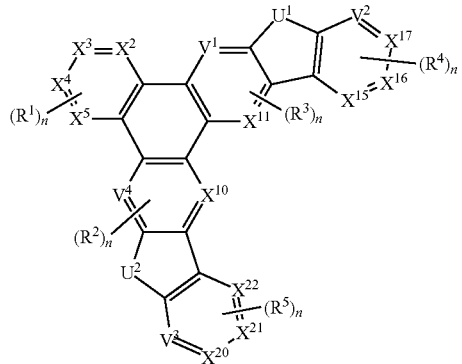
298
-continued
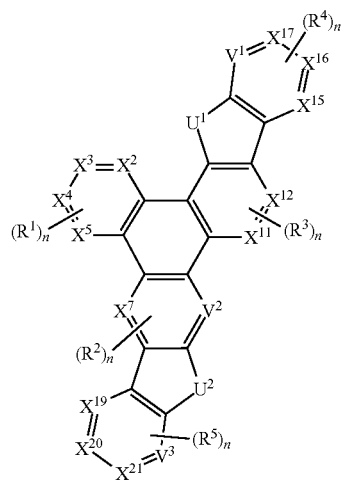
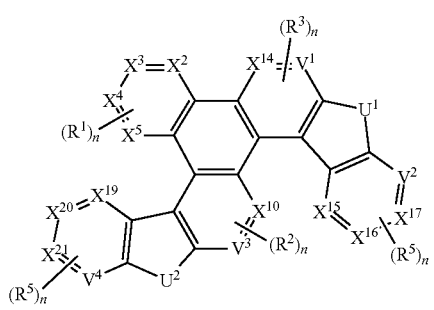
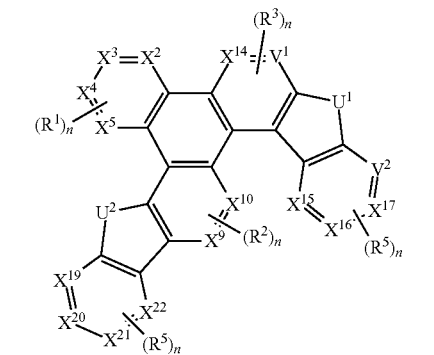
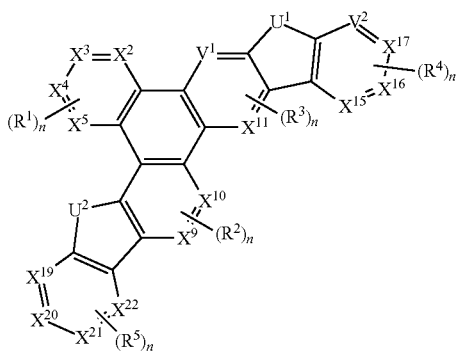

-continued
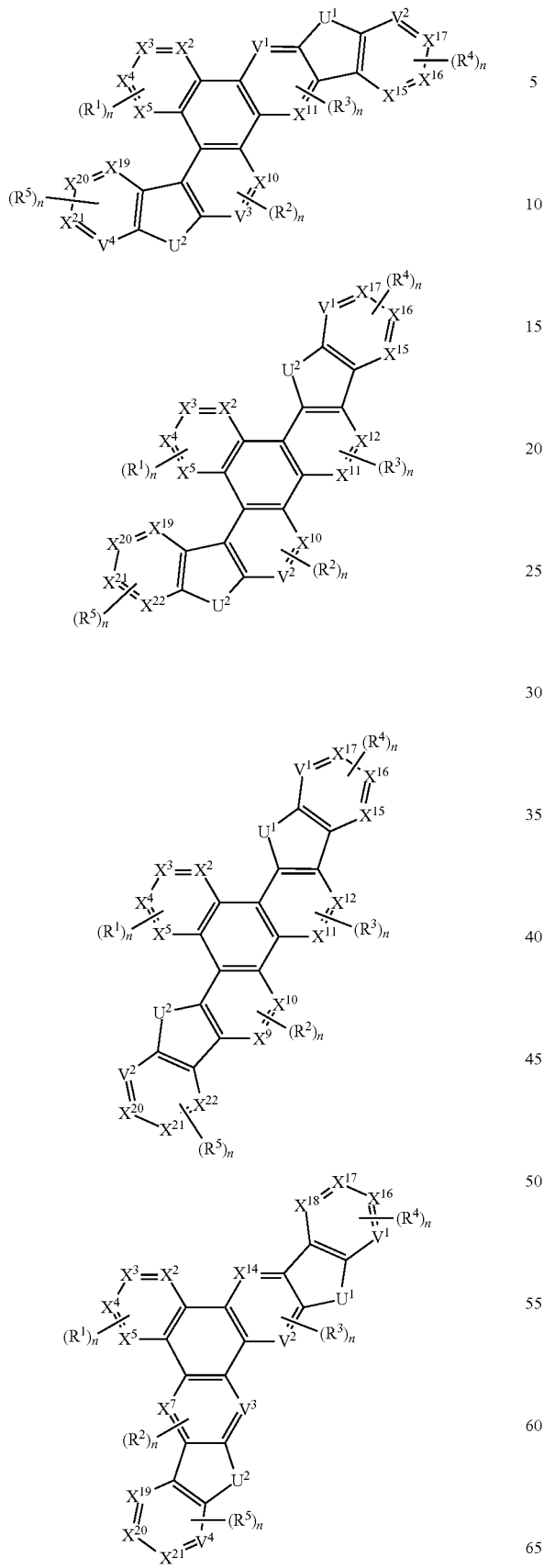
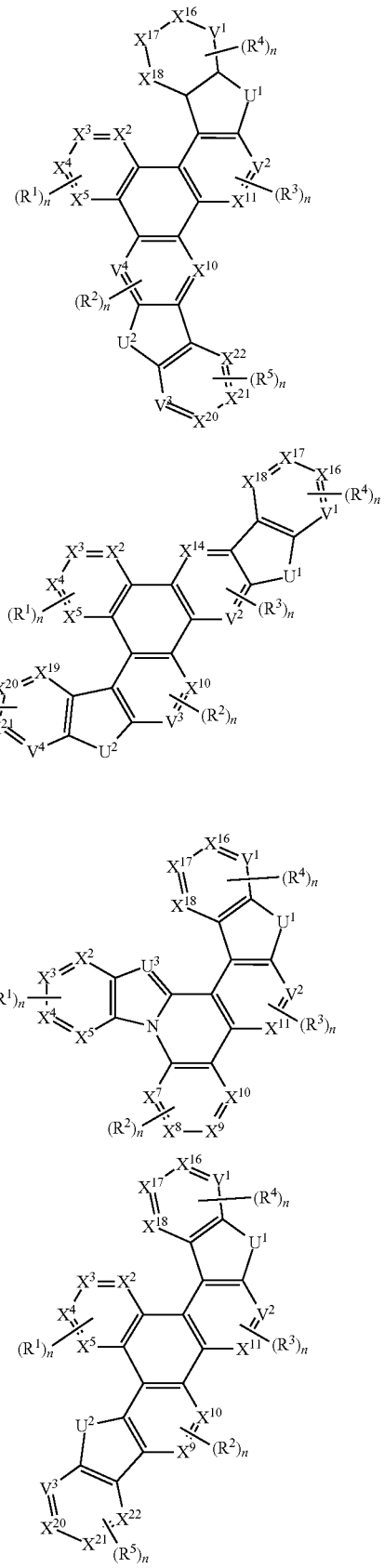

301
-continued
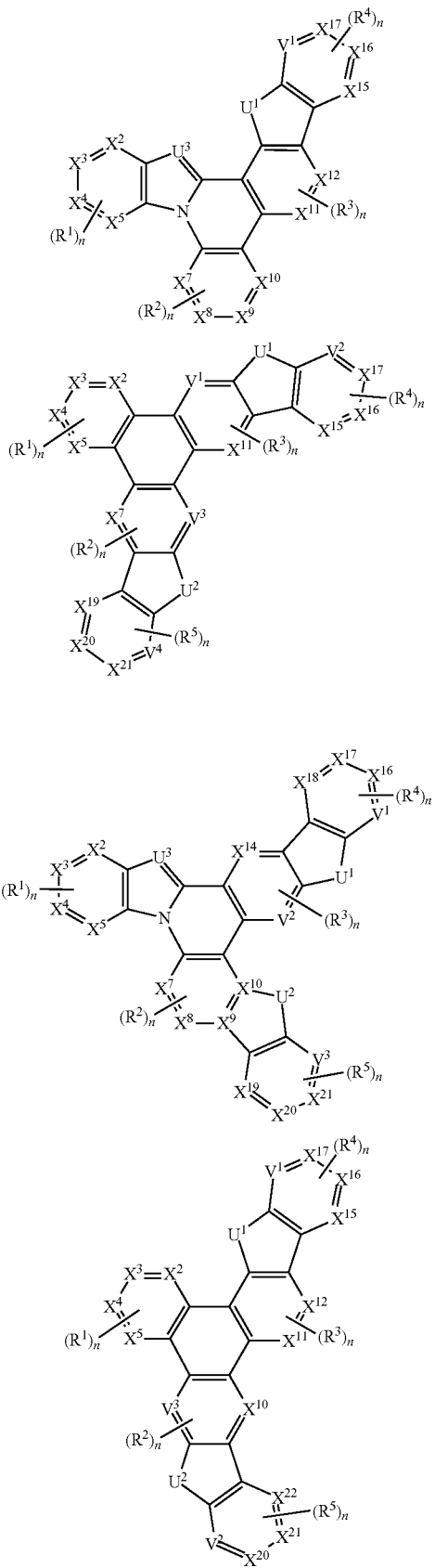
302
-continued
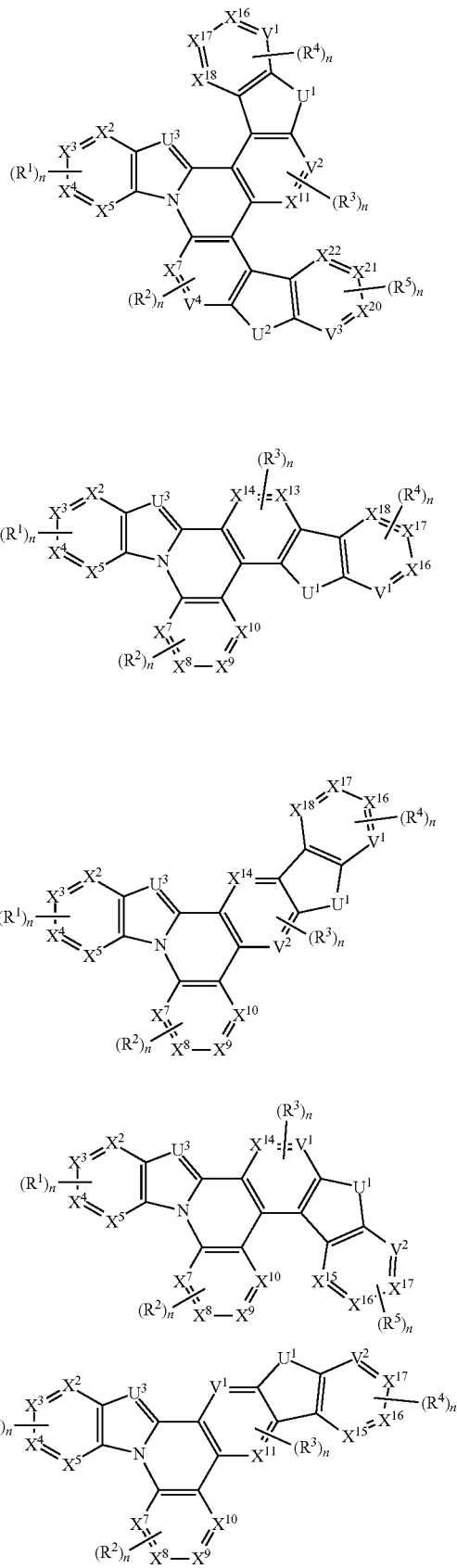

-continued
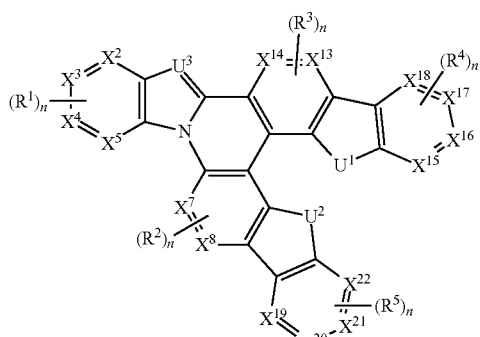
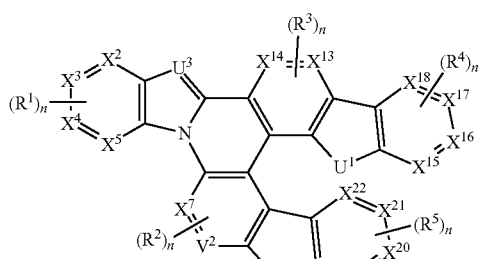
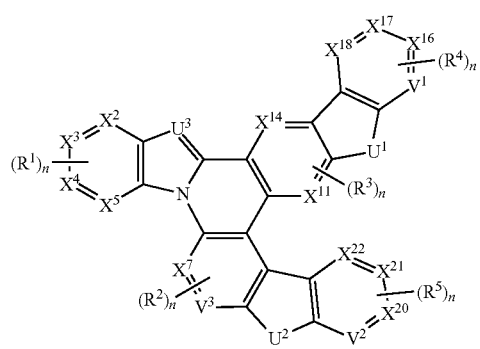
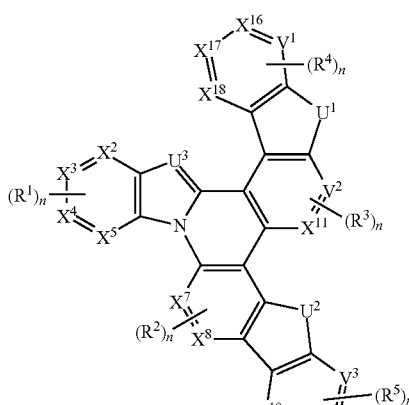
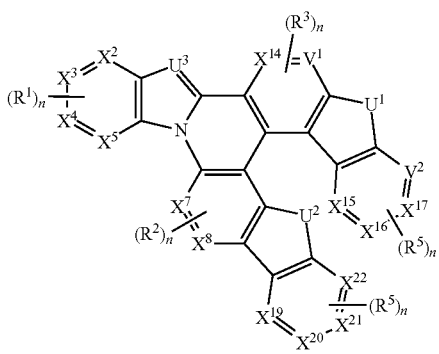
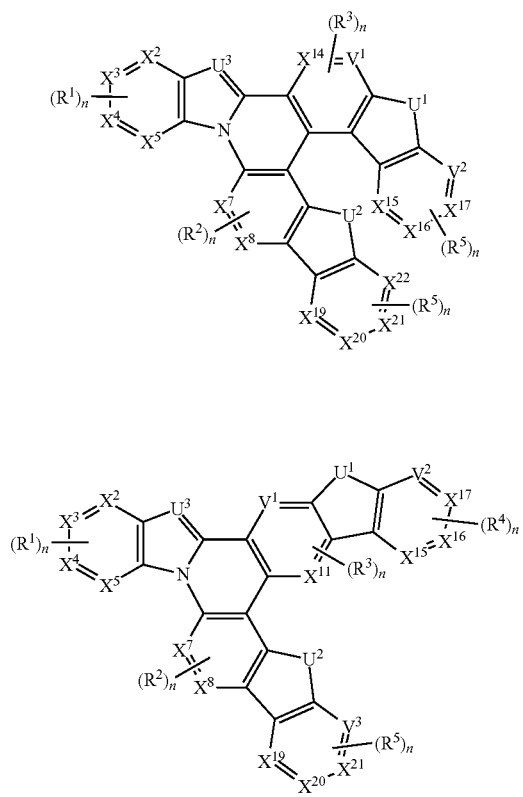

305
-continued
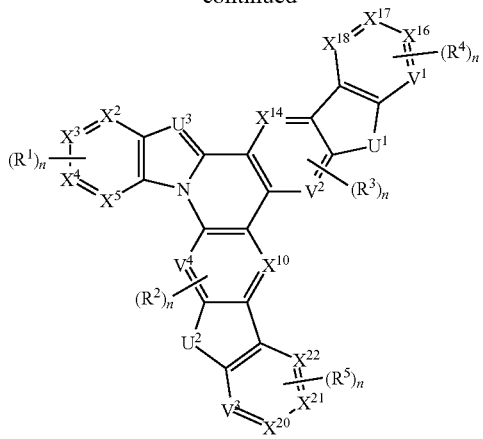
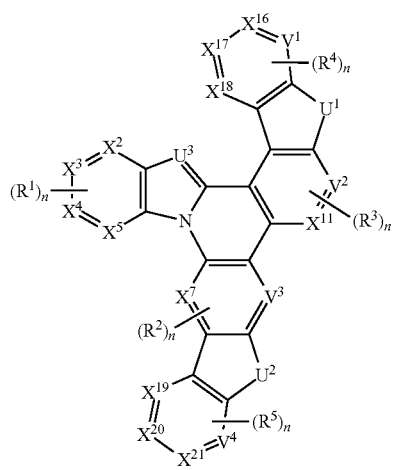
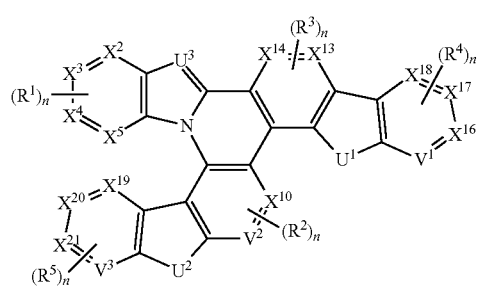
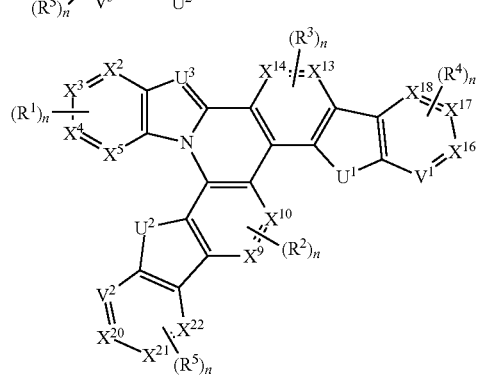
306
-continued
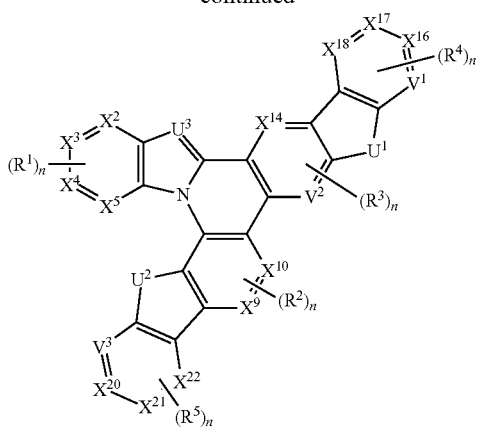
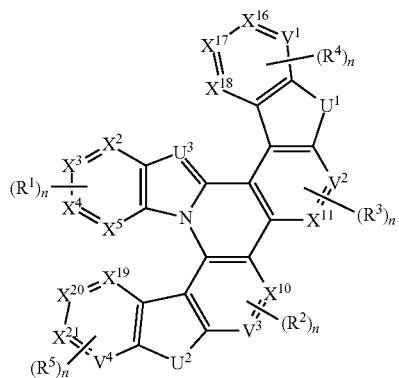
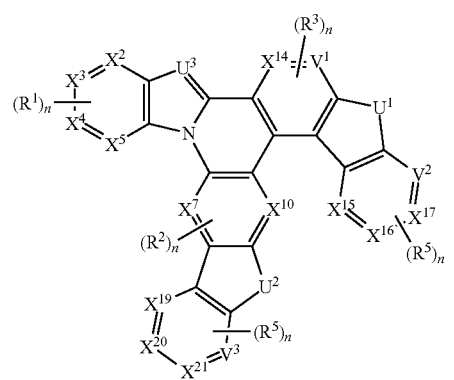
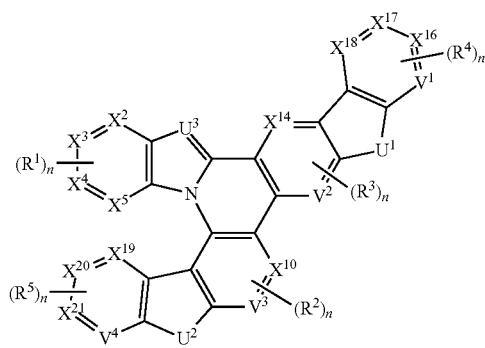

307
-continued
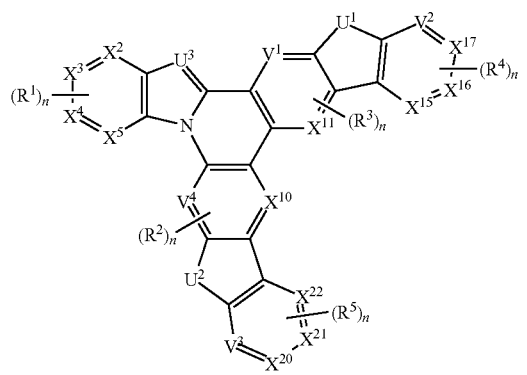
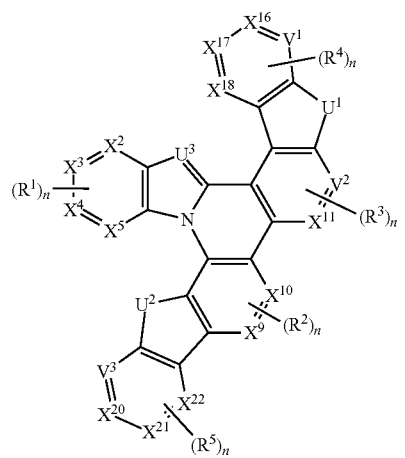
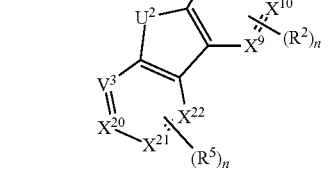
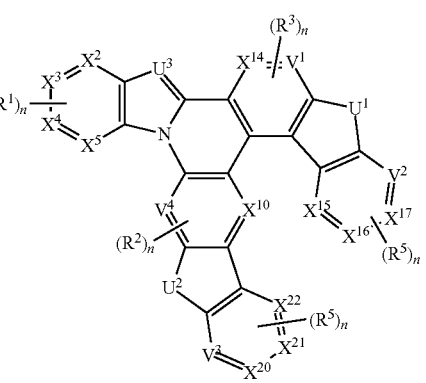
308
-continued
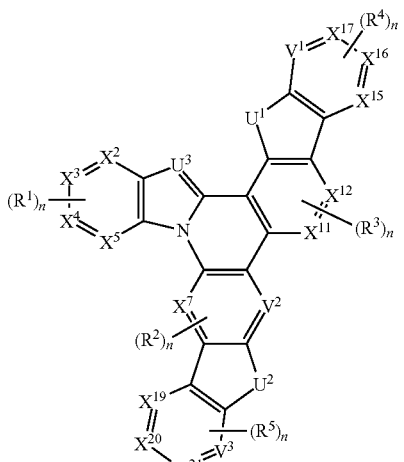
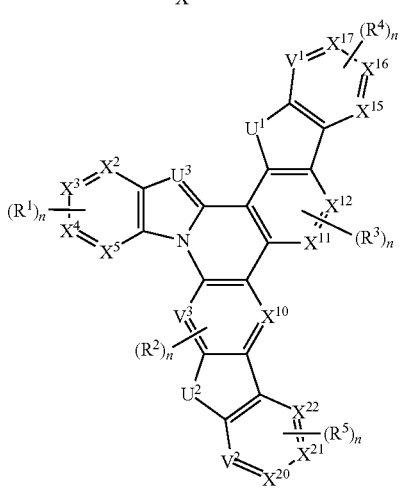
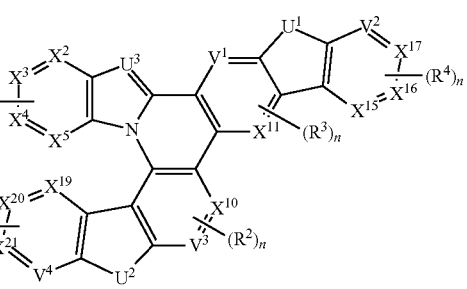
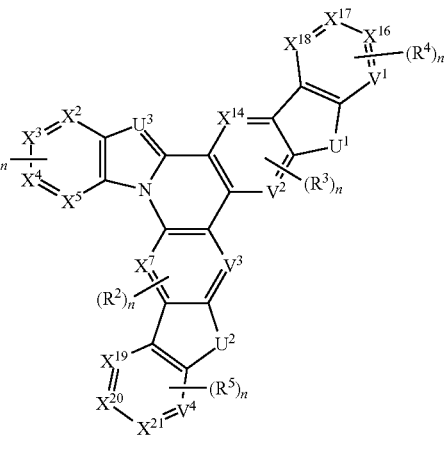

309
-continued
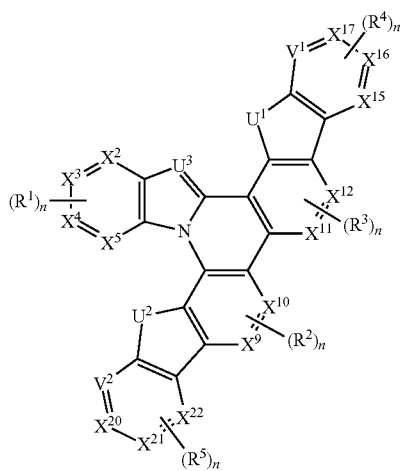
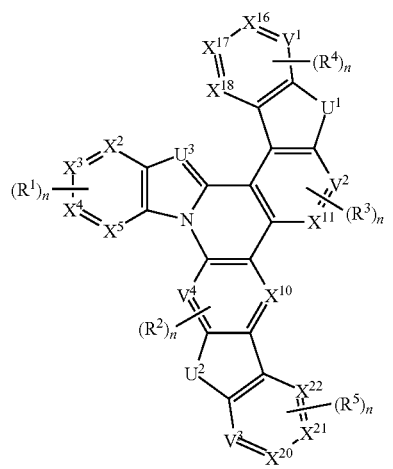
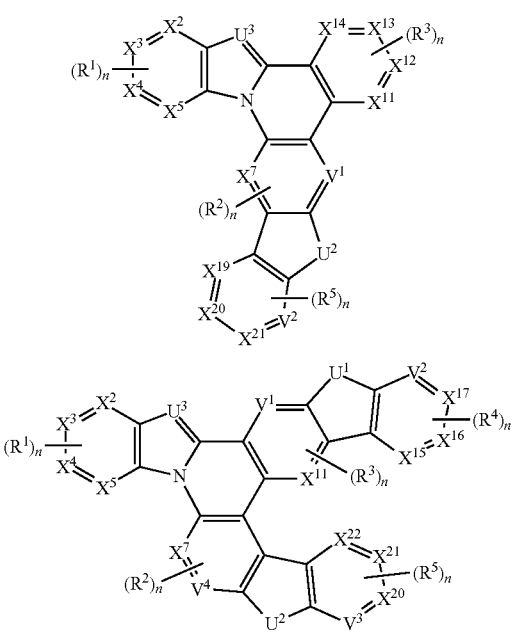
310
-continued
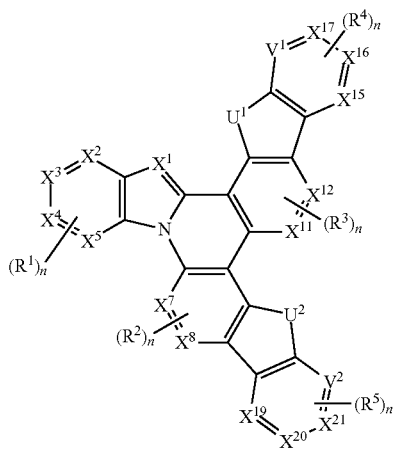
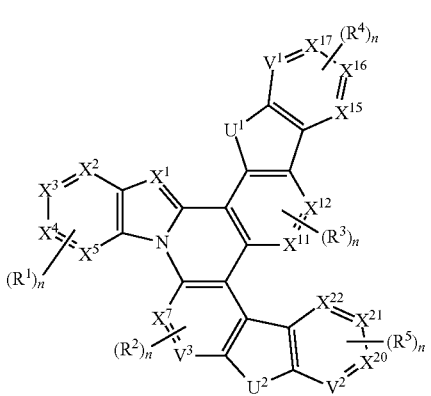
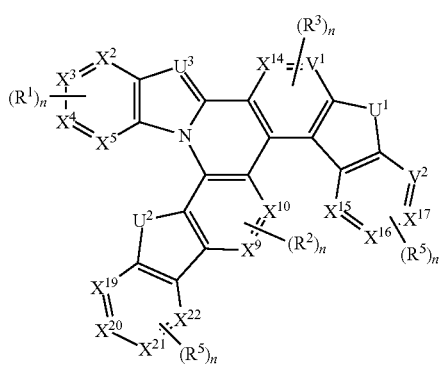

311
-continued
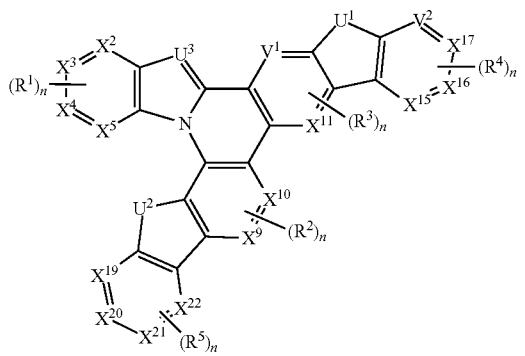
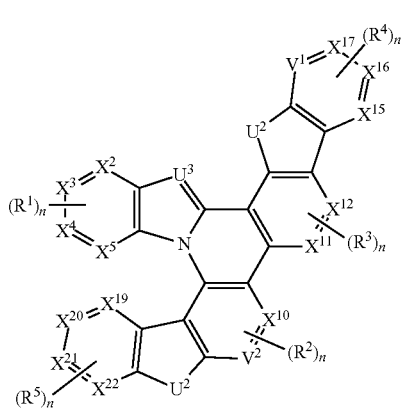
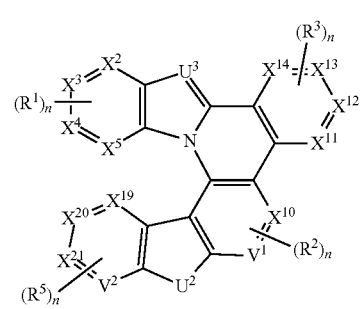
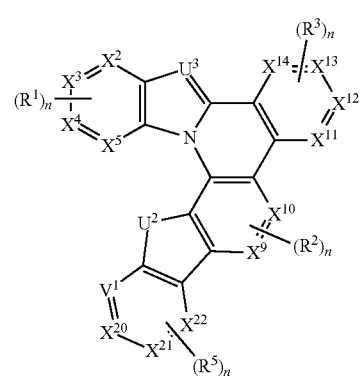
312
-continued
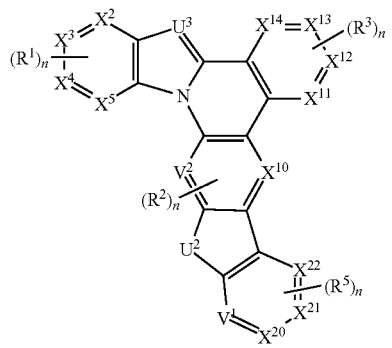
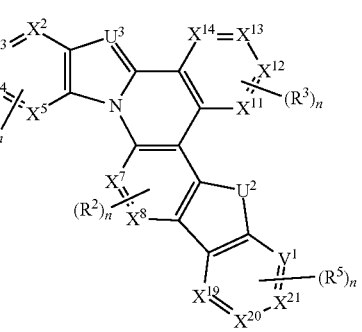
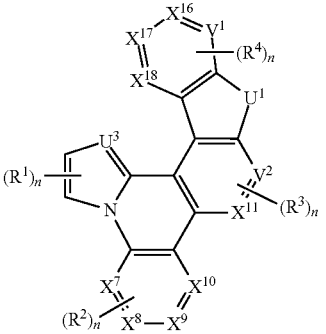
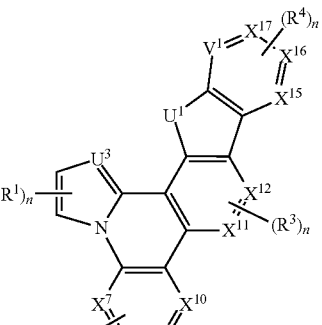
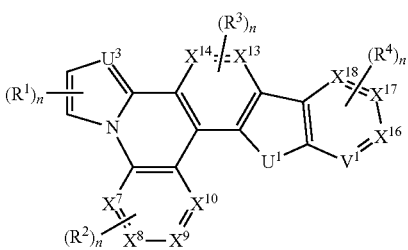

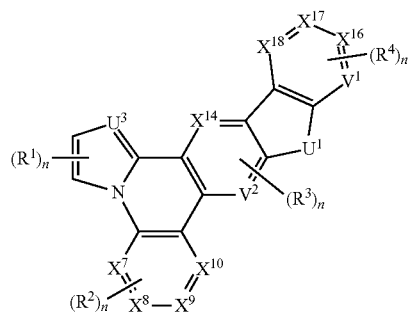
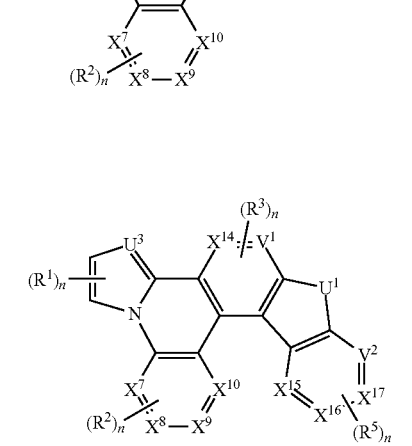
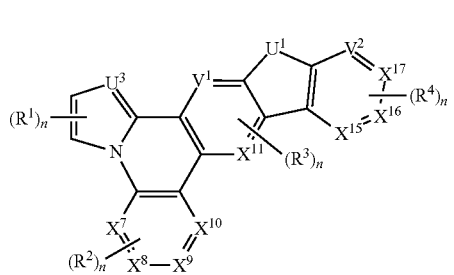
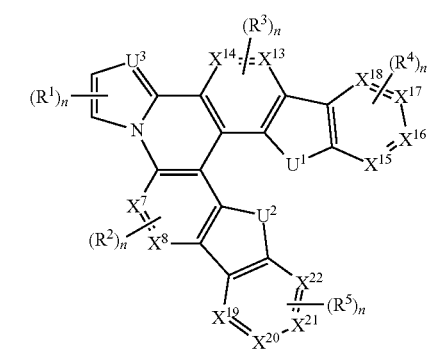

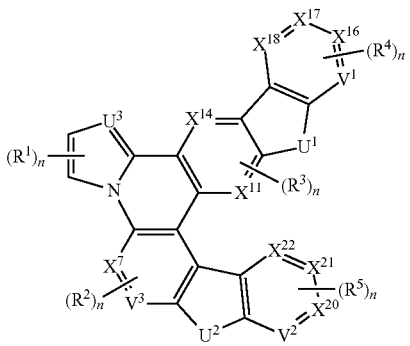
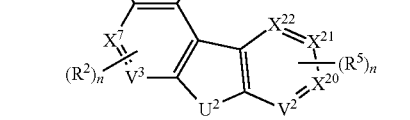
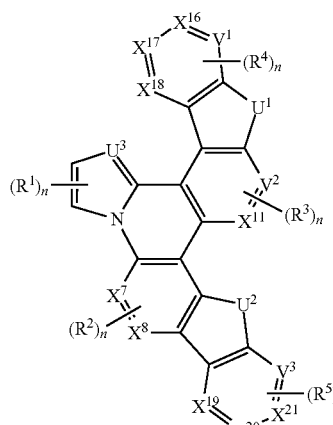
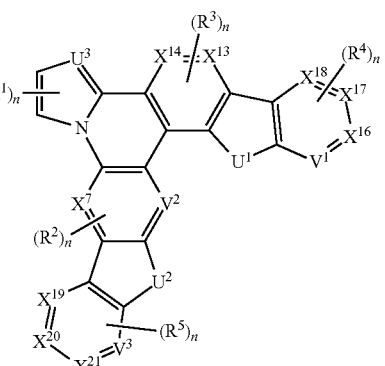

-continued
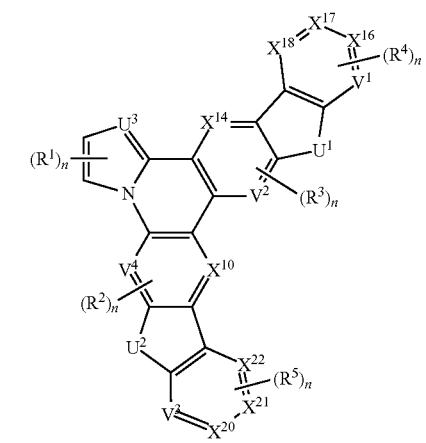
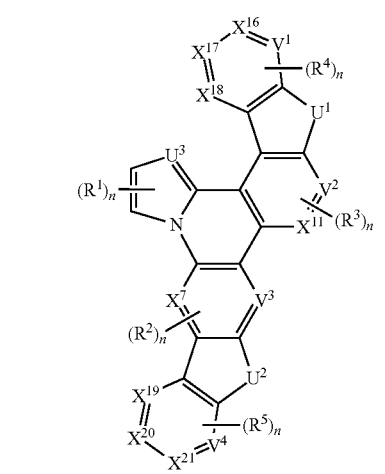
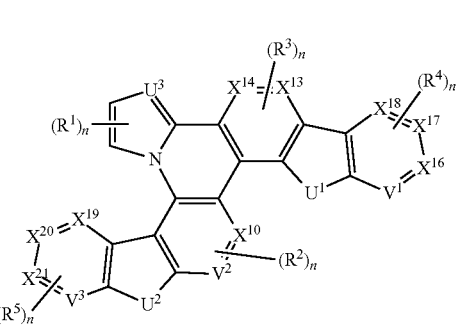
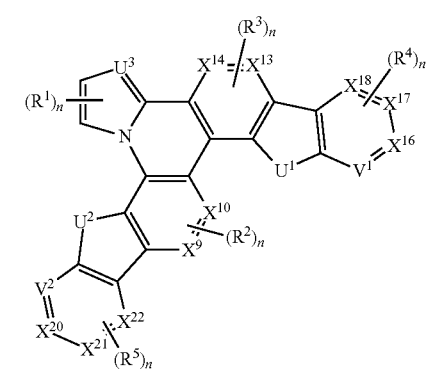
-continued
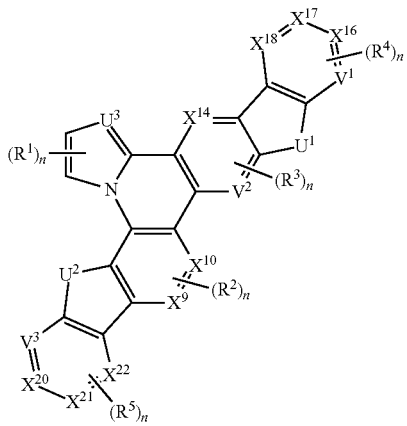
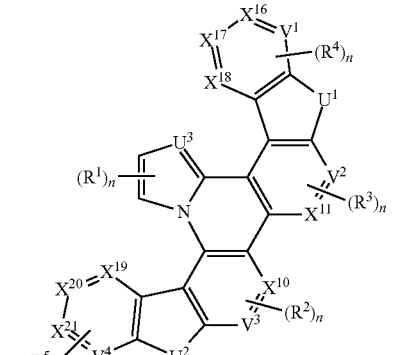
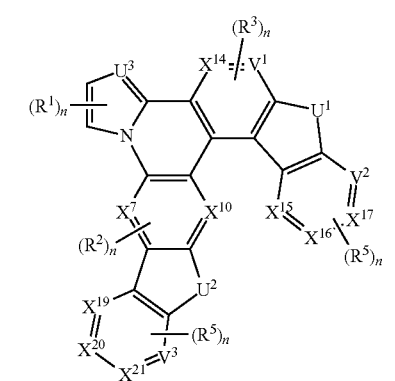
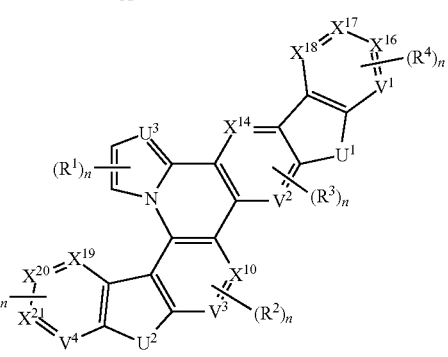

-continued
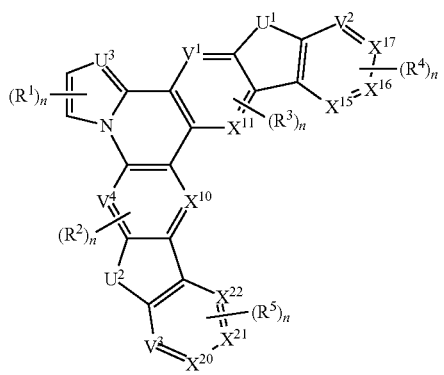
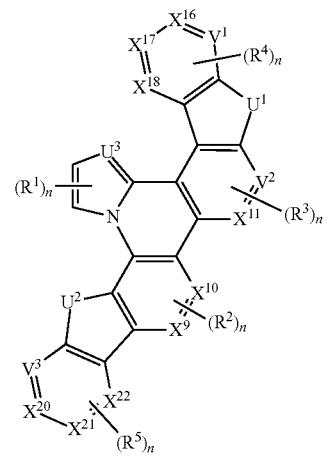
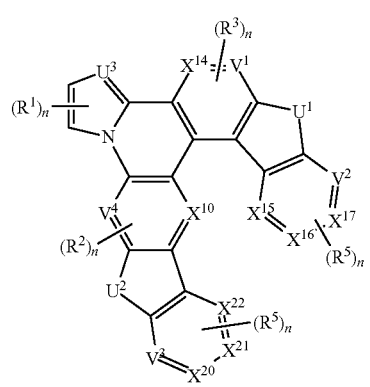
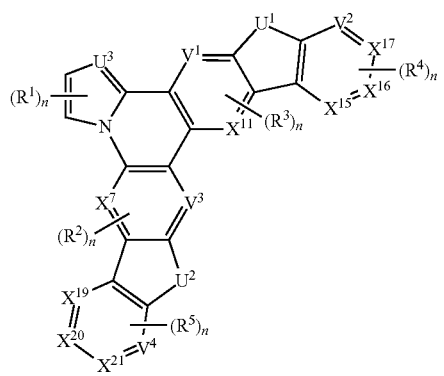
-continued
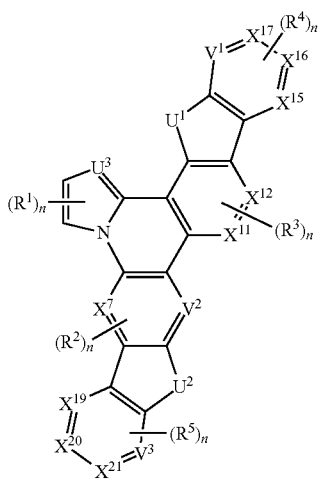
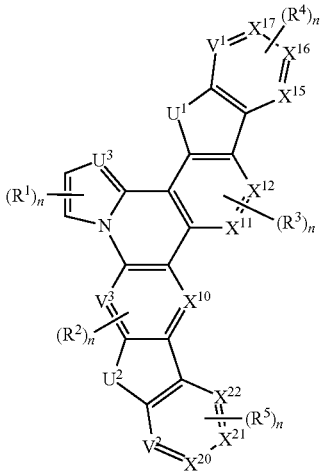
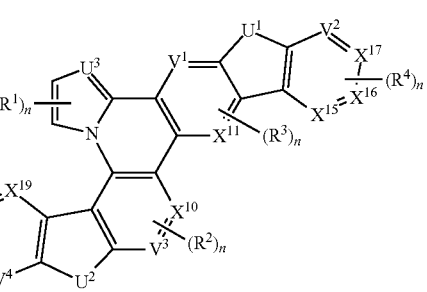
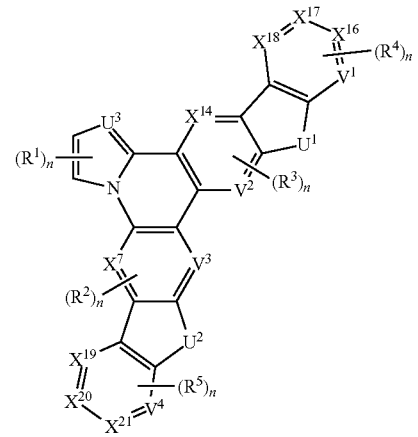

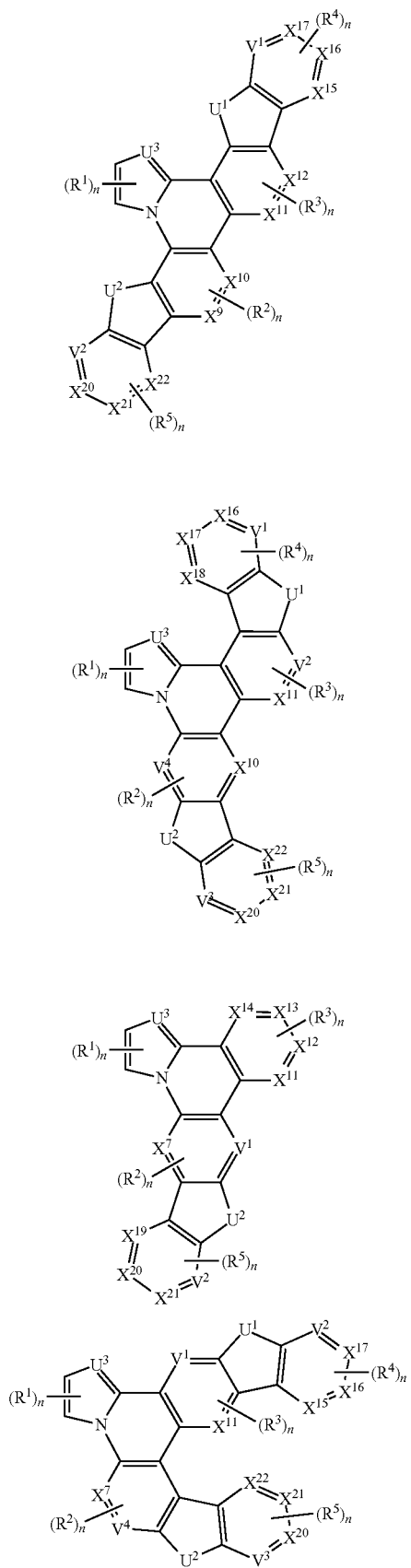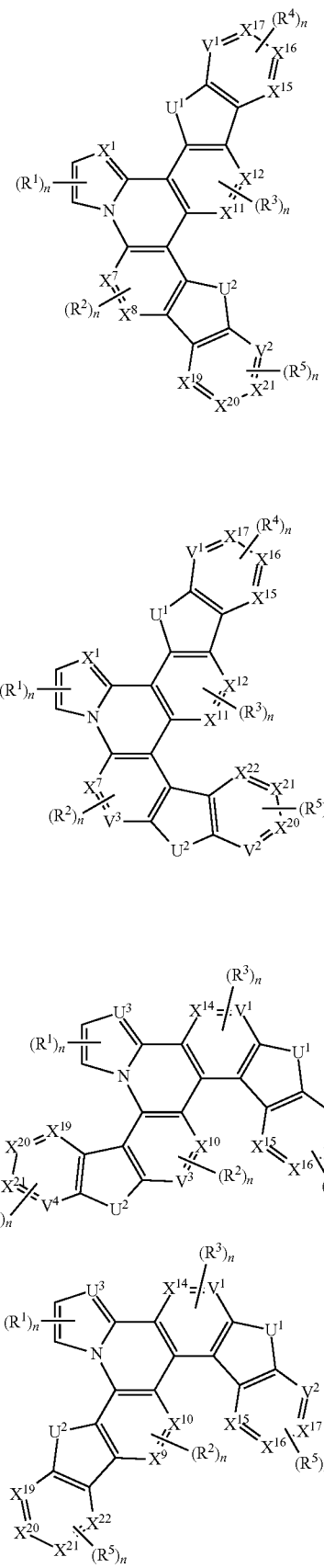

321
-continued
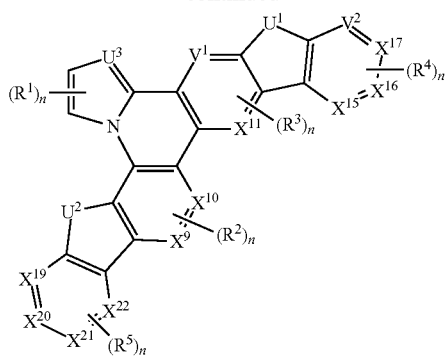
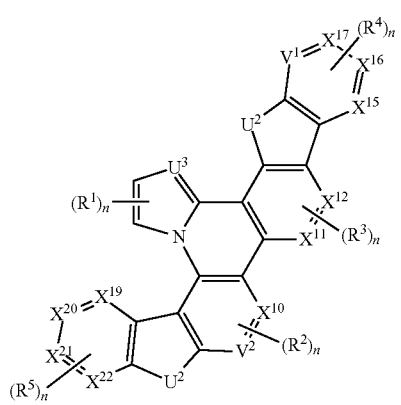
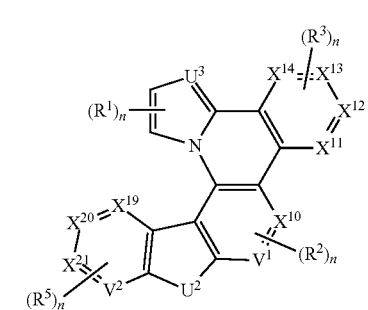
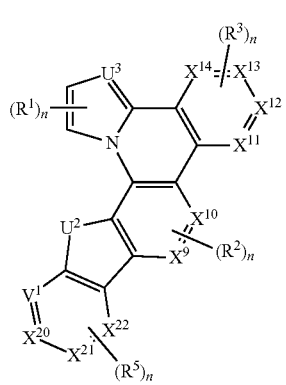
322
-continued
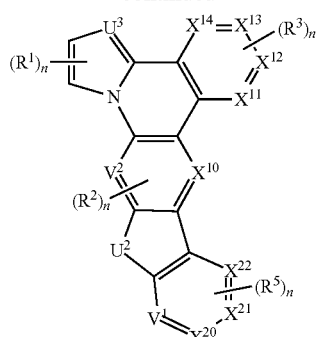
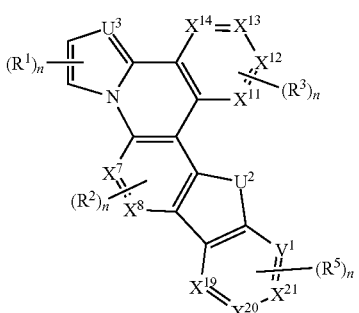
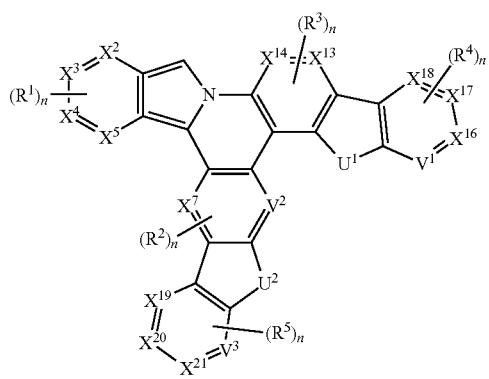
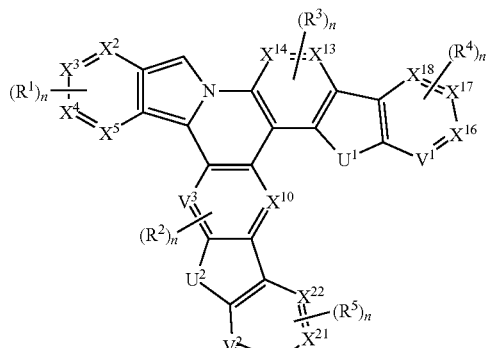

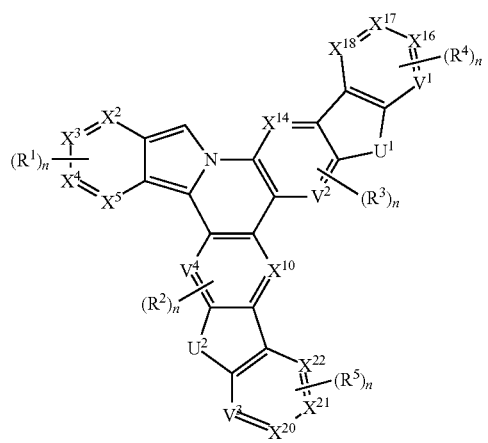
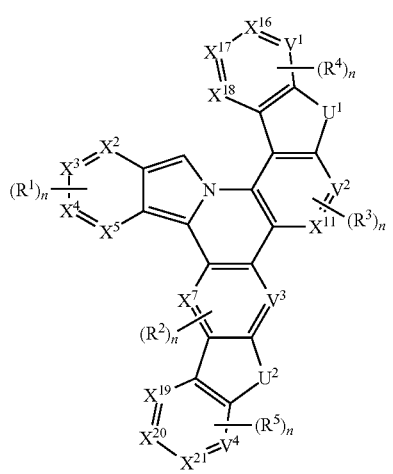
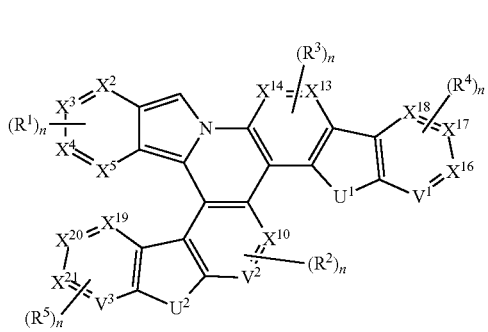
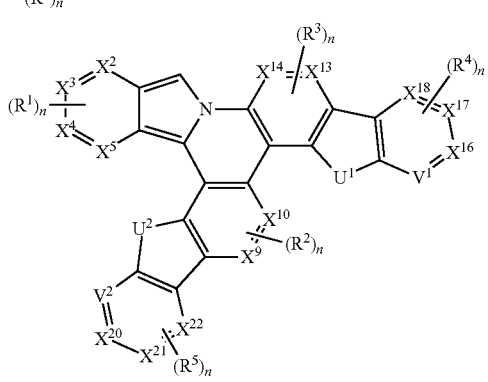
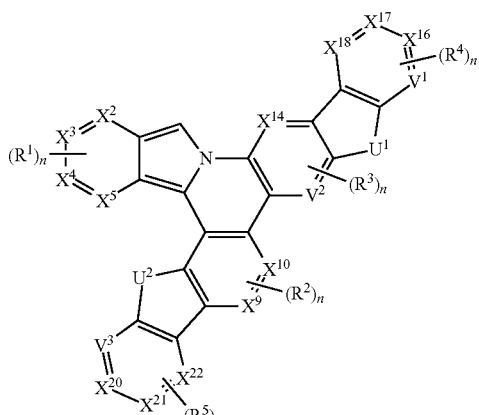
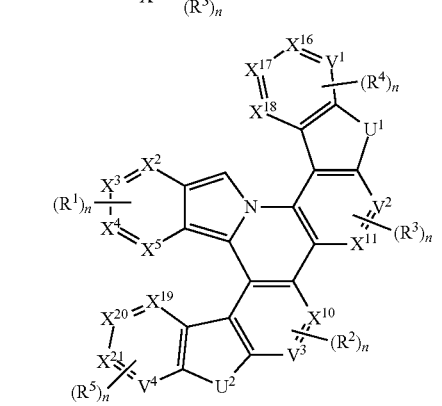
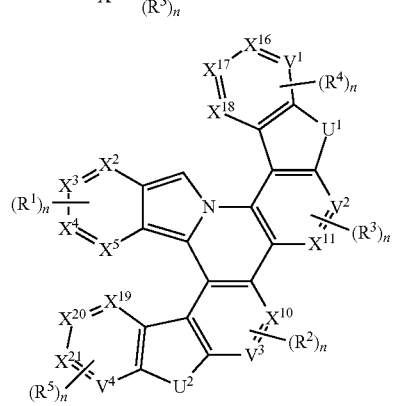

-continued
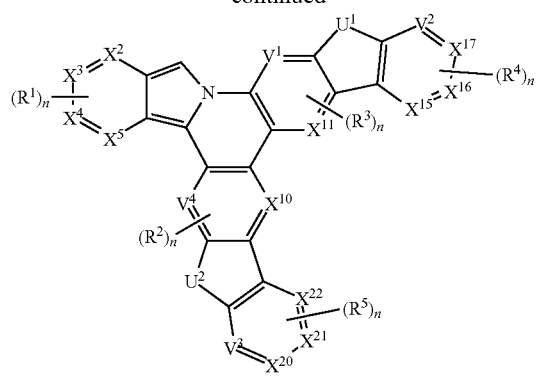
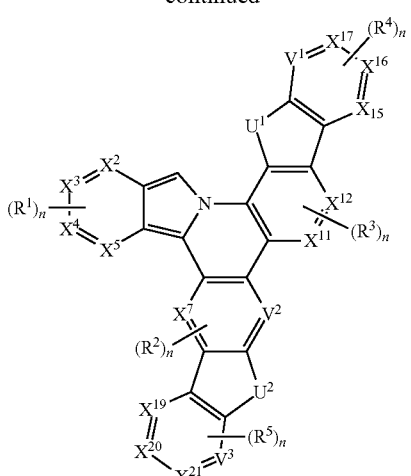
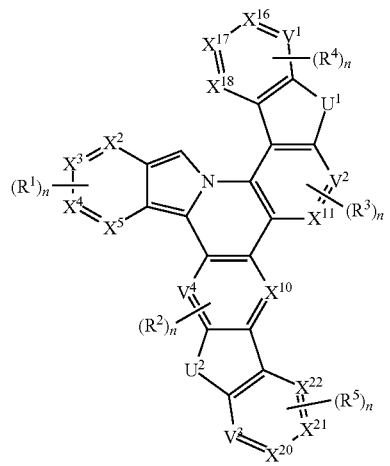
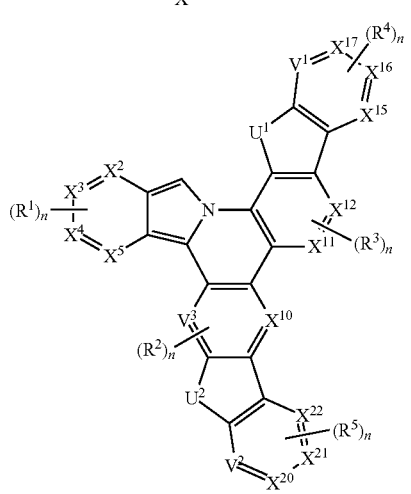
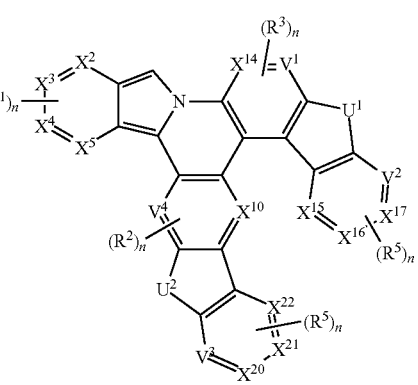
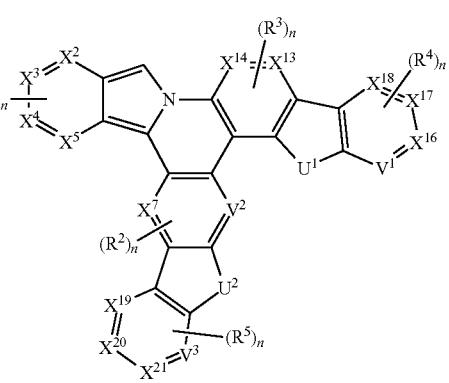
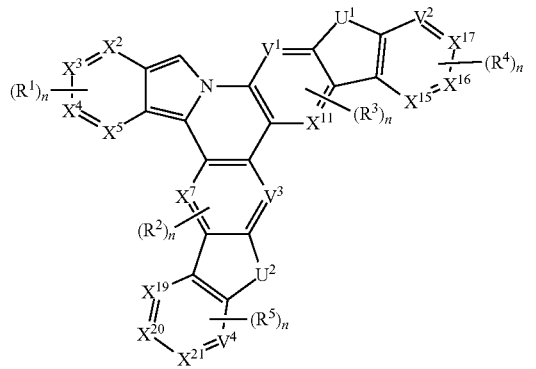
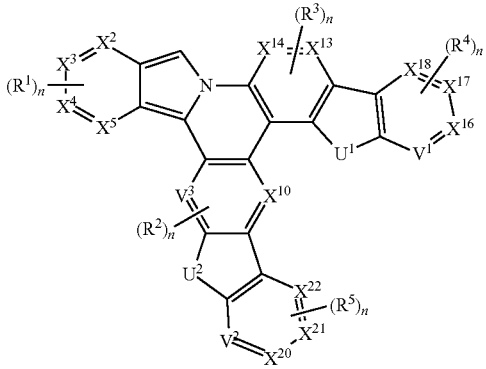

327
-continued
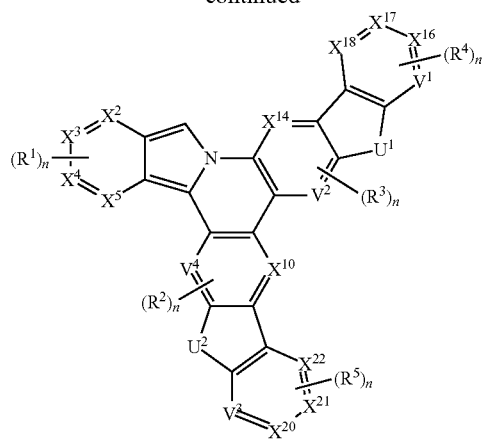
328
-continued
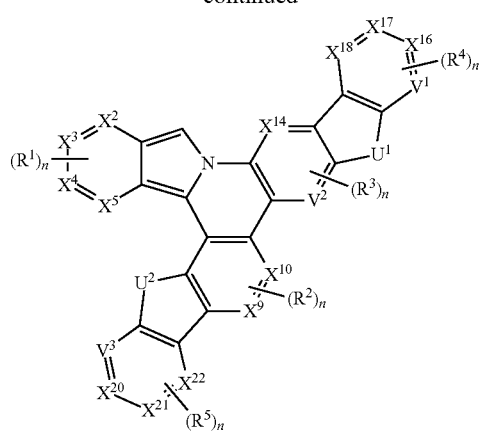
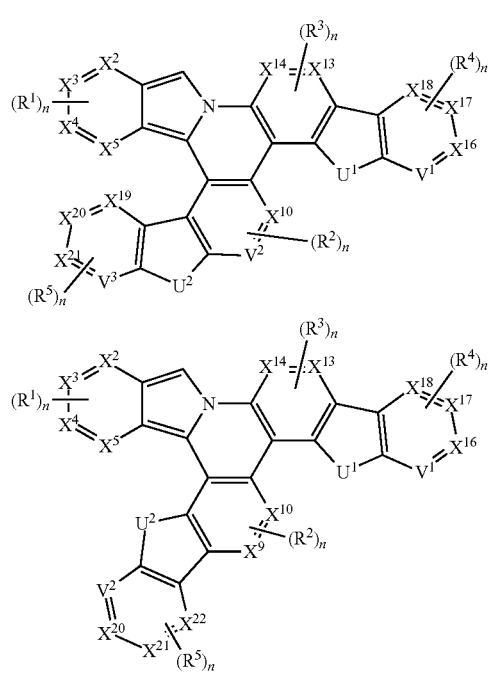
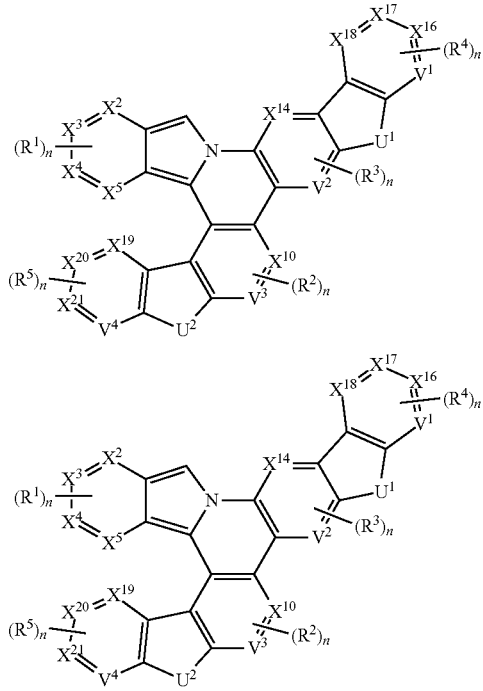

-continued
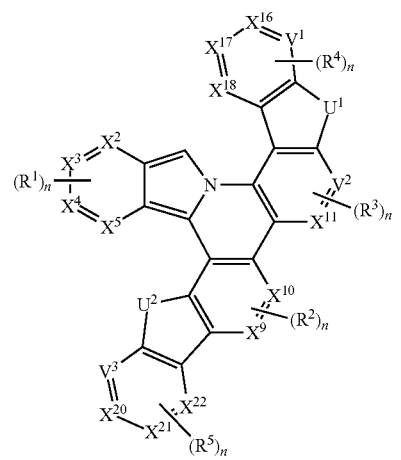
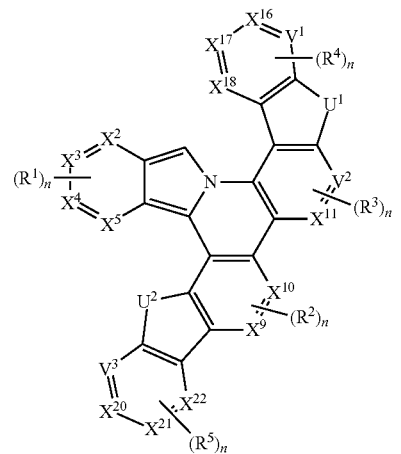
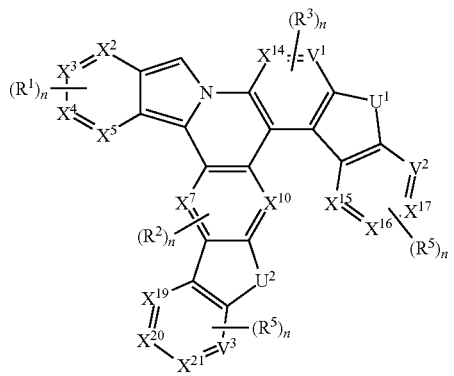
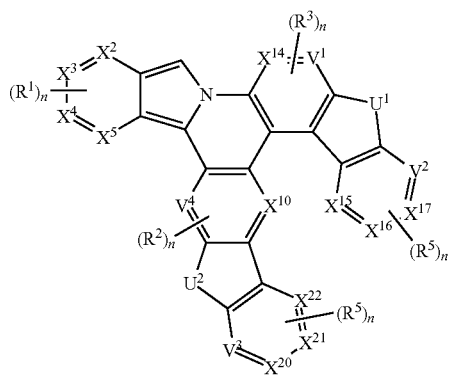
-continued
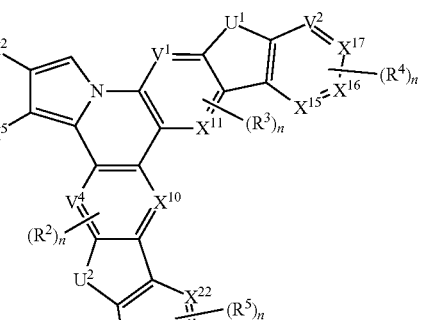
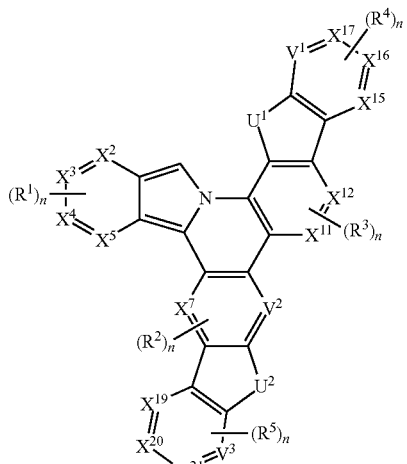
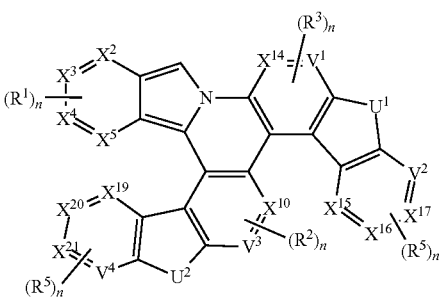
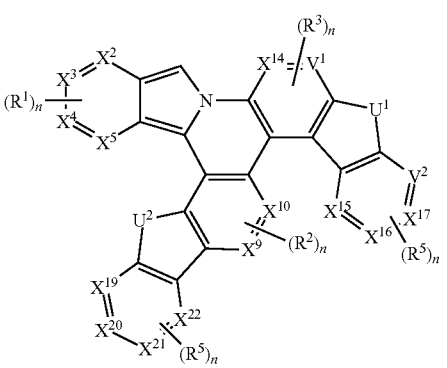

331
-continued
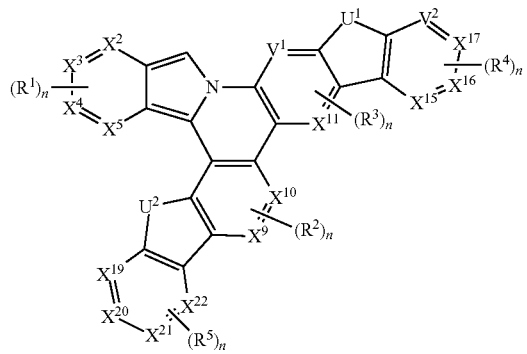
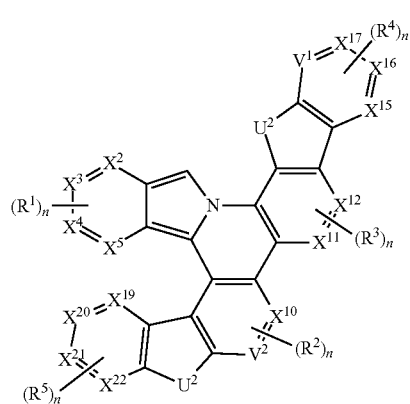
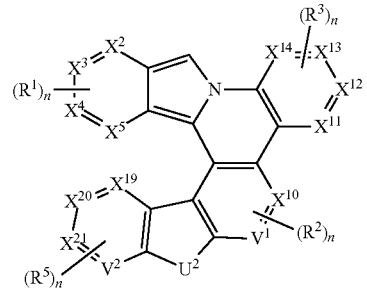
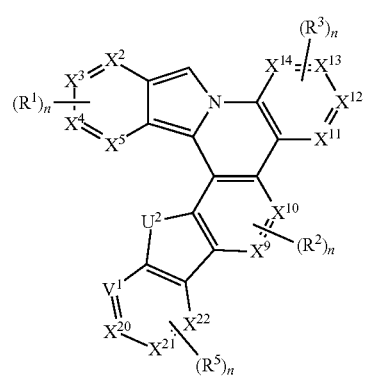
332
-continued
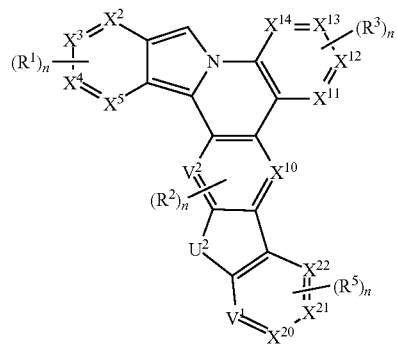
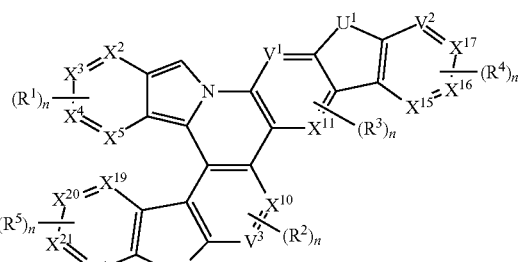
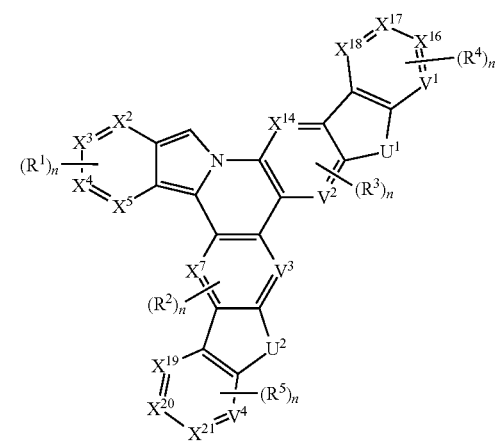

-continued

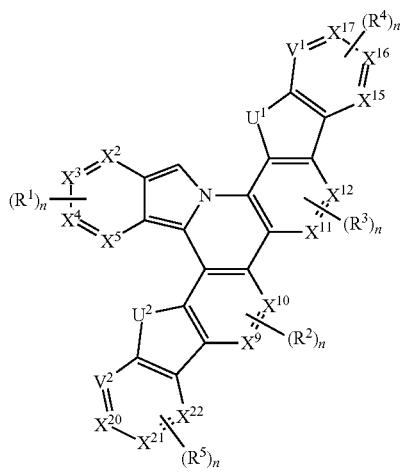

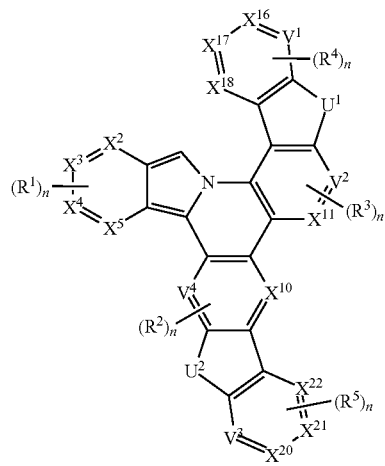

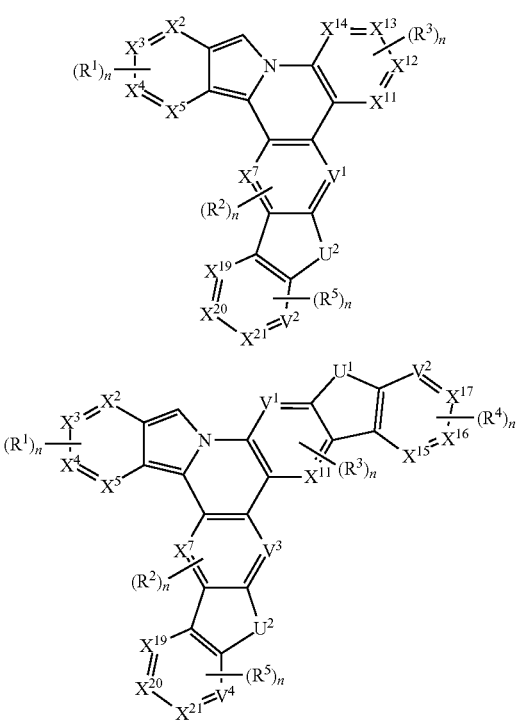

-continued

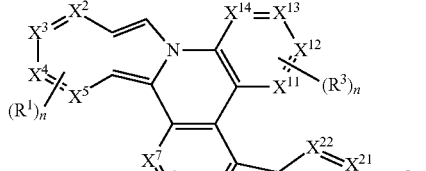

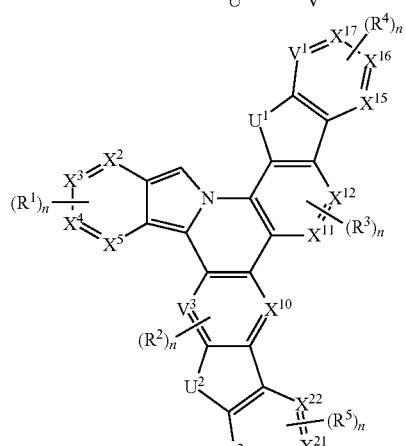

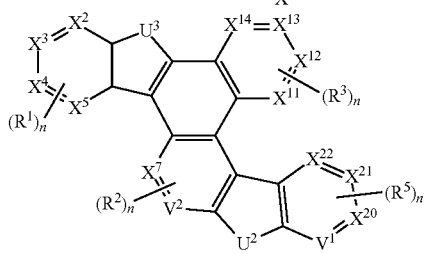

wherein:
$R^1$, $R^2$, $R^3$, $R^4$, and $R^5$ each independently represents hydrogen, cyanide, halogen, hydroxy, amino, nitro, thiol, or substituted or unsubstituted $C_1$-$C_4$ alkyl, alkoxy, or aryl, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, and $X^{22}$ each independently represents substituted or unsubstituted C, N, Si, O, or S, valency permitting, $V^1$, $V^2$, $V^3$, and $V^4$ each independently represents substituted or unsubstituted C or N, valency permitting, $U^1$ and $U^2$ each independently represents O, S, CRR', SiRR', or NAr*, where R and R' each independently represents hydrogen, cyanide, halogen, hydroxy, amino, nitro, thiol, or optionally substituted $C_1$-$C_4$ alkyl, alkoxy, or aryl, and Ar* represents a substituted phenyl, pyridyl, naphthyl, pyrimidyl, pyridazinyl, pyrazinyl, pyrazolyl, imidazolyl, oxazolyl, or thiazolyl ring, and Ar* is optionally covalently bonded to $V^1$, $V^2$, $V^3$, or $V^4$ to form one or more 5-membered or 6-membered rings, $U^3$ and $U^4$ each independently represents CR, SiR, or N, where R represents optionally substituted $C_1$-$C_4$ alkyl, alkoxy, aryl or heteroaryl, and each n is independently an integer as permitted by valence.

2. An organic light emitting diode comprising the compound of claim 1.

3. A light emitting device comprising the light emitting diode of claim 2.

\* \* \* \* \*